US012188020B2

(12) United States Patent
Rigo

(10) Patent No.: US 12,188,020 B2
(45) Date of Patent: Jan. 7, 2025

(54) METHODS FOR REDUCING ATAXIN-2 EXPRESSION

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/323,826

(22) Filed: May 18, 2021

(65) Prior Publication Data

US 2022/0162615 A1 May 26, 2022

Related U.S. Application Data

(63) Continuation of application No. 16/063,852, filed as application No. PCT/US2016/069406 on Dec. 30, 2016, now abandoned.

(60) Provisional application No. 62/273,689, filed on Dec. 31, 2015.

(51) Int. Cl.

| | |
|---|---|
| ***C07H 21/04*** | (2006.01) |
| ***A61K 31/7088*** | (2006.01) |
| ***A61P 25/28*** | (2006.01) |
| ***C12N 5/0793*** | (2010.01) |
| ***C12N 15/113*** | (2010.01) |

(52) U.S. Cl.

CPC ...... *C12N 15/1138* (2013.01); *A61K 31/7088* (2013.01); *A61P 25/28* (2018.01); *C12N 5/0619* (2013.01); *C12N 15/113* (2013.01); *A01K 2227/105* (2013.01); *A01K 2267/0318* (2013.01); *C12N 2310/11* (2013.01); *C12N 2310/315* (2013.01); *C12N 2310/3233* (2013.01); *C12N 2510/00* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |

(Continued)

FOREIGN PATENT DOCUMENTS

| | | | |
|---|---|---|---|
| EP | 0878543 | A1 | 11/1998 |
| EP | 1752536 | A1 | 2/2007 |

(Continued)

OTHER PUBLICATIONS

Elden et al. ("Ataxin-2 intermediate-length polyglutamine expansions are associated with increased risk for ALS." Nature (2010) 466: 1069-1075).*

Corrado, Lucia, et al. ("ATXN-2 CAG repeat expansions are interrupted in ALS patients." Human genetics 130.4 (2011): 575-580).*

Elden ("Ataxin-2 intermediate-length polyglutamine expansions are associated with increased risk for ALS." Nature (2010) 466: 1069-1075).*

Rogers et al. (A Glutamate Scavenging Protocol Combined with Deanna Protocol in SOD1-G93A Mouse Model of ALS. Nutrients 2023, 15, 1821).*

Ataxin-2 Wikipedia. Downloaded on Jul. 16, 2018 from http://en.wikipedia.org/wiki/Ataxin-2.

(Continued)

*Primary Examiner* — Kimberly Chong

(74) *Attorney, Agent, or Firm* — McNeill PLLC

(57) ABSTRACT

Provided herein are methods for decreasing Ataxin-2 mRNA expression. Such methods are useful to ameliorate symptoms of Ataxin-2 associated diseases. Such Ataxin-2 associated diseases include amyotrophic lateral sclerosis (ALS). Such symptoms include loss of motor function, reduced CMAP amplitude, denervation, and loss of motor neurons.

45 Claims, No Drawings

Specification includes a Sequence Listing.

(56) References Cited

U.S. PATENT DOCUMENTS 5,399,676 A 3/1995 Froehler
5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,801,154 A 9/1998 Baracchini et al.
5,808,027 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'O
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,582,908 B2 6/2003 Fodor et al.
6,600,032 B1 7/2003 Manoharan et al.
6,660,720 B2 12/2003 Manoharan
6,673,535 B1 1/2004 Pulst
6,770,748 B2 8/2004 Imanishi et al.
6,844,431 B1 1/2005 Pulst
7,015,315 B1 3/2006 Cook et al.
7,053,207 B2 5/2006 Wengel et al.
7,101,993 B1 9/2006 Cook et al.
7,262,177 B2 8/2007 Ts'o et al.
7,374,927 B2 5/2008 Palma et al.
7,399,845 B2 7/2008 Seth et al.
7,427,672 B2 9/2008 Imanishi et al.
7,491,805 B2 2/2009 Vargeese et al.
7,547,684 B2 6/2009 Seth et al.
7,569,686 B1 8/2009 Bhat et al.
7,666,854 B2 2/2010 Seth et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,888,497 B2 2/2011 Bentwich et al.
7,939,677 B2 5/2011 Bhat et al.
8,022,193 B2 9/2011 Swayze et al.
8,030,467 B2 10/2011 Seth et al.
8,080,644 B2 12/2011 Wengel et al.
8,088,746 B2 1/2012 Seth et al.
8,088,904 B2 1/2012 Swayze et al.
8,106,022 B2 1/2012 Manoharan et al.
8,124,745 B2 2/2012 Allerson et al.
8,153,365 B2 4/2012 Wengel et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,501,805 B2 4/2013 Seth et al.
8,440,803 B2 5/2013 Swayze et al.
8,530,640 B2 9/2013 Seth et al.
8,546,556 B2 10/2013 Seth et al.
RE44,779 E 2/2014 Imanishi et al.
8,728,736 B2 5/2014 Leamon et al.
8,828,956 B2 9/2014 Manoharan et al.
9,005,906 B2 4/2015 Swayze et al.
9,012,421 B2 4/2015 Migawa et al.
9,127,276 B2 8/2015 Prakash et al.
9,290,760 B2 3/2016 Rajeev et al.
9,994,855 B2 * 6/2018 Prakash ............ C12N 15/1138
10,006,027 B2 * 6/2018 Bennett ............... C12N 15/113
10,308,934 B2 6/2019 Freier
10,533,178 B2 1/2020 Bennett et al.
11,111,494 B2 9/2021 Freier
11,834,660 B2 12/2023 Freier et al.
2001/0053519 A1 12/2001 Fodor et al.
2003/0158403 A1 8/2003 Manoharan et al.
2003/0175906 A1 9/2003 Manoharan et al.
2003/0228597 A1 12/2003 Cowsert et al.
2004/0171570 A1 9/2004 Allerson et al.
2004/0220132 A1 11/2004 Kaemmerer
2005/0026164 A1 2/2005 Zhou
2005/0042646 A1 2/2005 Davidson et al.
2005/0100885 A1 5/2005 Crooke et al.
2005/0130923 A1 6/2005 Bhat et al.
2005/0209178 A1 9/2005 Pulst

(56) References Cited

U.S. PATENT DOCUMENTS

2005/0244851 A1 11/2005 Blume et al.
2005/0255487 A1 11/2005 Khvorova et al.
2006/0148740 A1 7/2006 Platenburg
2006/0270727 A1 11/2006 Melander et al.
2007/0031844 A1 2/2007 Khvorova et al.
2007/0224624 A1 9/2007 Pulst
2008/0039618 A1 2/2008 Allerson et al.
2008/0113351 A1 5/2008 Naito et al.
2010/0190837 A1 7/2010 Migawa et al.
2010/0197762 A1 8/2010 Swayze et al.
2011/0054005 A1 3/2011 Naito et al.
2011/0142789 A1 6/2011 Gitler et al.
2011/0177131 A1* 7/2011 MacLachlan ........... A61P 31/14 977/773
2013/0130378 A1 5/2013 Manoharan et al.
2013/0172399 A1 7/2013 Corey et al.
2013/0225659 A1 8/2013 Bennett et al.
2014/0107330 A1 4/2014 Freier et al.
2014/0303238 A1 10/2014 Linsley et al.
2015/0018540 A1 1/2015 Prakash et al.
2015/0141320 A1 5/2015 Krieg et al.
2015/0184153 A1 7/2015 Freier et al.
2015/0191727 A1 7/2015 Migawa et al.
2015/0259679 A1 9/2015 Bennett et al.
2015/0267195 A1 9/2015 Seth et al.
2015/0275212 A1 10/2015 Albaek et al.
2016/0053254 A1 2/2016 Kimpe et al.
2017/0175113 A1 6/2017 Bennett et al.
2017/0175114 A1 6/2017 Freier et al.
2019/0002887 A1 1/2019 Rigo
2019/0017047 A1 1/2019 Bennett et al.
2020/0056179 A1 2/2020 Freier et al.
2020/0087661 A1 3/2020 Freier
2022/0064639 A1 3/2022 Freier et al.

FOREIGN PATENT DOCUMENTS

EP 2399611 A2 12/2011
WO WO 1997/42314 11/1997
WO WO 2000/015265 3/2000
WO WO 2000/070039 11/2000
WO WO 2001/083513 11/2001
WO WO 2003/033741 4/2003
WO WO 2004/003201 1/2004
WO WO 2004/045543 6/2004
WO WO 2004/047872 6/2004
WO WO 2004/070062 8/2004
WO WO 2005/116204 12/2005
WO WO 2005/116212 12/2005
WO WO 2006/021814 3/2006
WO WO 2006/131925 12/2006
WO WO 2007/106407 9/2007
WO WO 2008/109379 9/2008
WO WO 2008/109450 9/2008
WO WO 2008/152636 12/2008
WO WO 2009/046141 4/2009
WO WO 2009/147684 12/2009
WO WO 2010/014592 2/2010
WO WO 2011/006121 1/2011
WO WO 2011/097641 8/2011
WO WO 2012/012467 1/2012
WO WO 2012/079578 6/2012
WO WO 2012/149438 11/2012
WO WO 2012/177639 12/2012
WO WO 2013/081864 6/2013
WO WO 2013/162363 10/2013
WO WO 2013/173645 11/2013
WO WO 2015/002971 1/2015
WO WO 2015/072438 5/2015
WO WO 2015/143245 9/2015
WO WO 2015/143246 9/2015
WO WO 2017/117496 7/2017
WO WO 2020/023737 1/2020

OTHER PUBLICATIONS

Becker et al., "Therapeutic reduction of ataxin-2 extends lifespan and reduces pathology in TDP-43 mice." Nature (2017) online Apr. 12, 2017, pp. 1-17.
Bezprozvanny et al., "Therapeutic prospects for spinocerebellar ataxia type 2 and 3." Drugs Future (2009) 34(12):1-17.
Branch et al., "A good antisense molecule is hard to find," TIBS (1998) 23:45-50.
Burke et al., "Huntingtin and DRPLA proteins selectively interact with the enzyme GAPDH." Nat. Med. (1996) 2(3):347-350.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Chiu et al., "Age-Dependent Penetrance of Disease in a Transgenic Mouse Model of Familial Amyotrophic Lateral Sclerosis," Mol and Cell Neurosci, 1995, 6:349-362.
Ciosk et al., "ATX-2, the C. elegans ortholog of ataxin 2, functions in translational regulation in the germline." Development (2004) 131(19):4831-4841.
Corrado et al., "ATXN-2 CAG repeat expansions are interrupted in ALS patients." Hum. Genet. (2011) 130(4):575-580.
Crooke, ST., et al., "Antisense Drug Technology" Second Edition, CRC Press (2008) Chapters 1-28.
Deleavy et al., "Designing chemically modified oligonucleotides for targeted gene silencing" Chem Biol (2012) 19(8): 937-954.
Duvick et al., "SCA1-like disease in mice expressing wild-type ataxin-1 with a serine to aspartic acid replacement at residue 776." Neuron (2010) 67(6): 929-935.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elden et al., "Ataxin-2 localization in ALS and FTLD-TDP and TDP-43 localization in SCA2" Nature (2010) 466: 1069-1075 (Supplementary Information).
European partial search report for 15765851.9 dated Oct. 25, 2017.
Extended Ep Search Report for 15765851.9 dated Jan. 30, 2018.
Evers et al., "Targeting Several CAG Expansion Diseases by a Single Antisense Oligonucleotide" PLoS ONE (2011) 6(9): e24308.
Frey et al., "Early and Selective Loss of Neuromuscular Synapse Subtypes with Low Sprouting Competence in Motoneuron Diseases," J Neurosci, 2000, 20(7):2534-2542.
Gautschi et al. "Activity of a Novel bcl-2/bcl-xL-Bispecific Antisense Oligonucleotide Against Tumors of Diverse Histologic Origins" J. Natl. Cancer Inst. (2001) 93:463-471.
GenBank: NM_002973.3, *Homo sapiens* ataxin 2 (ATXN2), transcript variant 1, mRNA, NCBI Accession No. NM_002973 (2015) (retrieved from the internet Jun. 28, 2017: https://www.ncbi.nlm.nih.gov/nuccore/171543894/).
GenBank: NT_009775.17 (truncated from nucleotides 2465000 to 2616000) *Homo sapiens* chromosome 12 genomic contig, GRCh37.p13 Primary Assembly (2013) (retrieved from the internet Jun. 28, 2017: https://www.ncbi.nlm.nih.gov/nuccore/NT_009775.17?report=genbank).
GenBank: BX410018.2, BX410018 *Homo sapiens* Fetal Brain *Homo sapiens* cDNA clone CS0DF030YB07 5-Prime, mRNA sequence; (2003) (retrieved from the internet Jun. 28, 2017: https://www.ncbi.nlm.nih.gov/nucest/BX410018.2).
Gurney et al., "Motor Neuron Degeneration in Mice that Express a Human Cu,ZN Superoxide Dismutase Mutation," Science (1994) 264:1772-1775.
Heuvel et al., "Taking a risk: a therapeutic focus on ataxin-2 in amyotrophic lateral sclerosis?" Trends Mol Med (2014) 20(1): 25-35.
Huynh et al., "Expression of ataxin-2 in brains from normal individuals and patients with Alzheimer's disease and spinocerebellar ataxia 2." Ann. Neurol. (1999) 45: 232-241.
Huynh et al., "Expansion of the polyQ repeat in ataxin-2 alters its Golgi localization, disrupts the Golgi complex and causes cell death." Hum. Mol. Genet. (2003) 12: 1485-1496.

(56) References Cited

OTHER PUBLICATIONS

International Search Report for application PCT/US2015/021607 dated Jun. 29, 2015.
International Search Report for application PCT/US2015/021608 dated Jul. 1, 2015.
International Search Report for application PCT/US2016/069406 dated Mar. 31, 2017.
Ito et al., "Treatment with edaravone, initiated at symptom onset, slows motor decline and decreases SOD1 deposition in ALS mice," Experimental Neurology, 2008, 213:448-455.
Kim et al., "Importance of low-range CAG expansion and CAA interruption in SCA2 Parkinsonism." Arch. Neurol. (2007) 64(10): 1510-1518.
Koshy et al., "Spinocerebellar ataxia type-1 and spinobulbar muscular atrophy gene products interact with glyceraldehyde-3-phosphate dehydrogenase" Hum. Mol. Genet. (1996) 5(9): 1311-1318.
Lajoie et al., "Formation and toxicity of soluble polyglutamine oligomers in living cells." PLoS One (2010) 5(12): e15245 1-15.
Lou Gehrig's Disease (ALS): Prevention | Florida Hospital. Downloaded on Jul. 16, 2018 from https://www.floridahospital.com/lou-gehrigs-disease-als/prevention-lou-gehrigs-disease-als.
Lovett-Racke et al., Therapeutic Potential of Small Interfering RNA for Central Nervous System Diseases. Archives of Neurobiology (2005) 62:1810-1813.
Magana et al., "Spinocerebellar ataxia type 2: clinical presentation, molecular mechanisms, and therapeutic perspectives" Mol Neurobiol (2013) 47(1): 90-104.
Maher et al., "Comparative hybrid arrest by tandem antisense oligodeoxyribonucleotides or oligodeoxyribonucleoside methylphosphonates in a cell-free system" Nuc. Acid. Res. (1988) 16(8):3341-3358.
New England Biolabs 1998/99 Catalog (cover page and pp. 121 and 284).
Nonhoff et al., "Ataxin-2 interacts with the DEAD/H-box RNA helicase DDX6 and interferes with P-bodies and stress granules." Mol. Biol. Cell (2007) 18(4):1385-1396.
Nonis et al., "Ataxin-2 associates with the endocytosis complex and affects EGF receptor trafficking" Cell Signal (2008) 20(10):1725-1739.
Parkinson's Disease—Symptoms and causes—Mayo Clinic. Downloaded on Jul. 16, 2018 from https://www.mayoclinic.org/diseases-conditions/parkinsons-disease/symptoms-causes/syc-20376055.
Philips et al., "Rodent Models of Amyotrophic Lateral Sclerosis," Curr Protoc Pharmacol, 2015, 69: 1-21.
Pulst S.M. (ed.) "Inherited Ataxias: An Introduction" Genetics of Movement Disorders. Elsevier, Inc., Amsterdam, published Oct. 3, 2002, pp. 19-34.
Pulst S.M., "Rare mendelian diseases: pathways to therapy development" Oral presentation, American Academy of Neurology Annual Meeting, Philadelphia, PA, Apr. 29, 2014.
Pun et al., "Selective Vulnerability and Pruning of Phasic Motoneuron Axons in Motoneuron Disease Alleviated by CTNF," Nat Neurosci, 2006, 9:408-419.
Ramachandran, P. "RNA interference therapy for the Spinocerebellar ataxias." Thesis, May 2014, University of Iowa, pp. 1-140.
Reynolds et al., "Rational siRNA design for RNA interference" Nature Biotechnology (2004) 22(3):326-330.
Ross et al., "Ataxin-2 repeat-length variation and neurodegeneration." Hum. Mol. Genet. (2011) 20(16): 3207-3212.
Sanghvi et al., "Heterocyclic Base Modifications in Nucleic Acids and Their Applications in Antisense Oligonucleotides" Antisense Research and Applications (1993) pp. 273-288.
Satterfield et al., "Ataxin-2 and its Drosophila homolog, ATX2, physically assemble with polyribosomes." Hum. Mol. Genet. (2006) 15(16):2523-2532.
Scoles et al., "Antisense oligonucleotides for the treatment of spinocerebellar ataxia type 2 (SCA2)" AAN Annual Meeting abstract published online Feb. 26, 2015; Neurology (2015) 82(Meeting Abstracts): S32.002.
Scoles et al, Antisense oligonucleotides for the treatment of spinocerebellar ataxia type 2 (SCA2), 5th Ataxia Investigators Meeting (AIM) meeting abstract presented Mar. 20, 2014.
Scoles et al., "ETS1 regulates the expression of ATXN2" Human Mol Genetics (2012) 21(23): 5048-65.
Scoles et al., "Treatment of Spinocerebellar Ataxia Type 2 (SCA2) with MOE Antisense Oligonucleotides." AAN Annual Meeting abstract published online Feb. 26, 2014; Neurology (2014) 82(10 Supplement): S47.006.
Scoles et al., "ATXN2 Is Regulated by a Promoter Associated Antisense Long Noncoding RNA (IncRNA)" Neurology (2013) 80: P05030.
Seth et al., "Short Antisense Oligonucleotides with Novel 2'-4' Conformationally Restricted Nucleoside Analogues Show Improved Potency Without Increased Toxicity in Animals." J Med Chem (2009) 52:10-13.
Shen et al., "Research on (CAG)n mutation detection of Spinocerebellar ataxia type 2" Chinese J Int Med (2000) 39(4): 259-261.
Shibata et al., "A novel protein with RNA-binding motifs interacts with ataxin-2." Hum. Mol. Genet. (2000) 9(9): 1303-1313.
Takei et al., "Edaravone and its Clinical Development for Amyotrophic Lateral Sclerosis," Amyotrophic Lateral Sclerosis and Frontotemporal Degeneration, 2017, 18:5-10.
Van Blitterswijk et al., "Ataxin-2 as potential disease modifier in C9ORF72 expansion carriers" Neurobiology of Aging (2014) 35: e13-e17.
Van Damme et al., "Expanded ATXN2 CAG repeat size in ALS identifies genetic overlap between ALS and SCA2." Neurology (2011) 76(24):2066-2072.
Woolf et al. "Specificity of antisense oligonucleotides in vivo" PNAS (1992) 89:7305-7309.
Yamanaka et al., "Transcription factor sequestration by polyglutamine proteins." Methods Mol. Biol. (2010) 648:215-229.
Zangemeister-Wittke et al., "A novel bispecific antisense oligonucleotide inhibiting both bcl-2 and bcl-xL expression efficiently induces apoptosis in tumor cells" Clin Cancer Res (2000) 6: 2547-2555.
Bennett et al., "Early Detection of Motor Dysfunction in the SOD1 Mouse Model of Amyotrophic Lateral Sclerosis (ALS) Using Home Cage Running Wheels" PLOS One (2014) 9: e107918.
Forsberg et al., "Misfolded SOD1 inclusions in patients with mutations in C9ORF72 and other ALS/FTD-associated genes" J Neurol Neurosurg Psychiatry (2019) 90: 861-869.
Lewis et al., "Microglia and motor neurons during disease progression in the SOD1 mouse model of amyotrophic lateral sclerosis: changes in arginasel and inducible nitric oxide synthase" J Neuroinflam (2014) 11: 1-18.
Pokrishevsky et al., "Aberrant Localization of FUS and TDP43 is Associated with Misfolding of SOD1 in Amyotrophic Lateral Sclerosis" PLOS One (2012) 7: e35050.
Therrien et al. "Worming forward: amyotrophic lateral sclerosis toxicity mechanisms and genetic interactions in Caenorhabditis elegans" Frontiers in Genetics (2014) 5: 1-13.
Extended EP Search Report for 21187734.5 dated Jul. 25, 2022.
European partial search report for 21187734.5 dated Mar. 4, 2022.
Gitler et al., "Validating ataxin 2 as a therapeutic target in ALS" Presentation for Target ALS Annual Meeting (Apr. 2015).
Amado et al., "AAV-based delivery of RNAi targeting Ataxin-2 improves survival, strength, and pathology in mouse models of rapidly and slowly progressive sporadic ALS" bioRxiv [Preprint] Feb. 2, 2024, 1-44.

* cited by examiner

SEQUENCE LISTING

<160> NUMBER OF SEQ ID NOS: 45

<210> SEQ ID NO 1
<211> LENGTH: 106001
<212> TYPE: DNA
<213> ORGANISM: Mus musculus

<400> SEQUENCE: 1

```
taattattca caggtggacc aggggtgtgg agctggagag gcaatgctat actccctatc     60
taaaactgac accccagatc catttttctc tctttttttt ttaaagtcat atttatggcc    120
agtcatggtg aagcaggtct ttgatctcag caggcaggtg gatctatgtg agttccagaa    180
cagccagggc tgttacacag agaaaccctg tctcggaaaa aaccaaacaa gaacaaaaac    240
caccaccgac aaggtcatac ttatattgct tatatatgtg tggcacaatc caagggtgga    300
gggctgggga caattccaag catttaagtt ttcttcttcc acatgccagc tccagggttg    360
agagttaggt ggtgagctta ggcagcctgg gcctttacct tctgagctat ctgctagcta    420
cttaaaaaaa aaaaaatcca tgtagaccaa caagtctgga actcaagaga tccagttgcc    480
tgtccagagc tgggattaaa ggcatgtgcc ataaccaggg gtaactcttc attgaattgc    540
cccttcttga gactgggtct cttgtagctt agcctggcct agaattccct catgaaggtg    600
aagatgacct tgactgtcta atcctccttc catttcccaa gtgctcgtac tacaggcaag    660
aacaccatgc ctgcctttaa ttcactggaa tgactttaat aggttgaggg tttttttttt    720
tccctcggcc catcaccttc ttaagcaatt tcacttagaa aagaaagaaa aaaaaaaaaa    780
ccaatttaaa ctcatttgaa aaaagttaac catttgtttc caatttaatt acaacacctt    840
aaaaaaaaaa acggaccagt gtttggtggc cttcccgagt taaagtaaaa gtttttaaaa    900
ggggtcaagg tctaaagttg acattcttgg gaaagtctgt ttagtcttca ccgagggaga    960
ccccatcacc cagttctact accaatcagg tccatttccc ttcgggtccc ctgaaggagg   1020
aactaagaag tccgagcgag ctagggggaa aaaaaaaaag agggttcaaa tgaaggtcag   1080
agacccaaca gttcgccggg gtgaataaag tggggcaaag tgaagcagct ggcggtggct   1140
tctgaggcgg caagcttccc cacgctggca gggcaagtcg gcacgcagtg gcacctgggg   1200
gcctactgtg tgccaggccc cgattgcagg tccccgcccc gaaggtgccc gcaggccatc   1260
ctctaagttg tgatttggtg gggtgggggt ggggtgaaat caaggtcctc caagggggtc   1320
gaggacaccc gagcagctca cggcgcccgt ccccgaagca gatcccgaag ttcagacccg   1380
ccttggcgag ggcggatccc tcctggcccc ctccacggcc ctagttcgac cccggggaga   1440
gcgaacgcgg cccagcgctg cgccccgctc ctcacgtgtc cctgatcggc cccccgggcc   1500
gtctcacgtt cgacttccgc ctgacccttc cgacttccgg taaagagtcc cccccccac    1560
ccccgacacc tccccggccc cgggtctgtt tcgcatctcc gcgccctcca ggcccgcgtc   1620
aaccccgtcc gcgtccgcca gcccgggtcc catgcgttcg tccaccgccg ccgctcagcg   1680
gcccgcggcg ggggaccccg agccgcgccg cccggcgggc tgggccgcgc ggcgctcgct   1740
cccgcggacg gcgcggcgcg gcgggcgggg cggcgcggtg gcgtatccct ccgccggccc   1800
tcccccgcgc ggccccggcg cccctccccg cgggccgcgc tcgccaccct gcgcctcaga   1860
ctgttttggt agcaacggcc acggcgcgtc ccggcccggc tcccggcggc tgctcggtgt   1920
ctgcgggcct ccccgcccct tcgtcgttgt cctgctgcct ctggcccccg cggccacgcc   1980
ggcccgcgcc tgcccgcccg gcgtccgcgc gtccccgccg cgctccggcg tctcctcctc   2040
ggcgcgcccg gcacccggct gtccccgccc ggcgtgcgag ccggtgtatg ggccgctcac   2100
```

```
catgtcgctg aagccgcagc cgcagccgcc cgcgcccgcc actggccgca agcccggcgg   2160
cggcctgctc tcgtcgcccg gcgccgcgcc ggcctcggcc gcggtgacct cggcttccgt   2220
ggtgccggcc ccggccgcgc cggtggcgtc ttcctcggcg gccgcgggcg gcgggcgtcc   2280
cggcctgggc aggtgggtgt cagctccccc agccccctcc gcgccgggcc gatcccgcgc   2340
cgctcgtccc ctcccccgcc tcgcgccccg tgaccggccg gcttcgcgat gtgccggggg   2400
gcccgcggag gggcgggagg cgccggcaga ttccttcggg cttctcgggc cgtgtccagc   2460
ctcccgcacc atcgcgtccc ctccccccag acggccaaga tggacggccc tggcggcccc   2520
ctgcccctcc cgggtgtgcc aggggcgatt ggtatcccgc cccacccccct tgctgcgccc   2580
cccccccga tagaagggcg gctgagcctg ggtgcgggtc gcagggggtg gggggatcct   2640
ctcctgaaat gagcctcttt gccgggtggg gagtcgggag ggaggagggg agattgaggc   2700
ccagccgccc caggtagggt caagccgggt gtcctgcata tctatccccc gccccgcaga   2760
ccctgggaag gtgggcgacg gaggcgaggt gggtgccagc ggcctaacgc acccatcccc   2820
ctttagatct ggggcggcgg ggttcccgca gcgggccgtt cttcccctcc ccccccccaa   2880
ctggggaagg ggtgggagtg cccggctccc tccaggcccg cctccctcct tccccgcaag   2940
gtcccctgcg cgcgggtggt ggccgatccg cattgctgtt cctcgtccgc ggagcagaag   3000
gcgcctttga atagaggtgg gcgagggccg gactcttgag gtgggttggc cgcgggctct   3060
ggacacgcac cgcattttcc ctcccaaccc cccccccccc cggcccagtt cctgcaattt   3120
ttaggggtga ggcgccgcaa cagaggagtt ggtgcgggtc cgaaggcaac aactcccgag   3180
tgttggcttg cgccctggtc cccctctccc cttccctggg cccgatctcg ttggtaggct   3240
ggggtgctgt cctgtgtgac tggactctgg agggtgtgtg cgtgcggggg tggggagtgg   3300
tgggggtgct tgtcagttcg tatttcacga actaagaaaa tgcttagtgt taaaacggag   3360
aggcagatgc caatagactc cattccattg tggccggtgt ccttaacttg ggaaacgccg   3420
ccgccagagc ttaccaaggg catgcaagtc cttttcccct gtgcccctgt gttacaggca   3480
ctactgtgcc tccctctggc ctaggcctgg ctggcagggc ctggagcagc ctcctcctta   3540
aatagacatc caggacttag gaggtgggca aggggatttt tcttgtacgg agttttcttc   3600
ttagccgcat tgtcctgctg tccgtttcca gagagtgttc ctctacagca gaagttaacc   3660
cctagggtga atcagagccg aggttttagg gaattcttct gggaacagta tgtttttttac   3720
tttattcctc cacactccca attttcccta acatgaggca tttcaaaccc tgcttagctt   3780
gcctcgttca agttaaacca tcattttatt tccccatctc tgtgaagtta gggttttgta   3840
agttgtttct tttctgtcct tgacttttag tgaaaaacga aaagatactt aaatgtaact   3900
ttaaggatgc atcctgtttt tctttgcttt ttcatgtttt ctctttagtt atcagaaagt   3960
gacgtgtatg tcactttcac tcaaatacaa attaaagcta aagttcctag gcttcaccag   4020
ctctctttag gcttaaacat tagatggtag ctgagttgac tccacaggga ggtgagcagg   4080
gtgtgagtgc cagcaatctt tttctgcagt tgaggtgctg caaaagtgaa aggcatttcg   4140
agtcttcctt gcttcaagtt ctttcacttg aagcctaggt tttttttttt ttaagagttt   4200
tcgtccaata ctggtactca gaatgtgtga gtttgttctg tacagagcct tggttaatgt   4260
cattctctca ttactgtctc tgtgggttcc ttgtaaatcc attataactt gtagagtttt   4320
gcttttgtgt gtgtgtgatt taaaatagga ctggctgcac tgaggaaagg aggtgtagca   4380
ttggggttgg tgaggtgctt cagggggtaa gggcaatcaa ctgggattcc cataccacca   4440
```

```
accaccacca ccaccaccac caccaccacc acctcagcag gaagcaactg actcctgctg   4500
caagctgtcc tctgacctct acacacctgc cagggcatgt tcccctcctc cacagtaaat   4560
aaacttaaaa aagaaaaggc gtcatgtttg agatagcaaa atgttcttcc cagcctagaa   4620
gctcactaaa gcagtctttc acttctgggc ctgcccagag cctggagcct aacccagggc   4680
cttgcttttg ctactcaggc agcctgggtc tgacttgatt tttgtgtgaa tggaattttg   4740
tgatttttga gaagagtttt ttcttgtcaa cactcaagag gccactttct tagaaaagaa   4800
ctgtgtgtga tcacttttta agaatcttac gggctggcga gatggctcag tggttaagag   4860
cgccgactgc tctttcgaca gtcctgagtt caaatcccag caaccacatg gtggttcaca   4920
accatctgta acgaaatctg atgccctctt ctggagtatc tgaggacagc tacagtgtac   4980
ttacatgtaa taaataaatc ttaaaaaaaa aaaaaagaat gttacacagt tgcactggag   5040
attctacttc ttactcttaa ctttgacctt ttgtgaggct gtgctcttgt gggatcgagg   5100
cttccccttt aatcgggagg gttttttttt tttttttttt ttttaaacag tagtgtacct   5160
gctaaactaa gtttctccct gccggctcgg actttggtct tgacgttcct ggttttgtgg   5220
aggtggtatg gtgaactttt tcatactcgg agctttttgt ttcatcttaa tttttcccta   5280
gagaaagtgc ccaggagtgg tttcactagg tcaaggactc ttaaggtttt atggctctca   5340
caagctgtgc catgctattt ctcagaagac tcagtgggtt ctggagccaa gaaggcagct   5400
ctttggggga tgggctctgt ggacttgttg gatgctcttg ggatgttgc attcaacaag    5460
gcatgtgctt tcatggatac gtttcctggt cgtttctact tttaaagatt tatttttgta   5520
tgtataagtg ctttgcccgt ttgtatggta tgtgtgccca gggtccacag agaccagaag   5580
aagagggccc tttattccct agaactgcag tgacagactg cagtgaacac catgtggtcc   5640
tctgcaagag cagccagcct ttctaaccct gagccattca tcctgtccct cttgattatg   5700
tctctttgaa gttttccagg attgtttttt atgtgtatgg atgttttgtg tgcatgtttg   5760
taagtgtctt catactttac tgatgcccac agagaccagg agtgggctct ggatcccctg   5820
ggatggagtt agggatagtt gtgaggccac catgtaggtg ctaggttcct ctgcaagagc   5880
agccatgccg ggcttggtgc cacatgcctt tcatcccagc ccaagagatg gggcaagtga   5940
atctttggaa cttgaggcca gcctggtcta tatagggagt agacttacaa caagtgctct   6000
taacctcttc agcccttgta tttgaatttt acatgagctt gcactgagac tgtgtatgaa   6060
gatgtttggg ggtctgtagt gtataatgcc agtgcagatc catggtttct gaaggaactg   6120
ttctaaaact ttctggctgt taaaaaattg ttaatccttt tttatttgtg ttattagctg   6180
ttagtttatg atcacttttg aaaaaaaaag ttagcttgtg gtgaagcatg gtggtaggat   6240
taactgaagg aggttgaggc aggaggatca tgagttacag gccagcctgg gctacacatg   6300
tactgttcag aggtggtgta cacctttgat cctaacaccg gggaggcaga caggcagtct   6360
gctgctgtac cgagcagcca gggctacgca gagaaaccct gtcttggaaa aacaagttta   6420
atttgtttat gcatacctct tgtctgtctg gtgcctgtgg aggtcagaag aggaggccag   6480
atgccctaga gctgtagtta tggacggtca ttgggccact gtgtggatgc tgggaactga   6540
gcccaggtcc tctgcaagag cggccagtgc tcttaactgc tgagctacct gtccacaacc   6600
atgcctttat tttttgagtt cagatctttt gtatccgatt gttcttgtcc ttgaaacttt   6660
ggtgtgcctg cccaaccccc tcccaactgt tgggattgta agtgtgcacc tgcctacttt   6720
atgcagtgtt ggggtggtca ttcagagctt gtctgcatgc taggcacacg ttgtagctac   6780
atcctcagct cctagttagt gactgcactg ggagtcatca tgggttaatt catatccctg   6840
```

```
ccttcctttc ctctttattg ggtttagtgg ttcgaggggc agcatctact ttgtagacca   6900
ggctgctcaa aattttgttt gctttctttg ttttgagaca aatttgtagc cttgggctta   6960
aaggcttgta tctgtcactc ctggcttata ggcttagaca tttttttaaa tttactttt    7020
aaaatttatg tgtgtatatg tgagcttgtg tggttgtgta ccacatgtgt gcaggagccc   7080
tgaggaaaac cagaccaggg cactgagttg gagatggagg cagttgtgag ctgccatgtg   7140
ggtactgtgg actgaacctg tgtcgtcttc tgggataggt aagcatttgt aaggaaggag   7200
tcagctctca agtgtgactt gtagcttttg tttttgtttt tgtattcttt ttcagacagg   7260
gtctcttaca caattgtgac aatcctgaaa gtcactgtgt agtcccggct ggtctcctaa   7320
ttcagagaga tctacctgtc tctgccttct caggtgcact ctcaagcctg ggttagtttt   7380
ggatttttag ttgttgttgt tgtttttgac agggtttctt tgtgtaatag ccctgctgtc   7440
ctggaacttg ctttgcagtc taggctgatc tctaagagat agacctgagt gctgggatta   7500
gaggcatggg ccaccattgc ctggcttgcc tggaactcct tgaagcatgc atcttcttgc   7560
ccctgcctca ggcaccatgg caggctccca cacttacttt aaaaaaaaaa aatgtagcct   7620
aggctggctc acaagcacat ttgggatttc aggtgtgtac caccatcctc tacacttcac   7680
actttaaaca cctttttttt ttctttaaaa ttacatttgc agggcctgga gaaatggttt   7740
agtggttaag agcactggcc actcttccag tggactgggg ttaagctcca agcacctaca   7800
agacagctcg caactgtctg taactcctgt tccagggatc tgactccctt acacatgcag   7860
gcaagacacc agcatacata aaatacaaaa taaattacat tttgagagag agagagagaa   7920
tacatgaatg tgtgtgtgtg tgttggtaaa tttcacagtt gtgtgattga agatcccagg   7980
acaacttgga ggagctggtt gtgggccagc gagatggaat ccaggttacc tgccagatgc   8040
cagaccgggg gcaaatgcct ttctctttaa gccttcttac caaccctctc actttttaag   8100
aactttctct gctttaatcc cagcatttag gaggcagagg caggtggatc tctgagttca   8160
cggccagcct ggtctacaga gttccaggac agccagggct acacagagaa acctcatctt   8220
ggaaaaacaa aacaaaaaac cccccaccaa aacacaaaga atgttctctg atttctcagt   8280
tttgtttttt cagttttttt atggctttaa tctctaaagt cattgcatct tagaaattgt   8340
tcatctcact tccattaaat gtcagagata tctccataag ttcatatccc tcaagtgctt   8400
acagcaccac acagcataca ttgttgagta tctgtctgta aggcagtgtt gagttctttc   8460
catgtactaa tgactaaacc aaaaatattt cctctcctgg agtttacatt cctcttttga   8520
gccttgaagt tagcgccatg tgtggccccg actgtcctgt gtcatccctg tcttctgggg   8580
atttcgggtg tggacaccac acctattttg ccttgaccga gaggcaggca gccttagaca   8640
gtgcaccagt ggcctgggat tagaggaagc agattaaggg ctggagagtt tgaggaagtg   8700
atggatgcaa atttaagtgg attagcggag cctccttgaa gaggtaacag tggagggtca   8760
ggtcctccag ccttaaatct tggttgcagt tcataaagtt aaaactggct cattttgtca   8820
tcttttgaag tgatattaat agttgtttga ttatgccaat ctgaagttag cagaaattaa   8880
tacttagatc attacagata aactactaaa gtaaagagac atgtttttgc tgttcttttg   8940
gatgtatata ttttactggg tttatccaaa tatgtggaaa ttagttacct gtgtttgaaa   9000
gaaacaatgt tggggctgct ttgagttctg catgctaaag tctagcaata gagacagtta   9060
tgggatcagg catggtggtc ttgctttgtc taaatgtgaa cttggggttt ttgtttctct   9120
aattaaacag ttgcagtttt acacagggtt tgggaactta ccatcctgat taagagccac   9180
```

```
atgatgcaga ttaaagaaca tctcattctt tttgttctaa ccagcttcat ctgtattgga   9240
acttcattct agtatagcgc tgggtgcatg cacacgcact gtctttagag acttttccct   9300
tgaattgtaa tgttctattt tggctaggtc gaaattgctt ttagtattat atagtgttga   9360
gcgggtacaa aagtctattt ttatagttat ttgaagtgat ggtgacagct tcagtggaga   9420
tgtaaatgga atttattagg ctaacctgct gctggagttt ttgaattgga aatgcatggg   9480
ggagggatgt agctcagtgg tagagggttt gcctagtatt caagaggccc tagattgaat   9540
actaccttct gtcaagaaag aaaaacaaac agcaacattg atttgaagtt gccttgaaaa   9600
aaaattaaaa atacatgggt gagtgagttt gaggacagcc tggtgtacat agtgaattcc   9660
cagccagcta gggctgcata gctagaccct gtcttggaaa ggtggggtgg ggtgagggaa   9720
tgagcagtga taagagtgct tgtgtgtttg gaatgggtgt tggggggcca tcactgtaag   9780
gggtgcagtt gcctgttttg gattgtgacc ctgagtgaca agccccgtgc tactcgcttg   9840
cctctgcttt cttagttgtc agacacagag tgtgctttca ggaaactgcc catcgatggg   9900
taggaagctt ggagttgttg gtgaagccta gaacaataag gacacttttg aatccatacc   9960
ttaaaactag tgccacatga tggaaaatgt gattatttat ttagggacaa ggcctttgcc  10020
aaggcttgtc tagaatctgt ggttctccta ctttagtttc ctgactattg ggatatagca  10080
ggagccatca tacctaaatg ctcttaagtg ggaagagagc ctcatacttt tgaatagtgt  10140
gctgcacttc ttcatgaggg gtgtgtgtgt atgtgtttct tgaagcacac atttagttct  10200
ataggtgctt gtgccaaaag ctgccttcct gtttaaaaca attgagatcc tgtagttgta  10260
tatatgctat gtctgagaaa tgtttggaaa aatagacatg tgaaatatgg tatataatat  10320
atatatatat atatatatat atatatatga cacagtctgt gatagagatg aacactgtcc  10380
tggaggcaga acaaatttat ttatgagata agtaagctga gtattcactt atttatagat  10440
ggggttgttt ttttgcctta taattggaac ttttaggtta cttccagaaa agcaaaatat  10500
tgacaggcat gttggtgcaa gcttttaatt cttggattcg agagacaggc aagtagtctc  10560
tttattttga ggctaagttc taggccaggc aaagctacaa aatgagaatc tcaaataata  10620
aaatctcact gggaagcaaa gtcaaatact gagagttttt cttttccttt attaagataa  10680
ccaacattac aggttcatat aggatacaaa cagagatatg gcacataggt tttttttctt  10740
ccctcaaggt aaggtttagc cttggctgta ctggacctaa aaatactttt aggttatttt  10800
atgtatttac aagtgttttt acctacatgt atatatgtgc accgggtgca tgcttgttgc  10860
ctttggaggt cagaagaagg cattaagtac tctgagaatg gagttacata gccaccatat  10920
gggtgctggg aagaccagct agtgcttttt accactgagt catctctcca gcctcttgtt  10980
ttaatttttt attggtgcac atttcttcag cctcttgctt taattttttt agtggaacct  11040
ttgtgtttct gggagtaatg tatatgaatg cagttttcct ggaggccaga aggtggtgtc  11100
aggccccctg gagctgaagt taaaggctgt gtgtgagctg atcaccttgg gtgctgggaa  11160
ttaaatttag gtcctctgca agagcactca ctgggtgctc ctaactgctg agccatcact  11220
ctagcctcat agattagatt ttgagttcag tagtttgtat cttaaagatt ttttttttct  11280
tgagatgata gaatttagag tatggaaaaa gaagaggaaa aaaaaatctt tcaaaataga  11340
aagagctaaa cctttcagct ttgggagatt gggcggcttg ccaaaagcaa ctgttgttga  11400
ttgtttttaa ttctgcccct cccttccata aatgcagaca gataaacaag atggtggggg  11460
ggctgtgcgg gcaacccact agagcagtgc tcgcccagct cgtgttagac tctgggttag  11520
atttctgccc agcaccacag aaaagaaaac gaaagggaaa acacagattg gagtttggct  11580
```

```
cacttaaata agttcctcac ttgtttttg ttttgttttg tttttcgag acagggtttc 11640
tctgtgtagc cttggctgtc ctggaactca ctctgtagac caggctggcc tcgaactcag 11700
aaatccacct gcctctgcct cccaagtgct gggattaaag gcgtgtgcca ccacgcccgg 11760
ctttccttgc ttgtttttag tttgtataat tctgcataaa tgtaatgtga cgtctactta 11820
aatgtttgtc ttttaaaggg cagggtctca catcctaggc tggcctgaca cttggtatga 11880
cctatcctaa gggaaacgtt tttttttat tcagtgcttc taggttgcca gtgaatcaaa 11940
aagcagaact ttcaggagca aatgtcattg agagcaatga caaacagtgt gagaggaggt 12000
tgagaaactg caggcttgta gtcagtcagg agaccttaga aagcacaccc tgcgggtgtt 12060
tgactgagtt gatgaccctg ggccttaggc cctagggcgt tactgcctta cagcacagtg 12120
tagttaacat gctcacagtg gtgactcata gtttaaatta tttttaatag ctttcaaaga 12180
agtatttttc aaactgcagg tcataattga ttagattatg aaatcttttt agttaaagtg 12240
gtcttggttg aggtggaggg tattcctcac tgtgcagctc tggttaggtt gcagtttgct 12300
atgttgacta ggctggcctc tgacagatgt gcctgccttt gcctcccgag tgctggaatt 12360
aaaggtacga gccagaatgt ctggccctac atttttctgt ttttgtaacc cactgagtcc 12420
agttggtgtt gtctgttgag atgtaggtgg atactggctt gctcttgtaa aggtcttgtg 12480
caagtgattg tagctgcagt gatctctcga gtgcaaggac catgttgtat tcagaagaca 12540
gcatttaaaa cacttctccc catcccctgc ttcttatctt ctttctgccc ctatttcatg 12600
gtgttgcttg aagcctgaga ccaggctcta ggtgtcctac ttaggccaag cactctgcac 12660
tcacttattt tcagcttctg accaggtgtg agtctctgca gtaactactg gccactgcag 12720
aatgaatatt tgcctgtcaa agttgaaagt agctctgact tttgggtata agctgcagta 12780
tttagaaggc agttggacta caagtcactt ggcagaacaa cagttacatt cttctgtatg 12840
gctatgccct ccttagccat tggctttgat caggtttaca tcatcacagt gtgagtagtt 12900
ttctggtgca gtagttgagg ctagagaccg attcacctcc tcttaactca gttaagctgt 12960
gagggctgca gctttgttgt ttgattgtat ctcttggcac agagaaggtg attgtctgtt 13020
tgtgtgaagg ctcagtttct gtgtctagta agaagtgttt cttagggttt tcataaggag 13080
cacaagtagg gtgggggtgt aggcctgtgg tggagtgcat gtgctgcctt catccctggc 13140
accccacaca aaaagtgagg cactgaattc tgtttacctt ctgtcttgtc aattccttac 13200
ctggccctcc aaaagtcaca cagatttgaa gctggaaggt tctggtggtt tttagtactc 13260
agttctattt acaggtgaag aaactaaggg caatgatatt tgctaagtct catgttgggc 13320
tgcataactg atgttagaat gaggtccacc ccctgatccc ccaaacctaa ttaattaatt 13380
aggctactcc aggacctcac atgctaaacc cgtgttccat ccctcctccc atacatgttt 13440
cttagcatgt ttcctgcttt tcttgttcta agtattccag cttactccag agccttagga 13500
atcattacag ccacattctt tggagagact taagtggttt tcattcttgc ctgagtcaaa 13560
tccagaccat tctctttggt agtgagttcc tccataggtg gaacacacag tattcattca 13620
gcatgagcta aagtctgttg ctcttgagtt tgtcttcttt tttttgtttg ttttgttttt 13680
caagataggg tttctctgtg tagccctggc tgtcctggaa ctcactttgt agaccaggct 13740
ggcctcgaac tcagaaatcc acttgcctct gcctcccaag tgctgggatt aaaggtgtgc 13800
gccaccacgc ccagctgagt ttgtcttctt aaatgtagtc ttcgtaggct ttcccccagt 13860
tcagttacac agtctcattg aaggagaaag ggccagttcc tgtgtccgtg cttctctggg 13920
```

-continued

```
aggtttagtt caggtggcgt cagtgcccag tgccttgcat taacagcctc tccatctggg  13980
ggcttcaact taacagtgag tgctgagata agagcaaagt cacacctgca gtagaagagg  14040
gttaatgcca ctaaccaaaa cagataggtg gctgtgccgc taatgagcaa atttaatcat  14100
acccacccac cactgttgtt ttaaaaatgt gtatgtgctt gaactcagct tattgtcagt  14160
gttgtcatac tcaggtgcag ccacagcaca cactgacggt gttacagaag ggagcagtta  14220
ctgctgcaaa tgcaggtttt tttttttttt tttaaagatt ttttaaaatc ttatttttat  14280
tttttgagat gggcctatga agtcctggct gtcttggaac ctgttgtgta gaccaggctg  14340
gcctcaaatt tacagagatc cttctacttt ctccctcagt gtaaaaagat taattttttt  14400
ttttaaattt gtgtgtctgt ttgggggtac cattagagcc cagaagagga tgttgcatca  14460
cctggcagtt gtgagtcctg ggaattgaac ccaggtcttt tgcaagagca gctattgctc  14520
ttaaactccg gggtcatctt tctcatccca agagtaatat ttagatagtg aacaatgaag  14580
tgattgatgg tgcaaggcag gaccttgggg aagttagtta gagtcttagt ttttgaggca  14640
gggtctctaa ctgtggttct cccagtaatt ttcccgtctc gccctcccaa ttacatatgt  14700
gagccaccat gcagatttag cttttaaata ctactcccct tgcctccagt aatggggata  14760
gggaccagag agtgtgctcc accatggagc tgcactagcc tccacctagc agagtaattt  14820
aaagtgaaga cttttgtagc taacctgtga ctgctgacct ttgttacccc cagcctagtg  14880
tgtgagcttt ctagttgtga ttgccctgcc agcaccttgt gtgctagccc tgcccttatt  14940
tagtaagggc tgctgtgcag tggccttcca gtgcatttct ctggagagat ggctgtgctt  15000
aagagtcttc tagaggacct gggcttaacg cctagcacct acatggtggc tgacaactgt  15060
ctgtaattcc agttccagag gatccaatac cctcttctgg cctacactgc atgcatgttg  15120
tgcacatatg tatatgatgg taaaaacacc catacacatg aaaataaaac ttaaaaaaaa  15180
tgtacttccc taatgcccag taatagtgtg catctttgtg cttatttata agcctttttt  15240
tgtatcatct ctgattgaga ccagcttgca ttagagcggg gacacagccc tataaaactt  15300
atgtggtttg taactggtta gttattgact ggtcgtggtt tcactgtgga aatcatgtgt  15360
taaagtcctc tctgcgtagt ttgtgtttcc cagaaattac ttgtgccagg cttgaggaca  15420
gtagtggaca ggtgagaccc aggtctctcc tttgagctcc cacattggtg cagacagcag  15480
aagtagttca gatgcctacc tgtctatggt attcaggcac ttgagctagt gtgttgtctt  15540
attgaactct tagacagctt aggctacata gtgggggtct cactttaaac ccctaagaag  15600
ggtctagcat atggctctgg taaaggcact taacctcaaa gtttggcgat ctgacttaaa  15660
tctgtaaacc cattcctgca ggttgctttc tggcctctgt acacatactg tgacaagtat  15720
acttcccctc aataaatata tgtaataaat ctattttttt gggggtgggg gtgggctgga  15780
gagatggacc agcagttaag agcactggct gcccttccag aagacacagg tttggttccc  15840
agcagcccca cagtggttca caactacctg tgactccagt tccaggggat ctcatatctt  15900
ctgggcaatc cacatacatg gtgcacagac aaaacaccca ttcacataaa tgtaattgag  15960
aaaaattttt tgaaaaagtt ccttaaaatg ttgaaaaata ggaatggaag acagaataaa  16020
ttcttcattt acagatgctt tttttttttt ttaaagattt atttatttat ttattttta  16080
tatgtaagta cactctagct gtcttcaggg gcatcagatc tcattatggg tggttgtgag  16140
ccaccatgtg gttgctggga tttgaactta ggaccttcgg aagagcagtt gggtgctctt  16200
acccactgag ccatctcacc agcccgcttt tttttttttt aaagatttat ttatttatta  16260
tatgtaagta cactgtagct gtcttcagac actccagaag agggagccag atctcattac  16320
```

```
gggtggttgt gagccaccat gtggttgctg ggatttgaac tccggacctt cggaagagca  16380
gtcaggtgct cttacccact gagccatctc accagcccct acagatactt tttaaaaaag  16440
atttatttat tttatgtata tatgagtaca ctgtagctat atagatggtt gtgagccttt  16500
gtgtggttgt tgggaattga atttaggatc tctgcttgct tggttggccc cactcacttg  16560
ctcaggccca aagatttatt tattattata aatatgtata ctgtagcagg gtgcaagacc  16620
tcattacaga ttgttgtgag ccactatgtg gtagccagga tttgaactca ggacctacag  16680
aagaacagtc aatgctctta cccgctgagc catctctcca gccccagata cggtttcatg  16740
tgtaaaagat cctaaggatt ccaccccaga atcctttggc actaaagaat attctcagca  16800
gagtgacagg atgtaaaatt aacataaaga tctgtagcct tccctcctgt atactagtga  16860
caaacttctt ctcatgaaga agtcagggaa acttccattc accttcaaaa acaaggtcgg  16920
atctgtccag acctcactgt tgatacttag tgcctgtttt cttttctctg taaatcatgt  16980
tctaaagtgc tcacgttgat gtctagcacg tatcagatgt tcagatcttt tttttttttt  17040
gtgttttgtt gttattgttg ttttttggtt tttcgagaca gggtttctct gtgtagccct  17100
ggctgtcctg acactcactc tgtagaccag gctggcctca aactcagaaa ttcgcctgcc  17160
tctgccttcc aagtgctggg attaaaggcg tgcaccacca cgcccggctg tttcactatc  17220
tcttagagta cagttatatg tccccaccaa gcatggattc attttgtacc tttgtatcag  17280
ttagaccagg attctttaaa aagatgaatg gaggtttgct tctctttcca ggttgtccag  17340
tgcagcagaa aaggagggtg ggcacacaaa tactgtgaac tgttagccct gctgtggact  17400
ggaatgactt ccttttcaga cagggtctta ctttgtagct cgggctgtcc tggaactcac  17460
aagtgctggg attaaaagcg tgtaccacca tacccagctg agtaagtcag cttcctccac  17520
acctctcttc acaagacagg ttttctttgt gtagctctag ctgtcctgag actctgcagt  17580
ctagacaggc ctcaaactga ggtcttccgt cttctgctgg gattaagggt gtgcaccact  17640
atttcttgtc actcacatgt aaaagtcgag caattaaagg acccttctgt acccttcagc  17700
cagttgtagc agcagtcagt cttctacttc agctgtaatt ccatctgtca tggtgttttg  17760
aagggcatta attttttca tgaggcataa gctattactt atgaccagtg ggtgaaacag  17820
tggaagagac ttgaggttac tacgtaaagc attcttggtg caggctggag gagcaaatgc  17880
ctccatcagc cttcctgtct ggagaagttg aaggaaaacc ttatgcttta taagtacagt  17940
atgggggctg atacccacac agggttagtt cagttaaaaa tggagctgtc agaaagtaaa  18000
gccgtggaaa gcctgcaaat tggacaaaat agagtggaag aagagaactc actcccataa  18060
gttgtcttct gaccaccaca catgtgccat ggtaacccct ccccctttat atactaaatt  18120
caaatgtgat tttttttttt aaagggctgc cgagatggct acagctggta aggaaaggtg  18180
cttactgcct gaagccctga gtgggttcca ggcaggaccc acatggtggg agaggagaac  18240
agactgcaaa ttaccctctg acctccatgt gcacccctgt acacacgcat gaacacatat  18300
gagtgtttga ttttttcaa gatggggttt ctgtgaatag cctaggctct cttgggactc  18360
actctgtaga tcaggctgct ctcaaacttg gagatcagcc tgcttctgcc ttctgagtgc  18420
tggggaagtt aaataccatc ccagctaaat acatgtattt aagaaaaaag aaataagggc  18480
ttagtagttg agagcattgg atgttcttcc agaggactca agttcaattc cctggtgccc  18540
ccatgacagc tcacaactat ctttaactaa tgcattgtgg tacacagata caggcaaaac  18600
acccatatat atacaaaaag cagctcagga tgagagtaac tgaaatgttc acgttacaat  18660
```

```
agctaagtca tgccagcctc gtctccagta ctcactgctg cttgtgccag tggttgtcat  18720
atttattgaa cagtgtgtgg tgtgacattt ccatcatcat ggtttctgtt gggacagcac  18780
tgggtctgtt cttatcccct gggtgtcaag aatcttgtgc tatctgcccc ttgtaaatcc  18840
ttacctcctg atagaacccc tttcctcccc ctgtgttata gatcttcaca tggagagaac  18900
ttgtttaata aagtttagtt atagggttac tctttaataa taaactcaaa gtgggaagag  18960
caaagtgact cagctcaagt taactgaaag tgctctgatt agatttttat gatgtactca  19020
gttgcttctt tcctgtgtgt gtgtgttcat gtgtgtgtgg gtacttgtgc tcaggtgaag  19080
gtcacaacaa tgttgagtgt tgcttacatt cttagagagc ttagagacag ggtctatcag  19140
tcattgtcca ttgtaggact gtcaccagcc tgcatttctt cgctgctggc attaaagtca  19200
tgtcatcatg cccaactttt tatatgggtt ctgatatcca aacttgagtc ttttgcttgt  19260
agggtaagta ctttataaat gagccacttc cccagccctg cctttccttg taactgctac  19320
atacagtttt ctttatagga aggagaattt gagtttgtca atacttgtca tgattcacat  19380
aaactatatt gtagacttta tttaacaatt caaaatatgc tcagccctct acagatcaga  19440
aattcttaga agtcaggctg gacctggttg tgcgtttatg taatcctcgc tcttgagagg  19500
ctgaggcagg aggatcacca aggctttaac tactctttgg gctgcatagt gagtttgaag  19560
cttctccaga ctaggtagtg agatccatgt caaacagaaa gtatgaaaga cacctgtcct  19620
tccaagtgct tggatgctga ggtcagatga gctgagcttt gtgagtttga gatgaacctg  19680
agttacacag taagccagcc ccgtgtccaa aaccatgcgt attgaatatg tgctgctctc  19740
taagcagtcc agtgggagca ctgcatagat ttcaactgct aggtctactt aggcttgctt  19800
agagtgtatg ggcaatgtct ataggccatg tacaaatgcg gccccattca ctcccactta  19860
ctcagtgcgt gcatgcatga gtgtgagtgt ctaggttaga agtccaggta ggccctcggg  19920
tagttgatgt cccccccccac ccccagctgt aagttccagg gagtaatcct gaccaaagtc  19980
tgtcttggtt agtatttaag aaacttgctt caaatttggc ttaaaaagaa aaagttggta  20040
cttaggaggt aaaggcaggt ggatctctct gagttcgaag ccagccttaa tctacaaagc  20100
aagtgcccag gaggccagga ttgatacaca gagaaaccct gtcttggaaa gaaaaaaagc  20160
atgattctgt agctcaggca ggtcttgctt gaactatggt catgaagtgc cgtatccagg  20220
agtacatggg gtttcacata gctgagtgta agtaggtaga gcagcagagt ctaaaggttt  20280
acactagctt gtattgtgca gttacctttt gaccttctgt gggtttgcat gtgtgattat  20340
gtgtgtatgt gttgggtttg ggggttggta tttgtaggcc agagactgat gtcagctgac  20400
attgtctctc attgagccta gagctaacaa gttggctggt ctggttggcc agtgagttct  20460
ggaatatgcc tttctgcttc ctcagtactg ggtatacaga ttgatgccac tatgcctggc  20520
ttttggcttt tatgtgggtg ctaggtatca ggaatcaggc tcccatatat tttgtggcaa  20580
gcactttatc tagtgaaaac aaacctggat ccttagctcc ttttttgttt gtgttggagt  20640
caaggaggaa gaataaatta gcatttattt agtgtttgtt tcaaccctaa agagtgtttg  20700
tttctggctc ttttgggcca ggtggtggcg cacgccttta atcacagcac tcgggaggca  20760
gaggcaggca gatctctgtg agttcgagac cagcctggtc tacagagttt ctggacagcc  20820
agggatacac agagaaatcc tgtctggaga aaacaacaaa accaaacaaa agagattcta  20880
ctctgctagc aatatattaa gaacttcttt agtgcataat gtatgtgcac acatgtgtgc  20940
tggcaggcca cattcgatgt ctagctctgt aactctgatt tactcctttg aggcaagctc  21000
tcaggaaacc tggagctagg ctggcagtgg acaataccca gtgaccttcc tcatagcgat  21060
```

```
aggggttgca gctctgtaga aatcagtggt gtagattgaa cagtaaatca gctccccaac  21120
gtcacaagtt ttgtgagaat gcctttttc gattaaaaaa gttttttag acggtctttg  21180
tatagccttg gaacttatta tgtagaacag gcagaactca gtttccccta cctacagagt  21240
tccccttacc tctgcctcct aaatgctggg aataatggta tatgccacca tgcctggctt  21300
tttaggtttg ctaatctgtg ttgtcccaca agtttttag ttatttcttg ccttgtttca  21360
gatgcttgtt gagctccttt agtgaatttc tgtcagttac gcttttcatc ttcaaatttt  21420
tttttccttt ttaaaaaatt atgcatattt ctgtgtatgc acacacacgt gtgtgtgtgt  21480
gtgtgagagc atgtgtgtta ggctggggcc ctcagatgcc agaaagatgg tgttggatct  21540
cttggttggt ggagttatag atggttgtga gttgccaagt aggttctggg aattgaactc  21600
agagcctttt gaagggcagc ttgtgctact gttgagccat cttttcagct catgtattaa  21660
gtcaatcaac taattcattt agtattcatt ttatggcagg gttctcacta tggttggcct  21720
ggaaccaggc tggccttgaa cacacagaga tcctctagac tctgccttcc aagcactggg  21780
gttaagtgca tgaatacctg cttcccttac tactttattg ttattgtgtg tacgtttgta  21840
tgagtgaggg caggcaggtg ctaagaagtg tttgaagtga ttaggaccat tggtagtagg  21900
ttcttctgtt cgtacctggg ttcaaactca ggtcatcggg ttcatgagga ttgattttac  21960
ccactggacc atctcactgc cagggatttc ttttcttttc tttgcccaag gccatgcatt  22020
caccaggtta gcactgtaac atagttgaag ccctgctgtc tccagtgact tctctttatg  22080
tagcttttg atgctgcatg gtaagttagc acactgtccc tgctgctggt cctgtttgta  22140
atgactgctt ttagttttgg agtcagagtc tttctattgt gtgtattcac tgctgcctgg  22200
tggctcttcc tgcctcagcc tcccaaactc aggcattgta gctgggggcg gactgcctgg  22260
ctacttgtag ttttactttt taaactgtat tttgggtcac aagaagcagt ttgtgttttt  22320
tgtttttctg cttagttggt gaggtcatga tttcctgggc tttgtaattt ttttattgaa  22380
aaatggatat tttagacaat accttgtagc aagtctggtt ctaggttgga gctagggact  22440
ggctgttact gtttacaatg gacagcacta caggaggata aagaaattgt gctattagag  22500
agtcttatag gactaacaca gtgtaataca tagcataggg cccgtgaagt tcttaggctg  22560
tctaatctta cgggatcact gtgcaaggca gatgttggcg catggctgga ggactagaga  22620
gaagtcaggc cacttcacac ctggcttgca ggatgcacat taactgtcgg ttggatgata  22680
ttattttttt tataattttg gtatgaatgt gtggatatgt atgcacagaa gtgtgtagag  22740
ggcagagctc gtccttgggt gctgccacct tgctgttttg aactgtctca gttaccttgt  22800
ggttgagcta ggctgtctct accaccaact tttttttttt aagatagggt ctttctgcag  22860
aaccctggct gtcctgaaac tcactctata ggccaggcta tataactcac acagatccaa  22920
ctgcctctgc ctcctgagtt taggaaatca aaggtgtgca gcatcacacc cggcactaca  22980
cccggctctc tgcaccagtg ctgggaactg agctcaggct ctcatgtctg cttgtcacgc  23040
cagcctgggc tgtgaccttc tccacatact gattggccaa atctgtacca ttgaaggaca  23100
gtttctgagt tagaaattag tttttctaac ttctccccg ttaccttccc acatgtgtcc  23160
atcaaaccta ctagaattac atttcttttg agctcgccaa ttttctctta gtgccttgac  23220
cacaagctgg atacttcttt tatttttat tttttattt ttggtttttc gagacagaga  23280
ttctccctgc caggtgctgg gattaaagtc tcgtgccaaa gctgccacaa aaccaattta  23340
atcgtcaatt ttctaaaaaa aaaaaaaaaa aaaaaagtca aattatatgt atatggatgt  23400
```

```
tttgccagca agtatgtcta tatactaagt gcatacttgt tgctccctga ggtcagagga  23460
aggtgttgga tcctgtggtc ctggagttac agttgtgagc tgccatgtgc gagctgggta  23520
ttgaactcag attctttgaa agaatagcca gttctttctt ttcaaagaaa gatttatttt  23580
atgtgttcag gtattttgtc tgtatgcatc tctgtgtata ccacatgcat gttttcttaa  23640
ccacgtagac ccaattttaa tcactttttt ttttaatcac tttttttttt tttttttttt  23700
tttggttttt cgagacaggg tttctctgtg tagccctggc tgtcctggaa ctcgctttgt  23760
agaccaggct ggctttgaac tcagaaatcc acctgcctct gcctccccag tgctgggatt  23820
aaaggcgtgc gccaccaagc ccagctaatt ttaatcactt ttaagttaaa tatgacactt  23880
aaattatatc actgctatct gcattgattt taaacacagt ttccatgttc agaaaggaag  23940
ttttgtatac ccaataagca gtggttcctc ttttttcccc tatatttggt tctgggaatc  24000
attttgtctt tgtgactgaa tgtaaggcct tgatgcagtt gagcaatact tgttttctct  24060
gttagcttgt ttactttagc atgcttcaag agtcctttgt gttgtaacat accagacctt  24120
catggagttg taaaatttat ttgtgttatt ttttaacgtt ttgtgtgtgt gtctgtattg  24180
ggtatgtggg gtatatgcat gtgagtgtag gtgcccgtgg tggccagaag agggcacttg  24240
ccctggagct ggagttatag gcagctgtaa gctgggaatt gaactgagat cccatgtaag  24300
agcagtaagt attgagccat ctctccagct ctagagagtt tatttctttg gatgaatgca  24360
gattttgttg taagccatca tgatgttgtt atccatcagt gtgcatttga atggtcttcc  24420
cttggtgagt gacctgctgg ggactgtgtg tgactatctg ctgactcacg gcttcaggca  24480
agggttttga tataagccca gaacctgaac tactggatct tgtgatcatt ctatttagat  24540
ttctcccaat tactttagtt tttatttatt tttgatgtat ataatgcctt tattaatttc  24600
tttgatgtac agagtgtcct ttggttgttt cccactcccg aaactctctt acccgattcc  24660
attcctgcta aaccccttc cccaaccaac cccctcctgt ttctgtgtct gtctgttgtt  24720
tggtgtttgg cgtccgctga cattgattag agttggttac gtgagtgtgg gatgggagtc  24780
actcactgca ctgcaggaaa ggcactacag cactgaagag aagacctacc tcctccagcc  24840
tttcctcctc cttcattccc agtaggtccc aaagagggct ggcaccctag gatcccatgt  24900
cctgtctgca ggattatagg cgtgcccagt cttggacagg taacccaact gcttaagttc  24960
ttgagcacaa ctgcaatgcc atatgtacat actctggcct taaactcccc gtgccctccc  25020
ttgtctggtc tgtctgaacg tggcggggtg actcacatgg aagtcttgtt ttaggcctag  25080
cgctcattct ctgcacttgg actagttgtt agcctctgac caaggcagag agcagctcta  25140
acctatagga atgaacaaaa atatttagag ataatttgat accacgtcca cttagaaaac  25200
aacactagat tgtctccgta tagcctgtaa ctctcctagt tgtggacttt tgcatagctt  25260
tatggtatca gttaggcata agcattctcc tgtggaacag gctttagata attagaaagt  25320
ggtaatgcca ttattgccac ataatgccac attacaacgg tgtgtacacc ttgactggtg  25380
ctggttgttt ggcttgtgtg gttcacttca gggctaagat tctgttcaga ttgatgtctt  25440
tcttcccagc agcttgtgga caccttcagg tagccatgaa agccagccag caggaggccc  25500
ctgactgtca cagtgcgctc tccttgtcct gcgtccaaag gctgtgctgg atttgtcttt  25560
attagcaaaa gttgtactat ctagttctgg tggcaacaga gtgattgagt gattgcaaga  25620
acctgaccga caactctctc tgtttggtgt gtgtgtgtgt gtgtgtgtgt gtgtgtgtga  25680
gagagagaga gagacagaca gacagacaga cagacactga ctgactgacc gactgaccga  25740
ccgaccatgc aagtctgtga cggtgctcag gccaggtctc tcccaatcac tttttttttt  25800
```

ttaaagattt acttatttat atatgtaagt acactgtagc tgtcttcaaa cacaccagaa 25860
gagggtgtca gatctcatat ggatggttgt gagccaccat gtggttgctg ggatttgaac 25920
tcaggacctt tggaagagca atcaggtgct cttacctgct aagccatctc accagccctc 25980
tcccactcac ttttatggat tccagggatg cctttattca gtgagctagc tgtctcaaca 26040
actgtgttta atgatttaag gagtagccat gttagccggt ggggcacact gtcttccctt 26100
tctgtcaatg gtacccaaga ttctgattct cccactgctc tcacctactt gctaacttct 26160
ggtattggtt agagacggtg ccagaaataa ttcatggctt cctgaaaggt aaatacttca 26220
atccctgcac tataagctgc cataatgggt gtgaaattta atttcctaaa aaactagtgg 26280
tacaaagaat attttatttt gccggacatg gtggcgcatg cttttaatcc cagcacttgg 26340
gaggcagagg caggcagatt tctgagtttg aggccagcct ggtctacaga atgagttcca 26400
ggacagccag ggctacacag agaaaacctg tctcaaaaaa ccaaaagaaa gaattttttt 26460
tttttgagg tagagtctca tggaatgcag actgctctta aactcattat gaagcaggga 26520
tgcacctcaa ttcctgattc tcttactcca tctcctgaat gctgagtttg cagggatatg 26580
ccactatatg cagcttgaac atctttttat ttttagatta atttcatgat ttatttatgt 26640
gtatgggtgt ctgcagaagc cagtaaagga tgctgtttcc cagaactgga attgtgagcc 26700
atccggtgtg agtgctggga tctgttccca ccctggctct ttggaagagc atgaggtgtt 26760
cttaattcac ctttgaacat ctttttgcag atcattgatt atctgggttt tgttgttgtt 26820
ggttttggtt tttgcttgct tttgcttttg ctgtttttga actaggttat tggttttatt 26880
tttgttaatg aattacagag ttcacacaca gctcctcctc aatattgaat attggcttaa 26940
agaggcatat tgtcatgttg ttgtcgaagc tggtgctaaa ttactgagct cgagaggatc 27000
ttcttggggc tggagagatg gctcagccag taagagcact gactgctctt tcagaggtcc 27060
tgagttcaag tcccagcaac aaccatctat agtggaatct gatgcccttt tctggtgtgt 27120
ctgaagatag ctacagtgta ctcatttaaa ttaaataaat aaatcttttt ttttttttta 27180
aagaagagca cattctttgt cagtctccca agcagctgag actgtatcat atatcactgc 27240
cctaggctga ctctccagtt ttacagtgct tttgatatca tatttaagaa tccaaagtca 27300
caaccattcg tagcagtcac accttttaat cccagcactc aggaggcaga ggcaggcaga 27360
tctctgagtt tgaggttatc ctggtctaca gagtgagttc caggacagcc agggctacac 27420
agagaaatcc tgtctcaaaa aacaaaaaac aaaaagcaaa acaaaacaaa acaaaaaccc 27480
aaagaattca aggtcacagt gctgttaagg agtttcatga ttttagattt ccttttttc 27540
ttttgaggct ggcccaggac ttaccatata ctctagattg ttcttaaatt caaagatcta 27600
cttacctctg tttcccaagc actgggatta aaagcatgca ctcccactca ggtttttctt 27660
tttttctttt ttctttgatt cttatgagac agggtttctc tgtgtatccc tggctgtcct 27720
ggcactcatt ttgtagacca ggctggcctt gaactcagaa atctgcctgc ctctgcttcc 27780
caaaggtttt tctttttaaa tgtgtgtgtg tgtgtgtgtg tgtgtgcatg ggtgcccgat 27840
gaggctagaa gtaggtgttg attccctggg accagagtta cagaaggttg agctgccatg 27900
tgggtgctgg acctgggtcc tctacaagaa gaaatgctct tgactgctgt gcagtctcca 27960
gtcccttcca tctgtttgtt tgtttattat ttagtgtgag ggcatgcagg cagacaggca 28020
cgtgcatgga aatgccatag agtgcacatg gaggtcagag aacacctttc tggagtggtt 28080
ttctgtccac cttgtgggtc tgggggattg aactcaggtt gtcagagttg gcagcaggtg 28140

```
cttttaccat ctgagccatc caacttccat tttatttatt tatttttaaa gatttattta  28200
ttttctgtat gagttcaatt cccatgtggt tgctgggaat tgaactctgg acctctggaa  28260
gagcaactgg tgctcttagc caccaatcca tttctccagt cccccattta tttcctaagg  28320
aaatcttttt tatgttgaat ggatcacatt ttagatttag ctgacaaatg cagcctacca  28380
gttggtggtt agaatctttt tttttttttt tttttaaaca actcagccgg atcctccagg  28440
aaaggttttt tttttttttt tttttttttt ttaatttttt tttttttaaa gatttattta  28500
tttatatgta agtacactgt agctgtcttc agacactcca gaagagggag tcagatctcg  28560
ttaggatggt tgtgagccac catgtggttg ctgggatttg aactccagac cttcggaaga  28620
gcagtcgggt gctcttactc actgagccat ctcaccagcc cggtggttag aatcttttgt  28680
gcttgtgttt ttctgtcctg ctagatatgg gtgcttgatg ggcgtctttt gtagcacttg  28740
gtgtctttaa gggatttgca ggaaagtaga cagactggta tgatgaccct tgaacacctg  28800
ctacttcaac acttagcaag tcacactggt cttgcttcat ataccatcta tttccttctt  28860
cctgttactc tgaagcagtg tagaagttat tttacgtgca ggttttcttg tgttaatata  28920
gccagcattg tgtataggtg tgtgtgtgtg agtgcacatg tgagtatgtg cacaagattc  28980
caggtccggg aggtatgggt gccctggagc tggtgagatg gttgtgagtc acctgatgtg  29040
ggtccaggga actgaactct gtcaccgtca ggaagagctt gaagagctct taactggtaa  29100
gctgttttc cagtcctcta ctctcctcct ttcctttcct ttcctttcct ttcctttcct  29160
ttcctttcct ttcctttcct ttcctttcct ttcctttcct ttcctttctt tgagatagtg  29220
taaaaaaatt actgtggttg ctctggaact tttatgtgtg tgtgtgcacg cgtgcgcacg  29280
cgcacactca gggtggtggg cacatacttg aggtcagagg atgatttgga gtaagttctc  29340
ttctatgatg tgggttctgg ggattgaact gaggtcatct gtaagtacct ttgcctgctg  29400
agacattttg ctactctgtc tttaccatgt ttgagagtta gtgtttgttt tagattgagc  29460
ctctctggtt gaaaaatgcc agaaagttca caggtcccaa agtctgaatg tgttggtgcc  29520
agcatgatgc tacaagtggg aagttctgca ccaagccaaa ggcaatgtgg tcagaatgtg  29580
tggccactta aggttctgaa tataggcacc ttcagcttat gtgcacagca caggtccata  29640
tgaaacatta aacttgggtt ccatcccaag atacctcctt agtctaaagt ccaaagaaat  29700
tggaaattca aaatccaaaa cctttctatt ccaagtactt ccaataaggc gtacttaagt  29760
taattctttg aattagatag atgattgggt ctagtgctag tgaagaaacg gagagctggg  29820
aatgtaactc agtgagcaga tgctcgcata ggatttagga ggagccggaa tgtgtcccgg  29880
ctttggacgt tgtggtgctc acctgtaatc ccagcactcg gatggtagaa gcaggatcaa  29940
gagtccaggg ttgcctctgc tacataccga cttcagggcc aacctgaggt acattagact  30000
catgtttcca cacccccaaa gccccccaaa ctaaaagtaa gtgggtcgag accccctatgg 30060
acaggagtgc cgaatgaccc ttcattcact ttaaagacca ttggaaaata tacatctaca  30120
ttactatttg taacaactgc aaacttacag tagtaaatta gtaaggataa taattgtatg  30180
tttgggcatc agtacaacat gagaactgca ttaaagggtg gcaacattag gagtattgag  30240
aaacactggt ctaggtgact ggaagggggt ttggtttgca gagcttcctt tgctgcacct  30300
cagtgaccct ctctgacatg tctgacttgt aggtcagttt tggttggtgg gtgtcagctc  30360
tttgacactt tgctgctgtg taacaactgg gactttttgt tttccttttg aactgtctgg  30420
ttctgagtaa actgggttgc ccagcaattg ctatgtagta ctcaaagctg tagttatagg  30480
cagcaaagag atgatatgtg tgccttctgt cagggccttg ttactttagt ttactcatag  30540
```

```
ctttgtggag aagtcaccca tgttcaggga tacttagtgc tgtctcagca atcaggaaaa  30600
gaaaactctc agcaaggcac agctgtttca tcttttctgt gtctgttttc agacagggag  30660
tcactgtgta gcttaggctg tcctggaact caccatgcag accagcctgg cctctgcttg  30720
aatgctagga ttaaaggcat gtgccagtat gcctgacttt cattttcatc ttttaggaac  30780
attctgtgaa taaatggaag taagagctga gttaataatt gaaaaggtgg aggaaatcgg  30840
taagacatag ttgtaaaatt ggacttttaa attttttttt gtttttttga gacagggttt  30900
ctctgtctag ctctggctgt cccagatctt gctctgtaga ccaggctggc ctcactcaca  30960
aaagatctgc ctgcctctgc caacagtaaa attggattta aaaaatttta tttttactat  31020
ttttaatttt gtgtgtgtct gctttggata atgtgcatgt tagtgtaggt gtccacagaa  31080
gccacaggtg ttagatgctc gtggagttgt agtcacaagt agttgtgagc tgctcgatgt  31140
aggtgctggg cattgaaaga gcatcttctc ccagtgctcc cagccactga gccttctctt  31200
gactatcaac cctcactttt tgagacaaag tctcattgtg tagccttggc tgtcctgggg  31260
ctcacttaga aaggccatcc ttgtcttgaa ctcagagatc ctcctacttc tacttcctgg  31320
ggctaatgac accataccag tgaatatctt tttctttttg atattataat aggattaaat  31380
aattcccttt ccttttccaa cttctcctcc cttgcctatt ctccttgctc catttcaaat  31440
tcatggcctc ttttttcatt aattgttatt tcgtgcatat atgtttatga gtatattcct  31500
aactataacc tgatcagtct gtatgtttct cacatgtatg ttttcagggc tgaccgtttg  31560
tcattgataa ccaattagtg tacactttcc tggagaagac tgtttctctc actcttagca  31620
ttcctaagtt gtctgtagtt cttgtataag ccttgtgggt tttctcccat ccactttgtg  31680
tctatcagtg ttgtctcctc tcatgttaag gcagccatgt tggtgagact tttgacatta  31740
ctaggagaca caatctcaca gcagactccc tgattctttg gttcttacag tctttctgct  31800
ttctcttctg caatgtttcc tgagccttag gtatgggaat gttttgtaga tgtatctact  31860
gggactaggc tccataatgc tgcattttga tgggttgaat gtttttgtaa tggtccccct  31920
gtctgagaag tttcctggat gaggtgtgag gactacactt atctgtggat gtaaggacaa  31980
ttttctagag ttaggggttc tgtgattctc tgaaatctga cttcacttgc actgagtagt  32040
tggctaggtt tccagtacca gggcatggtt tttctctcac tgagtggctc ttaagtccaa  32100
ttagagagtt gttggttact gccaaagaat gccactactg caagccttag ggtgatcacg  32160
tcatgccggt cattgtggtt cataggcatc atagctgagt aggcttagag ttagattgct  32220
ggaagctcgc ctcctttgta agcttgcaca gtggcaccgt gaaggctagt ccttaaaggg  32280
tgcaagcatt caggtcagtt ccagctcagg tgcttgtgtg tgggtcctga ctctaaagta  32340
catggtgtct tcagcagtag agacttactt atctcccacc tctggggtca cccaagggca  32400
gtagcaatag gctgtatgtt taggagtctg ggtttttttt tttttttttt ttttttgtt  32460
aggttgcctt tgactcttgg agaaagtgtt gtcagctcag atgaaactct gtatgtaatc  32520
ccctctctct tcctctgtta gttaccctct taaagattgc ccacccctc accatttccc  32580
tattatgccc agctcttgtt cccctccccc acaccctgcc aatggtcatt ttttgtttgt  32640
tagttttctg tttgtttttt gaggcagggt ctctgtagtc ctgtctgtcc tcagattccc  32700
tatgctgatc aggctagcct gatgacagac cctcctacct gtgtatttta aacactggga  32760
ttaaaggcgg cttcagtggg ttccttttta ctgtcctggt ttctgaagtt actccagaat  32820
atactcacat gtgaagattt ggaacctggc ttctttagag ataagattgc aggtgtgtgt  32880
```

```
cactgttcct gatttttgtg tggtactggg gataaaacca gggccagtta cagtctacta  32940
atcagcctgc cttttaagtc ttaattgtaa agtttgaagg gtgccaggaa gtttttgggt  33000
tgtgattccc aagagtgaaa aagcataacc cagaaacaaa agcttcgacg tagattaggt  33060
gcacctagtt gcagcaggac tttactgcat gtgaactggg ttgggtggtt tgggttaagg  33120
ttcatgtcca tcaactgtca aacagtggtt gatcagagtc cagtgcataa cattgtactt  33180
ggttcctagc aagatctgtg acaagtgaga agtcaggttc tttatgcttt tggcccctcc  33240
ccctccccct cccccctcccc ctcccctccc ctcccctctt ctcttctctt ctttcttttc  33300
ttttcttttc ttttcttttc ttttcttttc ttttcttttc ttttcttttc actccagact  33360
ggaatgtaca ggtcagagga ctacctgtga gagatctctc ctttaaattg tgggggtcca  33420
gaggatggaa tgcaggttgt caggcttggt tgcaagtgcc tttaactgct gagccattct  33480
gccaggtgcc aagaacattg caaatgtgtg aatcttaggg ttctagaatt tctgaaagaa  33540
atgagaggcc atccagcctc agacagcttt cctgagtgag tgaggtgagg aagacagttg  33600
aagggtggag aactaggtag tgggctgcct gggagttcct gctagtgtgc tgccacgagt  33660
tggcagccct gctctaggct ttcacctgtt tactgaattt tcaaatttgg actcaattgg  33720
agtgtgtggc tattgtatta aaatggcact tcaagggctg gacagaagac ccagtggtta  33780
agaacattgg ctgcttgtgt agaggacctg ggtttgtttt ctagaactca catggctgct  33840
tataattttc tgtaactcca gtttctgggg atccagtgtg ctgcttcagg ccctgtgggt  33900
atcaagcatg aacaaggtgc acagacatac aggccggtgc tcagctacat agaacattta  33960
ataacaaaaa aaccccagca actttaaaat gggattccag atgtgttgtt ccacaacagg  34020
tggaacagaa atgtagaatt ccttgttatt tgtgagaaac tcaatctttc cctttagaag  34080
aagccttcag ttgtacaggt ttaagacttg caggttgaac taacagtggg tagaaaggat  34140
cgggagaaac tgtaccagca aggactgtgg gtcatgtttt tttccccttg tcattctcta  34200
aataatacag ttgtgtatat gtaacatctt caattgacta gatattaaat aataaatgag  34260
gtatgtgggt catgcaaata ccatataagt gatttgaaca tcattgaatt ttggttctga  34320
tggaatcttg aaccaatccc ctagagtaca gaggaacaat ggtgttattt attatgattc  34380
agttcacttg aaaatagtcc acattacaaa ggcaccattt gatagcaggg ttttatgttg  34440
tttaatgtgg gttttgtttg tttctgcagt gctggaaact gagttgaggg ctcaaaaaca  34500
ataagcaagc agactgtagt cccccccccc ccccagctga ggacctctga ggcaagcact  34560
ctacctcgac ctaaatctcc aactcctaag caagcatact ctactgcaag ctatattcct  34620
aacctggtag ctgagttttg tgtactgtag cttttccaag ggagaaggtt ggtaaggaaa  34680
agacttgttg gacaattcct gaattttgac agtgtagccc aggctagcct caagtaagga  34740
agctactgcc tcagctgggg ttacagctgt gaaccaccag gcctgcaata tcatgtacca  34800
aatctgacag agacacatgg tatttagaaa taaaagtgtt tagaactatc tgatgtttaa  34860
acatttattt tccgtgtgtg tgtgtgtgtg tgtgtgtgtg tgtctgtttg tgtgtttgtc  34920
ccagcacaca tgttgtagtg gtcagaggac agattgtaga agttgggatg ggaagttgta  34980
tggatgctgg ggattgaatt caagtcttag gcttgcagca agtcccttta ccttctgagc  35040
cttctgacaa agccctgttt taacttattt ttggtagttt tttctgcagt tataaacacc  35100
tagctacttt agagatgggg agaatgagag ctgattgggg tgtcagttgg ccatgttgat  35160
cacaagtctg tgccaccact ccacacttct agtgctgctc ctttgcgtac ccttgtcctt  35220
cggtgcgtct ggggtgggga gacaaggtgt gctctacagc cctggctgaa ctcacaccac  35280
```

agcatcccac tgtctcagcc tctgaagagt gagtgcagcc acacaccact agacccggat 35340
aggctgtctt tactcttctg ttatacattt gtttttgttt atttatatat tagggtcaag 35400
gtctcgctca gctctggctg ccctggaatt cactgtgtag agcaggtgtc cggcttccat 35460
ctccctagag ttgggatcaa atgcatgtgg ttctccacct gccttaccta tttggttttg 35520
agaaaacagc agtcttgtct tttctttcct ctttgtggga ttctctcctg gcctggtagc 35580
acacagccac tgagatttcc tgtcacacta tattagatgg cgccttcaca gtcagcttgg 35640
cctgtgtttg agtagaatta taagattata ttttatgtac tcattaattt aaataaaata 35700
aaaattgaat ctaataaaac aatgtttaat ctttgcagag gtcggaacag tagcaaagga 35760
ctgcctcagc ctacggtgag taactttaat gttatttaga aaaatacata aactgtgatt 35820
tccaatcata gactcaataa taaagcaaag aattagattt ccagttgtac tacagatagt 35880
ctatagataa gtcagtttaa tacaaggttg ttgattcggg aaggcctctg aaatgaacac 35940
ttttctgtta gtggtatttg tggcttacat aatactgatg tcaagggttt tgatgttcca 36000
ggaccagagt ttgcagagtt ctctgggctt tttgttagga ttaatgtgct gtctgtttta 36060
actcagtcat ttttcctcct tggaaaacac cttccggcct gccgttttcc aacttttatc 36120
agtgaagtta aaatagacac aaagagcatg aaattccata taagaagccc tcttttattg 36180
gtgttttttt tgcttggttg gtgttttggt tttctgagat agggttttct ccatgttgtt 36240
aactgttgga actcctgtag accaggctag cctcaaactc agagaaatct gcctgcctct 36300
gcctcctgat tgctgaaatt aaaggtgtga accactactg cctacctgtt tgtttttttgg 36360 acacagggtc tactatgtag tcttggctgg tctagtactt gctatgtaga ccaggctagc 36420
ctcaaaaact cagagagaac tggttgtcac tgagttttga aacatggtct ttatcgctca 36480
ggctatctta ctgagagtca ggtggtcaca ccctgtgtag tccagcctgg aatggttttg 36540
ttgccttgat tcagacatgt tgagagaagc tggtcgtcgt gcaaggtgta ccctgctcag 36600
cacttctctt ctttattaag atgtactgcc cctctttagg acttgggttg ggaggtcttt 36660
cctcactacc ctgctaccct tggtgctcag gctctttaat gtgttaggga agcgctctgt 36720
catccagctg ctctccagcc tggctgatgt ttggttctgt tgtggcttat atttagtttt 36780
atttagtgtg ggggtagtgg gtgcaccatg atgcaggtgt aatagtcaga ggacctccat 36840
gtgggggctg aactcaggac atcaggctca tgtgccttga cccactgaac cattttacgc 36900
gccccatctg agggagtgtg tgtgtgtgtg tgtgtgtttt gagacaagga ctaaatatgt 36960
atcctggctg gcctgaaaac ttcctgtgtt gatcaggatg acctggaatt cacttagatc 37020
cacctgtttc tgcttccaga atgttggaat taaaggtatt tacaggcatg cctggctgta 37080
tcctacagcc actactgcac aacccttctc tacctggccg ctagctgtgc aaagcacaga 37140
ccctacaaat actgatttgt cttctccaga ggtttttgct ttctcacatg gaggtctgag 37200
tctcctgttt ttgtttgttt tatgtcatag taattattag ttggaatggt tggttgattt 37260
gtttaaaact ctaccttttc tcgtagggaa acaaaatgtg atagtaacca gctcttcctt 37320
cgtgcattat aatccaaata tcttagagct agacaaggtt agcttttgta tataggcaag 37380
tacaaagatc agcttacaat aatgtttatt ttttatacat tctagatttc ttttgatgga 37440
atctatgcaa acgtgaggat ggttcatata cttacgtcag ttgttgtaag ttacctgatt 37500
attggggata aactcctttg gagtgggatt ttacatggag ttaacatgta gataattctt 37560
aacctaatat tattaggcta tattaataaa gatggtttta aaaacatact agaatgctat 37620

```
tcagttaatt acaactcaca gtaaaaatac tcttgttaac tctgttgcat gtaaaatagt  37680
atttatagct gctggtcttt tgtgtgatat tttgttatct aatggtagtg gggacagaag  37740
tgtgtagctt taggatacag tttatattca ctttggagtt tccagtcctg taccaataga  37800
gaagtaggta taatgttaat gtgctgaaac ttgatcattg ccagtcaata tccaatactg  37860
aatgagacct tacagaaaat gaaagggaga cacccactat gggaaccaca ctcttgactc  37920
tgttaaattg tgtcttttag ggatcgaaat gtgaagtaca agtgaaaaac ggaggcatat  37980
atgaaggagt ttttaaaaca tacagtccta aggtaattct tactaagtat tagttcttcc  38040
tgtagcttcc tgagagtgtc ttgtcattgg ttgagctgac tgtggagttg gcagttgagc  38100
tcatgagata aaatacaaat gttttcctga ttaccacgct ctctacctgt ttgataacca  38160
cttgtttttt tttttttttt tttttcctct ctaataacaa attcttacta tttaatgact  38220
ggtttgtgaa gctgaaaata ttgtatgtgc ttgtactggc tggttttatg tgtcaatttg  38280
acacaggctg gagttatcac agagaaagga gcttcagttg gggaaatgcc tccatgagat  38340
ccagctgtaa ggcattttct caattagtga tcaaggggga aaggcccctt gtgggtggga  38400
ccagctctgg gcttggttct ataagagagc aggctgagca agccagggga agcaagccag  38460
taaagaacat ccctccatgg cttctgcatc agctcctgct tcctgaccta cttgagttcc  38520
agtcctgact tccttggtga tgagcagcaa tgtggaagtg taagccgaat aaaccctttc  38580
ctccccaact tgcttcttgg tcatgatgtt tgtgcaggaa tagaaaccct gactaagaca  38640
gtgcttatga ttttcaacca ttttcagatg ttgtgagcta gaagagggct gtacagagtt  38700
atgtcttttt tgttgttgtt gttgttttga gacagggttt ttctgtgtat ccttggctgt  38760
catggaagtc actctgtaga ccaggctggc ctcaaactca gaaatccacc tgcctctgcc  38820
tcccaagtgc tgggattaaa ggtatgcacc accactgccc ggcatatgtc tttttaaca  38880
ttagtgtgtt tcagatccgc tatagtaaga tcagctttta gatttgaggg tttttgtatt  38940
gtaggtgcat gacaagtcca aacaggatgt gataatcagg ttttcacagg atgcttttgt  39000
cataggctta aaagtaaatg gctttgatga gctaaatagc tctataaatg gctattaatt  39060
aatttttta atgttattaa tttctttatt ttagtgtgac ttggtacttg atgctgcaca  39120
tgagaaaagt acagaatcca gttcggggcc aaaacgtgaa gaaataatgg agagtgtttt  39180
gttcaaatgc tcagacttcg ttgtggtaca gtttaaagat acagactcca gttatgcacg  39240
gagaggtagg cttgggtttc cgaggtgacc ctaaccctgg tgtgattggc tcactccaac  39300
agcaggtctc cagcacccat acagacttgg tttccctcac ctcagacagg atcttgctat  39360
gtggctcagg ctgaccttga gctcttggtt ctcctgcctt tgcctcaaga cctaggaatg  39420
agattttctt ttcttttcct tttctttatt agtggtattt ttctagaata gctttttttaa  39480
taatctaata aaaatgtgag ttttaatgaa ttttttgtta gaaaatattt aaaacttagg  39540
tggaaaataa cttggtaatt ttagaagcat aaatatataa ttgcagtatg catttttga  39600
aaaacgtttt tagatttata tatctgagca ttttgtctga atgtatttat gtgtaccatg  39660
ggcatacctg gtgctactga ggtcagaaga tgtcagatcc ctaggaactg gagtttctga  39720
tggttatgag ttcactgtgt gggtgttcct atctactgag ccatctctgc agccccagtg  39780
tgcatcctgc taacataatg ttggccacta ctaggtaagc cttgggttca ggagctccgt  39840
ctgggctggc ctgggctggg ctgaacagtg ggactatctc aaacaggatg ctgttgtggg  39900
tgtggttgcg tattctgaga atttaaatgt acttacattt gtgtgtatat gtatatgcat  39960
gtgtccccta cctgttgcaa gtgttgatta aagaggggct tgtgaacatt ggtctatcat  40020
```

```
ctggagaggc acttgtagca ctgggaaagg acctttgcaa ttaaaaaatt cttgaatgat  40080
agattgtcac taactatagt tgatttagat tgtcattaat tacagttgat ttttgtgctt  40140
caattggtgc taatggctat ttgtgctttg tggttgaaat gtccatactg aaactctgag  40200
gcacaggaaa tttcagtgct ccctgactgt cctgtctcta atatctgcgt atctctgcct  40260
ccagagtgtt gggattaaag atgtgtcaca actaccagct gttaacagcc tatctcaaca  40320
caattctctc attacttttg gggggggtg ggcaggtagg gggacacctt agatttataa  40380
ttccttagag agccttcagt cacccatgaa ggagacagtg cttccttagt tgttgccttt  40440
agagtcagtt tcccttatgc tttgaagtac cacatcatat atatttatgg ttttgaaaga  40500
tttcatgttt ggtcatcaca caagggggaa gaccaaactg tgagtgaata tacagcactc  40560
tgaggagagg attggctgta gcagaaacag cacagtttca gaaacagcag aaacacagta  40620
ccggctgttg tactgtgttt gcagcgtgct tgttttggga gtgctgtgga ccaagcatag  40680
agtactgcat gcagttgatc atggttttgc tggaccccac caggtcccgt tggagttttt  40740
acagtgctgg aatgccccgt agccttacat gtgctaggtg aacctactac taagccccac  40800
ccccaacccc acacaccacc ccactctgcc ccagaacccc cagagcaggt ttcacggtgt  40860
agttctagct atcctggact catcctggac tcacagagat ccacctgcat ttgcctccag  40920
agtttggatt agaggtgtgt gcactatgcc ctgtgtttgt ttagttttat tttattttag  40980
tttttaaaga tttatttatt aaagatttat ttatttattt tatgtatatg agtacactgt  41040
aggtatacag atatggttgt gagccatcat gtggttgctg ggaattgaac tcaggacctt  41100
ggaaagagca gtcagtgctc tttacctgct gagccatctc accagcgcat ttataatgtt  41160
tagttttaaa gacaggtctt cttgtagtca ggactggccc caacgattaa acttcttgtc  41220
cacgctcccc agtattggca ttgcaggtgt gtgccagcat ctcgggtcct gtatagtatt  41280
agggattaac cctaggctct gtgagaatgg atactttact gtgtattaat ggttcaattt  41340
ttactatgaa gacatgagta ttgacataat ttcaagtagt ttgtagaaaa ccaggtatgg  41400
cgggaggagg agacagaggc aggcagatct gagtttgagg ccagtctggt cctcaaagtg  41460
agttccagga cagtcagagc tcctcagaga aaccaaaaga aagaaagaaa gaaaaagccc  41520
acagtggttt ggttaattat acagttgtat tttccagtgc tgggaaagag tgtgcagggc  41580
ctgtgcacac taaagagaat ctctgcctgt cttcaagagt ttaggatcct tgagccagaa  41640
ttgtctgcca ggtggacgtg gaggccaggt tacggttggg caggtggtct tcttcagaag  41700
ccatctgccc tgttttgaga caaggtctct cgctaggact gggtgctcac tgctgaggct  41760
agacagcaaa catgggtgaa tgcctggctc tgcctcccca ggtcaggcat tatgaacaca  41820
caaccatgtg ccatctttgg cttctgtgga tgctggggat tgaggctggc tcttggatct  41880
atattcttga tgattaaacc ttctcccaag ccctcgagtc aggttctctg tgtatatccc  41940
tgtgtgtgca aatatcatat gttggttgaa attgctcttt tttgtttgtt tgtttttgtt  42000
ttcccaaggc aaagtttttc tgtgtagctc tggcttttct agaacgccct cagtaggcca  42060
gtctcagaga tctacctgcc cctttctcct gagtgctggg attaccatgt ttttgagagt  42120
gaagtgttgc tgtgggaata ttgcttatgt atagaagttt gacctactaa tttggcatgt  42180
ttcattaatc agataaatta aggtaatcag tgctgcatta aaaggaatgg tctttacctt  42240
acggcttttt agtctcctgg agtgagagga gatctaatca gtgcttgcga gttttagtta  42300
cttaggaaca ttcccaagac attagtcttc acttccttat attctgtttt ttgtttgttt  42360
```

```
gtttgtttgt ttgttttgtt ttgttttgtt ttgttttttt taaagattta tttatttatt  42420
ataggtaagt acactgtagc tgtcttcaga cactccagaa gagggcatca gatcttgtta  42480
cagatggttg tgagccacca tgtggttgct gggatttgaa ctctggacct tcagaagagc  42540
agtcgggtgc tcttacccac tgagccatct caccagccct tgttttgttt ttcgagacag  42600
ggtttgatag ccctggctgt cctggaactc actttataga ccaggctggc ctcgaactca  42660
gaaatctgcc tgcctctgct tcccaagtgc ttccacgccc agctgtttcg ttatattctg  42720
atttacaaat aatcagcttg tgaaatgatg agtattggct gctattccag aagacctggt  42780
cgtgattcct aactcctaaa tggtggctca taactgcaac cccagtttca ggagacacag  42840
caccctcttc tagcctcctt gaacactgta ctcatatgat gcacagacat aagcaagcaa  42900
caaccccac ccccactccc cagcacaaac ataatacacc ttgcttgagg gtctgagcat  42960
gtgaaataga tgaggactga gccctaggct tctagtcctg aggaatggtg tggctctgag  43020
tcctgaagga cacacttact ttctttgact cagtgccttt tttttttttt ttgtctcagt  43080
taaccattat cttgtaaagt ttttgctgat acactaacta atatggtaga ccttgatcag  43140
agatggactg ataggtggta gtttgccatc caagcttgaa ggaagtcaag ttccccctgg  43200
agcttctgct ttcatcattt ttctttaaca ccactgtcag aatcttgagg ttgttagcta  43260
ggcatgatgg gctcactgtt attccagaat tcaggaagga cactgaggca ggagactgcc  43320
ttgagttcaa ggccagtgag atccatatct caaacaaaca aatccaacca aaccaaaaca  43380
aagaacctca gaaacaacaa tagacagggc tggagcaata gctctgtgct taagagcact  43440
ggctgctctt ctggaggact agggttcagt tctctttacc ttactcacat gaaggcttga  43500
ctctgcctat aatttcactt ccaggagaac tgacaccctc aagggccaac catgcacagg  43560
taaacatatc agcaaaacat gcatgtgcat gtacacacac acacacacac acacacacac  43620
cctgagatag tttgaatatg cttggaccag gaagtagcac catttggagg tgtggccttt  43680
ttggaggagg tatgtcactg tgggtgtggg ctttaagacc ctcaacttag ctgcctagaa  43740
gccagtcttt tcctaacatc cttcagctga agatgtagag ctctcagctc cttccacacc  43800
atgcctgcct ggatgctgcc ttacttcctg ctatgatgat aatggactga acctctgaat  43860
ctttaagccg gccctaatta aatgttgtcc ttataagagt tgccttgggg gctggtgaga  43920
tggctcagcg gttaagagtg ctgactgctc ttccaaaggt cctgagttca aatcccagca  43980
accacatggt ggctcacaac catccataac gaaatctgat gcccttttct ggtgtgtctg  44040
aagacagcta cactgtactt acatataata tatgtaatac atatatatat atatatatat  44100
atatatatat atatatataa ataaaaaaga gttgccttgg tcatggtgtg tgttcacagc  44160
agtgaaaccc taattaagcc ccccccctta atttaaaaaa taaaaaagca aaaaactcca  44220
gcaacagcac tgggaaatgt gtttgagtgg tatgcatgag atcttaggct caggcacagt  44280
catggagcaa taaaggtgaa gctggcagta ttttaaaggc tggttagatg gctcaaaggt  44340
aaaaaaaaac atttgctgcc aacccagaat tcaatccctg gaacacacat gcctgaggag  44400
agaaccaact ctacaggttg tcctctaacg tctacatgca tgcacgcact ctcccaacat  44460
aagcaataca tgtaaaataa aaacaattta aattcttgtt taaaagaaga aaaatcagct  44520
gagcatggtg gttctcattt ttagtccttg ggaggcagaa acagaggcag gcagatcttt  44580
ctaagttcaa ggccagcttg gtccacatag tgagtttgag gatagctaag gttacatagt  44640
ggagactcta aaaaaagttt ttagttttaa attctgtgta ttagtatatg ggctgatgga  44700
aggtattgga ttcccctaga cctggagtta aaggtggttg tgagccatcc agtgtgtaca  44760
```

ggtctctgta acttttactc ttaactgtca agccattgtc tctagtcctc tcaggttagg 44820
gcctgttgta acgtgggcat gatttttatc tacttgctcc ttggtaagaa aacagatgca 44880
tctgaggatg tggtcgagta gggacagagc ccagttcttt aaccctagct catcacggct 44940
gtccttcaca ttgtacagtg gtgatgagca ctgtgggggc agctctttat taacattaag 45000
gatgtagtca cagataaagc agagggtaaa gcatggtggc agacactgtg accctaattt 45060
tgcagaggct gtggcatatc agactaccta ctgagttcta ggtcagattg ttataaataa 45120
caagatcctg tttcaaaaca acaaccacca cctaaaacaa agccattgca ggcagtgtaa 45180
gctacagatt attgtatgat tcaggtttct ttttttttctt tttcttcttt tctttttgtg 45240
tctggctttt gcaggggaaa aaaatatttt ttgagacacg atctcactat gtagatcaga 45300
caggagtcac cactccctac gagctaaccc tttaaagcag gtagcgtcag tccggctttt 45360
gaaccctgat acatacttta ttttgtcagt gagttgtttt aaaatgtatt gcatgtatgt 45420
tcgcgtgtgt gcacgcatac cttgatgtac aaggggagct cagggggagc ttgtggaagc 45480
ctgttctctc ctcctaccat gtggttcctg aggtgcaaat tcaggttgcc aggttggtgg 45540
ccgtgccttt acctgctgag ccttttctgg cttgagttca gcaggtttga gaagtcactg 45600
ttccagcact agggattcag aggccggtgg atctgagttc caggacagcc agggctacac 45660
acagaaaatc cctgtttttt catacacatc ttttttggtt tttgagacag attttctctg 45720
tatagccctg gctgtcctgg aactcactct gtagaccagg cgtgcgccac caccacctgg 45780
ctttcataca catctttttt tagaactttt ttgtatacgt tttgtttttc tttctgtgta 45840
tgggtgtttt gccttcatta gtgtttgcac cacatgcatg cagtgcccat agggtccaga 45900
agatggtgtt ggataacctg aaactggagt tcctgatggt tgtggggcac tatgtgagtg 45960
ttgggtattg aacccaagtc ttttagtaga tcagccagtg ttcttaaaca ctaaactgtc 46020
ttcctcagca tctgatttta aaaataactt ttataggggc tggaaagatg gcttagtggt 46080
taagagcatt ggctgctctt cccaagttca attcccagca accacatggt ggcttacaac 46140
catctataat gtgatgtgat gccttcttct gatgtgcatg tgtacatgca gataaagcac 46200
tcatacatag aataaatata tctttaaaaa atgattttaa tgtgcatggg attttggtct 46260
gcatatctat gtctgtattg tttgtatgct tggagcccaa gagaccaaaa ccagggcatc 46320
caatgccctg gagctagagt taaagacagt tgttagctgc catcatgtac tttgatttga 46380
acaggggtcc tcaggtagag ccgctagtgc tcttaactaa ggcatctctc cagccccata 46440
ttcatctatc tttacagata tatgggaggc ttagaaatat ccctatgttg tgggccaata 46500
tggtttatgg actgagtaaa agtatcgtcg ctagagtctg tctcgctcac acataggtag 46560
aacaggtcat gagattcttt ttcatgaatg tgtagaccag ggtggctttg aaataacctc 46620
tgaagaggaa gctggtcctg aactcctgat cctcctgcct cacttgccca ggtggtgaga 46680
ggacaggtga ttgtcattca tcgttgctga aaagatcagc tcttaatgga aagttagctt 46740
tttaaaaact aaaatgttat aggtttgttt ttatttttaa aggattttat acctttagtt 46800
taatttatgt gtattagtgt ttggctgcat gtgtgtatgt ttgtgtacag cgtccacaga 46860
ggccagagga ggatgttgga cccattggaa ctgaaggtag agcctgttaa tagccctgag 46920
gttggtcctg gaaaggcact gtggtctttt cttagtaggg ctctgctgca aacagattgg 46980
aagcacttgc tttttctgtg tgcagcccgg atgttcagcc atagatggtt ttgtagcttc 47040
tctgctgtat tcagcagact agctgcaagt gtgagtttca gggatgcttg tcttcactcc 47100

```
caggtctcct taagaggagt ttagggacca caaaagctaa gtcaggctct taggtgagtt  47160
ctggggattc aaattcagat ccgcatgtgt acatggcaag tattgttact cactgagcca  47220
accttctagc cctagagcac tttgctgtgt gtactgtctg catgtgcttg tgtgcctctg  47280
tatccgtgta agtcagaagt agatgttgga tgaggttttg tcccaacccc tgttctttct  47340
tcttttagtt ttttgagata gattctctat gtcctagaac ctatttagat taggctggcc  47400
ttgaactcag agatcttcct gcctctgcct tctgaatgct gggattaaag acctgtggtt  47460
tcctcagtca tgtcctatct tatttttgga acagggttgt tactgaacct ggagttcact  47520
gactggctag agtgggtggc ctggggattt tcctgtctgc atccctagca cggagatgac  47580
agttgtgcag gattttgtgg gtcctagggt tcaagctcag gtcctcctgc ttgctctgta  47640
agtgcttcac caactgtgcc tgcccctgcc ctattttttc ctattttgca cctactttaa  47700
gagagctgga cgtggtggta cacgccttta atcccagcac tcgggaggca gaggcaggtg  47760
gatttctgag ttcgaggcca gcctggtcta caaagtgagt tccaggacag ccagagctac  47820
acagagaaac cctgtctcga aaaaccaaaa aaaaacaaaa aacgtgtgct gcttgtcttg  47880
gaatgggact tgtgtctctt gctctgttct ttccagtgtg tctggtctgc attttttttg  47940
ttttgttccc cccccccccc atcttcccat tgtcccctcc aaaggtcttc ttacatgcta  48000
acctcagctg tcactgcctg tttcccagtc cctagtgatt agtggccttc tgtttgtatt  48060
gtatcctttg ttttgatgac ctccctgtgt gttggatctc tatggcttct ctcttgcttg  48120
tctctcatgc tgccacttta ctgctttgtg cctttgtgtg gtctcagcca gcccggatag  48180
caggtcagca gatggacaca gtagtacaca aagttggatt gtaacagcga tgtgtttctt  48240
cattcatgtg ttggctgcag ctgctgtcct gtagagctgg aggtcagtcc taataacaga  48300
cagcaggcct tgcatataca cctcatctgg cctttgacag ggaagcttga caacccttag  48360
cctaaatcat tcttccttct gcattggagc tatttagagc tgatgtgtta aagagttaca  48420
tgctgttctg gtttggcgca ataaccgaac atgctttatg tctaatctca tattcagcgc  48480
tgatgcttgg ctctagtatt acatgtatca tctaattcag cttcttattt atgaccactc  48540
caattggagg cagcccaaag aatcacttgt gctttctaga tgccacattc agtaagaagt  48600
aatgagcaag tggtttattg ggagtgacct ggagcaacta caactaccta ccacttactc  48660
ctcctctgca aatttgattc tctttttct ggctttgtgg aaggaacaac taagcccccg  48720
tctccttgtg tttccccaca gcattcctac ccctcccgat ctttcatttg gcttttactt  48780
attttaagtg tgtgtagtgt gtgtctctgt cgtgtgtatg tgttactgtg tagagagaag  48840
aggacaacac ctgtgggctc tgggtgttgg actttagctt gttagccgta ggccatcatt  48900
ttgtgctttt ataccactta tttctggact ccacactctt cctgctactg actccttcaa  48960
ttctgcctga aaattattca agtccccttt ccctgaaaca agtcccttcc ccgttcctca  49020
tacatacagc cctacttgag gctgtgtgga gcttctattt cacaggtcct ttggggctct  49080
ttcagattct tatgccacat ttgaggcttt accagtacct gcatctcttt cataaacaca  49140
tcatctctct tctgactcac tcctggcttg tttcccctcc tttacactgc tctcttacat  49200
gcttgtgctc gcctggcctc gtggcttgtg tcagcccctc cccagtgccc atgcaactac  49260
tcttaggcca ggttgtagga gggtgatggt tttctcatta taatctgagg tcttaaatct  49320
gagtaatgtc tttatttttt attttatttt tcttagacaa gaccttactc tgtagcccag  49380
gctgtccttg aatttgctgt gaactctttg cagttctctt gtctgagctt cctcagtagt  49440
aggtttacag gcgtggacca cgatggcttt taatctttta aaaagtctca ttatctacca  49500
```

```
cagtgtcttg cttggcacgt agtacatggg ctcataatgt ctttgaattc atgatattta  49560
atagcctaaa actttttttt tggggggggg ggttggtttt tcgagacagg gtttctctat  49620
atagccatgg ctgtcctgga actcactctg tagaccaggc tggcctcgaa ctcagaaatc  49680
cgcctgcctc tgcctcccaa gtgctgggat taaaggcgtg cgccaccaca gcccggctat  49740
cctaaagcat ttttaaaaaa catttattca tttattttat gtatgagtat actgtcactg  49800
tcttcagaca cactacaaga gggtatcagt ttccattaca aatggttgtg agccaacatg  49860
tggttgctgg gaattgaact caggtggctc ttaacccctg agccacctct ccagcccatc  49920
ctaaagcatt tttaaagaac tacaattcta tatgaagtct aggaaattag ggctggagag  49980
atgattcagt gacctttagt gcatgctgga ccaccacaaa gaccctggat ctctacactg  50040
ttataacaag ccaggtgtgg tccagctctg tagggtgaga caggaggatt gctggagctt  50100
gctggcttcc agcctagtgg agaaaatgcc aagtccaaga tgtaggggag ggactctgcg  50160
tcagaggagg aggctgcatg acaggatgag tgacactgca ctgcctgctt tccagtccag  50220
atcgtgcacc tccttacacg tgctcacaca cgtgtacccc taaagtaaat gaaactagcc  50280
aaagatggct acagatgtct tgctgtgttc ctgtccctct gcttatggct ctggacagct  50340
cggcgagatg tagagattct taggagttct tttgagaact tctgtgaagc ttcctcactc  50400
tagggaacta cagacaaact tgtgcgttta aataccactt gagacaaata cagacgcttg  50460
tggaaataga cacacaaatg gaaaacattt gctaaagtta ctttcagaca ttcagaaaat  50520
acagaactta tcttctgtat tttttataca tatgcccaca tgttgtttga cagccttctg  50580
gggtgatata acacatcaac agaccatgac aatgactgtc gcagcactgt gaagttcatg  50640
aactaatgag ttttattgag attcctagag gtgagaagtt acttaaaagg attaggggta  50700
actcagaaaa gcagctctac actaacatgc gtaataacat gaatataata acatgtgaat  50760
actgcagcct tggagccttc tgtgtagttt gcaggcaggt ttgcttggct gtctctgtcc  50820
ttagcagctt tttacttctt tttatactgt tagtagggcc cccaggaatc tcacaagtcc  50880
tcatccctgt ttctcccccc atgtataacc atccgtagta aatgttctat ctccaaagag  50940
acaccatgac cacggcagct cttataaaag aaagtgaaca tttaattgga gtttgcttat  51000
agcttcagaa gtttagtcga ttatcatcat ggtggggaac atggcaacac tcaggcagac  51060
ctggtgccaa agaagtagcc aagagttctg ctttaggatc cagtagcagc aggtgagggc  51120
tgacactagg cctggcttgg gcccatcccc acatgacctt ctgttcactg gtctgtgaga  51180
accccctttc ctctggaggg gatgttggca ggtgtagaaa acctgctgta taacagcagg  51240
tcagagcatt aaaaacgaga aaggagtttt gctgggcctg gtagtgccta cccagaaggc  51300
acagaaggcg aggcaggagg attaagactg ctatttagtg ctagtaaaag taaggtgccc  51360
tgattgattt cttacgtatt ttacttttaa aaagttacat ttgtctatta tatatgtggg  51420
ccttggtgct gtggtatctg tatagatgtc agagacagcc tatgggaacc aattctctat  51480
tgtgttagtg ccctgcagca ataaaagttt cattgtgtgg tggtcggtag ctttacactg  51540
agccatttta ccgggctgtg tgtctgtgtg gtcccccacc ccatgggctc tcctgtattc  51600
ccgctgctgg ctctgtagcc aaggatgatc ctgactccag tccatggacg tgcgggagtc  51660
cagccgaggg ctggctgtat ggcagacagg actttgctag ctcagcacta actgctttcc  51720
tttccctgac tgggtcagtg cccagcttgc aaaaatcaat gctaaataaa tacaaacatt  51780
attaaagtag atttgatcat ttgaagattt tgtaatgctt tttgtggtcg gttcttagta  51840
```

-continued

```
tgctgatgtg atgctaaagg ctctgcactt ccatgtatta acaaagagaa gacatgtttt  51900
ctttcatagc aacagggagg acatgccttc ccagacatga aagtgctgta gagttcagtg  51960
tttgtagtga cagagaatag aaaaccccag acagactcat gtctaagtgt gcatgtgcgc  52020
agtaaaggta aggcttccat tgagagaagc atgccattgg ccagcagcat tggatagcat  52080
ttaggagagg ttggctttct gtttcccacg agttcagcac tgtatagtgt aaaacagcag  52140
tgagctgcaa acgtgtgctg ctacatccct ggcatttgag ttatctgaga gagaagagcc  52200
ttatgggcat gtgcttggtt ggttgacatg ttgggaagag agacctttag tgaagaggat  52260
ctttcatcac tttggccctt ggacaactct ataggacttt ttggtttttt aattttttat  52320
tgctgattgg aggaggatca atccctctct gtggaggtat gagctctgga caggaggctg  52380
ggctatctat gtaagagtgg cagactgtaa ggctggaagc aaaacagcca gcagcattcc  52440
accaaggtgt ctgcttcaag ctccttcttt gtattcctac ctcaactttc ctatgatcta  52500
tgggaggaac caagacagtt tgaagtagca aattgtattt tttaaagaaa cagcatgttg  52560
gtgtttgctc ttttatattg attgttttca gacactgtat aaaatggttc ctacatcaag  52620
tcctaaaagg aataatatgg gagaagataa gatgtctcag ttgatgaagg cgtacagtac  52680
caagcctggt gacctgagtt ctgtccctga gacctacatg gtagagagag aggtgtgctc  52740
cagggcacat atgttcacct gctctcactg ctgcccgata catgcataag cttaaagctt  52800
attttatttt attgcggata aaatgatttg gttggtgcca gttgttttgc tttgcttctt  52860
ctggccctaa gcttatagga tcttctgttc tttaacccag tcaggtggca gctgcagaag  52920
gccctccgtt tccttagagc acagtgcctg aggtgcttcc tcaagctgcc taccctgtgc  52980
tcggagtgca gtgctgctgc tgtcgagcta tgccttttta aaaacatgtt ttttattttt  53040
agatttattg tgtataagtt tgtgctactg tatgaggcca gtgtggactc tcctggagct  53100
agagttagag gaggttgtga aactgtcaga tgtggccgtg ggaaccgagc tcatgccctg  53160
tgaaagtgta tcaggtattc tccactactg aaccgtgtcc ccagctcttg gccctgaact  53220
ttggaagcta atatcccaca ccaaggtctg tgtctccacc aatccttctg gtcgcctctt  53280
tcctagactg cttatctctt cattgtgtga tcacaataaa agaataagtg ttgttctggc  53340
caatattatc atattgtaat caaaggatca aggcattttt ctcctggttg tgaatggatc  53400
ttggcaagag aaggatccac tatttctcct catggggttt ggttagtttc ctgttgccat  53460
gatgaacctg atagaaatgg cttacagggg gattatttag cctgagtcgt ggcttcagag  53520
cctgtagaat atggttctct ggctctgtga actgtgaaga gcagtaggtt gtatggtggt  53580
tgagggtttc acctcaagga ggcagaagga aagcaaaagg cgccaaccag ggcaacatgt  53640
aggtcaagga cagaagcccc atgacctgct accgctaatt aagcaccacc tccaggtaac  53700
tccaccatac tgtaaataac atcagggcta actggttaac ttctagccct caggagagaa  53760
ctctctggaa atggacttgc agacctaaca gagatactta ctaaccacaa tggtatttct  53820
tagtttagtc agttcattat ggagacaaac cacggtgctg tcagaagcta tcccatttga  53880
gtctgtacac ctataatcct gtctatttct gcatgccaaa aatgtcattt ccccagtgtt  53940
gtttgtgttt gctacaaaat ttgctttcat gtgttgttta tcattttaag aaattagtca  54000
tttgaagctt gttgttttga agtttttgtt ttgggaacag gtctgtgctg tgtagattag  54060
ggtgacctag ggctgcagtt ccttccctgt catctgcccg gtgctgggac atgctcactg  54120
ccatccatgc cctgcaatta gtcattcttg cttcctcccc ctcccctccc ctcccctccc  54180
ctccccttcc ctcctctctt ctcttcttga aattagatat tgtgttatgt atgtaagtat  54240
```

```
actatagctg tcttcagaca caccagaaga gggcatcaga tcccatcaca gatggttgtg  54300
agccaccata tagttgctgg gaattgacct cagaacctct agaggagcag tcagtgctct  54360
taaccatctc agtgcactga gctatctctc cagcccctct tgtttgagtt ttgattctcc  54420
agacagcgtt tctgtggctt ttctgaattc actctgtaca ccatgctggc cttgaacttg  54480
accagctttt taaattaact tttttttact ttagcaaaaa ttataccccc ccccccccca  54540
aaagtcccat ccacttgttt ttctttattt ccttacctat gaaagtttag cctatgaagg  54600
tttttattcc tgatcttttg tggtttgtat gcttacagtt ttatttatgt gagacaaggt  54660
ctagccctga ctggcctgga acatgatgct gtgtaggcca ggctgcactc aaactcacag  54720
aggtctctct gtctctgcct ctctgcctcc caagtgctgg aattaaaggt atgtgtcatc  54780
atacctaggt attttacctt atcttattgg atttgatttt gagatagggt ctgtgtgcag  54840
tcccagctgt cctggaactc actaagtaga ttagactgag ctgtttttat atatgcatat  54900
atggtttatt tgtgtctgct acatgtgtag atttccagag gccagaagag agcattggct  54960
cccctggagc tgaagttaca agaggttgtg ggtttctttg cgggtactgg gatctgaact  55020
tggtcttttg gaagagaaac actcttacca gctgagcctc actctcaaac cccagaactg  55080
attgagcttg tggcagattt taatttgact gttgatgtgg atatgtcttg tcaagcatcc  55140
tctgctatag aaactgtcct cctagggaag tgacttagtg cctttcctga cagtgaggct  55200
accagatgtc aagatgtgtg gcagctgcgg aggagaccga gtggttaaga gcacctgctc  55260
aatcttgcag aaaacccaga tctgttccca gtattcaaaa ggagttcata cctctctaac  55320
tccagttcag gggagctgat gtcctcttct gggctctgca ggtgctgcag gcatatatga  55380
gggcaaaaca ctcaaacata taaaattaaa tctttaaaaa atgatatatg aatttctgat  55440
tatattttgt tgcgccttgt gcctgattct gttcagagct gtggtgtctt gttactgtgc  55500
cagtgtagta agttgaaatt tttatggatt tattttacat gaatgagttt gcctgggtgt  55560
gcagaccttg tgttcttgag gtcagaagag ggcattgata tctggaactg gttatagatg  55620
acagtctctt tgtgggtgct gggattgaac ccaggcctct gaaagagaaa caagcactac  55680
tcctcagaat agatactctc aagctttttg agatagggtc tcactgtgta gctctggctg  55740
gccttgaatt caaatcgttc ctccactacc accaccatac catgaaggca gtggctccca  55800
cacctggcaa ggacttcata ttatgctctt ctttagggat agacttccag aatgacttct  55860
agtcaacatt ccttcccgtg actcttcaac cttgatggcc ttcttgagct tatctcatct  55920
gccctgttta tccttgggtt tgctttctac aaaagcccat gcaccgcaga gggtgctaga  55980
cgcgctttca gaacccagaa ccagatcaca cctttgctct tcagtcctga gctttttgct  56040
cacccaagtt gctcttcagc tggatacttt actattagtt tgctgggctg cacttgatgc  56100
agttgacatg gtttctgtgg gctgaggaga atgagggttt cttggagccc caggcagctt  56160
tttctcatga ctcctggggc acttgaggag atggttggag aagccgtggt ctgctggggg  56220
cgtagcaagc tttcctaggc tgtaacagtg tccctctcta gtccttattg cataatcatt  56280
cctcaagatg agttcctaat cctgggaacc aagccaatag cagtcatcta ttattttttt  56340
ataggcatat cgatacagac aaagattaca tttttgttta acattcagtt ctgggaaaca  56400
aaagatatct aaaaatgata tttttcagta gcatgatatt taagcatatt tttgtggttg  56460
cagatcattt ctagtcattt tgatttttag aaggactgat ttaatgtttt gatctctttg  56520
tttttgcttg caggcctcta tatacagcat gtgcatggct agtacccata gaggccagca  56580
```

gaggggggtta gatcccctaa ctggagttaa cataagattg tgagctgccc catgagtgat 56640
gggactcaaa cccacatcct ctgcaagaac agtgcatgct cctaactgct gagccatctc 56700
tccttcccca taatacactt tagacaataa aaactctaaa gcgttagatt tgacaagtaa 56760
taggctcagt acatgtaatt ctttctttac tgagaagcat tctagcataa gtaaagtgtg 56820
cctagcgatt tgagctcttt gacttttcct ttgtgtgtgt atatatatat atatatatat 56880
atatatatat atatatatat atatatatgt gtgtgtgtgt gtgtgtgtgt gtgtgtatat 56940
atgttgtggg ggtggccttt aaactacaac cgtgcattca gtgcatccac tgtgaaggaa 57000
tgcatgaaag tagcctagct gcttctttgt ttggagtcct aggattacaa gatcccctca 57060
agatcattca tatgcaaccc cttctagagc atgctgggga aatgaccctt tggcagccac 57120
caacgggtgg gttagacatc ccctgtaggt gtcagtgttc tggaggcagt tagatgtgat 57180
tctctgaaag tgtagcatcc tgttatatta tggttggaag tttgttgtct tgactttctg 57240
tttatacttg gtatttgggg gtggctcttc gtttctgcta tttgctgtgg tgcctgtcct 57300
gctccacaga aagttttgac acattggtgt ccacagtatt tgttagggtg atgtctctat 57360
ctgctagtga gtccaggtag ccattcagtt tcctttagtg caaagatctt taaagatgag 57420
ctgggactca gtgttgttcc cagagaggcc tggcttcctg tcccacctgg cctcagtgag 57480
agagtcagag atagcctggg gctagcttgg ttttattttg ataccttagt tctttctgtt 57540
tctctgcttt aaagtcttca gttgaagaaa caactctggt ctctgatggg actccccagc 57600
gccttgcatt ttgtggttat ggttgatgat gatctctaca gtgtgtaaaa caaactgttt 57660
cctgacattt aatcaggcaa atagtaaatg tgttatgttc agtgggctta gtcattcaga 57720
atggatggta tttgctattg gcctttttcc cccagacaaa acaggtgctg ttatgcagaa 57780
cagagctgtg tgtttctggc atgcagtgtg ttgtgcttag ggacttgatg catttgatgc 57840
aagttttcag tgacatgtgt ggcagagatc gggttttcca tataacctgt ttgttttgtt 57900
tccagcagag cagtatctca ctaggcacat tacccttcaa cattttgtgt agcagcttac 57960
acaggaccac agccatcatg ttcctcacga cactgctctt ctcttctcct gccctcctgt 58020
gtttcttttc ttggttgttt ttgttttatt tttaagatgt atttgattct tttatgtaat 58080
gaattaatta atcggttaat ttaatgtatg cgagtatact gtacctgtct tcagacacac 58140
cagaagaggg catcagatcc cattacaggt ggttgtgagc caccatgtgg ttgctgggaa 58200
ttgaactcag gacttttgga agagcaagtc agtgctctta accactaagc catctctcca 58260
gccccaaagt taacccatta aacctcaccc acccaaggac caggtaactt cctagaattc 58320
tggggattgt acagatggaa aagtatggtg gccatatggg tgtgtccttt aaaattccta 58380
caacatatgt ctcagggcca ctcaactggg aattataagg agagatcctg accaaagtca 58440
ttcctggtca gtatttgaat acatttggct caaaagtgtg gaactggttt cctattttga 58500
atctcaaaat taacatttgg aggcctcagt gagataggcc tttccatccc aaattctgga 58560
gctaggattt cactctggct cccccacccc catgttcatg ctgggaaaaa tgaaatagca 58620
ttttttatgg taattcatag aagccaaggg agacatccca caacagtttc tgtggccttg 58680
gctgttctag aattagcttc gtagaccagg ttagcatcaa actcagattt tgcctgcctt 58740
tgcctccatc tcctgagtgc tcgggttaac atcatgtccc accactgcct ggctttattt 58800
taaattatat atatgtgtgg tatgtgcacg tgctcatgag tgcccacgta gaccataagt 58860
tacattaaca gatggttgta ggccatccaa cattggtgtt gggaattggg tttgggttat 58920
ctggaagagc agtatgtgct gctgttaaaa tgcttgaggc atctctagtc ccttgaagat 58980

```
ttgcttgttt gggggacaag atcttactta tcatgggcta actcggaagt ttttatgtag  59040
ctgagcatgt cttttaactt ccgtttctcc tgtcctcacc ggatacatac tggggatggc  59100
agacattgtg ctgttatgcc cagtgtactt cagtattgtg taacagaaaa gagagatcat  59160
ttgtatgcca ttacatttgc ctgtgtagtg tgtatacttg tgatgcgggg gcttgaaaat  59220
agagccgtgt gcatgacagc catgcattct gcccctcagc catccccgat tcctgtctgt  59280
tctgtttaat ctggtcctcc ttcagcttct gccctttgct gtttttaatt aaccaggcat  59340
ggtggcacag gcacactgag gcaggagaat tgccatatgt tacagcttag tctaggtctg  59400
ctgagtttga ggtcattcta ggctgtttca gaatgagctc caatctcaag aacaaactca  59460
gctggatggt agtagcacat accataaata ccaacactta gtaggcaaga ggcagtcgga  59520
tctctgggtt caaggccagc ctggtcctca gatcaagtta ctagctacac agagaaaccc  59580
tatgtctaga gagaggaaaa acacccaaaa cacactcctg attctatgtg agcactcagt  59640
taccgtgtgt gaattccctt tctttatgta tgtagtcggg gaaatgaagc aggctgaata  59700
aaaatgccct cttagcagcc tacagtgtag acagcaagag gagcctgatc tgggaattct  59760
tttggcccac tcactcctcc atagctatct cctgaatagg ctgctatctt gtcttgctca  59820
ggatcagaac acaaaacagt aggtaaaagt ttgtgggttg gtttttgtag gttttttttt  59880
ttgttttgtt ttgttttgtt tttttttttt ttttggtcgc ttctcccctc cctgccccca  59940
accctcacag tggtatcttt gtgtggcgtg aaatactaaa aaatgcaacc catgatattc  60000
cagctggtcc cagccggcct tgttctcatc tttggcaaac tctctgacgt ggagctctga  60060
aatcttgcca caggactcgc taagttccca ctgggtcact accacgccag ccccgctctt  60120
ccaaattccc atggcctttt ggggtgcact tcttgcaaac ccatgctttg cagccctacc  60180
tttctttctg gaacccagtt gagttgccat gtgaaggaaa agaccacaca aacttagttc  60240
aggatcaaca gttaattcag ttgctgggca caacaactag aatcctaatc ttgtaagcca  60300
tattaaatat aaatcaccat ctaaatgggg gccacttgta gctacatctt gtcctcccac  60360
tgtccctgtc caaaagccct cttgcggaag ctgaattaac atcaaaatac aaacagcatc  60420
agggctatcc acaacacttt tgagaggagc ttttggttca tcccacacct gctgacattt  60480
ttatacacct cccccataaa caagaaaagg tccatttagg ccagctgtgg tagacatcta  60540
tattccctaa gtctgaagat ggataatcat agagttatag gctgttgtac cagactattt  60600
atttgacaga gttctgtctc caaaaaagga ttataatttg tgtggttgtg agacagtctt  60660
ctatgctttt aactttcatg ataatgtctt cctttcctat gttccttttt ctgtctgtgt  60720
ctgtctgccc tccttctccc tctctctctc ccttcctctt tctttttaag gtaggatctt  60780
attgtatgta ttgtacaata gtgaacctcc tacccaagcc tcccagtttg ggggctcagc  60840
tcccagcttt gagttctaac ttcctgaatt agaatgttag tttttttata ctgagtttgt  60900
gtttaaattc ctgcttttgc aacactggtg attaacatgt taacaggatt ttgtttttga  60960
acattgttgc agcttttgtg tagagatgag tctgaatgac tctaagtgcc ctgtaatcta  61020
cttctgtggt tttggttcct tgtagttgaa gagatcccag gatcctaaca aatacttgtt  61080
tgccattatt atcggaatca ctcctctttc tgaaggtata cacaagtaaa ttcaattgat  61140
tgttcaatca gactcactct cttttttttt ttttttaaga ataaatttat ttcatgaata  61200
cgagtacact atagctgtct tcagacacac cagaagaggc catcagatcc caaccccagt  61260
aaacctttta aaattgattt accggctgga gaggtggctc agtagttaag agcactgact  61320
```

-continued

```
gctcttccag aggtcctgag ttcaattccc agcaaccacg tggtggctcc caaccatctg  61380
taatgggatc tgacaccctc ttctggggtg tctgaagaca gctacagtgt acttatatac  61440
atgaaataag ttttaaaaaa gttttgctca ggtgtatctt gatctgagtg caggtgtctg  61500
caggaatcag aagaggaggt cagatctcct ggacttgacg agtctcccag tataggtgct  61560
gagagccaaa gctggatcct gcaagagcag ggccgtctct ccagctccac aacttaattt  61620
ttaccaatag ttgatagagt tgtcagatga tgtaggatag ggcttgagtc aagctagcag  61680
gaaataatga ggctgactag ttagggctgt ttgtagcttc cagttgctgg ggggttggga  61740
gatgagcaac atcttatgct ctgcaaaaag ctttatcctg agcgcagttc cattctactg  61800
ttgctcagag ggctccctgt gtgcactctt tgtccttatc attgatagta gcaggagaca  61860
tctgctggtg aggcctcgta tgtatggtgc acattcatgt ctatttgccc ctaatttggg  61920
aagacaggtg gttagggcta cctagccgtg cagatgtgtg accatgagca ttcctgatgc  61980
tgttcaactc tttaactccc agctgtagag cagtaaggtc agctgagcat gtaagtgcca  62040
aacattttca taagctagac tcctcaaggg atattacaag gagtgggatt gggtgcatgt  62100
cagtgagcct gggctgctag aagtacccat gaggctgccg gagacagcag cactgcagaa  62160
tctgaacagc ttcttgtttg gttttctgag acagggtttc tgtatgtagc tctggctgtc  62220
ctagaacttg ctctattgac caggttagcc ttgaactcag agatctgcct gcctctgcct  62280
cctgagtgct gggactaaaa ttgtgagaca ccactgtcct gcttgaatct gaacttctta  62340
aggtgatatt gaggaactgt tttggaaagg gacagatcac ttaggaatgg tcttacttat  62400
taatatctgt attgtcagga ggtacatttg gatactgcac agagacctaa gcttagaaag  62460
ttaaaaccat tctgcctagt cacacatggt gggcacttgc tagctatccc agaactgaga  62520
aggtacatgc aggaaggagt gctacaagtt caaggctagt ctgggctaca tatttcaggc  62580
tatctagggc tatatatagt aagactgcct caacacaaaa acaagacaac taatgtattt  62640
ggctatagat acttagtgtc gcctgcctgt tgttcttcac agatgctttt actgactctg  62700
ctctcagcgc aaaggtgaat ggtgagcaca aggagaagga cctggagccc tgggatgcag  62760
gggagctcac ggccagcgag gagctggagc tggagaatga tgtggtgagt gccctctgca  62820
ccccagcact cagtgtgaac gtggggagaa ctccacacgt gcagagcagc actttctctg  62880
ggcagttgct aaagagggag agaaggaaag aatttctccc tgactggagt cggagcactc  62940
ttaaattact tctttgtgat gatcagttac ttcagggaac tgatagttac aagatggcag  63000
cctgtttcgt tttgaatacc aaccgaaagc aggtagtgtt taattgtatg ttgacttcct  63060
tagaaatgag gtcaaggtgg ataaagagtt atcattaaga tagtttcagg ttgggtgtga  63120
caactgtgat gtcagcactc agtcgtagaa gaataagggt ttaagagttc aagatcagcc  63180
tccactaaag agaaagtttg aggctagcct gagctttata aagaccctga ctcaaaacaa  63240
aacaccaaaa caccaacaac aacaacaaaa aacccaagtc agctaggtgt tacctgcctt  63300
aataccagga ggcagagaca gacaggtcta catagcaagt ttaaggctag ctacggctac  63360
acagccagat agtggatgaa aaatagcaat cataaaagat aaatacttag gttacattaa  63420
aattaaagcc tggcctaaat ttcttgaact taaaattagt atcattctct ataggaactt  63480
gcttctaaaa tgaccatttg tcatacatta ttttttgttt tctcttggca ccccatctac  63540
aagtcaaata ttagtaaact ttgatggagc atagagctta ttatattttc tttaattaaa  63600
aattttattt tatgcatatg ggcatattgt atgtatgcct gtgacctatt cctaatgcct  63660
tgagaggcca gaggagtgcg tcagacccct agagctggag ttacagacaa ctgtgagttt  63720
```

ccatgtgggc taggacttgt actgggtcct ttggaaaagc agccagtgct tataaccgtt 63780
gagccctctc ctcagtcccc ttgaacatag agatttaatg ttatggagcg tcatgaataa 63840
gactgagtga gcaaagaacc ttctgttgtg cacagacaac caagtttact atttaagaca 63900
tagtaaggga ggaaatagta tctcttctct aagagctcag ccccctcaaa gaatagaact 63960
gccctgggaa gttgtcagtg ttaatcttca aagtttattt atttattttt ttgttttgtt 64020
ttttttgttt gtttgtttgt tttgagacac agggtttctc tgtgtagtcc aggctgtcct 64080
ggaactcact ttgtagacca ggctggcctc gaactcagaa attcgcctgc ctcagcctcc 64140
caagtgctag gattaaaggt gtgcgccacc atgcccggct taatcttcaa agtttaaaga 64200
atctcctaaa cttaatataa tggttttcat gtgtgcatca ctgcaccatt gtgatgggaa 64260
acaggtacag tttttacttt attagtggag agataagttc tttaatggtt tgagggggag 64320
actcaggcag tttatcagta tttaaaatgt aagtgtggtt tgttcccaat tagtcttact 64380
acaaagaatt taccttagct aggcagttgg gttctgagtt caaggacaac ctgatctaca 64440
tagcaagttc taggccttcc tagggtatcc tgtgaaaccc tgttgtttgt tttttgtttt 64500
tgtttttaag acttatttat atcatttatt ttatgtatgt gagtacactg taactgtctt 64560
cagacatacc agaagagggc atcagatggt tgtgagccac catgtggttg ctgggaattg 64620
aattcagggc ctctggaaga gcagtcaatg ctcttaacca ctgagccatc tctccaacac 64680
cccgtttttg gtttttcgag acctgtagta gccctggctg tcctggaact cactctgtag 64740
accaggctgg cctcaaactc agaaatccgc ctgcctctgc ctcccaagtg ctgggattaa 64800
aggtattggt taccacctcc tggcttgaga cccctttta aggggaaata tataaattta 64860
aaatagaaaa gaatttatct tagtcctaat atacctataa tacgtgtaaa ataattatat 64920
gtcatgatat tttttcaaca ttatttctat tagtagtttc ccatcagaaa agcacaatgc 64980
tgatacttaa tagacatttg tgtacctacc aataaccagt attcaaatag gaaagatacc 65040
tcatatattt attaacagga aaagcaagct gcagagtagc aataaaagta catagtgtgt 65100
gtgagagaga gagagagtgt gtgaatattc agtttatgtg caccataaaa tgttgcccag 65160
agctggcctc ggttacgggg agttgagatc tgccttgcag gtgctgctgc tgtacatcct 65220
ttttctaagt tctaagagca tactttttgt tgttgtttta ttggcggtgg tggtttttttt 65280 gtttgtgtgc ttgttttgaa acagggtttt tctctgtaga cctggctgtc ctggaacttg 65340
ctctgtatac ctggctattt gaactcagat cttcctgcct ctacctcgtg agtactgggg 65400
ttaaaggccc gtgccaccat gctgagctct gtagtaacag ctcttaacct tggaaccatt 65460
ggcctaagcc cgtgaaactc ctcatagtgg ttattcctat gccctggaac ttgaaatcat 65520
tagttttggt ggatattttt ctgttcagtg tgatggatca ctcaaattac tgaagttaga 65580
gtcttccaat taaaaaaatt atgtatctat ctatgtatcc attgcgaggg agagtgtgta 65640
tgtatcatgg cttgcatgta gattctaagg acagcttgta ggagttgctg ctcttcctcc 65700
accatatctt ccagaaaagt ccatgtcctc tagaaaagta atatgttttc ttgattactg 65760
agccctcaac ctgtcagact ttaaaaggag agtttgatgt gagatttgct ggggaccagg 65820
agttgcctca caaactacat gaacactgat atcagtcagt caggaatagt ttattgactg 65880
ttccccccag gactgatgca tgagggctgc agatgtgaca gtgagtcaga ttctgtaggg 65940
ctttcaagcc tgaaatctac aaacatgtgt gccatgatct tctgccagtc aggatgtggg 66000
gatagggata ggcacttcct taggagcttg tctttggtgt acatttactc tgcttccatt 66060

```
ggttggtgta ttcagcagtg gcaaggtctt gccttgccta acactcatgt cttaacttgc  66120
caatcaggat gtcagttacc catgtccata cctttttcta gcaagtagga tgtcaattcc  66180
caaggagatc ttggggactt aaactttact taacccctac tcaaaatgga agccttattt  66240
ttaaaaagct tcttatattg gtgcaggtgt ttctcttatg ttggcatcca tccaaggggc  66300
tgcttataaa agcaaaatcc atgaaagttt atacataggt gtaggaattg ctgctgggtt  66360
gttggtttgg gtccaagcta ttgtggctaa ctatacaaag cagttctgct gacttctgtt  66420
gcgattggtt tccaagaaca ccaaagcaca gaagttaaca gaatctgcaa tcgactagag  66480
catgagaaag tttccttatg gcattagtaa cttcacaaaa tggcagacta gaaagtaaca  66540
gttacctagg ccttaacaaa attaattggc accgaagatt ctcactttat tttcctcatt  66600
tcttcaggtt gacgagtcca acctatgttt tgagagtggc agtttagtcc ttcacctgtg  66660
gaggggaaca gcactgagtt tggaagttag gacaagggga cccatagctg ttgctgagat  66720
cttcaaacag ctttaaagct tagcatgtgt gacacccatt tgcctcccca tggctttgtg  66780
ctgcccttcc tcacctgcct agggaagggg aaggggttct ggcatggaac tcttggaggg  66840
aaagttttga ctctgcttgt agggaaggct gttaggacag gtgaaggaga gacctctgac  66900
ccagaggcac cggatctttg aaaactcatg taccggatct ttgaaaactc atgtaatctc  66960
cacggactta aaagataata tgtgtgagag aaaagctctt cctaaagagt tgtttttttgt  67020
ttttgtttga tatagggctt ttttttctt tttctcttcc tcttcctcct tctttattct  67080
tccttctttc ttctttcctc cgcctcctct tcctcctcct cctccttctc ttcttcttct  67140
tcctcctcct catcactgta gcccaggctg acccttgaac tcaaacattc tcctgtctca  67200
gtcccctaag tgctggtata acaggtatga gctctatctg gcttgtcttt aatgtttttct  67260
aaagtaaagt ttggcccttt tgtagggaag gagtcagagt tagagtcaac tagtatggtt  67320
tgctatatgt tcctataaac actaattgta gctaaattga aagttgacct tcattttcct  67380
tctagtctaa tggatgggac cccaatgaca tgtttcgata taatgaagag aattatggtg  67440
tggtgtccac atatgatagc agtttatctt catatacgta agttcacaga gttccctttt  67500
atacatttta gtgcatttgt ctttgatttt catcagctca aaattacttt gctaactaat  67560
tatttctttt aattttaaat taaacaacaa tatcacattg tttctataaa ctattcagac  67620
tgacagactc acattaaaac agggaataag tgttgtttcc ttacctatcc ttagttttct  67680
gatcaaaata catttttttc tgtttttaat ttgtaaataa aaaatgttaa attgacaggg  67740
ataagggtga accagttctt gaaatagtaa gtgttcttct ttataacata accacaaaaa  67800
atagtatttt gatttatgat agaaagcccc caactttgtc agtgtctttg accccatact  67860
atagagtctg ttaatagctg aggattaaaa tgatcatgca tgtcttcttg tctttgtgtt  67920
tagggttcct ttagaaaggg acaactcaga agaatttctt aaacgggagg caagggcaaa  67980
ccagttagca gaagaaattg aatccagtgc tcagtacaaa gctcgtgtcg cccttgagaa  68040
tgatgaccgg agtgaggaag aaaaatacac agcagtccag agaaactgca gtgaccggga  68100
ggggcatggc cccaacacta ggtattcaac atgattcaaa gtctgtgtga gaggatgtag  68160
tctgactgtt tccttttttt ttttttttgg tgaagctaag gagaaagtgc tccttgattt  68220
ggcttaatat tctgttggag agctgggcag tagtggtgca cgcctttaat cctaacactt  68280
gggaggctga gttcaatgcc agcctcaccc cccccccccc acacacacaa atttctgtta  68340
aaagattacg gtcattttaa tagtatcatt tgggattagc tctctggagt caagtgaccc  68400
atgtgaggag ccagcccaga ctctgaggag ctccttaaaa taaggttgga ggaggcagag  68460
```

gcaggcggat ttctgagttc aaggccagcc tggtctacag agtgagttca aggacagcca 68520
gggctataca gagaaaccct gtctcgaaaa aaacaaaaca aaaaaaaaaa aagaaaaaga 68580
aaaaaacaaa tccaaggttg gacagtgtgg cttgcatgat gaaggtcttt tcagagcagt 68640
agaatatcag aatggggaag aactagcatt gcctgtgtag ttcaagagag cctcaccagg 68700
aggtgacaag tttggtatga taatggatcc tgtctggccc tgggagtgtg gggggttatt 68760
tcacctctgt agaacatggt cctgtaagag aatctggcct cttccggtaa agactaagat 68820
cccaggatat tcttcatgct atgctggcag gtggcagaag catttgtgtg ccattcttga 68880
agagtagtct gtagggaaca gtgaggaaca aagacactga gtcagagagc ctgtcagtgt 68940
gacagcatta tagcagaaag tggcaagctg ccagacagac tcatggcgcg aaagctggaa 69000
aaactagaga gaggcgaacc ttacttgaaa attcagctgt tcatgatgct tgctctgaga 69060
acacatgagc taaaggcagt gtggggtgac ttagaaagga gaaacgatgg cgcagtggtt 69120
gcttgtattt gcagggctat gggtctgtca tttactcaaa aaagtagaat gcctgctgca 69180
ttgtgggtaa agctgattct accggcaagg ttccatagct gagtcttccg atttccctaa 69240
tcatcactgt gtcaggatga aagtgagcac accttttaa agtgctggtg gccgagacct 69300
gcagggctgt gtggccgtgt ggtgagactg aggcttgtgt gagagacagt cttctattta 69360
gtgtaccttt cagtgtgttt tgttagccca gtacttttta ggataaatga tttagaggat 69420
ctctcatttc cagggacaat aaatatattc ctcctggaca aagaaacaga gaagtcctat 69480
cctggggaag tgggagacag agctcaccac ggatgggcca gcctgggcca ggctccatgc 69540
cgtcaagagc tgcttctcac acttcagatt tcaacccgaa cgctggctca gaccaaagag 69600
tagttaatgg aggcaagtat tttgacctta tttgttaatg ttttgatgaa atacagaact 69660
atctaaacat ttaagagttg gcatacctga taggaatgtg catgccattt gtggattttt 69720
tggagtagtt tttattatct ataatgtagt ttgttttgtg gctactagac agtataacac 69780
tgtatctgtc attggcgcgt atagggtgac agcatgtcct gagctgtttc atcctctcat 69840
actcatttgg cctaagacac tccacagaca gacagaatgg aaacttgaaa gacactgggt 69900
gatgaggcag tgggcatagt tcatgagaaa gaccctgagt tagtgcagat tccttcatta 69960
actgtgatga ttccattctg cgtacttcag ggaagaactt agggtgattt gtaatgtcag 70020
aaatgagcaa gagtcaggtg acgaaagtca tcagagaact gcttacaaac acagcacaga 70080
caacctttga tttctgagag taggtattag agtgtagcag cttggagctt taagtaggaa 70140
ggaaggcatt ttgtgtagtg tccccagtca gttgaataca gattataggt gagtatagaa 70200
atctggaaga tgggacagca gaagcgaatc atttagaaat atggtagctg acagggaaaa 70260
agagtggaca gcagattcag ggttgaagtt tagagcaccg caagctgggt gaggcaagtg 70320
cctcatgctg agcagtcagg ctccataggc agtctgagcc agcctgggtt gtgtgagacc 70380
tcgtgtaaag aaagggagtg aagtatgtca gccatgtaag agcagaattc ctctccaagg 70440
aaacactctt gagtagttct cctgcttagt aacgatggtg acatttcttt gctcactgag 70500
tgaagatttt cagttgttta tgaatagaat tttcaagtta aaaacgtgaa gggggctgag 70560
aaatgtatga tactccagtg agtggagccc cctagactac tggagaggaa ccctggactg 70620
ttgactaatt accaggacaa ttgctgaccg gggcgggggg gggggggggg gttgtccgtg 70680
ccctgatgtc aggtttgggc cccgaggctt acaggcccct gtggtgtaca ggcagtagat 70740
agacggggcc attcattcct gtgcatcagg atgagattct tttaagcatt cgagaaagca 70800
atagaagtaa gctctcattt ctacctgaac aggatgtggc tagtgacctt tgaaactgat 70860
atttcagttc agatataggc ctgaggaagc tcaggtgaga gtaggagaag agcctggaca 70920
gtggcgttag aggctgctgt ttgtgtttat tgtttgggcc tgccttcccg agcaggagtc 70980
agtgtgttta ttgagggggt tatctgtgtg tgggacattt tcttcacaag tgatggctga 71040
caacagctga agaagtaggc atactaggca gagtcttaac tgtcttcttc agtagtatgt 71100
gtagatccta attaaccctt tgggaacgtg gattcatttc aacagactta attttaagga 71160
ggttaaagta aaatgtgaat ttgtgtcagt taagttgtac taaaacttat cacaaatcaa 71220
atgactgtcc tcaaagggtt aaatgtacaa gaaatcattt ttgtcatttt actttttttt 71280
ctgtttactt tttccctcat ttttttcttt agtttttata ctttccttca tatcatttgt 71340
tctgtcaggt gttccctggc catcgccttg cccatctcct tcctctcgcc caccttctcg 71400
ctaccagtca ggtcccaact ctcttccacc tcgggcagcc accccctacac ggccgccctc 71460
caggcccccc tcgaggccct ccagaccccc gtctcacccc tctgctcatg gttctccagc 71520
tcctgtctct actatgccta aacgcatgtc ttcagaaggt acaataccac gatttgttca 71580
tgtttttgtt tgtctttgtt tagctccttt gtgaggttat gattacaaaa tagtttcctc 71640
ttcattattt aataacctat aatttttgtg ttttaacttt agtttattaa agctatttct 71700
aataaccttt tgttcactag attaaaattt gataagtgct atgtataaag ccctgcactg 71760
ccctgcatat agagatgggc tccgacctgt ctggtaatag tactcctgtg cagcccagga 71820
aggtctcggc ctggacagta acagtgatga actgggcatt tctgctcctg gaggtgggtg 71880
gggttatgga ggctgccaca ttcagctcct tggtaatggt gccagcgaac cttcctgttg 71940
gccaaaggca ggagtactat tttggggttc ttagtgatcc atgacatccc ttgtagtggc 72000
cttgtacgtc tgccctcagg taacagtagt atttagagtg cctgaggaat tactaattta 72060
attgaataat tattttaaat tagttttata atatcactgt agtggaaggc tgctttaatc 72120
tgtggggaga cctttattta aagtttatca attacaaaac aggtatagat ttgagccttt 72180
tctgtctttt tggctcatgc caaattgtgt gtatttgttg ctgaattcac cattgttgca 72240
tgtcatatac tttgattagt ggcacatgcc tataatccca gtgcccaggc cacaggcaag 72300
aggattgctg aaagttgagg tcagtttgtc tcatatataa tgagttctaa ggctgccagg 72360
actatatggt gagaccctat cccagccacc ctgacaccct gcccgaaaaa ggtagcattc 72420
tgatttaatg caggttgtaa gttctaagta acaatgtcct ttgttcagag catttgtgtt 72480
tatattctaa tcaccttgtc ttggtaaaat catagtgaat ataactgatc aagaccatta 72540
aagttttcta aagaaggtgt ttgggaataa actatattgg ctactgttaa atttttgccc 72600
acacagaagg gaattcaagg cagaagaata caatgttgca aaggcagatg tcacagactt 72660
tcaatgcgtg cctctctggt gactcctagc agcaacaggg agctgttgca gacgtttggg 72720
tggaggtgct tattcctcga atgtgtcaga aagcattgca ttgtagtcag atgaaagggc 72780
tgcttttgga ctgcccagaa agcgtgccat gggaaaagtg caaaaagaga agtgactcca 72840
caaagatgac ttcacacaca cacacaccag cacatacaaa cccagtccat accacacata 72900
tcctatagta atgaatacat tttaaacatt aaataagggg aaattctaac atgagttagc 72960
atttcctcag agcacatgtc tgactgtgtt cccactgagg acacagcaga gagcatgtgc 73020
tagggtcctc atcatggcct ctgagaggag gggtagttct ggacttgtgt gctacaggct 73080
gtattcccag aagtccccat gggtggcaga gacagtgatg gtgactgtcg tcagctctca 73140
cagtgcagct ttctgcagac tttccttgtt ctgctcttac aagccaacca cgcacatgtg 73200

```
aggacggctt gggcaaaaga tggagaggag atctgaggtt gctgcttaaa ttcctttttc  73260
ccctggggcc ctgaaggatg tagctcagag atagaacact agcctaacaa gtatgggctc  73320
ccaagtttgg ttcctatcaa aaaaaaaaaa aggtttttgt ctcattttgg aaatagtaaa  73380
atctgttaga aagataaact gataatatcc catcatgcat ctgtgcttcc tacgaaaacg  73440
ttattataac ttatttttaa atgcatgtag ttaaacactg ttgggccatg ttgttatatt  73500
tctcaccatc aagtttattt cctccttgct ttaaaagtaa aaggaaataa ggctggaaag  73560
atgggtcagc tgtcagacag ctttctgctt tccagaggaa ctcaggtgca caccctcaca  73620
cagacacata cacacaatat aattaaaagt aaaacaaatt gtaaaagggg aaaataaaac  73680
atactgacat aattgacata ccacaaaaga attcttagtg tggccagaaa tcaataacag  73740
tgtgattcat attctaacca atgaaaacct gctaaggaaa taagagttat atctgtatct  73800
agtaggaaaa gcagtaaggt gggcaccgca ggactgatgt gatatcctgt ggcatccttc  73860
tgtcttcctc aggaccccca aggatgtctc caaaggcaca gcgccaccct cggaatcaca  73920
gagtctctgc tgggagaggc tccatgtcta gtggcctaga atttgtatcc cacaatcccc  73980
caagtgaagc agctgctcct ccagtggcaa ggaccagtcc tgcagggggga acgtggtcct  74040
cagtggtcag tgggggtagg tatgacactg cagagctgaa gatctgagat taaatacaga  74100
ttaaatgtgg tggcataagc agctgttgcc agttaccatg gttatcaaga cacgagttga  74160
aggaactgtc ccatccctct ggaactctga ccctgtatac attttgtaaa cctgcttagg  74220
tttcttactg ctgcgggttt ccatggcatc cgtgtgtgga gtaaacagat agtcgcttgg  74280
tgctcctcaa ggagtagtct gcgccaggag aggctcagct tttgttatga gtctctgacc  74340
gtcagcagct gcagccaagg tcctgcttgg agcagatttg gaattaggcc agactgcttg  74400
ggctgctgag ttggtcttgt tggtctgtag tgcttcctcc cgggagtcca gagctagagc  74460
ttgtgcctgt tcttttggcc ttaccaggaa aaggtcttta agcttaaaaa actagacaga  74520
cagtgcgctc acccctgtaa ggtgtgcagt tgtagtgatt gtcctgtaaa tttctttgtg  74580
ctattcttct tagcctttta aactgaagat taacaagaaa agaagcttga ggcgttttaa  74640
ccctattata aataagcaac cttttataaa tacaagaata gagacagttg agggatatag  74700
tgagaatcgt gttacggggt tggtctttcc atggaaagtt agagttgtga acagtttcct  74760
tctataatgt ttgattgaac cattttcatt gaccccttta gtctgaagcc tgcaaatagg  74820
tttttattgg attaggaagc attaagcagt tgtgtggaag gcgttcattc tgtgttacgt  74880
accccttgag gctaggtgcg tcctaatttc cttcagcact ggcggtggat ctttatattg  74940
caagtaaaag cacataggct tggcagcaag ctaccatcaa ttttatttcg tgtattgatg  75000
gaaggagagg agagaggcat ggtagagatc tctcaccttg aataaatgtt acactttgaa  75060
tgtcgtcttt ttttttaact taagtatgct ttggcttgcc attgaacttg actcaaatac  75120
ttaaaagttc actcatttaa ttaggaggga aaccacggtg gtacttagag attgttgact  75180
tctgccataa gatacttctg agaatttaat gagtatcttt ttgcttctag ttccaaggtt  75240
atctcccaaa actcacagac ccaggtctcc caggcagagc agcattggaa actctcccag  75300
cgggcctgtg cttgcttctc cccaagctgg catcatccct gcagaagccg tttccatgcc  75360
tgttcccgcc gcatctccga ctcctgccag ccctgcatcc aacagagcac tgaccccatc  75420
tattgagggt atgcaaccaa cacctttcct gttgtaatcc atgcatggcc aagagttgtg  75480
ttctcaatac acagtgatgc ttttgtggat gcaagattct gtctctggta gaactattcc  75540
```

```
atgtatatta actaatgtct ggcatcagag gctctggcct gtcctagtat gacgtgcctg  75600
ttgtatgagc atggttattg aattttgatg tgatgactaa cagggaataa actcagttta  75660
atgaaaccca ttttcccta agccagaagg ttagaagtgt ttggtattta ctcacactat  75720
tgtcctaatt tctgtctaat actagttttt tgctttttta aacttgtttt ctagcaaaag  75780
attccaggct tcaagatcag aggcagaact ctcctgcagg gagtaaagaa aatgttaaag  75840
caagtgaaac atcacctagc ttttcaaaag ctgacaacaa aggttagagt ttgttaaagt  75900
ttttttttt ttaaaagatt tatttgttta ttatatgtaa gtacactgta gctgtcttca  75960
gacactccag aagagggagt cagatctcgt tacagatggt tgtgagccac catgtggttg  76020
ctgggatttg gactctggac cttcggatga gcagtcggtg ctcttaccca ctgagccatc  76080
tctccagccc ttgttaaagt ttttagacac aattatagaa atagcaaagt gtttagccag  76140
acagatactt gcattgctag tctttacgtg atagatctgt cttcatttct tatttatctc  76200
ttcccctcag ccccagtgct gagattaaag atgttataga ggtgcaccaa cactcctggc  76260
ctctgttctc atttctaaca ttccatattt aacaatttta agtttaaagg taaaagtaaa  76320
ttggaatcta acaggttttg gttttacagg tatgtcacca gttgtttctg aacacagaaa  76380
acagattgat gacttaaaga agtttaagaa tgattttagg gtaagttctt tatcgactgg  76440
ttagaattaa aaaagaaata gcaaacataa tgatttttat ggccagttca caaaagtaca  76500
ctattaaaac acacgcacac acatacgctc ttgtcttaag tcatttgtac agcaagctaa  76560
acttcttttc agttgttttt catgcatatg agtgtttgca ttatgtattt gggctatggg  76620
tctgcctggt gtcctttgaa accagcagag ggcataggat ttcctggatc tgaagttgca  76680
gatcgtcatg agctaccatg taggttctgg gaactgagct caggtcctct ggaaaagcag  76740
ccagtgctct taaccactaa tgtctttctc cagcccacag ggtttgagag agtgtgtgtg  76800
tatgtgtgtg tgtgtgtctc tagtcttgtt tgtctgtgag taggtatgta catagtactt  76860
caagtgccct ctgagggcag aagaaattgt tatcatttgg aaatggggtt aaggcaatgg  76920
tgaaccgcct gatgtgggtg ttagaaattg aatttagatt ctctggaaga gcaataaata  76980
ctgttaacca ctgagccatc tcctcagccc cttgacaatt actcttaaag atgtctttgt  77040
ctgttctaag tacaataact taagatcaca aggtttttgt ttgtttttg gtgtgtgtat  77100
gtgtgtgtgt gtgtgtaaca agactgcagg taacaaagga tatgatctta ttttggaaac  77160
tgacacacta gagctcactg ctcagtagtt ctaaagttga agactgacca cgtcagtgct  77220
tgtagtgtgt gcagtagaag atgaaatgtg tcctgagtta gctcaccttc caatctgtga  77280
gtaaattcat tcacttgttc attcatcctt tttggtgttg aggattgaag ccagggctaa  77340
attcccttgg tgggcgtatt cctgtaacct cacttcatat cctaagacaa gcttccaagc  77400
cctccttggt tactctgtca ttcttccaca caaaatttac aaggagcttt agatactacg  77460
ttagcttata taacttttaa aaatgacttc tttgttttta ttttatgtgc attgatgttt  77520
tccctgtaag tatgtaagta tgtaagtatg tatgtatgta tgtatgtatg tatgtgtgag  77580
gatgccaaat cctcagaatt gttgttataa gcatacgtga gcagccatgt ggatgctaga  77640
aattgattct ggatcctatg gaagagtcac cagtgctctt taccactgaa ccatctctcc  77700
ttccccccaa attacgttta gaccaataac tttttatcct ttgaattcta tactgttggg  77760
gttttttgtt gttgttttaa ctatgagttt ccttttgttt tgttttgttt tgttttgttt  77820
ttttcatttt tttaagatat tttatttaca tttcaaatat tattctcatt ttccccttc  77880
ctagtttccc ctccgaaaat cccctatccc tttccccctc tccctgctgc tacccgaccc  77940
```

```
acccactggc attcccctat acctgggcat agaaccttta caagaccaag ggcctctcct  78000
tccatggatg accgactagg ccatcctctg cctgttggtt ttctttttttt tgtttgtttt  78060
ttgttttttt gagacagggt ttctctgtat agccctggct gtcctggaac tcactctgta  78120
gaccaggctg gccttgaact cagaaatccg cctgcctctg cctcccgaat actgggatta  78180
aaggcgtgcg ccaccatgcc cggcaggttt ttttttttta agatttattt attttaatgt  78240
atgtgagtac actgtatctg tcttcagaca gactgaaaga gggcatcaga tcccattaca  78300
gatggttgtg agccaccatg tggttgctgg gaattgaact caggacctct ggaagtgctc  78360
ttaatcactg agtcatctct ctagctccct atactgttgg tttttatttt tattattttt  78420
tggttttggt tttgttttgt tttttgtttt ccgagacagg gtttctctgt atagccttgg  78480
ctgtcctgga actcactttg tagaccaggc tggcctcgaa ctcagaaatc cgcctgcctc  78540
tgcctcctga gtgctgggat taaaggcatg cgccaccatg cctggctatt ttaaattata  78600
tgtatctgtg tgttagaata agcacatgaa tggaggcact cccagggact ggtggtgtga  78660
tatttttcta gagctcgtta gagctgccta gtctggtgct gggagccata atctactccg  78720
ttgggagaga agagttcatg atcttaacca ctgagtgagc cacccatcct ccccaccaag  78780
ttacattgaa atacctgttc agggagtctt gaaatttagc tattatttag catttatata  78840
cctatatata catgcttttg tatctctgta ttaaatctta aaactcacaa atgagagaaa  78900
acatgtaata attgtctttt ctgaatttgc ttaatctgat actctgatgt tatatttatt  78960
ttccaattgt tttttggatg actaaagctg tgaataccca tgtcacatcc ttctcagtca  79020
gtcctctgtt aatagacacc tggcttggtt ctgtaagtag ctattgtgaa tagccctgca  79080
agtgatgttg ataaggtaca ctatctgtga cacggctttg gagtcctttg agagttaatc  79140
gctgggtaaa atggtaggtc tatttttatt tttttgggtt tggggttttt ttcatgattg  79200
actttacaga ttttatttat atgttcatat gtgtgtgttt gcacatgtgc aggtgctctg  79260
gagctgaagt tgcagacagt tggtaagcct gagtccatgt gggtgctggg aattgaacct  79320
ggaagagtgg ccagtgctct taactactga gccatctttc ctgccaagcg ctttttagtc  79380
catagagact ggacagcttt acattcccac cagcattgtt ttctggtggg agcaaaaagc  79440
gttcttttta ctccacatcc tcactaccat ttgctgtttg tttctaatga ctgccattgt  79500
gactgagtta ggagagaaac tgagtgtgtg tgtatgtgta tatatcttgt ctaaaataag  79560
cgcatctctg tgtatgtgtg tgtgtttaag tattcatgaa tgaggatacc tggcggggtc  79620
acaggctttg gatctcccta gaattgtgtg attgtgtgct cagtggctgg tgttgtgtgt  79680
tgcatggtgc aggtgctgga aactgagctt gcatcgtctt ccagaggact tcatactcat  79740
aaccacttca aactccagtt tcctcaatgg agtttcaact caaatttctc tcgtgcctag  79800
tgatcttgaa catttgtcat ggattcattg actattgatg tgagtgtttt gagaacagtc  79860
ttgtgtgttt cattcgccta tgtaaatgat tttgttattt gagatacata caagtaagta  79920
cacacatgca cacacacata tgttgggagt actcagctgt cctttgttac acatcatgct  79980
ctgggttatt cttgcttcct tacaaggatg aataatgcca acagaaacac tgaggcttgg  80040
tatcatgtaa acatgtgtgg tcacttcttt aggattggaa agtctgtgtc atgtggtagt  80100
gtgttgagtc tttgcaggaa ctaccagtca ttgtaccatg gtagctgcat ggtctccatt  80160
gaacactccc tccaccatca gctagcaagt tctttttatt ttcattttgg gtttgttttt  80220
tttttttga aacagagact tgcattgtaa ctgcagctac ttcgtgtcac aggcacacac  80280
```

```
cacctggcca tgtgtgggga cagccattcc cctgaaggtg ctggggttca tggtcttagt  80340
tgtggtccat attggttttc atatgcagag ctctcgtggc cagtgatgtt tattgccgtc  80400
ctttgtgttc attgtttgct tgttttgttg ttgtttagat tgctgttttt tcatatcctc  80460
aactgtaaaa ctttagggtg ggcactggtg agctagctct gtgggttatg gcagcctaag  80520
ttgaactccc tagactcaca tggtgggtga aggaactgac ttccagaagt tgccttccag  80580
cttcccataa ccccttcct gtatgtgaga taattaatct ttgttctttt ttttcttttt  80640
tttaattttt ttttttaag gttcctctgt gtatctctgg ctgtcctgga acttatctgt  80700
agaccaggct ggccttaaac ttgcagatac tcctgcctct gcctcttgag tgctgggatt  80760
aaaggcatat gtgccatcac cacagctcag ctgctaagta atctctttta aactgggttt  80820
ttaattaatg aattgcagta ggctatgttc gtgttccttc tttttctttt cagacagtgt  80880
ctctgtgtag cccatgctga ccccagcctt taggtctctc tctctctctc actcggctgg  80940
ggttcttatg tactgtagat cccagtctgg tgccgtttgt ctaacacttc tgggatatta  81000
ggtttggcac ccagagtgac acagagctcc agccttggtc ctgtatccgt caaaggatct  81060
gggtgtgtga attgcttttc tcccatttca tgggctgtct tttcactttc tgtcccttga  81120
gacacagctt tatttaatga catcaaggtt ttttcctggt atcagttgcc ccttagcttg  81180
agagtttggt gtctggtatt gcaaatgact gtttaatctc ctgaagatgg cagcacttaa  81240
cctgctttct taggacttcc tgggagctct catctgtgtg gttcacctta ctgagcgagg  81300
ctcgcactca gttacactgg tgtctatcag gaatctcccc gtcatctgtc gaaaatggga  81360
ctgtattcac ctccactctg gctccaagtt gcttgcagat agggaagttt ggtattagct  81420
ctccatttct tcccatgtcc atgtgttgta gttgatacct ttttgaaaga ctattctttc  81480
tagacttaat atcgcatgcc tttaatcccg gcacttggga gacagaggca gaggcaagca  81540
gatctctgag ttcaagacca gcctggtcta tgtagtgagt tttaggacag ccagagctat  81600
gcagagaaac cctgtcttaa accaccctag cccccaggct gctctttatt tattgtttac  81660
ttaatattcc aaccactgat actagtttgc aactctcttt gtttggccct accttactaa  81720
tgaattcttt ctctgtcctg atacttatta ttttttccag ccttgatttg ggcttaggtt  81780
gtcgtcactc ttctgatatc ttcaggtaca gcattgttac ttattgagat cttatcaaat  81840
tctttttttt tataaattta actgaattta attattttaa tttttgttta attaattaac  81900
aattgggcat tacatttctt ctttaaatta aagttcaggt agcactggca tcaagagtcg  81960
gtctctagga gtggatcata cttattttgt tgagctcctg ggcagtgagt aaatgctagg  82020
aaacaaagca ggggttccag ggcagggttg acactgagtg cttcctgtgt ttcagacact  82080
tttctctgct tgtgtcctag cccctcctgt cacagtgatg ctctgaagca ggttctgtca  82140
ctgcctgcag tgtgtgcatc aggaaactga ggcagtgagg ttaaatcatc tgcccagggc  82200
cccatggata ggaaagggca agccttggct ctctggggta ctgcagtgtt cagccatcct  82260
cgtgacatgg aggtttggtt ttgaactgcc cttttcttga gagcagtctg cactctgcag  82320
tatagctgag tattggaaat ttgatacaga ggatttctct gtctgatctg ttaatgctta  82380
gtaactgaga ttatgcagat agagattttt ctttcacagt atattgccta gtgtcccaag  82440
cacagtaggg actggtagaa cctacttggg ttgcaggtgg cagcatataa ctgtgggccc  82500
tgcccttgct agtgtctgtg gtccacgctt gttactgggc atgacttcac attgccgagg  82560
tgtggtgact ggtcctgaca gttgcttttc tctgagttac aaaaaggcat gggtttgggt  82620
ggggtttagc tctgtgtgtt tactgtggac tagttgagtc cagtcccacc aaacacacat  82680
```

```
atcccttccc tacagaattt ttaaaaaata tttgtttatt tatcaaatgt aagtacactg  82740
tagctgtctt cagacactcc agaagacaac atcagatttc gttaaggatg gtcgtgatcc  82800
accatgtggt tgctgggatt tgaactcagg acctttagaa gagcagtcag cactcttaac  82860
cgctgagcca tctcatcagc cctccctac agaattttaa ttgcactgtt ttctccatgg  82920
gtttgccata aaagtaccta catcaaaatt taggccattg tgtggattaa acaaataaca  82980
caaacagttt ggatctatag gtaattttgc cattataaga atagaaatga gctgggcatg  83040
gtggtgcatg cctttgatcc cagacagagg caggtggatt tctgagttcg aggtcagcct  83100
gtctacaaac taagttccag gacagccagg gctatacaga aaccctgtc tcaaaaaaac  83160
aaggaaggaa ggaaggaagg aaggaaggaa ggaaggaagg aaggaaggaa ggaaggaagg  83220
aaggaaggaa agagagagag aaagaaagaa agaagtggaa aatgcttttt taaaatttta  83280
ttcctagcat gtttttgtat gatgtgggtg tgtgcccgtg agcttacatc ttcaggcttg  83340
agcaatctct tcagctcttt gcattttatg tagattcatt tttatttcat gtgtccggtg  83400
ttttgcctga atgtatgtgt attagtcagg gttctctaga gtcacagtac ttatggatag  83460
tctctatata gtaaaggaat ttattgatga cttacagtct gcagcccaat tcccaacaat  83520
ggttcagtag tagctgtgaa tggtagtcta aggatctagc agttgctcag tcccacatgg  83580
caagcaggtg aaggagcaag agcgagactc ccttcttcca atgtccttat atggtctcta  83640
gcagaaggtg tagcccagat aaaaggtgtg tcccaccaca cctttaatcc cagatgacct  83700
tgaactacct gtcttaatct tctggaatcc atagccacta tgcctcaaga tctccataac  83760
aactaagatc caggtcagaa acttctatct cccagcctcc agagaagggt cactggtgag  83820
ccttccaatt ctggattgta gttcattcca aatatagtca agttgacaac caggaatagc  83880
cactacagta tgtatgtaag tgcactacat ttatgcctgt acccagagcc caaagaggac  83940
accagatccc ttgaaactaa aattttagag attgtgacca tgcaagtgct gggaactgaa  84000
cctgggtcct ctgcaaaaac agaacgtgca aatgtctact gagccatcac tgcagcccta  84060
atttttaagt ttaggaagtt gtcgtatggt cattgtatat tgtcctaggt ttcataagca  84120
cattcatata aatgtcgatg atacactctg agcacattcc atctcctgtt ctctcccttt  84180
cccctttctc atgctgttgg gattttaaaa ttagtttttg tttagattag atgttgatct  84240
cttcaggagc tattccttca tggaggctgc tttttctttc tgcgccacat ggtagcttcc  84300
caccttcctg tgtctaggca gtcggaactg ttgcatcttg ttcactgtca gccactgcct  84360
ctgcctctcc aattctgaaa ttgcaggcat gagccaccat cagtctaata gttaattctt  84420
ttttgttatg ccttgggcga caggggcggg aggttgagac atggtctctc tacatagccc  84480
tgcttgctct ctgggaactc actatgtaaa aactaaggtg gtctctaact ctcagacgtg  84540
cctctgtttc atgagtgctg aacataaagg tttgtgccac catgttcagc ctggctaata  84600
actagtcttg gatactggtt cctaaaattg tgttgtgtat cattctgtta tttgtgcctg  84660
aaaaatgcat attctgagcc aggcatggtg gcctttagtt ccttccagca ttcaggaggc  84720
ggagaaaggc agatcacagt gagttcagga ccagcctggt ctacatagag agttccagta  84780
cagctacact caggttacac acagagaccc tgttctgtct taacaaacag acaagtccac  84840
caaaaaggcc atattctgaa aataatgaaa acagaaaacc tattcaaagt attttcattg  84900
ccatcacata ctacttggct tatacttaat gggaaattat ttcttatatt tagttacagc  84960
caagctctac atctgaatct atggatcaac tactaagcaa aaatagagaa ggagaaaagt  85020
```

cacgagattt gattaaagat aaaacggaag caagtgctaa ggatagtttc attgacagca 85080
gcagcagcag cagcaactgt accagtggca gcagcaagac caacagccct agcatctccc 85140
cttccatgct tagtaatgca gagcacaaga gggggcctga ggtcacatcc caaggggtgc 85200
agacttccag cccagcctgc aaacaagaga aggatgacag agaagagaag aaagacacaa 85260
cagagtgagt aacctgggtc tcagcacatg ctctctccga gtaacctgct ttaaggggtt 85320
ttctgttcca tagtaactgt tacatagagc tggggttaga aatctgagct gaatctagtc 85380
attgggttct tagcattctt cccattctga cttgtttgca gctgtggggg taagaaaagc 85440
tacttctatg gagataagag tttaaatttg aatgccctgt ctcggggttc tggttctgcc 85500
taaccctgca gtctgcaagg actatttgct gccccagttg aggaaatgtt tagttgataa 85560
gcacatcttt ataaacctta tttctgtgca tctggcattt aaaagcactt aaatagataa 85620
actagtgggt tagcctcaga cataatcacc actccctttt tgtgttctgg ataacaaaaa 85680
aaaaaactaa ttgtacttga actatttatt cttgatttgc agaaaaataa ttttactaga 85740
gcaatggtaa acccaaggca tgtgattaaa acattttgac acatttaaaa ttgctgcgta 85800
tgctacaggt ggtggaaggg ctttgttaac acagcacttg ggcatctgag gctgttgatc 85860
ctaagtttga ggccagcctg gatccattgc aaggcctaat ctttaaaaaa aaaaaaaaat 85920
tagaactact gtgaactcat taagcattgg tgttttatct gcctgtctgt ctgtacacca 85980
cacacttgct gtaccttcag aggccaaaag agggtgtcag atgcctgaaa ctgtagttat 86040
agatagatgg attaataaac ccagtcctat ggagtggcag ctgtttagct gtcacttaac 86100
ctcattaggc accctttttaa ggggctgcga cttaccagtt gaaatattcg gtgattgctt 86160
ttgagggatg tggtttcttt ggttttcatt tgttctcgta tggttagttt cttcatcaga 86220
ttaagcagca gaggtgtgtg tttcagtaaa ggagactgag acatggagag ttactcacat 86280
ctgctctatg tcagcaatcc tctgaaagct gacgagtgtg gcgcagttga gaaagccgca 86340
gccccatgat gtttcactgg cctgcttgtt gttttctttc tttcttaggc aggttaggaa 86400
atcgacattg aatcccaatg caaaggagtt caaccctcgt tctttctctc aggtaagcgc 86460
tagcctttta cagctggtct gaagagacgt cactgcgctc ttcatggctt tctcctgagc 86520
tcccatctga ctgagcccag ttgtaggacc ctgagacagc ctggcctcca ggcttgtggg 86580
atgtccccaa gcttgtcagt cctgctgtgc cgctgtgagg gacagctcag tgtaagctca 86640
caacgactga ggctgtcagg ccaaagaagc ccactcacta actacacaag agagtccatt 86700
tcctcgggaa ggcataggag aacatgcctg tattcttagc aaacaggaga ccggggcaaa 86760
agggtcatga ttttgtggtc agtttgggcc acatagtgag atccccaccc caaaacacaa 86820
aaatgaaaag aaaaaaatgg atagaccttt tctggttcct tgtaaaatta ttacaatttt 86880
tatatctttt tttcattgat aaatatttta gcttgattag atatgataca gtgttgatac 86940
caaatctgtg tttatgccag ccctctaaca ctgagaaatg tctgcagcct aagttttccc 87000
ttttttaacc cctggaaact gaatcaactt cttacatgct agcctctgga tgttttgttt 87060
gcctgtttgt ttgtttgttt gttttgcttt gctttatctt tagaataaaa aaatgctagt 87120
taaaaacaaa taggcagaac aatcagggaa gctgctttga atattgtttt catagatgct 87180
tttcatcttg acagagttga tgttgaattc tgtttttgtt gttgttgttg ttttgtagcc 87240
aaagccttct actaccccaa cgtcacctcg gcctcaagca caacccagcc catctatggt 87300
gggtcatcag cagccagctc cagtgtacac tcagcctgtg tgcttcgcac ccaatatgat 87360
gtatcccgtc ccagtgagcc cgggcgtaca agtaagttcc atgggttaca atttgctgga 87420

```
caccatagct tgcatttagc acaagtgtcc taggtgggca ctaagtggga cacctgatag  87480
caagtagtgt taagagtggg cagtgggtag gggtggtgta ttgtatcatt agcatgtgga  87540
tctaagtttt aggattaatt ttcagaaaaa aatgacttac atttactata ggccagagtt  87600
gttcctttta gttgtgggta ttaatttgaa tagctcacag ggaatcaaga aaacactggc  87660
cagatcacat taaaagacag tgatagaatg aatatattgt taccatatga atctaatgat  87720
gtgttttcaa ttccctcaag cctttatacc caatacctat gacgcccatg cctgtgaacc  87780
aagccaagac atatagagca ggtaaaggtg agaataaccc tgcctgtgtt tgcttgtgtc  87840
tgcatgctgc atgagtttag cacctgtgtg caatgaatag ttggcttcag cttgaattca  87900
cagggtatgt gttcacttgt gatggccaac gtgagtattc aagtgatcac atagtaatca  87960
tgtgagagaa aaaaatataa ataaactttg tatgtggtgt gtgggtatgt gcatgtgtgc  88020
actcagtata catggaggtt aaaagaacac tgtaggagtt cctcctggtg ggttctagga  88080
tcaacctcag gtcatcagat ttggccacaa ataccttac ctgatgagcc atcttgccaa  88140
cccaataaat gtccatcccc atcccagtca cctacacctt taccacccac actccaccct  88200
accctacccc cacacagagt ctctctctct cttaccttgt agccttgact agcttggaac  88260
ttactttata gaccagactt ttgtggaatt cctataaatc ttcctgcccc cccaagtgct  88320
ggcactaaag gtgtgcccac tacactcggc cttcttttta aagatgcatt ttgaggctgg  88380
agaattggat cattggttaa gagtgcatgc tgctcttgca gaggacccag gcttgatatc  88440
cagctctcac gtggtgcctc acgacttatc tgtaactaac tccagtccca gggaatccag  88500
tgccctcttc tggactccat gcataccagg catacacaca tgtatcaata tacatgcagg  88560
caaaacactc atacacatat aaatatctgt attttttttc tatatatgaa catttgcta  88620
gcgtgtttgt acttgtactg tatggacaca cggaagccaa aaaaaggcag cagaacccct  88680
gggactggta tcacagacag ctgtgagctg ccttgtacat gctgggaacc tgaactctga  88740
tcctctgtaa gaacatcaag tgccttaact gataattctc tctagcctct gtttggtatt  88800
ttttgccaaa agaaataaat tttagaaatt tcaagctgaa gtctaaattg aaattttatc  88860
agaatttttt ttttgtttgt ggtttatttg gaattgtttt cagccatagt ctcactgtgt  88920
aaccctcact ggtctggaac tggctatgta gaccaggtta acctcaaaca gcaatcctag  88980
agttaaaggc gtgcaccacc acactggccg ctctttattg ctgagaagat gctcctatag  89040
ccaggctggc ctcatcggac ttgctgtgta gctaaggcct cagatcaggt gttggctgtg  89100
ctggaactga gtctaggtgg cagtgagctg ctatgtgatg ctgcggacat tttccccaag  89160
tgctgtgtgc cctgcgcaca gctttactca gtgctcttgc cctgcagctg ttgtaatccc  89220
ctcttcccag cgtatcaatc ctgctgactc catccttggg cagtgctagt tcaaaggagt  89280
cttaaatgcc ttccaaccct ggaaagaggg attactacat aatagtcatt tccaggacaa  89340
agttgggtaa tttttttttt tttgtaggtt tgttgattag tttgtttttc tggtattgat  89400
ggtatttctg aggattgaac ccagggcctc atgtatggtg attgaggtag aggaaggaag  89460
ggagggaggg agggagggag ggagggaggg agggagggag ggagggaggg agggagggag  89520
ggagggaggg agggagggag ggagaagaga gcatttaagt tgcccagggt agccttacac  89580
tctgcatgtg ttccaagaag cctggagctc atgctgcagt caccgagtgt agtgttcttt  89640
cagtttgtgc tgtgttgtga atggtgtctg ttctctcagc acagaggtgt cctgtcatct  89700
ctcattgtga taactgttac agggaaactg aggccgaagg atcaggagtt caagtcagaa  89760
```

```
gcacaaggtc atcttgagct acatgacacc ctttacccac ctcccctgga cccccatctt  89820

tgcgcaccac atgccttctg tagctacttc ctacctgtgt tgctgccata gataaccatg  89880

gtgtagtccc aaattcagtc agggcactgt gatgtggtga aacttctttc atccatcttt  89940

gctttccagc aaagctttac ttcattggac ttgtggattg tcctgaagta gaatttgcat  90000

gagctggaat ggaagtacag acatgctcct cagtgccttt ttaaaggctg tctccaaaga  90060

taagagtgtg ttctatgcta gggcattgtc aacgtacggg atttcatact tgtttcccta  90120

gctggtattt tacagttaac ctagaggaga ttctctccct tcacagaggt gaaagtgagg  90180

ataaacttgt tctgtgtata aatggagaac ctcgtgcatt tccacaggtt ctgcgtctta  90240

agctgctgtg acaggaatat caactgtttg tgtcttctaa ggctcaactt agaaagtcct  90300

gggaaagtag ccatccctgc ctatgtgatt gctatatcct catactgctg tgctgctact  90360

gaacaaatgg aggtgctaga caaagacacg aagtcaagtt ctggcttctg agattctaca  90420

aaccatgtaa aagacacctc ttcttgcatg gcagtgaatc tttgcataaa accacatcag  90480

gttcccccttg ccataaatca cacctgcctt tcatgcaccc tgtgagaaca cgcctgtaag  90540

ggagctaaca taatggggat cacacacaca gagtcactga gcctactccg gcctccagtt  90600

ctccttgtag ctgtgtggat ttgaacttat gtactcaggc tctgagcttc atgcctacac  90660

cacactgcaa gggctgaagt aagttgtctg atgctgggca ccattgccat ctgtaactag  90720

tattcttttc tacagtgggg agaggctcct tgcctgactg cgggtgctta ttagcaatca  90780

ctagatctag tagtaacaac cctttagttg attaggatga caaaaaaaag tctctagata  90840

ctgccacatg gcctctgttg ggcacaattg ctcttaatag agagtcaatg acatgtgaaa  90900

tggctgaaat atggttcata taaagtgtaa tctaagatga atatccattc agttttggag  90960

aaatccacta tagccaagta aatatgatgt cttttgtgga gggcaggtat ccatggctag  91020

tttgttcctc gttttgcttt gtttgagtgt atttatttta cagaggttat ggatcccaaa  91080

acagcctcaa aagctgagga ccttgaacgt cattgtcctt gtctcccacc caaatttcct  91140

tttgttttct aacaatagca gttccattaa atgttcagcc aaccttttta aatatttaaa  91200

ataataagca catagacaat aatagttgct ttagctctgt gactgcataa acaagccagg  91260

ttacaggttc tctgtgctgt accctcatga ggcatgcagt tcccagaggt agcatgacat  91320

cagaaacaga catgacagct acaatcgatg tgtgcttacg ggaggaaatg cacgggtgat  91380

gcagaggacg tttgtgagtc ttacacgggt cttctttcct ctgtttcctg ggtgttgaga  91440

ttaaagattc atctcttagc tgacatcagg aaaagtaatt tttataggaa tatggaaaac  91500

acacagcaag caatttttcc tttcttaaat gcgctacttg gtgtacttgg tactgtatga  91560

tattggaaaa caggagagct gggcgtgggg gggggggggc tttcaagaca gggtttctct  91620

gtgtagccct ggctgtcctg gaactcactt tgtaaaccag gctggcctcg aactcagaaa  91680

tccgcctgcc tctgcctccc aagtgctagg attaaagggg tgcgccacca cacccagctt  91740

gtcatctgtt tttcttcaga aaggaacctt tcttgacctt cttaattaaa cacgttatga  91800

tttggagtat cagacagtcc ctgtgttctc ctcccattct aataccatct cttatgttag  91860

gaaaaccagg tgaagggaaa gtcactggac agctaaactc tgaaggatga gtcccttacc  91920

tgaagcaagt ggagcaatgg ctcaaagcag caggagaggg gtgggggctg ggtaagacag  91980

ctcagacagg cagaatcaga gtttggtaac acagagcctt tcagaccaca caggtgcatg  92040

aattataccg acaaggtttc attttctttt aatccgtttc tttttctttc gtgcagtacc  92100

aaatatgccc caacagcgac aagaccaaca tcatcaaagc accatgatgc acccagcctc  92160
```

cgcggcaggg ccacccatcg tagccacccc gcccgcttac tccactcagt acgttgccta 92220
cagccctcag cagtttccca atcagccttt ggtccagcat gtgccgcatt atcagtctca 92280
ggtaaggcca gtggaaccta actcacttca ctcctaagaa gagcatctta cttcgattgt 92340
ttatgggttt atgggttttt tggctttgtt ttatggtatc agatagttaa tggggccttt 92400
taaatatgtt tctttttatg tgtatgctta gttttgcgtg ttgtaaaccg tatgctgtgc 92460
ttggtgtgtg gtgcctgttg gagagggcac ttgctgttct tgcagacgac ccgaggcttg 92520
ttgtccccat acctatttca gaagatcctt cggtctccat ggacatctgc acacatacaa 92580
agcacaaata ctaggcacat atacataaag aaaataaatc ttaaattaaa aaggaaaaaa 92640
ttgaaaagga agcatctgag aaatagaact gtgaaatgtt tctgggaacc atgaagctag 92700
gagtcagaag tgactgggac agagcaatgg ctcagcagtg aggcgtgttt cctgctggtg 92760
atggggccca gcacccacat ggccactcac aagtccttgt aactcctgtt ccaggggatt 92820
cgtgtcttat tcaggcccct tgtagcactg cacatgtgca tgcatacact caacatatac 92880
agtgaatctt tttaaaaaag aaccttatct agacttcaca tcgttcattt tggcataatg 92940
gatgttcttt tgtctacata cagcatcctc atgtgtacag tcctgtcata caaggtaatg 93000
ccaggatgat ggcaccacca gcacatgctc agcctggttt agtgtcttct tcagctgctc 93060
agttcggggc tcacgagcag acgcacgcca tgtatggtag gaaccatttt attgtctttt 93120
ctgtgtgttt gactatagtt gctgtaaagc tctgtaaaga tattctgttt aagaatagcc 93180
tgcgataggt atagtggact ggatcctggc tattagtggt agtggggaga ctaaagtaca 93240
ggatcatttg agccaagagg tgagagacaa catagagact ctaccttaga aaacaagggg 93300
ggaaaaaaaa gaaaaaaaga aaagaagaag aaaagaaagg aggagtaaaa ataacctgac 93360
tctttgtgag agtgagtgtt gagagtctta aaacgaaagc aaacttatgt ctgacttaat 93420
ggcaatttat ctctactttg aatctacaat tcctctgtct tgatatgttt ctcctttaaa 93480
aaatgatgaa aagagctggg cgtgggggtg cacaccttca acttgggggt tcagggaagg 93540
ggcaggcaga tctttttgag tttgaggcca gcctggtctc cagagcaagt ccaggacagt 93600
cagggatata ctataagtaa gaccctgttt cagagaaaca aacaagcaaa cttgtgacgt 93660
gtaatgagag catctttggg ggaaagatgt acttaacgtc cttcctgccc aagccttgca 93720
gggaagggtg taccatacag tctttcttac ttcccacatc ttaccatgta gagtcgcctg 93780
ttcatcttac agtatgcttg tgtgcttttt acagtcacct taaattactc cgaactttaa 93840
atgacaacac tataccaaac ttagcacata ttttttctag tgacatttga attcttggga 93900
aagttagata agtttgggtt acttatcagt tgagaagtgt acacaatggg actgagagtg 93960
tgagtgcatg cagccttgta cacactgtgt ctcatcttag tctgacccct taagtgaaca 94020
tatgcagggc agtaaggtct gtgttgtggt gaacacttga tcattccgaa tgctttaaca 94080
ttatgtaggc taactaagag aacattggcc accctgagtg tcctccctgt gtttgtgatc 94140
acatgtgtac tgagcaggtg cacgcctgtc accagtgata catgcctgct gtcaaacact 94200
tgcctatgtg aaatcctgag gtctgcttgt tccacatttt gatcatggtc attgccatcg 94260
tcatcagtgt gtactgggca tttgaaataa agagtagggc aagtgctgta ctttagaaaa 94320
cattttcttt taagcagtca atccattggc ctggcatggg agagtgccta taaatctcag 94380
tcctgtgaac atcataaaaa aggaggatca ggtattgaga cagtctgggt ggcatagcaa 94440
gaccctgtcc agatcaaagt cctcctgtaa tttgatttat aaagagtggc ctggtttaca 94500

```
ttttcattga tttataaaga gtggcctggt ttacattttc atcatgatga gtctgtcctt  94560
cagtgtgtga tcagttgtac tccctgggat tagatcagac ctcacatgga aaggccctgg  94620
cggtgtctct cgctgacctt gctgtacctt gtatgcattc ccacagtctt ccagcttggt  94680
aaaaggcttg gttgaagtgc ttatgtttgg acactgctgc tgtgtgattc agaagtggaa  94740
gagacatttc tttcctcctg gttttctggc ccccactggg ttaagaggaa actctggagc  94800
tgaagtttgt agtgcttttt ggaacagcac tgtggctgcc agtgcagtgc tctgcagtgc  94860
tgccttcctg gttttgtcat gcagtaccta tataaaatgg gcactaggaa atgaactgtt  94920
tggggatttt cccatagtca aaaatcattt tttaatacgt tgacacagtt tgtcagtacc  94980
ttggctgctc catagatcag ttatgccaaa catacataca tataagacat atatgtatgt  95040
atacacacac agtttgaaaa ctgttgtatg gaaatactaa ttttgtgttc atttcctttg  95100
aaaagtatgt attttctata acccaagaaa taagacactt gaagctgttg atttacaatg  95160
cagtggtgct ttgtcctcag ttctgctgct gatctgcctc tctgttgtta ctggttctct  95220
caaggcaaag gccctccttg tgttgaggag gactacatgg tgtcaccttg tactctttgt  95280
gaggaaggac ttctattagc agactcccct tgttgcctct gccctgcaaa gtgatcactg  95340
tagcgtctgt cctgctcgtc tgagttgcta ttccagcagt ggttccattt tcagactcag  95400
tggtagagct gtctgactga caagtcagcc agaagaactg aatgtgctct cactagcccc  95460
actcccactc ctccaaaaaa agacagggtc tctgtatagc cctggctggc cttgaacttg  95520
ctatataggc caggctggcc ttgaattcag agatccacct gcttctgcct cccaagtgct  95580
aggattagag gtgtgaacaa ccataccagc taaatatttt ttaacatgta tagtttaatg  95640
cagataagtt tttttttaag tacaataagc ataaagaaat aggatttcct gtaatccttc  95700
tgcctgacat ctgcttgtta atattcatat attctcccag agctttaatt ataccctttt  95760
agacagacac attttagtat gaatagtgtg atacttaaat ttatattttt atgtcatgaa  95820
ccttgggatt tactacccaa gggcctgtgg tgacatttgt gttgctgtga aaaattatgt  95880
atcatgagtt tgcttaaata ctgttttatc tgggtacctt gcttatgaca aggctgtttg  95940
atggatgcca tgttggtctt tttatcagtt aacggttctc tatcagataa taatcttatt  96000
ctttttattt aagcaagtca gcgtgtggac ttgctacctc agtacagaag gaaagccttc  96060
cggttcagtc ctgttcgctt gtaaatctct gcagcaatgc ttatttacag tgctggtcac  96120
ccctgaccaa acgaactgtg cgtgaataca aaagatcact gaatgtgtcg gcctttccag  96180
agcatcagga atgcacacct caagaggcta atttaccttt ctatttccca cattcagcat  96240
gtcccaaatt accatacaac aaggagacaa gcccttcttt ctactttgcc agtgagttgg  96300
ggtttttata ctaattttaa ctacacagta aacactattt aagggatacg tgttaaagta  96360
gctaatttgt tggagaacat tttctttcta ccagacagaa ttattcaaag tatgcatgtc  96420
tgggctgggg atgtggctca gtggtggagt aacttgctct agcatgcacc aggccctgaa  96480
ttcattccct agtacaaaaa aaaaaaaggt aaagttaaga tttgtggctc tgtttgtata  96540
attcagagtt ttgacaaaag aactatgtct tatgtcatag cttaagaaaa ttggaatcaa  96600
agactgagtt ctttcaggaa gccattttga atacaacgca agagtgtagc tgtatgggaa  96660
ataccttgtt ttcctcattc tgggagactt tttctgaact gttggtagta ttttatacta  96720
agccacaagc ttgtgcaaag cttaaagtac tagtgagtag tgttctgggc tgcagagaag  96780
tgacctcact gagattcctg tagcacaggt gaagtagtta gagacacagt tctgtcttag  96840
cgctatttgc atgactagag gcttaaagtg tgaaggcctc tggaagtgtc ctgaagcctg  96900
```

```
taacaatgtg tggtctaggc taccttcttc cctaagggag cttaggagat ggagttttcc  96960
tgctttaccg ggaagcagat catgggcttt gataggctaa ttactaagag accttttaga  97020
aatgtgtgtg ctgatgtcac tttgtatgaa acatgagtcc taacaaacaa taagatttaa  97080
tgttattaaa tttgggacta aattttgggc tattttggaa tgactactca atcatcaggg  97140
ttttggaaac atttttacct taaattttca ttaattagtt gctacttttt ggtgcctggg  97200
ataagttaac aaatagagcc ctttcatgtg ctcttggaaa agtagtctta ttgagaatgt  97260
ccctgaggat ttcaggagca cagtttgagg tctctagtgc agttatcctt accatcctgc  97320
tggctgttac agtcatagtc atttccttgg cagatggctg aaaggtcttg aatcatccct  97380
aagcactaac agcctgagca cagcttcctc atgaaaggag tcagcactaa agccagcagc  97440
tgttgttggg gattttagtc accgcagtgt tctgccctag tccactgcgg ttttgcctcg  97500
ccttagtgtg atgtctttta tcccctctgc cccctaaaat ctccttgagt tatatcccct  97560
ttttggaatt attgaagttg gaggatcctg ttctgcttat tttcagtgtt tccagtgcta  97620
gtgatcacga atgacttgta catccaaggt caaaatgata gaaactattt acagagtgaa  97680
catctggtcc tgaggactga attcgctttt gttaacctca tgacttaggg gactgtttct  97740
ggaatctagt taatgttaaa aaaagagttg acatatttag aattttaaat acttaagtca  97800
agaagcgctt tgtcctctca cccaactctc gggagactgt ttgagccttg taagtagtag  97860
tttagctgct gaataacgat ttcagaacat ctgaggggat tcatggtctt tctagtctcc  97920
caagtagtta aattaaccag cagaggaaaa gccattcaat cctgcccttg gctgagagcc  97980
ttgcttgcca ctctccaaag actgctcttg gttaccttcc ccagtctttt ctgttctgtt  98040
gtttctctaa tttccctctc cctgattttt tttttaaaga tttatttatt tattatatgt  98100
aagtacgctg tagctgtctt cagacacacc agaagagggc atcaaatctc attacagatg  98160
gttgtgagcc accatgtggt tgctgggatg tgaactcagg accttcggaa gagcagtcag  98220
tgctcttaac tgctgagcca tctcaccagc ccctctcccg ctttttattg cccttagttt  98280
tgctgttgct ggaattacag tgttggttcc catttcccga tttctcacat tatagtcaag  98340
gggaaagggt tacataaggt acttgttttt taggcctctt tgagccagaa agtgagcaga  98400
tggaaacatt tctctggatg ctcctgaaag tgttttgtta aaatgcatac tagggcctgg  98460
agagacagct cagcagttca gagcactggt tactcttgca gaggattcag gtttggttgc  98520
cagcacccat gtgtaactat atctgtaact gtagttccat gggatccagt attctgtgct  98580
ggtctctgtg agcactgcac atgtgtgtgt tgcactggca aaacactcat atgcatataa  98640
taaaaatcaa tctttttaaa agatgtctaa tagggccagg aaggtggctc aatgataaga  98700
acacacttcc tgtgagagcc tagcctttaa atgccctttt atataaaaat aaaattttaa  98760
actggatgtg gtagtgaaag tgtggccctg ccatgtgaag agctaaggtg ggagggtcag  98820
ctgctgtcaa gcttgagggt tgcgtgggtt ccaccaagcc ctgcctctag ttattcaatc  98880
ttaagaacat ggctcagtgt agctcagtgg tagactgtgt acttaggatg caggaggctc  98940
tggctccaat cttaagcata aactatgagt aataaagctg tttgattttg atcctggctg  99000
ggtatggtac cccggtgcgg atccacttgg aagatggagt tggggagggt gggttccagg  99060
ccaacttaag ctataaaaga agaaaaacca aacaaagaag ggaaaggatc ttttaattct  99120
ctttccaagt gacagtatca agactttccc attttcccag ttgacagatg taattctgag  99180
acttgatgga catagttact atgactgcgg tggccgtgtt tccactgcat tttgctagag  99240
```

```
cttccttcag agttacttgt tttcccacct gttccaggac tggaactcag ggccttctgt  99300
gcaaagcttt gcactgagct gtgtctccaa gccttttatt tatgttttct taaacttttt  99360
tttagtttga atacttgagc tcctatatcc tctatcttta tgaaatctca taaataaaca  99420
tttagggttg ctttccctca gttggactta acattgctat aaaggaaaca cttactaaac  99480
actggatggg gctttaatgt ttgtggtttt agaatgagac atgtggacca gttatcacca  99540
tctagcagcc tagtctatag ttgcagacct gtagttgttg tctctaaaaa caaaagtcgt  99600
tcttaagtgc ttttcacagt cagggaatta gaggatggac tggtctccct gactcactga  99660
aaacattgtg acgttaggct gccgtagttt tctctttaca catctgttga ctaatacagt  99720
cagggaaact gtaccaggtt ctaaacacag ttgccttcat cagtctcacc tggatactga  99780
gggacactgg tgagtgaggg ctgtggcctt ggcaggtgga cacacaggcc atgccagctc  99840
cgaccattgg aaacagaatg ccctgccctg cactgtgaca tctcatgaat gtttcctgtc  99900
cctaacccgg gacaccactc agctggcaca cagccagagt cctccatgtg tgctattctt  99960
ggaagttttg gtgcttctct gtccacatca tagctgtgtt tgctgacata ttatctaaag 100020
tgcatgaaac tgtgacacat ctgtgtgtgg gcttggctgt ggagggctaa gggttcagtg 100080
ctgagagaga gatagagata gcttgagagc agtccatttt ctgcttgatg tttagtttgt 100140
gtcgtgagct gtccagagtc acaggagcag cgaccttcct ggagttctca ttcccaggct 100200
gctgctctgt aaaggcacag gttcacttaa tacttgatct ccttggttgg taccaaggtg 100260
gggcccctcc tagatgcata aagagcagcc tcagggtcat tgtcgtagag tcacatttta 100320
agagtgttaa gaaaaactgt tcctttggta tttttctagc taacaggata gagtggtcag 100380
tttcatctcc aggctttttg tcaggagctg catcattcag tagggaacag aatagtgagt 100440
gggtactgtg attgactgag atggcagtga cgttgtcctt gcgcccagcc tcactggtgt 100500
gtgtacaggg accgttccag agcagtagca tagcaatgta atcagatgct gaccttgaga 100560
gagaggctgc acctgtcttc atgtgggcca gtgtgattgg tggagttgtt tctacctaag 100620
cctccgagag gaacagggat tgtctgagta aatttaaact aagtcggtgt gagtgtagtg 100680
tgtagagcta tgtagcacac gggtcacgtg ctggccttgg tagacagagc ccttccgtct 100740
gtttccagac tgtgcttgct ctcatggctg tagagcgtgg cagtgattag agtgcagtga 100800
attaggcata gtgggctggc agtggtcgtc agaattgtac acattccttt ttctttttca 100860
tctcagtttc caccggctcc ctcgctcagc agtatgcaca tcctaatgcc gccctgcatc 100920
cacatactcc ccatcctcag ccttcggcca ctcccaccgg acagcagcaa agccagcatg 100980
gtggaagtca ccctgcaccc agtcctgttc aggtaaggag aggcgtggcc tgtgtgtgcc 101040
tagctgtgag cagttgtggg tacgggggag gccattccct aaggttgaat gccagaaaca 101100
taagtgttaa aaagctgctt gatcttgaag ttcttagtta agtctaaagc cctctggaat 101160
ttcattcctg aaggcaagcc gcaatgctgc cttcctgttg gcttcctcag tcccatgtgc 101220
taatggggca gtgaggcctt gtttggacct gtaactgccc ggctgaggct tgggcttgag 101280
tccccggaaa aggccatctg catgagagat gctttgtgct ctcctttctg cgcctcccgg 101340
ggtgggggtg gggtggtggc ctgtcgcctt cactctatga agtttcccat tgctttacag 101400
caccatcagc accaggctgc ccaggctctt catctggcca gtccacagca gcagtcggcc 101460
atttatcatg cggggctggc accaacacca ccttccatga cacctgcctc taatacacag 101520
tctccacaga gcagtttccc agcagcacaa cagacagtct tcaccatcca cccttctcat 101580
gttcagccgg catacaccac cccaccccac atggcccacg tacctcaggt aaaccagcac 101640
```

tagccaagtt tttgtgaagg ccacataggg agtggtggtc agataagcag caaggagcca 101700
gttgctcccc aagccaggaa accctgtgtg tggtgccatc tgcctgtctg cccctttcct 101760
gcttagcacg tgatcttctg gctctcagtg aatgttgcta tggttttgtg gtggatcagt 101820
gaaactgtga cttagcattt cccagctgag accttaaacc tctgagtctg gaatgcaccc 101880
cagtcctttc cttcctgtgt ctgcttcgct gcgtctctct agcctctcca ctgtgtatat 101940
atgtgcacac atgcagacac ctctacacgg gagcacacac gcgagcctta gagcagggtg 102000
gcaggcaggc cttcagtggc tctcactctg agggactgca ctaggattgt tggtttgcgg 102060
gttagcagtg tcccagctgt tgcctggttg cctctgtctg ctgtgattcc tgagcttgga 102120
ccttgggctg tggtgcagga gaactcaggc tctagagtag cccagaccgt ctggggcttc 102180
ccttccttcc ttcctccctt ccttccccca gtgtaaaggc tgagcttgaa agctgtggtt 102240
gctgagagag ccagggcagc ctgggccatg gagaggccct ctctgtagct gttaacgtaa 102300
ggtggctgga tcagatgtct gctacttttg atcacagttc cctgaggtgg gtctcactta 102360
gaagagttcc tgaatgattc tatttcctgt ctcagtgtgc cagtgaggct ctggcgaggt 102420
gtgagctaac gctgctgtgt agttgggtct cttgcagaag gctagcttgt tcctgtcctt 102480
cccccagagc tgagagtgta gaatatgctc ctgttggctg gcggcagtgg ggagggtagc 102540
cagtgtggtc agtgtgcttt ggtggagtga gacttaagag aatcagggtc ctctaagtgt 102600
ccagcagagg ctgtgaattt atgtgtaaga tgagctcatc ccaaacctca ctcatgtatt 102660
tgcataagag agtaagaggc taacagggaa agcagagagc catgggcctg tttgaaggtg 102720
tgaaccagtg cttcgctggg gtgatggtct agagcaatgc acaggatggg aggcaggaag 102780
ccgcctcttc ctgctctgcc cactccctgc agagccaagg ttgagattac cgaccaggta 102840
gctaacatca cctttctaac ttaaatttgc tgccatttgg tactgggttg acccagcttc 102900
agatcactct gtcatctcag tggagccagt gactcagcct ttgctccgtc agttaagctt 102960
ttaaagtgag gggcctaagt gctgcttcac cctacttttg gggaacccac tacaactggg 103020
gaagggcgga agaggagaga ctcaggaagc tgctgagggt gctggggagg cagtcccctt 103080
acaggccctt gtcagttgct ttctgactgg aaaagggcat tgatatatct ttggccatgc 103140
accatagcaa gctaagaaag tgcccttccc accccaatag cggctgcttt tggtgaagac 103200
cttgccttgt gtggtatctg agcagacgag ttggggacta ggaggcaact tccccatctt 103260
agccctgctg gatctacctc aaggttaccc aagaagtcca tcttgctcct tcaagagccc 103320
tagtccaatg aaaggaatag ctgacttgtt gtttaagaag gagatgttgc ctgtatgcgt 103380
aaaagagctc tctgtttcag gctcatgtac agtcaggaat ggttccttct catccaactg 103440
cccatgcgcc aatgatgcta atgacgacac agccacccgg cggtccccag gccgccctcg 103500
ctcaaagtgc actacagccc attccagtct cgacaacagc gcatttccct tatatgacgc 103560
acccttcagg tgaggcgtgt gtgtgcaggg gccgccgggg caccccgagc gttctgctcg 103620
cagaggtaga atggcaggca ggaccagtgc ttcaggctgc aaacctgact agcgaggccc 103680
atccaagtgt gcacaggagg gatcgtgacg gtcaggaaac atcaggctct gtgtgtgttc 103740
tgctggttca gggttggctt gagaagcagc agcctcattc tgggtagccg atgcatgccg 103800
aggactcagt tggccttcct ggttatgtat gtatgatagg ctggacaggg cagcgtggtc 103860
cgtcctgagt cctttatagg ctgatgtggg gggtttatgc ccatggccaa gtttgatcgt 103920
agcttggagg agagcactgg tgaacacgtg ctgtgtgcgg actggtctga gtgtagtgtt 103980

```
agccccagcc tgtgccctga cacaggacgc ccatgatgtc tcgtactgat ggctgctgtg 104040
acgacacctg tcttccctgt gacttggaaa gcagtggtgc ttggctagtg tagtgggagg 104100
gggtgtgaag gcctgctcca caagcagcaa gtccaggact tgtatctgaa gtggtttacg 104160
tctgactggt ttgtttctcc tcacccccttt ccctccccaa ccctaccttg gctgcagttg 104220
ggggagaggg gcagcattaa ccctccagtc ttactcacta gcacaggagt agttgacagt 104280
cgtgtgctgc ggacactagg ctggcgggca gtggtgcctg tgttgtttaa atagccactt 104340
ttcttttta cagtacaagc ccaccaccaa cagcagttgt aaggctgccc tggaggaacc 104400
gaaaggccaa atcccctcct cccttctcct gcttctgcca accggaagca cagaaaacta 104460
gaacttcatt gattttgttt tttaaaagat acactgattt aacatctgat aggaatgcta 104520
acagctcact tgcagtggag gatgttttgg accgagtaga ggcatgtagg gacttgtggc 104580
tgttccataa ttccatgtgc tgttgcaggg tcctgcaagt acccagctct gcttgctgaa 104640
actggaagtt atttattttt taatggccct tgagagtcat gaacacatca gctagcaaca 104700
gaagtaacaa gagtgattct tgctgctatt accgctttaa aaaaaaaaaa tcaagacttg 104760
gaacgccctt ttactaaact tgacagaagt tcagtaaatt cttaccgcca aactgacgga 104820
ttattattta taaatcaagt ttgatgaggc gatcactgtc tacagtggtt caacttttaa 104880
gttaagggaa aacttttact ttgtagataa tataaaataa aaactaaaaa aaaaaattaa 104940
aaaataaaaa aagttttaaa aactgatacc cagttagtgt gtgtttatgt tgactcctgc 105000
tgctgtggga ggtagacccc agggaagaca ggctggttgt gctgctccaa tctctgagga 105060
ggtgctgacc aaatgacttt tcttcttcac ctttagttct ggctcaaggt atctagaaaa 105120
agtcaagact gtgattccct ctcgggtgga ttagcagttg gcttcagcag aaggcaggct 105180
ggccagaggt gggcagcgtt caaaagtcca catctgcaag caggtgcaga ctgtaagctc 105240
acttttcctt gttgatctga gttatcccag ttcagttctg tgttaccagt agggggcaga 105300
agctccttct ttacagagga atctgaccag gctcaaggtg tggccacagt ggctaagcac 105360
ttgtctagta gcacagagcc ttgtccctcc tcagtgtagc cagggattgg ggaggggggg 105420
gcagcacaga atgaggccag gctgcccgaa agggaggcag gcaagtggga tgggtgtgtg 105480
gatgcagaga tcatggttgt aatactggaa acctttttaa ttgacataca gcaatttgta 105540
cattgtagca aaatttgcat tattcaagaa taagttactc atacagtaca taaaacgaag 105600
atttgccaaa taccttctgc tgtaatgata gaagatgaga ttccctgttt ctgtggtgac 105660
aatgctgctt attccggcca cacactggcc attagatgtg tcttcactag gaggcagtgg 105720
gtgacagttt atcacttggt gtttgcacca aggtaatatt aaacaagaga ctgagccctc 105780
agggaagggg tgaagcctta ctttaagaaa cttaggtaaa gatagtgttg tgtggcccga 105840
gattgtaatg atccctattc ctttctccta caccatccag aaatgatcag aggcagaaga 105900
tttatacaga taaagccata tggattgctg gtaaagtcaa ggcaggttag ttgacccaac 105960
tctttggtgc tggtgacttt tagtttgtag ttgagtactc a                     106001
```

<210> SEQ ID NO 2
<211> LENGTH: 4505
<212> TYPE: DNA
<213> ORGANISM: Mus musculus

<400> SEQUENCE: 2

```
ccgtccgcgt ccgccagccc gggtcccatg cgttcgtcca ccgccgccgc tcagcggccc     60
gcggcggggg accccgagcc gcgccgcccg gcgggctggg ccgcgcggcg ctcgctcccg    120
```

```
cggacggcgc ggcgcggcgg gcggggcggc gcggtggcgt atccctccgc cggccctccc    180
ccgcgcggcc ccggcgcccc tccccgcggg ccgcgctcgc caccctgcgc ctcagactgt    240
tttggtagca acggccacgg cgcgtcccgg cccggctccc ggcggctgct cggtgtctgc    300
gggcctcccc gccccttcgt cgttgtcctg ctgcctctgg cccccgcggc cacgccggcc    360
cgcgcctgcc cgcccggcgt ccgcgcgtcc ccgccgcgct ccggcgtctc ctcctcggcg    420
cgcccggcac ccggctgtcc ccgcccggcg tgcgagccgg tgtatgggcc gctcaccatg    480
tcgctgaagc cgcagccgca gccgcccgcg cccgccactg gccgcaagcc cggcggcggc    540
ctgctctcgt cgcccggcgc cgcgccggcc tcggccgcgg tgacctcggc ttccgtggtg    600
ccggccccgg ccgcgccggt ggcgtcttcc tcggcggccg cgggcggcgg gcgtcccggc    660
ctgggcagag gtcggaacag tagcaaagga ctgcctcagc ctacgatttc ttttgatgga    720
atctatgcaa acgtgaggat ggttcatata cttacgtcag ttgttggatc gaaatgtgaa    780
gtacaagtga aaaacggagg catatatgaa ggagttttta aaacatacag tcctaagtgt    840
gacttggtac ttgatgctgc acatgagaaa agtacagaat ccagttcggg gccaaaacgt    900
gaagaaataa tggagagtgt tttgttcaaa tgctcagact tcgttgtggt acagtttaaa    960
gatacagact ccagttatgc acggagagat gcttttactg actctgctct cagcgcaaag   1020
gtgaatggtg agcacaagga gaaggacctg gagccctggg atgcagggga gctcacggcc   1080
agcgaggagc tggagctgga gaatgatgtg tctaatggat gggaccccaa tgacatgttt   1140
cgatataatg aagagaatta tggtgtggtg tccacatatg atagcagttt atcttcatat   1200
acggttcctt tagaaaggga caactcagaa gaatttctta aacgggaggc aagggcaaac   1260
cagttagcag aagaaattga atccagtgct cagtacaaag ctcgtgtcgc ccttgagaat   1320
gatgaccgga gtgaggaaga aaaatacaca gcagtccaga gaaactgcag tgaccgggag   1380
gggcatggcc ccaacactag ggacaataaa tatattcctc ctggacaaag aaacagagaa   1440
gtcctatcct ggggaagtgg gagacagagc tcaccacgga tgggccagcc tgggccaggc   1500
tccatgccgt caagagctgc ttctcacact tcagatttca acccgaacgc tggctcagac   1560
caaagagtag ttaatggagg tgttccctgg ccatcgcctt gcccatctcc ttcctctcgc   1620
ccaccttctc gctaccagtc aggtcccaac tctcttccac ctcgggcagc cacccctaca   1680
cggccgccct ccaggccccc ctcgaggccc tccagacccc cgtctcaccc ctctgctcat   1740
ggttctccag ctcctgtctc tactatgcct aaacgcatgt cttcagaagg acccccaagg   1800
atgtctccaa aggcacagcg ccaccctcgg aatcacagag tctctgctgg gagaggctcc   1860
atgtctagtg gcctagaatt tgtatcccac aatcccccaa gtgaagcagc tgctcctcca   1920
gtggcaagga ccagtcctgc agggggaacg tggtcctcag tggtcagtgg ggttccaagg   1980
ttatctccca aaactcacag acccaggtct cccaggcaga gcagcattgg aaactctccc   2040
agcgggcctg tgcttgcttc tccccaagct ggcatcatcc ctgcagaagc cgtttccatg   2100
cctgttcccg ccgcatctcc gactcctgcc agccctgcat ccaacagagc actgacccca   2160
tctattgagg caaaagattc caggcttcaa gatcagaggc agaactctcc tgcagggagt   2220
aaagaaaatg ttaaagcaag tgaaacatca cctagctttt caaaagctga caacaaaggt   2280
atgtcaccag ttgtttctga acacagaaaa cagattgatg acttaaagaa gtttaagaat   2340
gattttaggt tacagccaag ctctacatct gaatctatgg atcaactact aagcaaaaat   2400
agagaaggag aaaagtcacg agatttgatt aaagataaaa cggaagcaag tgctaaggat   2460
```

```
agtttcattg acagcagcag cagcagcagc aactgtacca gtggcagcag caagaccaac   2520
agccctagca tctccccttc catgcttagt aatgcagagc acaagagggg gcctgaggtc   2580
acatcccaag ggtgcagac ttccagccca gcctgcaaac aagagaagga tgacagagaa    2640
gagaagaaag acacaacaga gcaggttagg aaatcgacat tgaatcccaa tgcaaaggag   2700
ttcaaccctc gttctttctc tcagccaaag ccttctacta ccccaacgtc acctcggcct   2760
caagcacaac ccagcccatc tatggtgggt catcagcagc cagctccagt gtacactcag   2820
cctgtgtgct tcgcacccaa tatgatgtat cccgtcccag tgagcccggg cgtacaacct   2880
ttatacccaa tacctatgac gcccatgcct gtgaaccaag ccaagacata tagagcaggt   2940
aaagtaccaa atatgcccca acagcgacaa gaccaacatc atcaaagcac catgatgcac   3000
ccagcctccg cggcagggcc acccatcgta gccaccccgc ccgcttactc cactcagtac   3060
gttgcctaca gccctcagca gtttcccaat cagcctttgg tccagcatgt gccgcattat   3120
cagtctcagc atcctcatgt gtacagtcct gtcatacaag gtaatgccag gatgatggca   3180
ccaccagcac atgctcagcc tggtttagtg tcttcttcag ctgctcagtt cggggctcac   3240
gagcagacgc acgccatgta tgcatgtccc aaattaccat acaacaagga gacaagccct   3300
tctttctact ttgccatttc caccggctcc ctcgctcagc agtatgcaca tcctaatgcc   3360
gccctgcatc cacatactcc ccatcctcag ccttcggcca ctcccaccgg acagcagcaa   3420
agccagcatg gtggaagtca ccctgcaccc agtcctgttc agcaccatca gcaccaggct   3480
gcccaggctc ttcatctggc cagtccacag cagcagtcgg ccatttatca tgcggggctg   3540
gcaccaacac caccttccat gacacctgcc tctaatacac agtctccaca gagcagtttc   3600
ccagcagcac aacagacagt cttcaccatc cacccttctc atgttcagcc ggcatacacc   3660
accccacccc acatggccca cgtacctcag gctcatgtac agtcaggaat ggttccttct   3720
catccaactg cccatgcgcc aatgatgcta atgacgacac agccacccgg cggtccccag   3780
gccgccctcg ctcaaagtgc actacagccc attccagtct cgacaacagc gcatttccct   3840
tatatgacgc acccttcagt acaagcccac caccaacagc agttgtaagg ctgccctgga   3900
ggaaccgaaa ggccaaatcc cctcctccct tctcctgctt ctgccaaccg gaagcacaga   3960
aaactagaac ttcattgatt ttgtttttta aaagatacac tgatttaaca tctgatagga   4020
atgctaacag ctcacttgca gtggaggatg ttttggaccg agtagaggca tgtagggact   4080
tgtggctgtt ccataattcc atgtgctgtt gcagggtcct gcaagtaccc agctctgctt   4140
gctgaaactg gaagttattt attttttaat ggcccttgag agtcatgaac acatcagcta   4200
gcaacagaag taacaagagt gattcttgct gctattaccg ctttaaaaaa aaaaaatcaa   4260
gacttggaac gccctttttac taaacttgac agaagttcag taaattctta ccgccaaact  4320
gacggattat tatttataaa tcaagtttga tgaggcgatc actgtctaca gtggttcaac   4380
ttttaagtta agggaaaact tttactttgt agataatata aaataaaaac taaaaaaaaa   4440
aattaaaaaa taaaaaaagt tttaaaaact gaaaaaaaaa aaaaaaaaaa aaaaaaaaaa   4500
aaaaa                                                               4505
```

<210> SEQ ID NO 3
<211> LENGTH: 4712
<212> TYPE: DNA
<213> ORGANISM: Homo sapiens

<400> SEQUENCE: 3

```
acccccgaga aagcaaccca gcgcgccgcc cgctcctcac gtgtccctcc cggccccggg     60
```

```
gccacctcac gttctgcttc cgtctgaccc ctccgacttc cggtaaagag tccctatccg    120
cacctccgct cccacccggc gcctcggcgc gcccgccctc cgatgcgctc agcggccgca    180
gctcctcgga gtcccgcggt ggccaccgag tctcgccgct tcgccgcagc caggtggccc    240
gggtggcgct cgctccagcg gccggcgcgg cggagcgggc ggggcggcgg tggcgcggcc    300
ccgggaccgt atccctccgc cgcccctccc ccgcccggcc ccggcccccc tccctcccgg    360
cagagctcgc ctccctccgc ctcagactgt tttggtagca acggcaacgg cggcggcgcg    420
tttcggcccg gctcccggcg gctccttggt ctcggcgggc ctccccgccc cttcgtcgtc    480
ctccttctcc ccctcgccag cccgggcgcc cctccggccg cgccaacccg cgcctccccg    540
ctcggcgccc gcgcgtcccc gccgcgttcc ggcgtctcct tggcgcgccc ggctcccggc    600
tgtccccgcc cggcgtgcga gccggtgtat gggcccctca ccatgtcgct gaagccccag    660
cagcagcagc agcagcagca gcagcagcag cagcagcaac agcagcagca gcagcagcag    720
cagcagccgc cgcccgcggc tgccaatgtc cgcaagcccg gcggcagcgg ccttctagcg    780
tcgcccgccg ccgcgccttc gccgtcctcg tcctcggtct cctcgtcctc ggccacggct    840
ccctcctcgg tggtcgcggc gacctccggc ggcgggaggc ccggcctggg cagaggtcga    900
aacagtaaca aaggactgcc tcagtctacg atttcttttg atggaatcta tgcaaatatg    960
aggatggttc atatacttac atcagttgtt ggctccaaat gtgaagtaca agtgaaaaat   1020
ggaggtatat atgaaggagt ttttaaaact tacagtccga agtgtgattt ggtacttgat   1080
gccgcacatg agaaaagtac agaatccagt tcggggccga aacgtgaaga aataatggag   1140
agtattttgt tcaaatgttc agactttgtt gtggtacagt ttaaagatat ggactccagt   1200
tatgcaaaaa gagatgcttt tactgactct gctatcagtg ctaaagtgaa tggcgaacac   1260
aaagagaagg acctggagcc ctgggatgca ggtgaactca cagccaatga ggaacttgag   1320
gctttggaaa atgacgtatc taatggatgg gatcccaatg atatgtttcg atataatgaa   1380
gaaaattatg gtgtagtgtc tacgtatgat agcagtttat cttcgtatac agtgccctta   1440
gaaagagata actcagaaga atttttaaaa cgggaagcaa gggcaaacca gttagcagaa   1500
gaaattgagt caagtgccca gtacaaagct cgagtggccc tggaaaatga tgataggagt   1560
gaggaagaaa aatacacagc agttcagaga aattccagtg aacgtgaggg gcacagcata   1620
aacactaggg aaaataaata tattcctcct ggacaaagaa atagagaagt catatcctgg   1680
ggaagtggga gacagaattc accgcgtatg ggccagcctg gatcgggctc catgccatca   1740
agatccactt ctcacacttc agatttcaac ccgaattctg gttcagacca aagagtagtt   1800
aatggaggtg ttccctggcc atcgccttgc ccatctcctt cctctcgccc accttctcgc   1860
taccagtcag gtcccaactc tcttccacct cgggcagcca cccctacacg gccgccctcc   1920
aggcccccct cgcggccatc cagacccccg tctcacccct ctgctcatgg ttctccagct   1980
cctgtctcta ctatgcctaa acgcatgtct tcagaagggc ctccaaggat gtccccaaag   2040
gcccagcgac atcctcgaaa tcacagagtt tctgctggga ggggttccat atccagtggc   2100
ctagaatttg tatcccacaa cccacccagt gaagcagcta ctcctccagt agcaaggacc   2160
agtccctcgg ggggaacgtg gtcatcagtg gtcagtgggg ttccaagatt atcccctaaa   2220
actcatagac ccaggtctcc cagacagaac agtattggaa ataccccccag tgggccagtt   2280
cttgcttctc cccaagctgg tattattcca actgaagctg ttgccatgcc tattccagct   2340
gcatctccta cgcctgctag tcctgcatcg aacagagctg ttaccccttc tagtgaggct   2400
```

```
aaagattcca ggcttcaaga tcagaggcag aactctcctg cagggaataa agaaaatatt   2460
aaacccaatg aaacatcacc tagcttctca aaagctgaaa acaaaggtat atcaccagtt   2520
gtttctgaac atagaaaaca gattgatgat ttaaagaaat ttaagaatga ttttaggtta   2580
cagccaagtt ctacttctga atctatggat caactactaa acaaaaatag agagggagaa   2640
aaatcaagag atttgatcaa agacaaaatt gaaccaagtg ctaaggattc tttcattgaa   2700
aatagcagca gcaactgtac cagtggcagc agcaagccga atagccccag catttcccct   2760
tcaatactta gtaacacgga gcacaagagg ggacctgagg tcacttccca aggggttcag   2820
acttccagcc cagcatgtaa acaagagaaa gacgataagg aagagaagaa agacgcagct   2880
gagcaagtta ggaaatcaac attgaatccc aatgcaaagg agttcaaccc acgttccttc   2940
tctcagccaa agccttctac taccccaact tcacctcggc ctcaagcaca acctagccca   3000
tctatggtgg gtcatcaaca gccaactcca gtttatactc agcctgtttg ttttgcacca   3060
aatatgatgt atccagtccc agtgagccca ggcgtgcaac ctttataccc aatacctatg   3120
acgcccatgc cagtgaatca agccaagaca tatagagcag taccaaatat gccccaacag   3180
cggcaagacc agcatcatca gagtgccatg atgcacccag cgtcagcagc gggcccaccg   3240
attgcagcca ccccaccagc ttactccacg caatatgttg cctacagtcc tcagcagttc   3300
ccaaatcagc cccttgttca gcatgtgcca cattatcagt ctcagcatcc tcatgtctat   3360
agtcctgtaa tacagggtaa tgctagaatg atggcaccac caacacacgc ccagcctggt   3420
ttagtatctt cttcagcaac tcagtacggg gctcatgagc agacgcatgc gatgtatgca   3480
tgtcccaaat taccatacaa caaggagaca agcccttctt tctactttgc catttccacg   3540
ggctcccttg ctcagcagta tgcgcaccct aacgctaccc tgcacccaca tactccacac   3600
cctcagcctt cagctacccc cactggacag cagcaaagcc aacatggtgg aagtcatcct   3660
gcacccagtc ctgttcagca ccatcagcac caggccgccc aggctctcca tctggccagt   3720
ccacagcagc agtcagccat ttaccacgcg gggcttgcgc caactccacc ctccatgaca   3780
cctgcctcca acacgcagtc gccacagaat agtttcccag cagcacaaca gactgtcttt   3840
acgatccatc cttctcacgt tcagccggcg tataccaacc caccccacat ggcccacgta   3900
cctcaggctc atgtacagtc aggaatggtt ccttctcatc caactgccca tgcgccaatg   3960
atgctaatga cgacacagcc acccggcggt ccccaggccg ccctcgctca aagtgcacta   4020
cagcccattc cagtctcgac aacagcgcat ttcccctata tgacgcaccc ttcagtacaa   4080
gcccaccacc aacagcagtt gtaaggctgc cctggaggaa ccgaaaggcc aaattccctc   4140
ctcccttcta ctgcttctac caactggaag cacagaaaac tagaatttca tttattttgt   4200
ttttaaaata tatatgttga tttcttgtaa catccaatag gaatgctaac agttcacttg   4260
cagtggaaga tacttggacc gagtagaggc atttaggaac ttgggggcta ttccataatt   4320
ccatatgctg tttcagagtc ccgcaggtac cccagctctg cttgccgaaa ctggaagtta   4380
tttatttttt aataaccctt gaaagtcatg aacacatcag ctagcaaaag aagtaacaag   4440
agtgattctt gctgctatta ctgctaaaaa aaaaaaaaaa aaaaaatcaa gacttggaac   4500
gcccttttac taaacttgac aaagtttcag taaattctta ccgtcaaact gacggattat   4560
tatttataaa tcaagtttga tgaggtgatc actgtctaca gtggttcaac ttttaagtta   4620
agggaaaaac ttttactttg tagataatat aaaataaaaa cttaaaaaaa atttaaaaaa   4680
taaaaaaagt tttaaaaact gaaaaaaaaa aa                                 4712
```

<210> SEQ ID NO 4
<211> LENGTH: 151001
<212> TYPE: DNA
<213> ORGANISM: Homo sapiens

<400> SEQUENCE: 4

```
tcccaaagtg ctgggattac aggcgtgagc caccacactg gccaaaactt gttcttaaga     60
ttgtattctg ggaccttgat tccaatcaga gaaaagtgat tgtatttttt tatttttatt    120
tttttagat aaagtttcgc tcttgttgcc caggctggag tgcagtggtg ccctctttgg     180
tcactgtaac ctccgcctcc tgggttcaag cgattctcct gcctcagcat cctgcgtagc    240
tgagatcaca gatgcccacc accacgccca gctaattttt tcgtattttt agtagcgatg    300
gggtttcacc atgttggcca cgctggtctt gaactcctga cctcaggtga tccatccgcc    360
tcggcctccc agagtgctgg gattacaggt gtgagccacc gcgccaggcc aagtgtttgt    420
atttctatta aagaaagaat ataacgggac accattgacg acctgctcca ttgcaggcct    480
ccttgctgtt cctcagactc ccccctcaga gcctttgccc tcgctgtgcc ctccacctgg    540
agcgtttctc cccaggatcc tcatgcccat gctcatttgg gtccctgccc catgtcaccc    600
tctccaggag cttcccctca cagcagccct ggcctgtacc acagccgggt acaggtattt    660
ttttgtttca actggttttt tagttccagt ttcctttagg ttactttatt tatttattta    720
tttatttatt ttttgagacg gagtctcgct ctgtcgccca ggctggagtg catgatctcg    780
gctgactgca acctccacct cccggattca agcaattctc ctgtatcagc ctcccgagta    840
gctgggatta caggcgccca ccaccacacc cggctaattt ttatattttt ggtagagacg    900
gggtttcacc atgttggcta ggctaggtta atttttaaag ggttttgcaa tggtcccttg    960
atctactttt taccttagat gggaaataaa actgatttcc tacattggca gaatacaatg   1020
atcatttttg cctggactat ctaggaggtt aatttcagtt ggactactga aaactgctgg   1080
ttcaatcatt ctccacgttt atctaagtct ttacctttat ctggacagtt ctaggacatt   1140
gaggggaatt ttggtgtttc ttcccctatt atttcctgaa gtcatttcac tttaaaaaac   1200
aatagattca ctgctcaaaa aaaaaaaaaa aagttaccta ctttctactt gcttccagtt   1260
taactgcaac acattttaaa aagagtctac tgtgctggct gggtaagtta aattaaaact   1320
tctaaagggt ccaaggtcta aagttcgcac attgttttga ggtcggctct gtctctaccg   1380
agggagatcc cattatccgt agttctacca gtcccaatcc catatatttc ctttagaatc   1440
tcatgaatga ggaaaaagaa gttcaagtga gggaacatag gttcaaatga aggtcagata   1500
cctaaaagag ttttctggtg actgtgcgcg gctggggtgg aaaaagtggg gaaaaggtac   1560
ccagatgtgg gtggccccgg agggttgctc cactccagcc ccggcagggc aggacagcgc   1620
ggcctgcctg gtagatgccc cgagccactg gagcgcctac tgtgtggcgg gcgggggacg   1680
gcaggaaaac ggcaggatgc tgtgtcccct gaatctggca gggttctagg tgctttacac   1740
gtagcaagac acattctccg ccccaaggca ctcgcagtca gtccattttc tgggttgcat   1800
caggtggggg caaactaggt ccccgcagaa gtgaagatgc tgaaggaata cagtaggaga   1860
agaaatgctt ctctcctgtc ctccacacca ggcaggcccc agaggctgag accgacacgc   1920
cctcccccgaa gggcagaccc gccttgagga aggcggatcc gggtagggac cgccgcctgg  1980
ccctcacccg acccccgaga aagcaaccca gcgcgccgcc cgctcctcac gtgtccctcc   2040
cggccccggg gccacctcac gttctgcttc cgtctgaccc ctccgacttc cggtaaagag   2100
tccctatccg cacctccgct cccacccggc gcctcggcgc gcccgccctc cgatgcgctc   2160
```

```
agcggccgca gctcctcgga gtcccgcggt ggccaccgag tctcgccgct tcgccgcagc   2220
caggtggccc gggtggcgct cgctccagcg gccggcgcgg cggagcgggc ggggcggcgg   2280
tggcgcggcc ccgggaccgt atccctccgc cgcccctccc ccgcccggcc ccggcccccc   2340
tccctcccgg cagagctcgc ctccctccgc ctcagactgt tttggtagca acggcaacgg   2400
cggcggcgcg tttcggcccg gctcccggcg gctccttggt ctcggcgggc ctccccgccc   2460
cttcgtcgtc ctccttctcc ccctcgccag cccgggcgcc cctccggccg cgccaacccg   2520
cgcctccccg ctcggcgccc gcgcgtcccc gccgcgttcc ggcgtctcct tggcgcgccc   2580
ggctcccggc tgtccccgcc cggcgtgcga gccggtgtat gggcccctca ccatgtcgct   2640
gaagccccag cagcagcagc agcagcagca gcagcagcag cagcagcaac agcagcagca   2700
gcagcagcag cagcagccgc cgcccgcggc tgccaatgtc cgcaagcccg gcggcagcgg   2760
ccttctagcg tcgcccgccg ccgcgccttc gccgtcctcg tcctcggtct cctcgtcctc   2820
ggccacggct ccctcctcgg tggtcgcggc gacctccggc ggcgggaggc ccggcctggg   2880
caggtgggtg tcggcacccc agccccctcc gctccgggcc cggcgtcccc tcccccgcgg   2940
cccgcgccgc cgtccccgcc ccgtgacccg ccgggctacc cggggtgggc tgggggccgg   3000
cagcgcgggg gagactcgct cgggcctgag ccccgaggct cggccggtgg gcgcagccgg   3060
ggtcctctgg gattgtcagg cctgtccagc ctcccgcagc atccccgccc cctcccccgg   3120
cggtcaagat ggagggagcg ggcggcctcc cctccccacg cgtgttggga ggggttctcg   3180
ggtagcggcg atggtcagcc ccggctcccc cttccgcacg atcctccgcc cgcagcgtgg   3240
ggatgctcgg gcagctcctc cactcccggt ttaggtgtga acgttggagg ggtctggagg   3300
ctgtggtggc gttttccgga acatgtcccc ctccatgggg gacatctctg gaggggagaa   3360
gttagggccg cgtcccccgt gccggttaaa ggggtaggca ccgggctcct ccggaatcat   3420
cagggtctgt cggggctctc tccccgcccc ctccgagtcc tgggaaagat cggaggacgg   3480
ggtggagaca agtgggcctt ggcccccgca cccctctgcg ttcgtgtccg aggcggcggc   3540
gggggctccc gaactcccct gaaatcgtgg ggctccatgt ggcctccggc agcgttccac   3600
cctcccccac ctggggaagg gaaggggtgg ggagtgcccg gccccgtccc ggccttcctc   3660
cttcccccgc cagacctctc cggcgcgcgg gtggtggccg atccgcattg ctgttcgagg   3720
ccgcagtgga gaaggcgcct gtggaacatc ggtgggtgag ggctggaccc aggctggacc   3780
ctggagatcc ggggtggcgg tgctggtggc agggggcggg caccctgcgc acttatccca   3840
acccccgccc caatttcgga aatgctagga gagagagatt gcagcagggg acgtggtcgg   3900
gttcctgaag gcagaaaggc gggtgtttac tagcgtcttt ttccctccta agccggggtt   3960
gtagtagggg ctgggggctc agtgttgtcc cggctaactg ggtttgactc gagggtgtgt   4020
ttgtgcagga gggcctgttg ggggtggcgg gcggttgtca gttcgtattt cacgaactaa   4080
gaaaatgctt agtgttcaaa gggagaagga aacgtcaata gactccattc cattgtggcc   4140
ggtgtcctta acttcgggag tgccgccaga gcttaccaag ggcacgcaag tccatttccc   4200
ttgtgcctca agtccatccg tgttgtaggc actactgtgc cttctttagg cctaggccgc   4260
cggcttgacg gcgggtgacc ggcgtcctcc ttaaataggc atcttgggct ttggaaggtg   4320
gaataagagg atttttcatt cacccgagtt ttctttttga aaacacattt tcagcaaccc   4380
atttccaaag aatttttatt tacagcagaa attccccatc aagaggaatc agctggtttt   4440
taaggaattc tgctgccttc aaagggggcg gaaacagtcg gttatttgac tttacacgcc   4500
ccgccccccc ttccccttct ctgagtctga agcatcccaa acactactta gccaaactag   4560
```

```
ttcagatgaa gtgatcgttt ccccaagtag ggtaacttca gtttcccttt ttcgttggca   4620
tctagcgaaa aatgaaaaaa tttaaaatac aacttttata gaaaaggatg tattctgttt   4680
ttactttctt aggtattagg aagagatttg gcagataatt caacatgttc aaatatataa   4740
acattaaaac taaggttatt aagttgcatt gactactagg cttaaaaatt agattataag   4800
agaatttgct cctgagtagt ttgagtgatc aaagatattt ggaatgtttt agtaccacaa   4860
ggtctttttt ctgttccttg aggctttaca acaatttaag gttaatttag atttttcctt   4920
gctttaagtt cttttacttg agacctaaat ggcagccctt attctttctg atgaataggt   4980
gaaattttgt ttactgtgtt ggatttgtgt aatgtgaagt tttattcttg aacagatcgt   5040
taatgtactt gtagaattac tttgaatttg aatcactttc ctgcattcct tgtaaataag   5100
tttcagcttc tagaatctcc tcacttaggt ttgtgcgtat caacagtgaa aataagtctc   5160
tgagagcaag ggtgaaaaaa aatgcagcat tcggtttgac aagtttcgag atagcaaaat   5220
atgcttgaaa gtctggaaat tcacatctgc tttaagaaac atttcataat ttgactttgt   5280
gtgtgtgtgt gtgaatagtt tttcatgact ttcagaagtg atttattttg ttctttgtta   5340
tatatatttt tgaaggtggc tgttttagga aagataatgt aatcacaata ttagaacata   5400
attttactgt aatctaattt tgtgtgtgtg tgtgtgtgtg tgtgtgtgtg tgtgtgtgtg   5460
ttttggatgg aatctcactc tgtcgcccag gctggagtgc agtggcctga tctcagctta   5520
ctgcagtctc tgtctcctgg gttcatttaa gtgattctcc agcctcagcc tccccagtag   5580
ctgggattac aggttcgtgc taccacacct ggctaatttt tttgtatttt tagtgaggac   5640
gggattttgc catgttggcc aggctggtct cgaactcctg acctcaagtg atccgcctgc   5700
cttggcctcc caaagtgctg ggattacagg cgtgagctac tgcccctggc caatttttgt   5760
atttttagta gagatggggt ttcaccatgt tggccaggct ggtctcgaac tcctcctgac   5820
ctcaagtgat tcgccagcct cggcctccca aagtgccagg attacaggca ggaatgagcc   5880
actgccccca accatcagtc taattcttat ttttgctttt taccttttca tttttatgta   5940
gtagaggtga ttgtgtatgt tattttgtag ttagcttttt tcccctgaac gttgtattgt   6000
aaatgtaaat tttttttttt ttttttgaga cagagtctcg gtgtttgccc agtctgaagt   6060
gcagtggtac gatctcagct cactgcagcc tctgactcct gggttcaagc gattctccca   6120
cctcagcctc ttgagtagct ggggctacag gaatgttcca ccacgcttgg ctaatttttg   6180
tatttttggt agagacaagg tttcaccatg ttggccagtt tggtctcgta ctaccgacct   6240
caggtgatgc gcccgcctcg gcctcccaaa gtgctgggat tgcaggcgtg agccactgcg   6300
cccggctgta aggtttttac ttaaccattc tattgttggg aattgggttt ccactttttt   6360
gttatagata gtggtgcagt gaacattttt aaatagcttt ttgcttcagt gtaattattt   6420
ccttagagaa agttaccaag agtggtttta ctagttcaga gggcttcagg atttttatgg   6480
ctcttgctag cggtgctcta ttattcttta gaagacttgt attacttcca gtgtcaagaa   6540
ggttgctctt ccatggaatg gtttctttgt agtttgtcaa atattgtggg gaatttttaa   6600
aggaaaaatt gcatttttac tgtcaagtgc atatattatt aagtgctttt gttagttact   6660
ggattattga tatttgagtt taatttggtt cctctgagga tttaataagg taatatatgt   6720
gaagatgttt tgaaacctgt aaccattatt attaatgagg gtacttggtt tatctgtcgt   6780
gctgatagta ctgagtaaag tgcaggaatg aaattcctga ggaactgttc taaagctttg   6840
ttgttgttgt taacctttct ttttcatctg aaagtgtttt ttattagctg ctagcctatg   6900
```

-continued

```
accaagttat ttttggtaac ttttttgtaa tttcatggca ctattgggaa ttttcgctgg   6960
ttgactcttc ttcttctaca ttcccttccc cattaaaaat aaaaatatgg atttacaatt   7020
gttactctat tcctaaacct aaataatatg acattagaat tgcttgggat acaggattca   7080
gtctgaataa aatatttttc ttttagtgat tttcagctta gtatttttac tgcttctttc   7140
tcttgaggca ttgcaactta aaaattgtgc tgtttagcca ggcgcctgta atcccagcta   7200
cttgggaggc tgaggcagga gcatcacttg agcccaggag gcggaggttg cagtcagctg   7260
agattgtgcc actgcactcc agcctgggag acagagtgag actctatctc aaaaaaaaaa   7320
aaaatgtgct gtgatttaat gtagttgttc atcatgcttc catttaaatt tcagtgagac   7380
tgttcatctt ttgcagttaa atatcttgta gaagggccta aaatatctac gttgaataca   7440
gctttattga agcatctatg tacatggggt ttttgggatg aatcagtgaa taaagcaaac   7500
atattgtcct tttggagttt acattctaat gtgactaggc agacaatgag acattaaatt   7560
accagcctat gtataatagt gtataagagc tatggaatta gaagaaagca gattaaaggt   7620
atagggagtg tggggagggg aatgagttac aattttaaat ggattggggg aacttaattg   7680
aggagctaac atttgagcaa agatttgaag gttgggtatt tagccgtttg ctttttatct   7740
aggttaatta gtcatgtggc ttcattagta atttataagg tttaaatggc atcatccttt   7800
gttattcttt tatgtgcaca ttgatactaa ccatctctga agttagacca aaaaagttaa   7860
ttgacattga gggtcattag aggtaaattg tagatggcta ttactaacca aagagacatg   7920
ttttgttttt cttttgggct tacgtatttt acctaattag tttagttttt gtttcaagta   7980
tgtggagaaa ataaactttt taagtttggg ccaaaacttg ctttggtttt ctttttcttt   8040
ttcttttttt ttttttaaga gaaaaatgta agcctgtagt tgcttaaaga ttccacattc   8100
tgaaacagtg aaaacatggg atcagtcatg gtgttccttt ttttggttaa atgtaaactt   8160
gtattttcag tgttactcta attagcaatg gtttatactt ctacataagg gatgttaact   8220
catattgtag ctatttaata gccatatatt ttgacttaaa ggaggatctc aaggccaggc   8280
gcggtggctc atacctgtaa tcccagcact ttaggaggct gaggcgggtg gatcacctgg   8340
ggtcaggagt ttgagactag tctggccaac atggtgaaac cccatctct actaaaaata   8400
caaaaattag ccgggcatgg tggtgggcgc ctgtaatccc agcttcttgg gaggctgagg   8460
gaagagaatt gcttgatccc ggaggttgca atgagtgcgg aggttgcagt gagctgagat   8520
catgccatta cactccagcc tgggcaacag agcgagactc tgtctcaaaa caaacaaaca   8580
aacaaaaaaa ggaggatctc attttttttgt cctaaatagc tacagccgtg ttagaactgt   8640
caccttagca aagtattgtt tttttacttt gaaacgaatt ttaaggtttt agaagattgt   8700
tctctagaat tacaattttc tgttttgact agtgatagta ttttgatgtt gtgtaaatag   8760
ttgagcatga acaaaaccct attttttttt ttagctattt caagtgattg tgacaacttc   8820
aacggagatg taaacagttt attaacagtc acacctatta tcttttttttt tttttttttt   8880
ttttgagacg gagtcttgct ctgtcgccca ggctggagtg cagtggcacg atctctgctt   8940
actgcaacct ttgcctcccg ggttcaagtg attctcctgc ctcagcctcc tgagtagctg   9000
ggtctacatg cgcacaccac cacgcctggc taatttttgt atttttagta gagacagggt   9060
ttcaccatgt tggctagaat ggtctcaaac tcctgacctc aggtgatcca cctgcctcag   9120
cctcccaaag ttctgggatt acaggcatga gccaccgtgc ttggccgctg ccgtatcttt   9180
ttaaatgaaa gtacttgtgt ttttttttgtt tttttccaaa ggatatctgg gtcatctatg   9240
atgttactgt taccatctaa gggttttttt gtttgttttt gagacagagt ctctgtcgcc   9300
```

```
caggctggag tgcagtggcg tgatcttggc tcactgcaac ctccgcctcc caggttcaag   9360
caattctcct gccttagccc tcccgaatag ctgggattac aggcacccgc caccatgcct   9420
ggctaagttt tgcattttta gtagatatgg agtttcacca tgttggccag gctgctcttg   9480
aactcctgac ctcaggtgat tcgcttgcct cggcctccca aagtgctggg attacaggcg   9540
tgagccaccc ccgcccagcc tcatgagcta aggtgttttt tttttttttg agacagtttt   9600
gctctttccc aggctggagt gcagtggtgc aatctcagct cactgcaacc tctgtttccc   9660
gggttcaagc gattctcctg cctcagcctt ctgagtagct gagattacag gtgcctgcta   9720
ccccactcag ctaatttttg tatttttagc agagacaggg tttcaccatg ttggttaggc   9780
tcatctcgaa ctcctgacct taagcgatcc acctgccttg gcctcccaaa gtgctgggat   9840
tataggcatg agccaccgtg cgcagcctac cctgtctctt aaaaaacagt aacaacaaca   9900
acaacaacaa aaaatcctaa atcttaaaaa tggaaggcaa aaactctaag ctttgagaga   9960
ttaggggact tgcccaaagc aatatttgta ggattttatt acacctctcc ctttatttat  10020
tttttagag tcaaggtctc cctctgtcac ccaggctgga gtgcagcctc aatctatggg  10080
gccaagcatt tctcctgtct tagcctcctg agtagctgga actacaggtg tacaccagct  10140
ggctaacatt taaatttttt gtagagacag ggtcctgcca tgttgcccag attggtctca  10200
aactcctggg ctcaagtgat cctcctgcct cagcttccca aagtgctgag attacaggtg  10260
tgagccactg caccgagccc cctcccttta tttttatttt taaattttaa gttctggggc  10320
ccctcccttg aaataaatag aaacgtaata tatacacaag atcatgctgt gtattttaag  10380
gcaatggtcc tcaacctttt taacactagg gaccggtttt gtggaagatg gtttttccat  10440
aggggcaggg gatgattttg agatgaaact gttccaccgg ccgggcacgg tggctcacgc  10500
ctgtaatccc agcactttgg gaggccgagg cgggcagatc acgaggtcag gagatcgaga  10560
ccatcctggc taacatggtg aaacccccct ctactaaaaa tacaaaaaaa ttagctgggc  10620
gcggtggagg gcgcctgtag tcacagctac tccggaggcc gaggcaagag aatggcatga  10680
aacccgggag gcagagcttg cagtgagctg agatagcacc actgtacttc agcctggggg  10740
acaaagtgag actccgtcta aaaaaaaaaa aattgttcca cctcagatca ttatgcattt  10800
gttagattct cataaagagc atacaaccta catctcttgc tatatgcagt tcccagtagg  10860
gtttgtgctt ctataagaac ctaatgctgc acctgatcta acaggtgggg ctcaggtgct  10920
aatgctcaca cagctcctgt tgtgcagtct ggttcctaac aggcctgttt tttttttttt  10980
aattagatgg agtctcgctc tgtcaccagg ctggagtgca gtggcacgat ctcagctcac  11040
tgcaacctct gcctcccggg ttcaagcgat tctcctgcct tagcctccca tgtagttggt  11100
actacaggcg cacactgtga tgcccagcta atttttgtat ttttagtaga gacggggttt  11160
caccatgttg gccaggatgg tgtcgatctc ctgaccttgt gatccgccca acagcctccc  11220
aaagtgctgg aattacaggc gtgagctgct gcgtccggcc ccctaacagg cttgttttat  11280
ggaatacagt cacggacagt acttgccctt caggatatct ttttgtaacc ttgattttgg  11340
cttgctaaaa taggaggtct attttctttt ctttgttttt aatgtatgtg gttctgtact  11400
tacgtggtgt gaaatctaca taaatgttaa atccttggtt atttatttat tttgagacag  11460
agtctcactc tgtcacccag tctggaaagc agtggcataa tctcggctca ctgtaacctc  11520
cacttcccag gttccagtga ttctcctgcc tcagcctcct gagtagctgg gattacaggc  11580
atgcaccact acacctggca aatttttgta ttttttttta gtagagatgg ggtttcacca  11640
```

```
tgttggccag gctcgtcttg aactcctgac cttaggtgat ctgcctgtct tggcctccca  11700
aagttttggg attacagcat gagccactgc gcctcgcctt attttttga gacaggttct  11760
agctctgtca cccaggcggg agtgcagtgg tgccatcatg gctcattgca acctcgagtt  11820
ctcaggccca agtgatcctc ctatctcagc ctcctgagta gctgggacca caggcatgcg  11880
ccactatgcc cagcaaaatt tttgtttcac tctgttgcct agggtggggt gcagtggcag  11940
gatatcggct cagtgcaacc tctgcctctt gcgttcaaat gattctcatg cctcagcctc  12000
ccgagtagct gggattatag gcatgcgcca ctacacctgg ctaatttttg tattattggt  12060
agagatgggg ttttatcatg ttggccaggc tggtctcgaa ctcccgacct caggtgatcc  12120
atataccttg gcctcctgaa gtgctggaat tacaggcata agccactgcg cctagctttt  12180
ttgtttgttt ttattttgta gggacagaga ttttacctgt tgcccaggat ggccttgaat  12240
tcctgacctc aaacaatttg ccctccttgg cctcccaagg tgctgggatt acaggtgtga  12300
gccactatgc ctggctggtt ttttaaatta ttattattgt ttgtgtgtgt gtgttgcagg  12360
atcttaccct gtcacccagg ctggaatgca gtgatgtgat ctcggcttac tgcaacctcc  12420
gcctcctagg ttcaagtgat tgtcctgcct cagcctcctg agtagctggg ataacagctg  12480
tgtgccacca tgcctggcta atttttgtat ttttagtaga gatggggttt catcatgttg  12540
gccaggctgg tctcgaactc ctgaccttag atgatccacc cgcctcgtcc tcccaaagtg  12600
ctgggattac aggtgtgagc caccgtgacc agtttggttt agtttttttt tttttttttt  12660
tttttttttt tttttgagaa atctcgctct gtcgcccagg ctagagtgcg gtgacacaat  12720
ctcagctcac tgcaagctcc acctcccagg ttcatgccat tctcctgcct cagcctcccg  12780
agtagctggg actacatgcg cccgccacca tgcccggcta atttttttta tgcattttaa  12840
gtagagatgg ggtttcactg tgttagccag gattgtctca atctcccgac ctcttgatct  12900
gcccgcctcg gcttcccaaa gtgctgggat tataggcatg agccaccgcg tccggcctgg  12960
tttggtattt tttttatgag tctgggttgt ttatgaaaac ttgtcacagc tgttaacctt  13020
aacttttttt ttttcttttt tttccgagac ggagtctcgc tctgtcacct aggctggagt  13080
gcagtggtgc gatctcggct cattgcaacc tctgcctccc aggttaaagc gatttttctg  13140
cctcagcctc ctgagtagct gggactgcag gcacgcacca tctcgcctgg ctaatttttg  13200
tattttagta gagatggggt ttcaccatat tggccaggct ggtctggaac ttctggcctc  13260
aagtgatcca cctgccttgg cctcccatgc ctggcaacct taactttta tttgctggta  13320
attatttgtg tttgcattca tgtgaaaatt tgaaattctc attaacattt aaagattctt  13380
acatagattg cttgtaattt taaccctgaa gttgtgtcaa gtgactttac aatgtcaatt  13440
tgttttattt atttatttat ttatttattt atttattttt gtgataggat ctggctctgt  13500
tgctaaggct ggagtgcagt gttgcaaata cggctcactg caacctctgt ctcccgggtt  13560
caagccatcc tcccacctca gcctcccaag tagttggaac tactggtgcg ccccacagtg  13620
cctgcctagt ttttttgtat tttcagtaga tgtggagttt tgccatgttg atcttgaact  13680
catggcctcg agtgatccac cccacttagg cctcctaaca tgctggtgtt acaggtgtga  13740
gccactgtgt ccagcccgaa aatgtcagtt tcgtgccatg attaatagct aactacattt  13800
tgggaatgta ataaaatttc attctataat gaagtctttg taaaactcat tagttgtggt  13860
atgaggcttg tcggcaatat aagtgaacgt ggtttatttt tattaactgt atcagaactt  13920
tagaatgttg gtctcctgaa accattgcct tgagaggctt tattgaacag tgttgccaat  13980
gatcagtttt tttttaaatt tcctttttt tgagactgag tcttaccctg ttggccaggt  14040
```

```
tggagtatag tggtatggtc atggctcact gcagcctcaa catcctgggc tcaagcagtc  14100
ctcctacctc agtctcccga gtagctggaa ctacaggtgt atgccaccat gcctggcttt  14160
tgtatatttt gtagagacag ggtttagcca tgttgcccag gctggtctca aactcttaaa  14220
ttcaaatgat ccacccacct agttttccca aagtgcttta attacatgtg tgaggcaccg  14280
tggctggcca ggtcaaatat ttttcattga cgtttttcat attgcttttt aaagtcatgt  14340
taaaatattc ttaataattt ttctaagtgg aattaatctt gattataatt ttagtttttt  14400
ataaagggcg ggttttgaaa caagtactgc atttttcttt tcgggtttat aaacatttgc  14460
tgtggacttt gtgcagttaa ctattttcat tcctgaaaca catttcgaaa tcaggaattg  14520
aagactaaat gtcttttcac tgaagcttga gcagatttta gaaaggggag ttcttttttt  14580
tttttttttt tttggtagaa atgggggtct tgttatgttg cccaggctgg cctccaactt  14640
ctgggcttaa actgtcctcc tgctttagcc tctggtctgg agagttcttt atggcctctt  14700
tgagaacttt tactttacac atgattctat ctagctttct tttctgatgt acatattggc  14760
agcaagtaga aaagcaatgt tttcagaggc agatatatta acagcaatga gaaataacag  14820
tagcgtgata gaaagttgaa agacttagct gggtgcggtg gctcacgctt gtaatcccag  14880
cactttggga ggccaaggag ggtggatcac ttgaggtcag gagttcgaga ccagtctggc  14940
caacatggtg aaaccctgtc tctactgaaa aacagaaaaa gggccgggcg tggtggctca  15000
cccctgtaat cccagcactt tgggaggttg aggagggcgg attacaaggt caagagattg  15060
agaccattct ggccaacagg gtgaaacccc atctctacta aaaatacaaa aaaattaaat  15120
gggcgtggtg atgtgtgcct gtagtcccag ctactcggga ggctgaggca ggagaattgc  15180
ttgaacccgg gaggcagagg ttgcagtgag ccgagatcgg gccactgcac tgacgacaga  15240
gggagactcc gtctaaaaaa aaaaaaaaaa aaaaaaaacc agacttgggg ctgggcgggc  15300
gcctgtaatc ccagctactt gggaggctga ggcaggagaa tcgcttgaac ccgggaggtg  15360
aaggttgcag tgagctcaga ttgtgccact gtgccccagc ctgggccaca gagcagagtg  15420
agactctgtc tcaaaaaaaa aaaaaaagtt tggaagactg gtggctgggc atggtggctc  15480
acacctgtaa tcccaacact ttgggaggct gaagcaggca gattacctga gcccaggagt  15540
tcaagtccag cctgggcaac acagggaaac cccatctcaa caaaaaatat taatacaaaa  15600
aatttagcca gtcatggtcg tgcacttctg tagtctcagc tacttgggag gctgaggcag  15660
gtggttcact taagtctgga tgtcgaggtg agccatgatt gcaccactgc actccagcct  15720
gggcgttaaa atgagacctt atctcaaaaa aacaaagcaa agagcctggg aactactaaa  15780
atgggaacta ctaaaaaaca gacacaagag ctcaacaagt ataccattct gggaggtttt  15840
tttttttttt tttttttttt tttttgagat ggagttttgc tcttgtcacc caggctggag  15900
tgcaatggcg ccatctctgc tcactgtagt tccgcctccc aggttcaagc agttctcctg  15960
cctgactcct gagtagctgg gagtacagat attggtcaca caccgggtta atttttgtat  16020
ttttagtaga gacggggttt ccccattttg gccaggctgg tctcgaactc ctgacctcag  16080
gtgatccgcc tgcttcagcc tcccaaagtg ccgggaccac aggcgtgagc caccgcacct  16140
ggcttttttt ttttgacata gaatcttgtt ctgttgccca ggctggagtg caatggtaca  16200
atcttggccc actgcaacct ctgcctccca gcttctagcg attttcctgc ctctgactcc  16260
tgagtagctg ggattacggg tgcccgccac cacacccgga taatttttgt atttttagta  16320
gagatggggt tttgccatat tggccaggcc ggtcttgaac tcctgacctc agatgatcca  16380
```

```
cctgcctagg cctcccaaag tgccgggatt acaggcgtga gccaccactc ccggcctggg  16440
agttttgact gtaagtttat agctgtatat cttaggccct aagggcatta ctgttttata  16500
gcacagtgta gttagttaat gtgctcataa tggtgactca taacaccagg ttaaatgatt  16560
ttttatatct cccaaagaag tatttttcaa tctgcagatc atgacccctt agtagattgt  16620
gaaacacatt agtggattat gacaagcatt tttagaaaaa tgaaaaagaa taagaagtgt  16680
taggatgcat tgcattattg aaataattgt ttttgagatg gagtttcgct cttagttgcc  16740
gaggctggag tgcaatggcc cgatctgcct cccgggttca agtgattctc ctacctcagc  16800
ctcctgagta gctgggatta cagacatgct ccaccatgcc tggctaattt tgtatttagt  16860
tttagtagag atggggtttc tccatgttgg tcaggctggt cttgaactcc tgacctcagg  16920
tgatccactt gcctcggcct cccaaagtgc tggggataca ggcatgaacc cctgtgcccg  16980
gcctaatttt tgtattttta gtagagatgg ggtttcacca tgttggccag gatagtcttg  17040
atctcttgac ctcgtaatct gcccacctcg actcccaaag tgctgggatt acaggtgtga  17100
gccactgcac ccagctgcca agaattgttt taagctttgg tttgagttaa tgtatatata  17160
ccgcattgta attcaaaatg taatttttgg ccaactctgg gcacattgcc tatggactag  17220
tcctgctctg ccacgagcag caacagttca atgaattttt tttttttttt tttttttttt  17280
tttttttttg agacagggtc tctgtcacca aggctagaat gtagtggtgc agtctcggct  17340
cactgcaacc tctgtttcct gggctcaagc gatcctccca cctcagcctc ctgagtagct  17400
gggagtacag gagcacgcta ccatgcctgg ctaatttttg tatttttga agagatgagg  17460
ttttgccatg ttgttcaggc tagtcttgaa ctctggagct cagatgatcc acccaccttg  17520
gtgtccagaa atgctgggat tacagggatg agccaccgtg cctagccaaa aattttttttt  17580
taagtaattt tttattgata tagtcaaaaa agttactgct ttagagccag agaaacgcag  17640
taaaaggatt gagaaagagt tttgaggtta tatctaagct agggttgtca gatttggcaa  17700
atagaaatac aggacactca gttaaatttg aatttttgat gaacattgac cagtttttta  17760
gtataattgt gtattaaatt gcatagaaaa aagttattta tctaaagttg aaatttaact  17820
gagcatcttg tattttatct ggcaactcca gtctaagctg gaatcatggt tcactgtttt  17880
tttttttttt tttttttttt gagtcggagt cttgctgtgt tgcccaggct ggagtgcaat  17940
ggtgcgatct tggctcactg caacctccac ctcctgtgtt caagtgattc tcctgcctca  18000
gcctcctgaa tagttgggat tacaggcacc caccaccatg cccagctaat ttttatattt  18060
ttagtagaga cggggtttc gccatgttgt tcaggctggt cttgaactcc tgacctcagg  18120
tggtccgccc acctgggcct cccaacgtgc tgggattaca ggcatgatct accgtgcctg  18180
gccatggttc actcttcagt aactaaaatt taagctctat gaaagcagga actttgtttt  18240
gttcactatt gattgtatcc ctatttcttg aatggttggc acttaactgc ttggtcacat  18300
gtttgaatgg gcaagttact cagccactct caggcttagt ttatttacct attaaaagag  18360
aaagaatatc ttccttggct gggcgcggtg gctcacgcct ataatcccag cactttggga  18420
ggctgaggcg ggtggatcac gaggtcagga gatcgagacc aacctgggca acattgtgaa  18480
acctcatctc tactaaaata gaaaaaatta gctgggcatg gtggtgcgca tctgtagtcc  18540
cagctactcg agaggctgag gcaggggaat cgcttgaacc caggaggtgg aggttgcagt  18600
gagccaagat tgtgccactg cactccagcc tgggcgacag aacgagactc tgtctccaaa  18660
aaaaaaaaaa aaacaaacaa aaaaaaaaac tgagatactg gccgggcgcg gtggctcgtg  18720
cctgtaatcc cagcactttg gaaggccgag gcgggtggat cacgaggtca ggagatcgag  18780
```

```
accgtcctgc ctaacatggg gaaaccctgt ctctactaaa aatacaaaaa attagccagg  18840
cgtggtggcg ggcgcctgta atcccagcta cttgggaggc tgaggcagga gaatggcgtg  18900
aacccgggag gcagagcttg cagtgagcgg agatggtgcc actgcactcc agcctgctgg  18960
gcgacagagc gagactccgt ctcaaacaaa caaacaaaca aacaaaaaaa ctgagatact  19020
aaagtcttaa tattttctgt ttttatgtat ttattttttg agatgggatc ttgctgtatt  19080
gcccaggttg gagtacagta ttgtgatcat ggcttattgc agcctttaac tcctgggttc  19140
aagtgatcct cccacctcag cctcctgagt agctgggacc acaggcacat gcaacatcac  19200
accctgcagt tctttttttt tttttgagac accgtctcgc tttgtcaccc aggctgcagt  19260
gcgtggtgca atttctgctc actctaacct ccacctcccg agttcaagca gttctgcctc  19320
agcctcctga gtagcttggg accacatgtg tgtgccatca tgcctggtta attttttgta  19380
tttttagtag tgacagggtc ttaccatgtt gcccaggttg gtctcaaact cctgagctca  19440
agtgatctgc ccgccttcgc ctcccaaagt gtctgcgccc tacaatttaa aaaaattttt  19500
gtagagacag tctcactgtt acccgggctg gttttgaact tctgccctca agtactcctc  19560
ttgccttggc ctcccaaagt attgaaatta aggccatgag gcagcacacc cagcctaaat  19620
tcttcttatg ttctgttctt ggcacatagt agatgttcaa caatgtagag tcaaacgcat  19680
ttggagttgg aatggctctg gtgttttttt ttttttttta aaccagaaac acgtgcagtt  19740
tattgaatgc cattgtagaa aagtgtgtga ggataaacgg ctgatagaga acttggctct  19800
gggggcaggg cgaggaatgg agggtggatg gagtacatgg gaatcagatc acgggcagag  19860
ctcctggcct agataatgcc tcctgatctg ttgatagact tgaaagatca acactgggat  19920
gatgctgagc agaatggtcg taatgatgcg cacaatcagg gcccagatgt tcaggcactt  19980
ggcggtaaag gcataggcct gggccctgat caggtcgcca accatcttct tgtccctaga  20040
cttcacggag taggccaatg ctatgaagcc caggcagcag gagttcatga agtgggtgtt  20100
gaacagggac cagacgacat ggtcgggcac ggagttctcg ctgtggatgg ggatcacggt  20160
ggacattggg ggagcagggt tgtggggtgc ccccagcaca gccacctctt gctcctcctt  20220
gagcatctca tagttagggg gatggccgat gttggcagga gtgaagaggt ttggacattg  20280
tggttcatgg tgtccaggga agaccagctg tggtcgggtt gctggggtgg ttctcagtgg  20340
gcccctccct ttccctggta gtttggattt ctctggctct ggtggttttt tagtactcat  20400
tctatttacg ggtgaagaaa ttgagaccaa gagggttatt taccagagta tctcatcatt  20460
ggctgcataa ctggcattag aatctgatgt acttttattt ctaatacatt tctttttttt  20520
tttttttttt tgagatggag tctcgctctg ttgccgagcc tagagtgcag tggggcaatc  20580
ttggctcctt gcaacctcca cctcctgggt tcaagctatt cctgtctcag cctcccaagt  20640
agctgggact acaggcacct gccaccacag ccggctaggt tttgtatttt agtagagatg  20700
gggtagcacc atgttggcca ggctggtctc gaactcatga cctcaggtga tccacctgcc  20760
tcggcctccc agtgctggga ttataggcat gagccaccat gcctggcctt tctttgtcgt  20820
ttcctttctt tctcttcatc cctcctctcc ttttttcccc tccccgctgc ctcctcctgt  20880
cttcccttct ttccttcctt tctctccttt ttattttttc ctttcttttt ctttctctgt  20940
ctctcccaac ccttcctctc tccctccctc cctccccttc tctctccccc cctccctccc  21000
cttctctctc cccctcccct tttgttccta agagacaggg tctccttatg ttgctgaggc  21060
tgaccttgaa ctcctgagcc cagatgattc tgcctcctta gtagctggga ctacacccac  21120
```

ctcccgttcc gttgtcatct tttttttttt tttctttttt ggagacagaa tcttcctctg 21180
ttgctcaggg tggagtgtag tggcacgatc atagcttact gtaactgtgt aacctcgaat 21240
tcttgggctc aagcaatcat cccatcatcc cacctcagct tgctgagtac ctggggctac 21300
aggtgtgtac caccatgtcc ggctaattac ttttcttatt tttaattttt cggagatagg 21360
atcttgctct gttgcccagg ctggtgtcaa actcctgggc tcaagtgaaa ctcttgcctt 21420
ggcctcccaa agtgttggga gggattacag gcatgagcca ctgcacccag cctcctcttt 21480
cttcccattt aactcctaac cacaccgaac tttctgtctg cagagaggag cattggtcag 21540
cagttcacaa aatggctagg tgtgatggcg tgcacccata gtcccagcta cttggggagc 21600
tgaggtggga ggatcgctgg agcccaggag ttcaaggccc tgggcaacac agcaagacct 21660
tatctctggc tgggcccagt ggctcacgcc tgtaatccca gcactttggg aggctgaggt 21720
gggtggatca cctgaggtca ggagttcgag accagcctgg ccaacatggt gagaccctgt 21780
gtctactaaa agtacaaaaa ttagccaggc acggtggcgc gctcctgtaa tcccagctac 21840
tcgggggggc tgagacagga gaatcacttg aacccaggag gaggaggttg cagtgaacca 21900
agaacacgcc actgcactcc agcctgggtg acatagtgag actcttatct caaaaaaaaa 21960
aaaaaaaggt cgtctgtact attgcatgtt agtagtttct ttctgcttat tgttgagtag 22020
tagtctattg tatgcatgta ccagtttgtt catctagtgg tggacattga gttagcaggt 22080
tttggctatt aaaaataaag ctggaggccg ggtgcgatgt ctcacgcctg taatcccagc 22140
attttggaag gccgaggcag gcggatcacc taaggttggg agtttgagac cagcctgacc 22200
aacatggaga aaccccatct ctactaaaaa tacaaaatta gccaggcgtg gtggcgcatg 22260
cctgtaatcc tagctactca ggaggctgag gcaggagaat cgcttgaacc cgggaggcag 22320
aggttgtggt gagccaagat tgcaccattg cactccagcc tgggcatcaa gagtgaaact 22380
ccgtctcaaa aaaataaata aataaagctg gtatgaatat ttatgtacag gttttgtgtg 22440
aacatatgat tttatttctc ttggttggaa tgcatagaaa tgagattgct gggttttgtg 22500
gcaagtgttt atttttccag ggtacatata atcctgtgag tgtttattta attttaaaag 22560
taattgctaa actgtttgct aaagtgactg ctatattttc tttccctagc agtgtatgaa 22620
tttttttttg aggcagggtc ttgctctgtc acccagggtg gagtgcagtg gtgcgatatt 22680
gtctgactgc aacattgacc tcctgggctc aagtgatcct cctgcctcag cctcctggct 22740
gggaccacag gcatgtacca ccacacctgg tagtttgctt tgatttttag tagagaagag 22800
gtctcactat gttgccctgg gtggtgttga actcctgggc tcaagtgatt catctacctc 22860
agcctcccaa agtgctggga ttatagatat gagcccctgt gcctggcctc attgtggttt 22920
taatttgcat ttccctaatg cccagtgata ttgagcattt tttcatgtgt ttatttgaca 22980
ttcataccat ctttggtgat gagaaactat gtttatgcat tgcttaatga tggggatgtg 23040
ttttgagaaa ttttttcggt gatcttatca ttgtacaaat atagagttta cttacacaag 23100
cctagatggt atacctacta gacacatagg ctgtcgtaca gagtattact cttaggctac 23160
aaatctgtat agcatgttgc ggtactgaac actgttggca gatgtaacat aatgttaagt 23220
atttgtgaat ctaaacatat ctaaacatag aaaaggtgag taaaaataca gcgtaaaaga 23280
taaaagtggt atatctgaat aggtcactta ccatgaatgg agcttgcagg acaggaagtt 23340
gcttgggatg agtcatttat cagtggtgtg tgaatgtgca ggcctaggac attactgtat 23400
gctactgtag acaaacactg aacagttagg atacactaaa ttgataaata tctttcttat 23460
tttgtttttt gagatggagt ctcgctctat cgcccaggct ggagtgtagt ggcgtgatgt 23520

```
tggctcactg cagtctctgc cttctgggtt caagcgattc tcctgcctca acctcctgaa  23580
tagctgggat tacaggtgcg tgccaccaca cctggctaat ttttgtattt ttagtagaga  23640
cgggggtttc accatgttgg ccaggctggt ctcgaactcc tgacctcagg tgatccaccc  23700
gccgtggcct cccaaagtgc tgggattaca gatgtgagcc accgcacctg gccagagatg  23760
aggtcttgct gtattgccca gggcgttgaa ctcctgggct ccagcaatcc tcccacctca  23820
gcttcccacg tagctgggac tgtgggtgca cgccatcatg cctagccgtt ttgtgaactg  23880
ttgaccaatg ctcttttctg cagacagaaa gttcactgtg gttaggagtt aagactttta  23940
acctctgacc tcaagtgatc tgcccacctt gacctcccaa agtgctggga ttacaggtgt  24000
gagccatcac gcctggtcaa aaatatcttt ctttaagagt aaatttacct taacttactg  24060
gttgatcatt gtatataggt ctgttgttaa ttgaaacatg cgggccgggc ccggtggctc  24120
atgcctgtaa tcccagcact ttgggaggcc gaggcgggtg gatcacaagg tcaggagatc  24180
gagaccatcc tggctaacac ggtgaaaccc cgtctctact aaaaatacta aaaattaacc  24240
gggtgtggtg gcgggcgcct gtaatcccag ctactcggga ggctgaggca ggagaatggc  24300
gtgaacccgg gaggcggagc ttgcagtgag ccgagatcgt gccactgcac tccagcctgg  24360
gcaacagagc gagactctgt ctcaaaataa ataaataaat aaataaataa ttgaaacatg  24420
cggtgcatgt gtttatttgc gatctgactt gtttggaaat atttgcatta tcttccttct  24480
agatttagag catcttgaca gtaggaacaa gtgttttgta caactttgta tgcttagtaa  24540
gttatcaatt aacttgtcgt ggccaggcgc agtggctcac gactgtaatc ccagcacttt  24600
gggaggccga ggcgggcaga tcacctgagg tcaggagttc gagaccagcg tggccaacgt  24660
ggtgaaaccc tgggtttgtt tgtttgttta tttatttatt tattttttgg agacggagtc  24720
tcgctctgtc gcccaggctg gagtgcagtg gcgtgatctc ggctcactgc aacctccgac  24780
tcccaggttc atgccattct cctgcctcag cctcccaagt agctgggact acaggagccc  24840
gccaccatgc ctggctaatt tttttatttt tagtagagat ggggtttcgc cgtgttatct  24900
gggatggtct cgaactcctg actttgtgat ccgcccgcct cggcctccca aagttctggg  24960
attacaggcg tgagccacca cacctggcct accctgtgtt tattacaaat acacaaattg  25020
gccatttgtg cgtggctcat ctacagtctc agtgactcag aaggctgagg caggagaatc  25080
tcttgaaccc gggaggcaga ggttgcagtg agcagagatc gtgccactgt acttcagcct  25140
gggtgacaga gtgagactgt gtctcaaaat aataataata atttgttgaa tatgtgactg  25200
ttggtttaat ttttattttt atgagatgga gtctcactct gttgcccagg ttggagtaca  25260
gtggcgtgca gtggcgcaat cttagctcac tgcaacctcc gcctcctgtg ttcaggtgat  25320
tcagcctccc aagtacctga gactacagac gtgcactacc gtgcctgact aatttttgta  25380
tttttagtag aaatggggtt tcaccatgtt ggtcagcctg gtctcaaact cctattctca  25440
agtgatccgc ctacctcgac cttccaaagt ggcggaatta taggtgtgag ccgtggtgcc  25500
cggccagact attggtttgg tttggtgtga tgttatgtta tgttatgtta tgttatgtta  25560
tgttatgtta tgttatgtta ttttaagaca gagtttgtct cttgtcgccc aggctggagt  25620
gcagcggcat gatctcggct tactgcaacc tccgcctccc aggttcaagt gattctcctg  25680
tcttagcctc ccaagtagct gggattacag gcgcccacca ccgtgcctgg ctaatttttg  25740
tatttttagt agagacaggg tttcaccatc ttggccaggc tgttctggaa ctcctgacct  25800
catgatccac ccgccttggc ctcccaaagt gctgggatta caggcgtgag ccactgcgcc  25860
```

```
tggctgacta ttggttttat tattaagcag tagtagttga ccctgtcatg tagaaagcat  25920
ggcatttata ggcataccac gtttaatttc ctccccttttt tttatttttg gagtacctcc  25980
tgcttgtgag gcttgggaat acagtagtga ataagccaga tgaggtctct ctctttttgg  26040
agcttatgtg gtagtataga ctaggcagaa agttctcatt gcccctgcca ccttatggca  26100
ttgaggtgtt tgagatgctg atgtttactt ctgtctcata aaatcttgaa aggagttctt  26160
ttagatgaag aggaaaacaa aatcagaaga atgggcctgg gtcatgtctg taaacctccc  26220
cacgtcatgg ggaggctgaa atgggaaggg ccaggagttc aagaccaggc tgagaaacat  26280
aacaagaccc catctctaca aaaaatattt tttaattaat gggggatggc agcacacacc  26340
tgtagtcgca gctactacga ggctgaagcg agaggattgc ttgagctcag gagttaaaga  26400
ttgcaggagc tatgatcaca gcactgcgct ccagcccctc ttatcagcag tctggtatgt  26460
tgctaagggt cttgttcttt ttagtgcttc agggacagcc actggctatg cccagaaata  26520
agtatgtttg agaagctttc tgacctcagc ttgaaaaatt gattagggtc ataattaaaa  26580
agggagggaa acaggattga gtgaaccgga cgctaccgtg agtttattct cccagggcat  26640
acataatctc atgtgattac cacatagccc tgttagataa tctgttatcc tgtcctcatt  26700
ttacccatga ggaaatgaag gcccagagag gttaaatgac ctattcaaat tcactcagaa  26760
ggtggcagag atgagttact atcattgtat tttggatctc tggaaagaaa gaaaactagt  26820
gatggtatta aaaaatgtta ttaatagttt cttttaatca accaggaact tgagtcacta  26880
gcttctctgg gtgaaggact atacttcaac agtatgaaaa acggaaaaga aaatgaggaa  26940
ttttggctgg gcacagtggc tcacacctgt aattctagca ctttgggaag ccaagggagg  27000
agggtcgctt gagctcagga attcaagatc agcctaggca acatagtgag gccccatctc  27060
tacaaaaata aattagctgg gcatggtggt gcatgcgtat agtctcagct acttgggagg  27120
ctgactcagg agggtcactt aaacccagga attggaggtt gcagtgagct atgattgcgc  27180
cactgtatac catcccaggc gacagagtga gaccctatcc ccccaccgcc aaaaaaaaga  27240
aaagaaaatg aggaatttac atttgtgaca gatacggaat tcagggaatt tagttgttca  27300
tagtctataa atgctataag aagtctccat acctttttt tttttttttt ttttttttgg  27360
agacagagtc ttgctctgtc gcccaggctg gagtgcagtg gtgcgatctt ggctcactac  27420
aagctctgcc tctcgggttc acgccattct cctgcctcca cctcccgagt agctgggact  27480
acaggtgccc gccaccacgc ccggctaatt tttttgtatt tttggtagag atgaggtttc  27540
actgtgttag ccacagatcc cgacctcatg atctgtctgc ctcagcctcc caaagtgctg  27600
ggattgcagg cttgaatcac cgcacccggc cggaagtctc catacttttt aacccaatct  27660
aaaatggtaa ggaaatatat aagaatgtct atttattatt aaattttttc tatataaaac  27720
atttcagaaa ataaagacta gcatttctga gccaagtggt agtagtggcc attttttctg  27780
gaaaaaaaaa aaaaaagaaa gaaaaaacac atttagctat ctatgatgtg aaaagatgaa  27840
cattttattt aggtaataaa tgttatgtca taaaatacca tttattgtgt gcctattagg  27900
tttcaggaga gctgtgccaa gagcattact tgtatatctt ttaagcctta caacagccca  27960
gcctgtcagg ctggtagtgc catatctgtt ttacagatga ggaagtgatg gattggagaa  28020
attaaggaaa ttgcctttag gtcaaagaga taggaagtga caaagctgag atttttaacc  28080
ttgtgagatt tcaaagtctt tgctttttaa taactgttcc attgcttcta atatagagat  28140
atgacaaaaa caagtaaaaa tcagtgaaga aggctgggag cagtcgctta tgcctgtaat  28200
cccagcagtt tgggaggccg aggcgtgtgg atcgcctgag gtcaggaatt tgagaccagc  28260
```

```
ctggccaaca tgacaaaact ccgtctctac taaaaataca aaaaagttag ccaggcgtgg  28320
tgacaagcac ctgtaatccc agctactcag taggctgagg caaggagaat cgcttgaacc  28380
tgggaggtgg aggttgcagt gagctgagat cgctccattg cactccagcg taggcaacaa  28440
agcaagactc cgtctcaaaa aataaataaa taaataaata aaaataataa caataatgaa  28500
gaaaacaatc cggtgattat tgtcagcaat aaaatttctt caatcaacca tgctttagtc  28560
ctggcagttc tctatcagtg agtttcaatc aaaaagtttg tttataattt ttttttttt  28620
aaaattttga aatttggaaa caacatcata aatgatggtt agttttctgc agctccctat  28680
tttggcagat agtctgttgt tactcataat taatttgaac taaaaagtag tgttgtacga  28740
tatcatgggc tgtgaatgtg tttgtgactt gatctgagaa cccacacacc acttaggatg  28800
cttctgtagg aaaattagag tatggaactc acttgcccac gctttccctg tctcagtcca  28860
tgttggtagg ctgcaaagtc tggggctaga aggacactga acaagacttc agcagtacat  28920
gttagtcttc cagagggaag gaatataata gttgagagaa taattccttt cctctgtgac  28980
tttaggcaaa ttcttggcta tgctgttatt tatttgggcc aaacaatatc aggaggttgt  29040
acattttatt cttaattact gcgatacatt aattttatcc atgggtttaa cctagcctac  29100
cttttgctgt tagacttcaa ctctacttgt gttgggttac ccctctgctt aaaaatcacc  29160
ctattcccaa gcctgaggga gtctaccttc aaagctttct atgacctaat ccaaggcctg  29220
tcaaacttcg taaagggcca gatagtaaat ttgttttttt tttttgagat ggagttttgc  29280
tcttgtcacc caggctggag tgcaatggtg ccatcttggc tcactgcaac ctctgcctcc  29340
caggttcaag tgattctcct gcctcagcct ctcaagtagc tggggttata ggcatgtgcc  29400
accacgctcg gctaatttct ttgtatttag tagagatggg ggtttcacca ttttggtcag  29460
gctggtctcg aactcctgac ctcaggtgat ccacctgctg cggcctccca aagtgctggg  29520
attaccagtg tgaaccaccg tgcccagccc gatagtaaat attttaggct ttgcagtcca  29580
tatacagtcc catttttttg tgtatgtttg cacgttttct ttacatattt taaaagcccc  29640
ttttttttt tttttgagac agagtcttgc tgtgttgctc aggctggagt gcagtggtgc  29700
aatcttggct cactgcaacc tctgcctcct gggttcaggc gattctcctg tctcagcttc  29760
ccgagtaact gggattacag gcacatgctg ccacgcccag ctaatttttg tatttttagt  29820
aaagatgggg tttcgccaca ttggccaggc tggtctcctg atctcaggtg atctgcccac  29880
ctctgcctcc caaagtgctg ggattacagg tgtgagccac cgtgcctgac ctaaaagctc  29940
tttacagtgt aaaaaatatt ctgagcttta agccatgtga aaataggcca tgggcatttg  30000
ctgaccccta atagaactcc attttacctt tctgatcatg tttcccatta actcttcaaa  30060
aatatgacct ccatttaaat caagatggtc tccttcctca ctgcttgtgg aggtccagtg  30120
cccagtgtct gcctcttgct tgctcctcca tcattgttct gccattcgag atcctcatac  30180
ttacccttta agatctagcc caaattttcc atgaaactaa ttctaataat taaaaacttc  30240
ctgtagaact taactttgtc tagtacaagt tagctttctt attcagtagt agcttactat  30300
aaattacaag aataaaaaga ttaccatttt ccctcacact gttttgtgga gaatgcctaa  30360
agttactttt tctttttaca ggtcagtatt cctatttggc atcctaatcc cctttcccaa  30420
atctgaattt tgggatttga agcttgcatt tgagattatg atttgtcttc cttgttgtac  30480
acaggagcag ggactttaca attagtattc gcatccctgc tccttcatac ttcgtgatgt  30540
aaggcaagtt attttcactt atgcttaagt ttcttcccct gtaaaaaggg gatggaagag  30600
```

```
gattaaatga attaaacatg taacacgctt aaagcaatgc ctggcaagta ataagtgctc  30660
agtaactttt agctgttctt attagcatgt ttggaaacca gtagaaacta caccagcaag  30720
ttaaggttga aaagtggtat tgatgggctt ggggtagtac agtatgaatg gctacagttt  30780
agcgtttcat taagtttgta tattcattaa ttcattacac atttgatgct gtcagactag  30840
gacagagaca aagatgaatg aaacattatc tctgcttcca ggttacccag tgtagtagag  30900
aaggcaggca tgcagatagt ttaaattggt agcactggga ggggactgcc atgggtgggc  30960
agtgaagaaa aagggcttca aaataatgag agttgagatg gatcttcaag gaagataagc  31020
agttttcagt aaggccatga agagaggagg aagttccagg cgggaagagt ttgtgctaaa  31080
gtacagggat tgctatacac atggtgtatg tagaaaaaat ttggttcaca gtgtgataga  31140
agaattggag ggggtcctca ctgaaagtaa ggaaacacat ttggaagaat atgtttcagt  31200
tagaaaatga aatgagctta aagtaaacgc taataaggtt tttaaaatgt aaaatttcaa  31260
cgtatttaga aagagaacag ctggatgaat cttatgtacc tgtcactcag ctttagcagt  31320
tatcagtaaa tggccaacgt tgtttcagct atactcccct ctcctccact gatagtcttt  31380
tgaaggggaa tacaattgtt ttgtggcctc cagaaaggga taagtttatg agcaacgggt  31440
agatcgttgg gagagacttg agtttcctgt caggaagcat tcttggtgca taagtcagag  31500
gtgatatgaa tgccgtggaa gggggtggct tactgtctgg agaactcgag aagatgggaa  31560
tgggcactgt ccagtattgt ggctacttcc acacatggtt ctttaaattt aaaattatgt  31620
tgattaaaat ttaaatattt cagttcctca gccatactaa tcgtatttca agtgcttagc  31680
tgccacatgt gcctaatggc tgcaatattg gacagcatga cataggacat cttcatcatt  31740
gtacaaagtt ctcttggaca gcatgggact agagccctaa gatccttttc tacctgagtt  31800
gtttggattt tttggtgtgt ctaggttgga tctagttgtt catggcttca tgaccaagcc  31860
ttttatccct ttctctagag ggactcaagg ggtaaaggca ctgaaggggt aaaacttcat  31920
atgaagagtg tggtggtggt ggtggtgttt taagacaggg tctcgctctg tcactcaggc  31980
tggagtccag tggcatgatc ctggctcact gcagcctcga cttcctgggc ttaagtgatc  32040
ctcccacctc agctcccaag taactggaac tgtaggcatg agccaccaca cctgcctaat  32100
ttttaaaact ttctgtagag acgagatttc gccatgttgt ccaggctggt ctcaaattcc  32160
tggactcacc ttggcctccc agagtgctgg gattgcaggt gtgggccact gcgactggcc  32220
tttttttttct cctttactac tctagtgtat gctggaatat gaggaaataa ttatattagc  32280
tagcagttat taaacactta ataacatacc aggcactgtt ttaagctatg cgatctgtat  32340
ggaatattac ttaatttcca caaccttatg aaaagatact attttttttc ttttgagaag  32400
gtactatttt catcttcatt tcatagatgt tgaaattgaa acacagagag ctgaagtcac  32460
aggattaagg ccacagagct gagaagtgat ggagccggaa tttgaaccca agcaattaat  32520
gctgatatta gttcttgtgt gaatggtaat tgttttgaaa caatgatcct agatgattat  32580
atgaccggat taatctggca gttgttctgt gtgaatttag agttgccttc ccacctcagt  32640
ttcctaaaaa caaaacaaaa caaaacaaaa caaaaaaaac tctagcttca ctgtgtttgg  32700
gttgtcatgg cctacccccct cttgccacct catttgactc aactttttag ggagaaaata  32760
ttcaatacgt ggtataggat ttccctttct aataataatg taaacaacaa caagaagtct  32820
gaaattggaa gaacaaaatg actcacctaa gtgagttaac cttaagaggt ggaacttgat  32880
ttctagattt tagttaattg tctaactgat gtactaaata ttagttactt aagtattaaa  32940
acgggtagac ataatagttg gggagctgct gtagaggggg tagtttgaga aggcttcttt  33000
```

caggaggtga catttaagtt ggtaactaac aagaaagggg cagccatgtg aatagctgga 33060
gggaagagca ttcttacagt tttactggaa gggggttaga ggtatgtggt acccttatgc 33120
caaagaaaat tagttacttc tatacaacca gtctgattct agaaacctgg atcaatgaaa 33180
tattttgatt atataaaaaa atctgttacc caggtcttgt tgaaatagca ttagaaacta 33240
ctgaaggaca tatagaggag gagtgttgaa aaatggtgat ggatgagcag aatggtgaaa 33300
aataaaaaga catgaagctc tataattata ttgtatggtg acagtaccaa tagagattgc 33360
atgtttttc tccccagttt tttttttgt tttgtttttt gtttttgaga cagagtctca 33420
ctgtgtcact caggctggag tgcattgtcg tgatattggc ttactgcaac ctctgcttcc 33480
tgggttcaag cgattctcct gcctcagcct cctgagtagc tgggattaca ggcatgtgcc 33540
accacgcccg gctaattttt gtatttttat ttgagagggg atttcaccat gttggcaagg 33600
ctggtcttga gttcctgacc tcagataatc cacctgcctc agcctcccaa agtgccggga 33660
ttacaggtgt gagccactgc gcccggcctc ccccagttgt tgaaacaata atggaaggta 33720
attttattct tagattattt aatgtttttc agttatcagg atgtgttaga ttgtttgtgt 33780
atattgtttt gcttgttaat taagtaacac agtgaataag acagacaaac atacgaaaat 33840
gtacatttat tttatttttt tgagacagtc tgttgcccag gctggagtgc agtggcccaa 33900
tctcggccca ctgcaacctc tgcctcctga gttgaagcga ttctcttgtg tcagcctcat 33960
gagtagctgg ggccatgggt gcacgccacc atacccggct aatttttata tttttagtag 34020
agatggggtt tcaccatatt ggccaggctg gtctcgaatt cctgacctca ggtgatctgc 34080
ccgccttggt ctcccaaagt gctgggacta caggcatgag ccactgtgcc aggccatttc 34140
atttttggaa cgttcttttt tttttttgaa atggggtctc gctctgtctc ccaggctgga 34200
gtgcagtggc tcaatctcag cttactgcaa cctctgcctt ccgggttcaa gtgattctcc 34260
tgcctcagcc tcctgagtat ctgggactac aggtgcatgc caccacgcca ggctaatttt 34320
tgtattttta gtagagacgg ggtttcacca tattggtgag gctggtcttg aactcctggc 34380
ttcgtgatct gcccgcctca acttcgcaaa gtgctgggat tacaagtgtg agccaccacg 34440
cccggcctgt ttctggaata ttcataatct tttgttgtca tttcaacagt gctcacagca 34500
gcttcaccag gtgtagattc catcttaaga aaccactttc tttgcttatc catgagaagc 34560
aacacctcat ctattcaagt tttatcatga gattgcagca attcagttac atcttctgac 34620
cccacttcta attttagttc tcttgctttt ttaccacatc tgcagttact tgctctactg 34680
aagtcctgaa cccctcaaaa tcattcatga gtattagaag caatttcctg gttgggcacg 34740
gtggctcatg cctgtaatcc cagtactttg ggaggccaag gagggcggat cacctgaagt 34800
caggagttca agaccagtct ggcaaacgtg gtgaaacccc gtttctacta aaaatacaaa 34860
aattagcggg gatgtggtgg cgggcgccta taatcccagc tacttgggag actgaggcag 34920
gagaatcgct tgaacctggg aggtggaggt tgcagtgagt tgagattgtg cccttgcact 34980
ccagcctggg caacaggagc gaaactctat cttaaaaaaa aaaaaaaaga aaagcaattt 35040
cctctaaaac tcctgttaat gttgatgttt taacctcctc ccatgctcat ggatggcatt 35100
ctcagtggca tctagaatgg tgaatacttt ttagaaagtt ttcaatttat tttgccatca 35160
gagaatggct atgaatggca gtagtagcct tacagaatgt atttcttttt tttttttttct 35220
ttttttttga gatggagttt tttttgctct tgtcacccag gctggagtgc agtggcatgc 35280
tatctcggct caccgcaacc tccgcctccc gggttcaagc aattctcctg cctcagcctc 35340

```
ctgagtagct gggattacag gcatgcacca ccatgcccac ctaattttgt atttttagta  35400
gaggcggggt ttctccatgt tggtcaggct ggtcttgaac tcccgatctc aggtgatctg  35460
cctgcctcgg ccttccgaag tgttgagatt acaggcgtga gccaccgcgc ccggccgtat  35520
ttcttaaata aaatggctta aacgtcaaaa ttatcccttg atccctgggc tatggactga  35580
ttcttgtgtt agcagttatg aaaacattta tgtccttgta cattcccatc atagcttttt  35640
gtcaatgaga agtaattttt tttttttttt tgagacagaa tctcactctg tttcccagcg  35700
tggagtgcag tggcatgatc tcagctcagt gcatcctaca actctgaggt tcaagcaatt  35760
ctcgtgcctc agcttactga gtagctggga ttacaggcgc ccaccaccac gtctggctaa  35820
tttttgtatt tttagtagag atggggtttc acgatgttgg ccaggctggg ctcgaactcc  35880
tggcttcaag tgatccacct gccttggcct cccaaagtgc tgggattgta ggtgtgagcc  35940
actatgcctg gcctaattgg cctaatttca atattgttat atctcaggga atagagaggc  36000
acgaggagaa agagagacaa gctgactgct ggttcgtgga gtagtcataa cacacaacat  36060
ttattaagat tgctgtctta tatggaccgt ttgtggtgcc ttaaaagaaa tcagggtaac  36120
atcaacgatt actgattaca gattactata acagatacaa taataattgt aaattattat  36180
ttacaattgt aaaatacaat cttttcttta ttatttacaa ttattgtaaa atacaatctg  36240
attacagatt actataacgt atacaataat agtggaaaag tttgaaaata ttgtgagatt  36300
tatgagaatg tgacacaggc gcaaagagag cacatgttac tggaaatacg gcactaatgg  36360
acttgcccga ctcggggttt ccacagacgg tcagcttgtc aaaaatgcag catctgtgaa  36420
tttcaataaa gcaaagcaga ataaaatgag gtatgcatgt attgccatca catgtacact  36480
agtaaaatac gttttttttt tcagtaggtg gatcaacctc aaattttaat ataaagcatt  36540
acttaaagga gaatatgggg acattcatga catttcttat atgtacataa aacttcatga  36600
aaataattta atgctatcca gcagtttatt ttagaagtac tggaggctag gcatggtgtc  36660
ttatgcctgt aatcccagca ctttgggagg ctgaggtagg aggatcactt gagttcagga  36720
gctggagacc agcttgggca atatagtgcg accccatctc tacaaaagag aaaagaagta  36780
ctggagtgtt gcagctctta cagaatttgt ctagcaggtt ttccagtctt taccagaaat  36840
gcccccatgc agaagtagta aatactgatt catgtaaaat aataaacaac tttatctttc  36900
agtttttaaa agacagggtc ttgtaacgtt gcccagactg gcctttaatt cctgggctca  36960
agcgatcctc tcacctgagc cttttgagta gctgagacta caggctgcac ctctgcacct  37020
ggctctgctt gatttttaat tgttgtattg ctgttgcagc tatgtttttt tttttcttca  37080
gtgtgaggat gggcaaactt tttatgtaaa gtctcaggta ataagtattt taggctctag  37140
ggccatatag cttctctgtt gcatatcctt tttttttttt tccatttccc ctcaaattcc  37200
ttttaccata agcaactctt gaggaacata aaaatcattc ttagcccaga agccagacca  37260
aaacaggttg tgggctgtag tgtcctgacc cctgatttaa agattgatag ctttgaaatg  37320
gaaagtttta actttctttt tttttctttc ccttgttctg attgggctgt taattcatta  37380
ggtatttact cagtgtgtat catatgaggc atgattcctc tgctaatttt ggtagtggta  37440
gaaagatact tttgccaagc ttggttgtta ggttttcatt tgtccaagag ttcctgacca  37500
agtgtgaatg gatgttgaaa tcaaggtgtt tctttggcca cacaatgtgc ctttgggggc  37560
tatatctatg tgcttctggt accttctttt aattttcaca aagacactgc ttgccgacca  37620
cactgttttg tctaatgtgg ggctatgacc ccctggaaga ggcatcattt tctgattttc  37680
acagaagcat aatatggtca ggtgatggtc ctgagtagtg ggtatatgac agatacacta  37740
```

```
gtaattataa tacagatcta aactggagag ttgaaaacag catcgtatat ttgattgaga  37800
taatcgaagg aagacttcct gaaaagatgg catttgagtt tcaaggctga gtaggattaa  37860
gtattattat ttaaaaaatg ccttggacaa tgcattaaat agagttaaca aatcacatca  37920
cttatagtct ccaattaaaa acattttact taaacataat tttagacttt tagaaaaatt  37980
gcaaagatat tataaagaat tctcctatat atctcacctg tattcttcaa gtaacatttt  38040
accatattca ccttaacatt ttctctgtat tggtaattgt atatgtaaga tttaatataa  38100
aataaaaatt cttattaaac atatgagaga catgatgcct ctttagccct aaatacttca  38160
acttgtatgt actaataaca agggcattct atttcaaaac cacagtacag ttgtcaaaat  38220
aaggaaatta ataattgtgt caaactgtta ttctgtttat agaccttcta atgtccttta  38280
aaacaatcaa caaatcaaca tttttctggt caagaaccag taaatatgta tattctacat  38340
atatatatac acatatatat acacacatat attctacata tatatgtgga atatacgtat  38400
ttactccctc tgtccaagaa ccaatccagg attgttacct tcggttatca tgtatctttg  38460
gtctccttta atccaaagca gtttctttgt cttttatgac ttgacacttt tgaagattac  38520
aggttatttt gtagactgtc cctcaactag ggtttatctg aggtttcctt atgattagat  38580
tcagatattt atttttggca ggaatacaac agaaatgatt tgtgtgtttt tctcattgca  38640
tgatatcaga aagtgcattg tatatattta tcccattact ggggttgtta actttgatca  38700
cttggttaga gttgtgtcta ctaagtttct tcactataaa gttatttttc acttggtcat  38760
ttcatcagta tcttgtgggg agttactttg tggttatata aatactctgt ttctactttc  38820
ccttactata tttagcttct gtggacactt ttgcctgaaa cagttattta ctatggtgtt  38880
accaagtagt gatgcccttt tcttccatca ttctgtctac attttttttt tttttttttt  38940
tttttgaga tggagtttcg ctcttattgc ccaggctgga gtgcggtggc ctgatcttgg  39000
ctcactgcaa cctctgcctc ccgggttcaa gcagttctcc tgcgtcagcc tcccgagtag  39060
ctgggattac agacatgcgc caccactcct ggctaatttt gtatgttcag tagagacagg  39120
atttttccat gttggtcagg ctggtctcca actcccgacc tcaggtgatc cacccacctc  39180
agcctcccag agtgctagga ttacaggcgt gagctgccac accaggcctt ctttttctct  39240
tttaagagat agagtcctgc tttgtcacca aggctggagt gcagtggcat gatgatagtt  39300
cactgcagcc tcaaactcct gggctcaagt gaacctccca tctgtagctg ggactacagg  39360
cacctgcata acacctgact gttttttaaa actattttag agatggggtc ttgcgaagtt  39420
gctcaggatg gtcttgaact ccgggtctta agtggtcctt ctgcctcagc ctctggatta  39480
gttggcatta caggcatgag ccattgtacc tggcaagtgc atattttctt tttttttttt  39540
taaggtggag tctcgaggcc gggcgcagtg gctcacacct gtaatcccag cactttggaa  39600
ggccgaggtg ggtggatcaa gaggtcagga gatcgagacc atcctggcta acatggtgaa  39660
accctgtctc tactaaaaat acaaaaaatt aactgggcat ggtggcacac gcctgtagtc  39720
ccagctactc gggaggctga ggcaggagaa ttgcttgaac ccaggaggtg gaggttgcag  39780
tgagtcaaga tcatgccact gcactccagc ctgagcgaca gaggtagact ctgtctcaaa  39840
aaaaacagaa agacggagtc ttgctctgtc acccaggctg cattgcagtg gcatgaactc  39900
cgcctcctga gttcaagcaa ttcttgtgcc tcagcctccc aagtagctgg gattacagac  39960
atgtgccacc acacgtggct aatttttata gttttagtag aggtggagtt tcaccatgtt  40020
ggctaggctg gtcttgaact cctgacttca ggtgatccac ccgccttggc ctcttgaagt  40080
```

```
ggtgggatta tgagtgtgag ccactgtgcc cagccaagtg agtatttgct tatgtagtat  40140
tttaatttta tgattttttt ttctttgaga cggaggtttg ctcttgttgc ccaagctgga  40200
gtacagtggt gccatctcgg ctcactgcag cctccacctc ctgggttcaa gccgttctcc  40260
tccctcagcc acctcctcct gaatagttgg gattataggc gcctgccacc atgcctggct  40320
aattttttgt atatctagta gtgatggagt ttgagcatgt tgccaggctg gtcttgaacc  40380
tctgacctca ggtgatccac ctgccttggc ctcccaaagt gctgggatta aggcatgagc  40440
caccatgccc ggccagagac tgttcattta tttttttttt ttgaggcgga gtctcgctgt  40500
attgcccagg ctggagtgca gtggcacaat ctcggctcac tgcaagctcc gcctcccaag  40560
ttcacaccat tgtcctgcct tagcctcctg agtagctggg actacaggtg cctgccacca  40620
cgcctggcta attttgtttt tgtattttta gtagagatgg ggtttcagcc cgccttggcc  40680
tcctggagtg ctgggattac aggcgtgagt cagggcgcct ggccaatcat accttctttt  40740
actgcattaa ttatggtttt ctttcgttct taaaacatgt ttatagtgac cacttttgaa  40800
attcttatta agtcagacat ctggttatac aagcaatttc tattgcctac ttctttttcc  40860
agtgggtggg gttatacttt cctgtgtctt agcttgtcgt tttttttttt gttgttgaaa  40920
actggacatt ttaagtaatg tagtaactct ggatacctca ttagcctatg gttgggggtg  40980
gtggttgtta ctgttatttg cttatttgtc taatgactgg ctgaatgatt ttagtgttct  41040
atccttcttc cctccctgta cagtgtgaca cgtctgatgc tagttttctt gggatgcagc  41100
cttgggtatg cctaccatca ctctagaatc acagtgattt tggcatggct ttgtctcttt  41160
tcctgactgt acccagctgt taagctacac taattactag gtgatgctgt gtagtcattt  41220
cttggtgtcc ttggggggatt ggtcccagga cccccccgtt ggatataaaa atttatggat  41280
gctctagtcc ctcataaaat ggcacagtat ttgcatatac cggtgcacat cctcctgtat  41340
gctttgtcat ttctagatta cttataatac ctaatatggt gtaaacacta ggtaaatagt  41400
tgttatatat tttttatttg tcttattttt attgtattta tttttaagtg tttttaatct  41460
cgagtgattg aatctgagga tgtgaaatct gcagatatgg agggcctgca ttgttttccg  41520
tggagctttg ggcctaaact gctccacaga ctgatctgat caaatttgcg cttctttgaa  41580
gggatagttt ctgagatcag tgtttgaaat ttgttccaat ccacagagga gtcctcccag  41640
ctctctttcc ctagttctgg ccaccaaact agacaactac aatttagcac ttatctccaa  41700
tgattctcct cctaccaagt gcctttgaaa gcatcattaa ctctttcata ccttgttgca  41760
aatgaaattt ctttgggaag agattgtgag ttttttttct cctaaattat ggtgcaatat  41820
aagtaatata ccattttaac aattttaagt gtattaagtg tttttttttt ttgtagtttt  41880
tttttttttg ttttttgaga tagtcttgct ctgtcgccca ggctggagtg cagtggcacg  41940
atctcggctc actggaacct ccacttcccg ggttcaagtg attctctggt ctcagcctcc  42000
ccaaatatct gggattacag gtgtgcacca ccacgcctgg ctaatttttc tatttttagt  42060
agaaacgggg tttcaccata ttggtcaggc tggtcttgaa cttctgagct cgtgatccac  42120
ccacctcggc ctcccaaagt gctgggatta caggccttag ccaccacacc tggcctatgc  42180
attgctttta tatgtatttt aaaattcata agttctcctc ctatgatgtt tttgtcccat  42240
gtgatttatt tgttaaaccg tcatctttgg ccgggcgtgg tagctcacgc ctgtaatccc  42300
agcactttgg gaggctgagg tgggtggatc acaaggttaa gagatcaaga ccatcctggc  42360
caacatggtg aaaccccgtc tctactaaga atacaaaaat tatctgggca tggtgacgcg  42420
tacctgtagt cctagctacc tgggaggcgg aggttgcagt gagccaagat cgtgccactg  42480
```

```
cactccagcc tggcgacaga gtgagactct gtctcagaaa aaaaaaaaaa caaaaaactg  42540
tcatttttta tgttgcattt actgcattct ggatttaaac tgtgaggaac ctcatggtat  42600
cagttaatat attcttccat cttaatgttt ctcgtaaact ggtagatctg taaacttgat  42660
taggtctatc ctattgtatc acatcagaag cagaaggtgc tttttttttt ttttaaggga  42720
aattgtgtga aagtagacag aatggtaaag tgaacccctg cacacctatc acccagcttt  42780
aatagttatc agctcatacc attcttgttt gatttacaac cccattcatt tctcccttct  42840
gtattattat tatttagtta attatttttt gagacagggt tttgctctgt caccaatgct  42900
ggagtgcagt ggcataatca cagctcactg ctgtcttgac ctcctgggct caagtgatcc  42960
tcccacctca ccctaccaag tagcggggac cacaggcgtg tgccaccatg cctggctagt  43020
tttttatttt ttgtagaaac agggttttgc tttgttgccc agactgatct caaactccgg  43080
cactcaagtg atcctcctgc ctcagcctcc taaagtgctg ggattacaag catgagctac  43140
cacattcagc atgtaaattt ctttatatta atttgactgg cattttaagt cacacttgaa  43200
tttcatattt ggcaactatt aaaagcatag agtcctggat attagtgttt tgttaaacct  43260
gatctatcta atcataaata tacttaggtc taaaatatgc tcttggcctt tgtttattgc  43320
ggttcagtat ttgttactat attaaatagt aaaatatttg gtttgagata ctaatgaaaa  43380
gattaaaagt aaagcataac ttgaatggat acaaaaagaa acaagaattt agacttcagt  43440
ggatttcaga gaatactgct tcgatatgct aacattcctg ttgggtgtcc aaccgtgtca  43500
tagatcagtg gaaattagtg gtttctgcac tttactgtac tgttttttta tatgataata  43560
ttttcctggt tgaatgattc gttcttttga gtaaactcca tggtcaaaca attacttttt  43620
attagtcaaa gatgtaacca cataatcact aaaaagaaca gtgtgactta tttaaagggg  43680
attatgtttt taagtctttt atatagcttt gtagggaggc catatgagtt taaggacagt  43740
tcgtggcatt tgttcaaggt tttgtaactt ggcatctcag cagccaccag gataccagat  43800
catcgttcta agtaagattt aggcatttta gccttcatgt acagactata agtacacccc  43860
cccacacccc taccaaaact gtaaattcaa atgatgtttg aaaaagcata gaatttttgt  43920
taggcgaggt agtttattcc ttgtgataca gttccagaga ggcagcataa cctaggaatg  43980
aaaaacttag acgtggaatc agatacacct ggtttaaata ccagctctac tgctcatgaa  44040
ctggatgatt ttggtcaaga tacttgactg ctgaggttca gtttcctcac ctgtaaagta  44100
gaggtgatag attagacatg ttgcatgtga agtacttagt atggtgtctg gttttgtagt  44160
aagatctata aaagataaat tattagtcat attccttaga cttcaggaat ttatctctgt  44220
gccatgtttg aggcaaacag ttacagaatt agaatgttag aaatgaaagg aatcctagat  44280
gtcatttaat tcaagtccat tgttttctgg atgagagaag aaagtgagga aaagtgacag  44340
agttggagac caagctagga ctggcctcag aatgttaaga gtactcttct agggatcgac  44400
cagtcgtgtt actagacttt ttggatctga attgtgcttt tccttgaatg ttttgaattt  44460
tggcttgagt gttgtgatta ttttattaaa atgagattcc agtcctattg tcatgactaa  44520
tgtttatgag aaatataaca tttcacttta atgatgtttt ttaattattc taaggggcct  44580
aatctttttc agtggaataa gctttaggtt gtattatatt ctataattca cttgaaaata  44640
gaattcatct ttacttgaca gccaaatttt gtgtactgca tcttttctga gggagagagt  44700
tggcaaggaa aggcacttgt tacaacgatc cacacatata gacgcatatt atttagaaat  44760
gaaagtgctt tgaatgattt agcttatttt cagttttttt ttttctgcag ttgtaatcat  44820
```

atgacctgtt tttctttctt tttttttttt tgagacagag tcttgctctg tcaccccggc 44880
tggagtacaa tggggcggtc tcagctcact gcaacctcca cctcccaggt tcaggcgatt 44940
cttctgcctc agcctcccta gtagctggga ctacaggcgc atgccaccac acctggctaa 45000
tttttttatt cttagtagag atggggtttc actgtgttag ccaggatggt ctcgaactcc 45060
tgaccttgtg atctgcccac ctctgcctcc caaagtgctg ggattacagg catgagccac 45120
tgcgcccggc ccatatgacc tgtttttctt ttatagatgg gggagaaata tgggaagtga 45180
cttggtgtca gtcatctgtg ttggttaaat caagaatata atccgtgttt tgcttctgaa 45240
tagctcttta taacagtgat tggttacttt gggagtaaag attattattt agagacagag 45300
tcttgctttg tcgcccaggc tagactgcag tggaatgatc gtagcctact gcagcctcag 45360
actcctggac tctggtgatc ctgcctcagc ctcctgagta gctaggacta gaggtgcatg 45420
ccacatgcct ggctataatt attattaatt tacgtttagc attagttttt ttcttccagt 45480
aggctatttt actttattta tttgattttg atgaagtttg attatttcta gtttgcttcc 45540
ttctatgacc cctacctgtt gtgggtctcc aggcaagcag tgcataggta gagccatcct 45600
taggtagcct ttagacttaa tattaggtga gctctcccca cagatagcct ctcctttatt 45660
tgaatggaat tatattttaa gtttggaaat atttttcagc ttatttagcc tgttgaattt 45720
aataaaaata atatttaatc ttttcagagg tcgaaacagt aacaaaggac tgcctcagtc 45780
tacggtgagt aactttaatg ttacttattg gggaaaatta gtagctaaaa catgatctct 45840
aaccacagac caaatgccaa ggcaaaagat tcccttcttt tgaattttgt catagataac 45900
ttgactgttt aagtatgtta ttagcctata tgtgtttttt taatgactct gtataaaatg 45960
tacaattact tgttgtatta gtccattctt acactgctaa taaagatata cctaagactg 46020
ggtaatttat aaaggaaaga ggtttaattg actcatgctc tgcattgctg gggaggcctc 46080
aggaaactta caatcatggt ggaaggggaa gcaaacacat ccttcttcac atagcgacag 46140
gagagagaag tgctgagcaa agcagggaaa gccccttata aaaccatcag atctcctgag 46200
aactcactca ctatcatgag agcagcgtag gggaaactgc ccccatgatt cagttatctc 46260
cacctggtct tgcccttgac acacgagaat tattataatt aaagataaga tttgggtggg 46320
gacacagaac caaaccatat catttgtaaa tagtattttt gtcacgtgta ataacaagaa 46380
caagtcgctt gttcttttct aaatgactaa gtgcaaatct aagtgaaaaa cctccaaaag 46440
atacgtagaa caccaagagt ggagtctgca gagttcttta tgctttttat tttgaattaa 46500
tgtgcttttt ttctgctgct ttcatttttc tcctttggct ttctggtctt aaattttgga 46560
atgttatcaa tgaaattgaa ccggacatga agggcagaaa ctataagtcc cacatgatgg 46620
aagaaataaa tgagaagcta tcacaaattt ttgagacttt gcctttatta gattgtttta 46680
caagaatcag gaagatatac acgtatatgg tagtaatatg gagtagtgtg gttgatcaga 46740
cttaagcact gtcactgatg ctgatatgct gggagaacct agtcagggtt cttctatgaa 46800
ggtatgacct ggcttcctac cccatttatt tatacttcac ccttcttagg gtacatttct 46860
gtgagtttta acaattgcat acaatcagtg taactaccac cacaatcaag ttaatagaac 46920
agtttcattg cccaccaaaa tccctcaaat cacttttcag tgaaccctcc tctctctcca 46980
accattgatt tgtcttccat ccttacggtt tgtgtccttc ctcctctatg gaagtttact 47040
cttgcttttt tatgtcatgt ttagtcaaaa caccattagt tggtttgact gataacactt 47100
gaaaacctga ccttctgttc cttctgttct ctatggaagc aaaatattaa ataaacaaaa 47160
tcttccctta atacatgtaa gatatcataa acctaactaa acattttgca acaaataata 47220

```
aacgttagct ttatatgcaa atgtaaatac aggctgagca tccctaatcg gaaatgctcc  47280

aaaatttcat attttgaatt agggatgttc aagcactaag tataatgcaa atatccccaa  47340

atccgaaaaa aatccgcagt ctaaaatact tctggtccca agcattttag atgaggaaga  47400

ttcagtttgt actaatttct aatagttttt ttttttttta atattccaga tttcttttga  47460

tggaatctat gcaaatatga ggatggttca tatacttaca tcagttgttg taagttatta  47520

gattattggg gataaactgc cttgggggta gaataaagta attccatgaa gttaaaatgt  47580

ggataaatga ttgtcaaagt aacattgctt agatcatgtt tagtcaggat gatttagaga  47640

aatagattag aactcctttt atccagtcta atataattca ttgtaaaagt acagttggtc  47700

ctctgcatct gtgggttcca tattcatgga ttcagccaac cttggatcaa aaatatttgt  47760

taaaaaggcc aggcacagtg actcacgcct gtaatcccag cactttggga gtttgaggtg  47820

ggcagatggc ttgagctcac aagtttaaga ccagcctggg caacatggca gaactccgtc  47880

tctacaaaaa gtaaaaaaac tagccgaacg tggtggtacg tgcctgtagt cctagtgact  47940

tgggaggctg acgtgggagg attgtttgag cctgggaggt ggaggtttca ctgagctgag  48000

ataatgcccc tgcactcagc ctggtcaaca gtgccagaca gaccccttct caaaaaaaaa  48060

aatttttttt tttttttttt tttttttttt ttttgagaaa aaagaggcat ggttgcgtct  48120

gaaccaaaga tgtacggacg tttttcttgt cattattcct aaaacaatac agtatgacaa  48180

tttacatagc atttacatta tattaggtat tacaagtaat ttagggatag tttaaagtat  48240

ttgggagaat gtgcttagtt atatgcaaat actattacat tttatgtaag tgacttaagt  48300

attatgtaat tcggtatctg aaggaggtcc tggaaccagt cccctaccaa taacaacaga  48360

tagctgtatt cttgttaacc ctgctgtgtg tgtaaaataa tgttagtagt tgattgtctt  48420

ttgtacatta ttttgtcact taaaatagct ggggtcagaa atgtttgact tcagtattaa  48480

aattcgtact gcaaactctg agtagagcct cctgaagaat ttcaagagtt cagtgtattg  48540

ttaatgtttt gaaatttttt tattgttttg ttagtgaata cctaatattg aatgaagcct  48600

gatgaggtat aaaaagtaaa atgaaaacaa atatccctgg tgaccgggta gtatactgtt  48660

tctttgataa ataaattata tgtttttagg gctccaaatg tgaagtacaa gtgaaaaatg  48720

gaggtatata tgaaggagtt tttaaaactt acagtccgaa ggtaattttt actttttttc  48780

tttttcttac aaagtaaaag aacattttca tagtcagtgt tttacctagt ttttaaagcc  48840

actttgaatg attttacttc tcagtttcaa atactgatta ttttatagac tggtttgtgt  48900

aatcagagag gcttcttgat gtgtgtgctt attaaaatat ttcaaccatt tttaagcatt  48960

gtgagctaat agagggatgt ggtggtttgt tttttcctct taaaaattat tattaatgta  49020

cttaagacaa accatagaaa caaaaaacat ttagatatga ggatttttaa atgatggaat  49080

ggataataga tcatatgcct gggaaaaagg gtatgattct cttgagatta tttttgtcaa  49140

aggcatataa gaactggtac cttgatgagc taaagaattc ctaacaaatt ttattttgta  49200

aaggtttgga gtacttactt gtgtttttca ttttagtgtg atttggtact tgatgccgca  49260

catgagaaaa gtacagaatc cagttcgggg ccgaaacgtg aagaaataat ggagagtatt  49320

ttgttcaaat gttcagactt tgttgtggta cagtttaaag atatggactc cagttatgca  49380

aaaagaggtg ggttttgatt tcctaaatat gcctcatggt ttattagatt tattcaagca  49440

aagattttca cagtgatctt acaaactttt tttaaagaaa tatctgggct gggtatggcg  49500

gctcattcct gtaatcttag cacttaggga ggctgaggcg ggtggatcac ctgaggtcag  49560
```

-continued

```
gagttcgaga ccagcctggc caacatggcg aaaccccgtc tctactaaaa atacaaaaat  49620
ttatttttgt gtgtggtggc gtgcgcctat agtcctagct actagggagg ctgagacaga  49680
attgcttgaa cccaggaggc agaggttgca gtgagctgat accgcaccac tgcactccag  49740
cctgggtgac agagcaagac tccgtttcaa aaaaaaaaag aaagaaaaaa gaaatatcta  49800
ctttctagaa tagcccaagt aaggtaattt tttagaaaaa tgagaatgtt aatgcatttt  49860
tgttggaaaa caattagaac tttagagaaa aattaaatag agtttttgtg atctcttaaa  49920
aaattagttt gtaaagcatt ttctacagtt ttgtggtcaa gaatgctact gattatattc  49980
aactgaaaat ttcttgtccc atttggccta caatgcttta gtttataagt gggcatgtgg  50040
caaatctgga aagaaatcaa agtataaggc taaggaagaa aggtagagaa cggttggtag  50100
aaaacaattg tctaatgaaa atgaaaaagg gtgaagaagt agaacatacg tattttaaaa  50160
atattcagag tatgagacaa ggttttgaga atttaaaagc gattatgtag ttatattaaa  50220
aatttagtct ctttttaagt gtccattgat gaacaaagtg ggaattcctg ttactcattt  50280
gcaaggcatt attgagtgtt cagtaacacg ttgcaaggca cttctgggca atcctgaact  50340
tggttctcaa attctttttt tttttttttt tgagacggag tcttgttctg tcccctgggt  50400
ggagtgcagt ggcacgatct cggctcactg cagcctctgc ctcccaggtt caagcgattc  50460
tcctgcctca gcctcctgag tagctgggac tacaggcgtg tgccaccaca ccaagctaat  50520
ttttgtattt tttgtagaga cagggtttca ccatgttggc caggatggtc tcgattgttt  50580
gacctcgtga tccgcccgcc tcggcctccc aaagtgctgg aattacaggc atgagccact  50640
gcacccagcc ggttctaaaa ttcttttatt tatttgtata tgccaaattc tgtagtgaaa  50700
tacgtaattc tgttgtaaat tgtagttcag tacaatttga ttttcactat tcaaatctat  50760
accaaaagct gtttttattg ttgggctgat tcttctacac tgttacttgg aaataataat  50820
ataccaggat tctttctctt agacttagga gtctttctct ttgcttgctt tttcagaggc  50880
taacagtact gggtattctt taactgtctt gatatgctga tgaaagcaca gtgttctgtt  50940
tttgaatctt ctcaaatgtc cttgtctttg attcacaact ttttgtctta agaggccttc  51000
agcatcccat acaaggaaac aagtcttttt ttagctgcta cctttggagt tgattttgtt  51060
tatgtctagg agcactaaat tatttatact tatactattg aaatattcct ctgttataaa  51120
ttcaaaaatt gactttggaa gataaaattt tagttgaatt taatacatag cactctggaa  51180
agagtattgg ccacaacaaa aaaaaaggtt ccctactcta ttggatacca ggtcatttaa  51240
cagccattta cggtatgcat tgtctttttg tttttatgat gaattgatat ttcccaaatg  51300
tggaagagtg aatattactt tgagatgttt gtgatagtcc attccttgct cctcttcaaa  51360
attaatgtca ttaaattttt attactttat tagatcttca tttctcagat aattttagtt  51420
cattatagaa aggcaagaaa atacagatca gagtgacaac tttgaaaatc tcactctact  51480
cataagggga tgggtgtatt ttgctatata ttacaaaatt agttttcttg atgaggacat  51540
ccactattgg agtaatttca ggtatcttat tttttctttt ctctctcttt tttttttttt  51600
ttttggagac ggagtttcgc tctgttgccc aggctggagt gcagtggcct gatctcggct  51660
caccgcaacc tctgcctcct gggttcaagc gattctcttg cctcagcctc ccgagtagct  51720
ggttactgag gcatgtgcca ccatgcccgg ctaatttttg tatttttagt agagacgggg  51780
tttcactatg ttggccaggc tggtcttgaa ctcctgacct tgtgatcctc ctgccttggc  51840
ctcccagagt gctgggatta taggcgtgag ccaccacgcc tgggcaggta tcttatttca  51900
aaacttacag tggtttagtg aattatacaa ttgcgtccag tgcgtagtat cctgaaaata  51960
```

gtattaagtc atgtgtttag gacatcaggt ctcttaagct aagactatcc aggcagaaat 52020
tgccctcttc tataaaagaa gaaaagtatt aattaggaag tactatcagt atggagaaaa 52080
ccattttaga attattaatt ggcatggttt ccttcttttt ttttttattt cgagatggag 52140
tctcactcta tttcccaggc tggagtgcag tggtgcgatc tcggctcact gcaacctctg 52200
cctcctgggt ttaagcgatt ctcctgcctc agcctcccga gtagctggga ttataggcac 52260
ataccaccat gccctgctaa tttttttttt tgtttgtatt cttagtacag actgggtttc 52320
accatgttgg ccaggccgca tggttttcct taataacaaa attaaggcat ttattactgc 52380
atctagattt tttttatttt ttattagaga cttactcaga ttactcccaa agtaaaggaa 52440
ggtatggttt aatcaatgct tcttaatgct gggttcacgt ttagtcacct ggggagtttt 52500
taaaaatgtt ctcacttcta gggatcctgg tttaattata attagcctgg gtgaggctct 52560
ggacagtcag ggtgtgagct atgggtttca tgtgatgaga tcccaggagt ggctctgttc 52620
tgtggccttg agaatttgtg ctttctaggc caggtgcggt ggctcactcc tgtaatctca 52680
ctttgggaga ccaaggtggg cagatcattt gaggtcagga gttcgagacc agcctggcca 52740
acatgttgaa accccgtctt tactaaaaaa gtaaaaaatt agcgggacgt gatggcacat 52800
gtctataatc ccagctactt ggggagaggc tgaggcagaa gaatcgcttg aacccgggag 52860
gcagagattg cgagatcatg ccactgcact ccagcctggg caacagaata aaaaaagaat 52920
ttgtgcttta ttttcttgcc tcacagtccc ctttctgtct cagaattggc aactgcctga 52980
aatagtctct gctgttatca tttgatagta cttttccaca tcttgaatgg atagatagag 53040
tgtttttttat aatagaagtg gatgaatgat tagagtatac taatatgaca ttgtattttc 53100
ctaaaagata tgaattgatt tcatttctga gcttttataa ttctcttctg taatagtctg 53160
tcaaattatt aaggttgata atattaacta aaatttgagt gcatattcta tgtgccagac 53220
tctgtgctaa cagatttacc tacatttgtt cacataatca tcacaagttg tttctgtagt 53280
agatacagct attatccacg tcatagatga ggaaacaggc atatttagga aacttgctaa 53340
agtgaggaca caaatctagc ttttctactc taactcatgt tcttaacatt atactgcagt 53400
gacataaatt atgtggtttg gtttgttgtt tatctcagtt gtcataagtc gaattaatgt 53460
ttgtttgttt gttttgagac agagtcttgc tctgtcgccc aggctgggta cagtggcgtg 53520
atcttggcgc actgcaacct ccacctcctg ggttcaagca gttatcttgc ttcagcctcc 53580
ctaataactg ggattacagg cacgtaccac cacacccggg taattttttgt atttttagta 53640
gagatggggt tttaccatgt tggccaggct gatttcaagc tcctgacctt aggtgatcca 53700
cccacctggg cctcccaaat tgctgggatt gtaggcatga accactgtgc ccagccagta 53760
agttccatgg ttgttaaagg atttctccac aaataaagct aaaagtaaaa aaaaaaaaaa 53820
aaaaaaaaaa ttctcaagca atataagatg cagactatta tgttgttcaa gttttttttt 53880
ttttttttta atctttggct ttatttttgg ggaaaccttt tttttctttt ttgttttcct 53940
tgggacggag ttttgctctt gtcgcccagg ctggagtgca atggtgcaat cttcgctcac 54000
tgcaacctcc gccttctggg ttcaagcgat tctcctatct cagcctcccg agtagctggg 54060
attacaggca tgtgccacca tgcccggcta actttgtatt tttagtagag actgggtttc 54120
tccacgttgg tcaggctggt cttgaactcc tgacctcagg tgatccacct gcctaggcct 54180
cccaaagtgc tgggatcaca agcgtgagcc accgcgccca gccagggaaa cctttatttt 54240
gaggcggagt ctcgctctgt cacccaggct ggagtgcagt ggcgtgatct cagctcactg 54300

```
caacctctgc ttcctaggtt caagcaattc ttctgcctaa gcctcccgag gagctgggat  54360
tataggcgtc tgccaccatg cccagctaat ttttatattt ttagtagaga cggggtttca  54420
ccatattggc caggctcttc tcaaattcct gacctcatga tccacccacc ttggcctccc  54480
aaagtgctag gattacaggc gtgagccacc acactcggct gctggggaaa ccttttaaca  54540
tgagtaaggt cagtgtgact tttaagttct tgatgctaac atcattgatt tcaataaagt  54600
ttaaaagtta tattcatgca tatatgcaaa tgaataaaag gctttgaaat agtgacttct  54660
tacggtacag tgaataagtt tcctttggtc tcttgaatgt tatacatgtt ccagtttgat  54720
ttactgagaa actgaaagta cctttacgtc atatgagctg tgagtcacct tggcacattc  54780
ataattagaa gagaccatca gattatcatt ggaaaatcag tttgtattta tcctttattt  54840
gaattccagt gcagacagat ctgaggttct cttcattttg ctaaaacttc ttagggcctt  54900
cagtcgcttt tggctctgta ttcgtgtatc tttggaattg tcctgttatc tctgcttgtt  54960
ttttacttga ttttccatcc atttccagta ttcctttctc ctctattttt ttccttcatt  55020
ttctttctgc tcttcctgtt gcgccattat tcatgttttc ctctttactc caactcaact  55080
atggctttac ttctgtttcc ttattccatt gttcctcata ctttttccta ctgcttcatt  55140
ttctttgcag tattctcagc ctagatgata ggggtcagca aatctgctca tcagtaaata  55200
aattttattg tagcatagct atgcccatgc gtttgtgcat tgtctatggc tgttttgatg  55260
gctgtagcca tagagttgag tagttgtagc tgactgtagg acttgcaaag ccagaaaatt  55320
tgactgtctc tttacagaaa agtttgccag ctcttggcct aaatcatatt ttccgctgca  55380
tttagggctt tttaggactg atcaaaaata catgctatac tggctttggt gaagtaacag  55440
aatgtgctct gtcctttaaa cttacaacta attgcatgct ttgattctaa tactgtataa  55500
tatcctgcga ttcttattca tgaccattct aattggattt agtctgaaga attacttttg  55560
cttaacagat tctttgtcac atttagtgaa aaatcataaa aggggaaggt tggttaatgg  55620
aaaagatctc catcaactaa ccactacctt ccttatctac aaatttatct tcttcctccg  55680
tgccatcttt tttttttttt ttttcagatg atcttgctct gttgcccagg ctggagtgca  55740
gtgatgcaat cacagctcac tgcagcctcg acttcccagg ctcaggtgat cctctcacct  55800
caacctccta cataactggg actgtatgtg cacatcacta tgcctgacta atttttttata  55860
tttatatttt ttgtagagat ggggtttccc tgtattgcac aggctggtct caaactgctg  55920
ggcctaagag tcttcccacc ttggcctccc aaagtcctgg gattacatga gtcaccgcac  55980
ccggcctcat tattattttt cctctggttt tagtagagag gatttttaag ccaacttcaa  56040
tcatgccctt gactctctcc cttctactta cctccttgtt ctctttttct ttttcttttt  56100
ttttagatgg agtctcggtc tgtcacccag gctgaagtgc agtggcgtga tttcagctca  56160
ctgcagcctc agcctcctga gtagctgggg ctataggtgc ctgccaccac gcccggctaa  56220
tttttgtatt tttagtagag atggggtttc accatgttgg ccaggctggt ctcgaactcc  56280
tgacctcaag tgatcacctg cctcagcctc ccaaagtgct gggattacag gcgtgagcca  56340
ccacgcctgg ccatcttttt ttttctcctt gctcttttat accacttctc tgtttctggg  56400
ctcttcaaca tctgcctttc tagttaatct ttccctttag catgaaaacc tattcacttc  56460
ctgctcatcc taaaaaggat tcttttttgt tttgttttgt ttttgttttt gagacagagt  56520
ctcgctcttg cccaggctgg agtgcagtgg cactatcttg gctcactgca agctccgcct  56580
cccgggttca cgccattctc ctgcctcagc ctcccgagta gctgggacta caggcacctg  56640
ccaccacgcc cagctaaatt tttgtatttt tagtagagat ggggtttcac cgtgttagct  56700
```

```
aggatggtct cgatctcctg accttgtgat ccatctgcct cggcctccca aagtgctggg  56760
attacaggca tgagccaccg cactgggccc aaaaggattc tttttaatcc tgaattcttc  56820
tagccattat cctgcctaag gctacgatta acctctaact gccaggtcct ttggaatctt  56880
tttctgtctt tattgctgca cttgaatgtt ggtttcaccc tccttcagaa tttcctcttc  56940
tgtatttttt atgtttattg atcattcctt ccctgcctca ttcctgggct tcttttcctt  57000
cacacacccc ttagatgtgt gtccccagtg tttgtttctt tgcctgctgc tcttgccaca  57060
tgacacacac tgccagctac cacacacaag ttccctccta tcatgtgtgt atcattgccc  57120
ttataccatg ttgtattaaa attatatgct tgtctcccct gttacagttt gagctctttg  57180
tgctccaagt aaagacagtg atactgtctt tattatttat tctcatggtc tagtatagtg  57240
ctttggcaca tagtacaggc tcaatataaa tgtgtttgaa taaatgaaat tcagtgcctt  57300
aatacacttt tgtagaagca ttattttatg gaaagaatga aaaagctgta agtggtctta  57360
catatatagt catccagcag atacttagag agctctggga tgtgttcctt gctgtgcttg  57420
ttgctatgga cagtacggag aaatacaaga atctattttg ggtccctttt gagaacctag  57480
tgaaactgtg tacctagtga aactgtatac cctcacccta gaaaaattta cacacatgta  57540
gattttacat gtaattcttt taaaaattaa tttttttct tttttttaaa gaaacagggt  57600
catgctctgt cactcaggct ggaatgcagt ggtgtgatca tggcttactg tagcctcgac  57660
ctcctggctc aagcgactct cccacctcag cctcccaagt agctggggct acaggtgcac  57720
gccgctatgc ccggctaatt tttaaaaata ttttatagac actggttctc actatgtttc  57780
ccaggctggc ctttacctcc tgggttcaag caatcctcta ccttggcctt caaaagtgat  57840
gggattatag gtgcaagcca ctgtgcccac gctaatgtaa tttcatggtg ttcacagttt  57900
cttcagggag ttcatatacg ccatgtactc tattctaagc atttttagag ttagagatag  57960
caaagcacgt gaataaattc aagaaaaatg gaatgttgta ctgcatgaca ttgaatatca  58020
aatggagtca gcgatgcaaa taattgtcta gattttacaa aaaaaattag cctggtgtgc  58080
tggtgtgcgc ctctaatccc agctactcgg gaggctgaga caggagaatc atttgaaccc  58140
agaaggtgga ggttgcaatg agctgagatc gtaccactgc actccagcct gagtgacaga  58200
gcgagactcc atctcaaaaa taaaaaataa aagaattgtg tagattttag tagttggaag  58260
aagttggagt gttaatgtgt aattagagaa cagtgagaaa taaaattcta cagattgttt  58320
tattctggtg tgctgttgtg ttctcatatg gttgtctttt tggtcttgat agtgtatcag  58380
taacagagta cgagtaacaa acagggatct cttctgaacg gcgtgacatt agaaaagctg  58440
tttacggcct caactttgct gtggtttatt aagacacaga tatgtgttca ttctggggcc  58500
aagcagtaac tggagagtgg cacttattga ggccagtatg gaggcagtac agagattatt  58560
gagattaaaa gaaagaaaca ggtggaacgg atctatgtaa tggaaagcta aacagaatag  58620
ttcgtggtac acagtagaaa agcattacat gtttattaag atatggtcat cttccattta  58680
ttaaagttac atgttttata atttttagag tatatagaaa ttctctaccc tatcatgttt  58740
gccaaagtca gaacaataac ttcatttatt aaatataaaa aaaataaaaa cctctagcat  58800
aaaatagaat tttatttgga caaacgataa aaaaatactg tgtggtacta gtaagagtaa  58860
ggttgattca agatacatgg gagcagaatc caaagtgtag aaataggcca ggtgcagtgg  58920
ctcatgcctg taatttcaac acttttggag gctgaggcgg gaggatgagt tcaggagttc  58980
aagactcgcc ttggcaactt ggcaaaaccc catctctaca aaaagtacaa aaattagccg  59040
```

ggtgtggtgg tgtactcctg taaacccagc tacttggtgg gctgaggtga gaggttcact 59100
tgcagccagt aagtcaaggc tgcagtgagc tgtggttatg ccacggcact ccagctgggt 59160
gacaagcaag accttgtctc aaaaacaaac cagccaggcg tggcggatca cctgaggtaa 59220
ggagttggag accagcctgg ccgacatggc tctactaaaa atacaaaaat tagctgggcg 59280
aggtgacggg cacctgtaat cccagctact tgggaggctg aggcaggaga atcgcttgaa 59340
tccaggagac ggagtttgca atgagccgag atggtggtgc tgcactccag cctgggtgac 59400
agagccagac tctgtctcaa aaacaaaaat aagcatagga catggggata aattgaagat 59460
ttatgaagac acagctgaag gagacataaa agtagatttg gctaaatgga aacatgccat 59520
actttgaatg gaattattta atactacaac gttgtcaatt ttcctcaaat aaatctctaa 59580
agataatata ttcagttttg gccgggcacg ttggctcacg cctgtaatcc cagcactttg 59640
gaaggctgag gtgggccgat cacttgagga cgggagtttg agaccagcct ggccaacatg 59700
gtgaaaccct gtctctacta aaaatacaaa aatcatctgg acatggtggc aggtaccagc 59760
tacttgggaa gctgaggcag gagaattact cgaaccccgt aggtggaggt tgcagtgagc 59820
tgagattgca ctccagccgg gtgactccat ctcaaaaaaa aaaaaatttt tataatatat 59880
atatatatat ccgtttttgt agaaattgac aaaatgattc taaagcttat tagattatgt 59940
gtattaacag aagaactttg gaaatttttt tccacaagag tcataaagga ggacttgccc 60000
tacaaaatat gtcagaatta aaacataact tgtcagctgg gtgcggtggc tcacgcctat 60060
aattccagca ctttgggagg ctgaggcagg cagatcatga ccagcctgac caacatggag 60120
aaaccccgtc tctactaaaa atacaaaatt agccggtcat ggtggcgcat acctgtagtc 60180
ccagctactc gggaggctga ggcaggagaa tcgcttgaac tcgggaggtg gaggttgcag 60240
tgagccgaga tcgcgccatt gcactccagc ctgggcaaca agagtaaaac tctgtttcaa 60300
aaaaaaaaaa aaaaaaaaaa gaattataac tgtcacagtg gctacgtatg gagcatccaa 60360
aactgaattt atgtgggtat tttattaata tgcaatatag cactttaatt ctggaggaaa 60420
ggtggattat tcagtaaatg attctgggac attggggaca aattagatac ctacttcaca 60480
ctgataaata aaaccaaata gattaatgag aaaactgtga ttaaacaaaa caacacccag 60540
actacactgg agcaaatctg tgaatttgtt taattttgag tggagaagga ctttataagc 60600
atgactacca gagcaaaaaa atcatgaagt aaaagatcga tacctttgat tataaagaga 60660
ttaaagattt aggccgggtg tggtgctcac gcttgtaatc ccagcacttt gggaggccaa 60720
agcgggtgga tcacttgagg tcaggagttt gagaccaacc tggtcaacct ggtgaaaccc 60780
catctctact aaaaatacaa aaaaattagt caggcatggt agcacatgcc tgtaatccca 60840
gctactcagg aggctaaggc aggagaattg cttgaatttg ggaagtggag gttgcagtga 60900
gccgagattg tgccacatca ctccagcttg ggcgacagag tgactccatc tcaaaaaaaa 60960
aaaaaaaaaa gacttagacg tgtccaaaag taccatacat ttaaaaagac atgccacaaa 61020
ctgggaaaag tagaaaaata gttttaaaaa tgaccagtga atgtatgaaa aggtggccct 61080
cctcacttgt aatgatttaa gaaatgcagt ttatttttat tttattgtat ttttaaagaa 61140
attcagtttt aaagcagtgg aatatgattg tctatcagct tgcgctgaat ggtaaatgtg 61200
agaaagatta ctactactta gtggtactga gggagttgca aaacacttaa cactgctagt 61260
gggatggttt aagtaaaaca agtagcattc ttaaactctc tattaggtaa agaataggta 61320
agtaatgcat atgtttccag gacattttca gtaagactgt ttactgatag ggttgtgtaa 61380
tgctaatata cttactatct agttttagta ttattttttt ctcttgtctt ggatggtttc 61440

```
aatggagtct tatgcatgca gatatattaa aactagtaat aaagcaagag aaggaatgtg  61500
gataaattat ctctaatttc tattttgttc tatttctatt tcatactcct gggaaagaat  61560
attaagtggg catgtgtact tgaacagttg ttctgttttt tattagaaaa gaatccgaat  61620
ctataaaatg ttttacatat ttgccaggga aacagaaaag atatttgtac agctgtaaga  61680
attggaatta atttcatttt actgactttt ccttaaccta attctgaaca cttttgccat  61740
aggtttgaga ataagttgtt ataaaatgac tactattctt cactaatagt attggcattt  61800
caattcctaa attctgtttt ttgattcttg aacatttctg aatttacttt ttttgtctta  61860
gttcttctac agaatcattt tcttcttttt tcttttttta tttttatttt ttatttttga  61920
gacagagtct tgctctgttg cccaggctgg agtgcagtag cgcgatctcg gctcactgca  61980
agctccgcct cccgggttca tgccattttc tcctgcctca gcctcccggg tagctgggac  62040
tagaggtacc cgccacagcg cccggctaat tttttgtatt tttagtagag acggggtttc  62100
accgtgttag ccaaggtggt ctcaatctcc tgacctcgtg atccatccgc ctcggcctcc  62160
caaagtgctg ggattacagg catgagccat cgcacccggc cttctttttt tctttctctt  62220
taacttctga gctgaaaata gtacctttta taaagaagtg ctcaaacgat gattggactg  62280
atttctcctt atttctctct ttctctctgt ctctttcact ctctttttag aatttttctt  62340
ttttaagtag agacgaggtc ccactatgtt gcccaggctg tcttgaactc ctgagcccaa  62400
gcaatcctct ttgcctcagc ctcccaaagt gctcggatta caggcttaag ctatcacacc  62460
aggcctaggc taatttcata ttttgagatg gcacaaattt ctttcaggta gctagctttt  62520
cctcctcctc cccacttaaa atagatcctg atccagaagc ctaatggaga aaatgaaaac  62580
agaatgttca cccataaaca gtatctttgt attggaatct tttctaaaac ttcttttgat  62640
ctttttagga gatagtgtgg gaatcagcaa tctagtatta cgtacgtgga atctgtcacc  62700
ttgttttttt aaatacagca aacctcatga agtgaatttc catatttttt cttgttcttg  62760
ttagttttgc accactcagg ctttgctgta gaatttgatg tatatttgat tctgtagagc  62820
atgggctatt gatcttcact cagctttcag aggaatctga ttagtaagtt tgagtttttt  62880
attatttttt agttgatttt gaagtaaaat acagcaccat tttaactgat accatttcta  62940
aacaatttc agttcaaatt ttaagttagc taatttagag cttaagaaaa ttgctttaaa  63000
aacataaaat tactggctgg gtacagtggc tcattcctgt aatctcagca ctttgggagg  63060
ccaaggcaga tgaattgctt gagcccagta gttcaagacc agcctgggca atatggtgga  63120
accccgtttc tacaaaaaaa atacaaaaag tagccagaca cggtggtatg tacctgtagt  63180
cccagctatt cgggtggcag aggtgagagg atcatctgag cgcagggaga ttgaggctgc  63240
agtgagccaa gtgagaccct ggtttcaaaa aaaaaaaggt tactaattgc agtgcctttt  63300
atcttattta atgggcttag tcaaactaag atgatgtatt ttatcttata aatgttttcc  63360
cttgaatttt aactgaagaa tccaatttgt acctctcaca aacagaatgt attagtaagg  63420
aaaataaata ctgcttttta ttacttaaat aggatatatt tttctcttag ggattttttt  63480
tctattttat ctcactttat cgtagtgcta gaaaatttaa tcattcattt gagataggga  63540
gaaaattagg tttttttttt tcttctattt tgagacaggg tctcattttg ttgtccaggc  63600
tggagtgcag tggcgccatc gtagctcacc ataacctcaa actcatgggt tcaggtgatt  63660
caccttagcc tcctgattaa gctgggactg cagatgtgta tcaccactcc tggctaattt  63720
ttgttgttat tttttgtttg atgaggtctc attatgttgc ccaggctggt ctcaaactct  63780
```

```
gggcctcaaa tgatcctcct gccccagcct cccaaagtgc tgggattaca ggcatgaacc  63840
tctgctccca gcccattttt taaaatatat tcacagcatt gtgcaaccat cactacaatc  63900
aatttacatt ttcatcaccc tgaaaagaaa ctctgaaccc cttagcagtt cctctctgtt  63960
tgtttcaatt ttccccagct ccaggcaact attgatttat tgtcttcata ggtttgccca  64020
ttctggacat tgcgtattaa tggaatcata taatatatag cctttttttt tctttttttt  64080
ttttgaaaca gagtctcact gtgtcgccca ggctggagcg cagtggcatg attgcagctc  64140
actgcatcct ctgcctccca ggttgaagcg attctcctgc ctcagcctct tgagtagctg  64200
ggactatagg cgcctgccac cacacctact aattttatat ttttagtaaa gacggggttg  64260
caccatgttg gccaggctgg tctcgaattc ctgacctcaa gtgatctgcc cacctcggac  64320
tcccaaagtg ctgggattgc agccatgagc caccgcatct ggccatatat attatgatag  64380
gcttgtttca cttagtatgt ttcttccatg ctgtagcatg tattagtact tctttctttt  64440
tcatggccaa atattccatt atacagttac acaggtacac tacattttgt ttattcatca  64500
gttggtggac attttcattg tttccacctt ttgatttata cataatcctg ctgcgaacag  64560
tgacttttaa agtttttgtg tgggccgggt gtggtggctc atgcctctgt aatcccagca  64620
ctttgggagg ctggggctgg cagatcattt gaggccggga gttcgagacc agcctgccca  64680
acatggtgaa accctgtctc tactaaaaat acaaaaatga gctgggtgtg gtggcgtgca  64740
cctgtaatct cagctactag ggaggctgag gcagagaatc acttgaagct gggaagccga  64800
ggctacagtg agccgagatc acgccactgc actccagcct gggtgacaga gtgaaacttc  64860
atctcaaaaa aaaaaaaaaa aaaaaaaaac tgcgtgtgga cataggtttt caattctcat  64920
gggggtgtgt gtgtatgcat actcatacat acatacacat acctgcaaga taattgctgg  64980
ctcgtatgct aaatctatgt tgaacctttt acataactgt tgggctgttt tgttttcttt  65040
ttattatttt ttgaaaatag agttggggtc tcactgttgc acaggctgat ttcctgggca  65100
tagtggctgt atcattttac aatcctacat agctgtttcc aacgtagctg tatcatttta  65160
caatcctact agcagtgtct gaggtttctt atgtttttca catcctcacc agcatttgtt  65220
attgtctgtc tctttgatta tacccatcct agtgggagag taagaagtag tatctcactg  65280
tagatttttt ttttctgttt acaactttac tttaaaaatt atatatgcac acatggtaaa  65340
aagttcaaaa cgtgtgtacc aaaagattta acagtgaaaa tagaaaataa gtgtggtcct  65400
tgttttcttc caccaaggca aatattgtta taatctccta aacaacttgt cttccagatt  65460
tctcattttc agtcaatctt gggcattgac ataaagaaat tcttagacat tgcttttatt  65520
agatcatctc atcccttgct caaaatcttc agtggccact gttgtttaca gaataaagtt  65580
gggatgctat acagggccct tcccagtgga acttctcttt ttcaacctta tctctcatta  65640
tttcccaatg tttttttttt tttttttgag acggagtctc gctctgtcgc ccaggctgga  65700
gtgcagtggc gggatctcgg ctcactgcaa gctccgcctc ctgggttcac gccattctcc  65760
tgcctcagcc tcccaagtag ctgggactac aggcgcccgc cactacgccc ggctaatttt  65820
ttgtattttt agtagagacg gggtttcacc gttttagccg ggatggtctc gatctcctga  65880
cctcgtgatc cgcccacctc ggcctcccaa agtgctggga ttacaggcgt gagccaccgc  65940
gcccggccta tttcccaatg ttaatctact tattgaccta ctaagctggc atgttctgtg  66000
tgttagacat caccaacttt gtgccttctt tttttgtttg tttttgagtt ggagtctcac  66060
tctgttgccc aggttggagt gcagtggcgc gatcttggct caccacaacc tctgcctccc  66120
gggttccagt gattctcctg cctgagcctc ccgagaagct gagacgacag gcgcgcgcca  66180
```

```
ccatgccctg ctaacttttg tatttttagt agagatgggt ttcactgtgt ttcccaggct  66240
ggtctcgaac tcctgacctt gtgatccacc tgccttgggc tcccaaattg ctgggattac  66300
aggcgtgagc caccgcggcc ccctgtgcct tcttctttta ctcctggatt taatcccaac  66360
gtgaagaatc taccttacta actagagttt tagatacttt ttcaaaacca agcccacatc  66420
tgtccttttt agagtcttct ctgaccttcc ctgctcattg tggtttgttt ttattgcctg  66480
taacaatggc tgttaaactt tacattttaa attaatttat gtttgtatgt atttatttgt  66540
tgagaaaggg tctctctctg tcacccctac tagaatgcag tggcgccatc atggcttact  66600
gcttcctggg ctcaagctgt tctcccattt cagcctcccc atgcaccacc ctacctggct  66660
aatttttttg tttgtttttt ttagtttagt ttttgtagag acagatgtct cactgtgttg  66720
cacaggctga tcttgaactc ctgggctcac ttgatcctcc catctcagcc tccccaagtg  66780
ctgggattac aggtgtgagt caccatgccc agactttaac attttctttt tagtatagaa  66840
taggtcagtt tttttccctc tgatgagatc ccatgctgac tcttagttaa aacaaggctt  66900
tggttggaag aagagctagt gatgtcctag ctccctactt actccacttt cccttgcctt  66960
ctggggtgtc ctgaagacat catagggtgt catgaagtac agttggagaa ccagtggtct  67020
ccatcatgta ccaaacactc atcttcacga agcagtatgt agtgtctttt ttaccggtat  67080
attttctctc tcccaatgca ttaaactttt ctggagttca gaaaacaaat ttatagaatt  67140
aaggaaatgc gtcccccccca accatggtgt ctagtatata tacagtgact tacagataac  67200
aggtgttcaa catatatata ttcctttgat tgatttttga aaagtttaca tgtatatatt  67260
ttttatatac ggggtctcac tctatcactg aggttggagt gtggtgatgc agatcttggc  67320
tcaccgcaac ctcctcctcc caggctcaag tgattctccc acctcagcct cccgagtacc  67380
tgggaccaca ggtgcgcatc accatgcctg gctaattttt tatatttttg gtagagacag  67440
gattttgccg tgttgcccag gttggtttcg aactcctgag ctcaggcagt ccacctgcct  67500
tggcttccca agtgtgagcc accactgaaa tacttatatt tttaaactta atttatttat  67560
atttattata tttttatgtt tttatatttt aaaaaaatatt tttatactca ctagacccaa  67620
ttttatactc ctaaaccagg gaataactgt tttttttttct cttacatagg catgatacca  67680
tagacaatga ttaaaattgt aattaccatt catttcttag ttttgtggct gggacactga  67740
tgtcttcaaa tgttagtttg caaatacagt cagccctctc tatccatggg ttacacagct  67800
gtgaattcaa ccaaccatgg atccaaaata tatgggaaat acgctggggc tgtgggtcac  67860
acctgtaatt ccagcactta gggaggctga ggcagatgga tcacctgagg tcaggagttc  67920
aagaccagcc tggccaacat ggcaaaaccc tagctctact ataagtacaa aaaattagct  67980
ggccatggta gtgcacatgt gtaatcccag ctactcgaga ggttgagaca agcaatttgc  68040
ttgaacctga gaagtagagg tttccatgag ctgagattgt gtcactgcac tccagcctgc  68100
gcaacagagt gtgagaagaa aagaaaaaaa actgtctgaa aagaaaaaaa aaaattatat  68160
gggaaatcaa aagcatctat actgaacatg tacagacttt ttttcttgtc attattcctt  68220
aagcagtacc acaactattt ccgtagcatt tactttgtat taggtattat aggtaaccta  68280
gaggtttaaa gtatgcgaga gtatgcaaat actacaccac tttgtatcag ggacttaagc  68340
atccctggat tttggtatcc ctagggggta ttagaaccaa tcccccatag atgctgaagg  68400
acaactgtag tgtgtgttgg aataatttat tttcaaatgg atcatttgga gaacactatt  68460
ctttaggaaa catagcctcc taagttctgt tccatacatc cctttcacct ccacggcgtt  68520
```

```
gtagcatcct gctttcatga ctgtgtcatc actcggaagg aactgcttct cttccagaat  68580
gcttttcaag atctactctg accacagcta taaactttac acttctattc tcttcttgcc  68640
cctcacagtg ttctctgttc ctctaagatc ttaaactctg tctactccta atccagcctg  68700
ctgggtgtgg ctggagaaag tcccactggg gggctgatta gttaggaatg tagggtttcc  68760
agctcttgct ggagcctcag aagagttcag cagacttttt tttttttttt tttccttaaa  68820
cctatttctg cagccttgat gaccactcct tccagtccct cacctatttg ctttattcat  68880
ggcagaggct ctttcttcct gcttgtcagt acaaagaggc aggattcttc acctggatct  68940
gtggattctc aaagaatttg tggagagaat tcagggcatt gatgaccttg gatgaagaga  69000
aatttacatc tttatttaca ctaaccttca agtgaaattt agcatttttt gccatttaaa  69060
aatatgggca acaaacaact agtagtatta gcagtattta tgacttaagc acctatagaa  69120
ctcagttaat ttcatatcgc ttgatgttat gggtatctca aattattatt ttatgtatat  69180
atatttttga gatggagtct cgctctgtct cccaggctga gtgcagtggt gcagtctcag  69240
cccattgcaa cctctgcctc ctgggttcaa acgattctcc tgcctcagcc tcctgagtag  69300
ctgggattac aggcgcacac caccacgcct agctaatgtt tgtattttca gtagagaagg  69360
ggtttcacca tattggccag gctggtcacc aactcctgac ctcaagtgat ccgcctgcct  69420
tggcttccaa agtgctggga ttacaggtgt gagccaccgc acccggcctc aaattatttt  69480
tagaaacaga atcttgatat ggtatccgct ctggccttga acttgtgggc tcaggcagtc  69540
ctcccacctc agcctcctga gtagctggga ttataggcat gtgccactgc accaggcttc  69600
aaattattat gtatgttcat cacctcttta aatttataat agttattaaa cctgttactg  69660
gatcttaata tttaatgctt taattaagaa catgtatgtt actatgccaa cagatttttt  69720
tagtttttga taactgcatt tcattgttac ttgttctcat ttgatttcct gtgtatttta  69780
cgaatttaag tacattctga atacggtttc ataggcttcc ctaaaatatt gaaggggccc  69840
atggattaag aaaaaggcta agaatcccta atctagaggc tccccacagt cctcttttgt  69900
catcataccc ctaccccatt ctagcctgag gagcgtggct ccacctgtgc ccttggtttt  69960
gttgttccag tccatacatc ctgcaccctt aactgtgttt cttatcccca acttgtttct  70020
ttgtgttatt cttcagtatt atagtcttta atataatctg tataatacat ggtgtagtag  70080
tatatgctcg tagtatacaa ttcagttaga acagatgagt attcaatgaa aagataatct  70140
cctctctaac ccccagtccc acttccctgg ggaagcctgt gttcttgtgt acaattcaga  70200
aaatgtttat acacatattt tttatttatt tattttttga gacggagtct cgctctcgcc  70260
aggttggagt gcagtggcgc aatcttggct cactacaacc tccgcctccc tagtagttca  70320
agcaattcaa ggttcaagca attcgcctgc ctcagcctcc cgagtagctg ggactatagg  70380
cgtgtaccac cacgcctacc taatttttgt atttttagta gagacagggt ttcaccatgt  70440
tggccaggat ggtctcgatc tcttgacctc atgatccacc cgcctcagcc tcccaaagtg  70500
ctgggattac agatgtgagc cactgtgccc agcctgttga tttaatttta aacagagttt  70560
cgctcttgtt acccaggctg gagtgcaatg gtgcgatctc ggctcaccgc agcctctgcc  70620
tcccaggttc aagtgattct cctgcttcag cctcccgagc agctgggatt acaggcatgc  70680
accaccatgc acagctatat ttagtagaga tgggggtttc tccatgttgg tcaggctggt  70740
ctcgaactcc ggacctcagg tgatccgccc gcctcggcct cccaaagtga tgggattaca  70800
ggcgtcagcc actgcacccc gcctatacac attttttgt tttttgtttt tttgagatgg  70860
agtctcgctc tgttgtccag gctggagtgc agtggcgcga tctctgctca ctgcaagctc  70920
```

tgcctccctg gttcacacca ttctcctgcc tcagcctccc gagtagctgg gattacaggc 70980
gccggccact acgcccatct aactttttgt atttttagta gagatggggt ttcaccgtgt 71040
taaccaggat ggtcttgatc tcctgacctc gtgatctgcc tgactgggcc tcccaaaatg 71100
ctgagattac aggcgtgagc caccgctccc agctatacac gtatttttaa tgccactcca 71160
gtctatgttg gaaccatttt acttcccctt tcttattttc ttcttgtgtt cttgaaggcc 71220
tagatcagct gttgctgata ggctgtcact gtcactttag aaagcccaga gccttttgtt 71280
ccttagaact ttgtttttaa ttgtattgta gcactcattg tattcgattc taaaagattt 71340
gcttcatttc tgtaactagt ctcttacacc caggagctcc tagttcctac aggaaatgct 71400
gggaattgta tcagtcaaat gtgaatcccc acctcgtcca gacttatgag tgcattgtag 71460
gtactcagta agtgctaaaa atgactaaat agtcccactg ataccaatct atatactgat 71520
actttatata gtatatagat tggtccacat ataacgatga cacataatga gaaactgtct 71580
taaaaagttg ttgaaagtgc cgcaggaata ggaattgatc aaaacaatat gatttttttag 71640
gtttatatgg aactttgatg tttgagaaaa ggctgattta gttgagaaga aatggttagc 71700
tgaggatttt gatgacttct ctggaagcac atttgagggt ttgtgatgtt aaatctgatg 71760
ttaatgatta tttcatccag ttttatgtca ttttatagtt tttatacatt taagtatatt 71820
tatttctaat gtttaacact accattttag ttatttgacc attattctgg ccctttaaaa 71880
aatgctcaga caagtttgaa tgatttttca gaggcattat tggctcagag gtaaaagagg 71940
aaagattgag aagctgaata tgtactctgt ttcctgggta tggggctggg gatacccaga 72000
agaggttcac acgttggtcg agacatttct ttatgaccac cagcaggtgg catcaccggc 72060
ccaaaatgac taagtttctg cccagaatca gaagagaagg tgttgagagc ccactgctgt 72120
gggggtagca tggaggtggg atacaggggc tggaggtgat acaattttgt ttcttcctcc 72180
aacatcgcct gctagtctag aggcttttat aaattgaaaa actaattctt tatcatctca 72240
tctgatggtt tttatgtttt tcctttttttc tctctatacc tgtagttcct tcagaaacag 72300
gtaacacttt tctaatagtc acgttgtatt cttgcatctt gttgttacaa tgcttttgtt 72360
tctcaccata ggggatgatg gaaaattaat attctttgac ttatggcatt ggtaaaatct 72420
gcatgcaaat tcccacagtt gcctgtagat tagagccagt tgttttttttc tcaactttgc 72480
aggaatcctg gttacaacat tgtactattt actaccaaca gtgtttttttt tttttaaaat 72540
ccagacttgc tgggcatagt ggctcatgcc tgtaatctca gcgacttggg aggctgaggt 72600
gggaggattg cttgagccca gggctgcagt gattgcggca ctacactcca gcatgagtga 72660
caaagacccc atctctgaaa aaacaaaaac aaaaacaaat tttttttaaa gaaacagaaa 72720
caaaaatcca aacttgtaac cactgtaaaa caaatcagaa tttacgatag tggatattat 72780
taatagtgca gaatggatac ccagatcttg cttcctttct agctaatgat gcaatgttgg 72840
cctgaaatgc attacttata gccagggatt ttctcagcat cctgatgata tagcctcatt 72900
tcgtgctaac tctccacttc tgcacatctt cccctaagtc ctttactcat ctttagaaag 72960
agctactttt ggtgaaattt taaaaccaag gaatatcatt ctttatagaa tcacacttct 73020
gtgttttccc cttccccatt tctgtctcga aagcgacaga ctgctacata acctgtgaat 73080
actttttttt aaaaaaagtt tggtattgta aacagaagat ttaagattaa aatgtagcat 73140
tgagaaaaat agatttatta ataatgccct cttaacacaa cctaaattct ggtcagtgga 73200
ataaagcctg ggtcctaaag ttttagacgc ttgcttgctt ttccacactg gctcttactt 73260

```
ggggatcctt ttagaaattt gtttagaata atactgtaaa aacatattta agctactttg  73320
tgtgtacatt tgggatcttt tggtttgaag acggcttgac tcaagacttt ctaaatattt  73380
tcacacacac acacataccc tgtagtgaga aaaaaatccg tttatatggt tctataaaaa  73440
tctctagctg cttcgagctt taatttcttg aatcaaaaga gtattgtttt taatactgag  73500
cttctatcta aataaatgct ttatttactt aaatgtgtgc ttttcaaaaa ctagtatgat  73560
taagacatta acaggatctt agacgtaaag gaacagtcct gttgcttctt ccagaagata  73620
atatgactcg tttggaattt tcctatagtg tagtttttg tctagtgttg tgagaattaa  73680
agggatttca ggatcttaag gtaggttatt atttgatgtt ttcttggaac attttacatt  73740
cttgaaaata cacatggcta aattaatttt tgccagcaat ccacataact ttaagataat  73800
gtagagaaga acgtgattca ggttagtatc aaataaggtc agatttctag tgccatcagt  73860
agctttcagc aaagatgagg tgttggtaag atagcattag tctcttagaa tctcttagag  73920
agattttcca aaattcagcc atttctagtg aatgctccat tccaccccca gctgagtcct  73980
gctgctctgg ggaactccct cagcacactc ttggctctta gaattgctag caatgggagt  74040
agtgctgctg gtggagctgg cagctaagcc cagaggtgga ttaatgcttt tattccctga  74100
tgtacaggta cacacactca tacctaccca cacctagttt gggataagaa gaggttagaa  74160
ttagctaggc ttgaagttcc atgcttaaat ttgctggctc agatttctta ttttggcatc  74220
actttgccca ttagggagac aatgacagtt atagaagcat tgccaaataa aaaatccatc  74280
tggaataacc tcttttgtag gagtattgtg tgtttagttg ttgattcgtc ccttcctcct  74340
cttagtggca acttacagta ctgggaagga acagtggctg ggagcttata ttcctcagca  74400
gagccagatc agcagaagta ttactcctta gttcgtagta ggtggtaccc tatgggtcca  74460
gtcatttaaa tgcaagcctg tatctacaga gcgtttccta gtgccatcat tgcccagtgg  74520
gcctttattt agctgagtct aactcccaac tagagaaaat ttcctgtgcc agacagcagt  74580
atggtcagct aacatgtgga tgctacattt gctttcataa gtcagtactc ttcaataaca  74640
ttagtagaag agaagaggac acaaagtgag agtgtgttaa taggaagtcc aggtatgcct  74700
gctacctgaa ctttctgaga caggtaatac tgtagggcct gaactttgta gcagagtggt  74760
tatatatgaa gaagtgggtt ctgggagggg ttaaaccact tagaatggct tcatttacta  74820
atggcaagag tttgctggga tattgaccac tgtacataga catgaatatg gaaagttaaa  74880
aacaaaatcc acatatattt ggctgcaagt actccgaagg tatatctaat tagtgcatcc  74940
attaaacaaa agagatattt taggccgggc atggttgctc acacctgtaa tcccagcact  75000
ttgggaggcc aaggtgggtg gatcacctga ggtcaggagt tcgagaccag cctggccaac  75060
atggtgaaac cctgtctctg ctaaaaatac aaacattagc tgggcgtgtt ggtgggcgcc  75120
tgtaatctta gctacttggg aggctgaggc aggagattcc cttgaacctg gaaggtggat  75180
gttgcaggga gccgagatgg tgtcactgca ctccggtctg ggtgaaagag caagctccat  75240
ctcaaaaaag aaaaaaaaaa aaagagatat ttttgatgga ttgatagaaa ttttcttttt  75300
ctttttttt ttgagacagg gtctcactct gtcgccaggc tggagcacag tggcgtgatc  75360
tccattcatt gcaacctcca cctcccgggt tcaaacgatt ctccttcctc agcctcccga  75420
gtagctggga ctacaggcat gtgccaccat gcccaactaa tttttgtatt tttagtagag  75480
agagggtttc accatgttgg ccaggatggt ctcgatctct taacctcatg atccacctgc  75540
ctgggcctcc caaagtgctg gtattacagg catgagccac cacatctggc cagaaatttt  75600
cttggtcact tctgagacat gcagagtaat tacctgtaat ataatttaat gaattatgtc  75660
```

aatatattaa aatatgcttc atgtgggctg ggcatggtgg ctcatgcctg taatcccagc 75720
actttgggag gccaaggtgg gggtatcact aggtcaggag atcaagacca gcctggctaa 75780
cacggtgaaa ccccgtctac taaaaataca aaaaattatc cgggcgtggt ggtacacacc 75840
tgtagtccca gctactcggg agactgaggc aggagaatcg cttgaacccg ggaggcagag 75900
gttgcagtga gccgagatca cgccactgca ttccagcctg ggcaacagaa cgagactcta 75960
tctcaaaaaa aaaaaaaaaa tgcttcgtgt ggcttaaaat tatatgaaaa gaaaatacct 76020
ttactgatag tcatctgtga ttccatttgc taaattaaac gtgaaagcat acttttactg 76080
aatactatat attccgtatc agtttagata gcagtttatc ttcacataca taagttttaa 76140
gtttaccttt attatagtgc attggtcttt tgttttcatc aacctaaatt atgttcaata 76200
aatgtttctg ttagatttta agttaaacaa ttatgtgaaa ttcatttttc gtaattgttt 76260
tttaacatat gtctttgttg gtaattcacg tgtgtgagtg taactgattg ccagattata 76320
taaactttca accaaaacca ttctttgcag atgcttttac tgactctgct atcagtgcta 76380
aagtgaatgg cgaacacaaa gagaaggacc tggagccctg ggatgcaggt gaactcacag 76440
ccaatgagga acttgaggct ttggaaaatg acgtagtaag taacatcttt gtaattattg 76500
ctagactctg gtcagtatga catcctgtca cttggttgta atttaaatgt gcttttgttg 76560
ttgttgttat tgtagtgagt gtatttagag cagcaggttt gttgtataac tagagacttt 76620
ctcccaagca atatataaag aaaaatgttt gtcattttac ttgtaggggt taagcaggag 76680
tactgtctgt tcttgtggat gctcatgaat tacttctttg tgattaaaat aaataataag 76740
aagtagctta aattaaaatt agaaaccatg ggaaatgccg gtgtgttttg ctttaacacc 76800
cagccaaata aggtagccta aggaaagtgg tgtcttaatt gttgacttca cctagagaag 76860
aggttgaagt aggacatttt aagcctcttg tctgaagaaa aggttgtcat taagataaat 76920
aattaggtta cattggaatt aaagcattac ataaatttct tggtcttaaa tttggattat 76980
tctccacaaa attcttttat ttctaaaacg cctcttgtca catactagtt ttgtttctct 77040
ctttaatgca ttatctgtac ttgaagtgct tagctgggta tgctggcaca tgcctgcagt 77100
cccagctact tgggaggctg aagcaggagg atcacttgag cccaggagtt ggagtccagc 77160
ctgaatgaca taaggagacc ccttctctaa gaaataaaaa taaaaacaaa tacttaataa 77220
agactctgtc tttaggatag agagcataga gatataaagc aaagtgtctt gccaaaaatg 77280
agtgttatgg taccaatatt tgagtagaat gaagaatctt ccattgagta gaaagagaat 77340
ttgtaacata tctgtgtttg atgtttaagg cataacagct taataatgac actcttcctc 77400
agacaggaag cctgaaatgt cctactttga cctaaagtct agtaataaaa ctggacatac 77460
acaggcaaca tgtcattaat tctcaaactt taacaaatca tatataacct aatataatgg 77520
ttctcaagtc tgtacatcac gtcacctgta tgaaaaatat gaggaaacag agacttcttt 77580
tacactattg gtgaggtgga taaattgata gagtctttct ggagagaatc tggcaatgct 77640
aatcaaaatt taaaatgcac atacactttg ttccagcagt tctatctcta gtaatttatt 77700
tttgccctca tatatccata agacatgcaa ataattatat gtgaagattt tttttttttc 77760
tttttctgca gagacagggt tttaccatgt tgcccagggt gatctggaac tcctgagctc 77820
aggtaatcca cccacctcag cctcccaaag tgctgggatt acaggtgtga gccatcatgc 77880
ctgaccagga tttttttttt tttcagcatt atttcttttg ttgttgttgc tgttgttttg 77940
agagatggag tctcactctg tcacccagac tggagtgcag tggtgcgatc tcggctccct 78000

```
gtaacctcca cctcctgggt tcaagtgatt ctactgcctc agctttccaa gcagctggga  78060
ctataggcgt gcgccaccac acccagctaa tttttgtatt tttagtagag acggggtttc  78120
accatatgtt ggccaggctg gtcttgaact cctgacctca ggtgatctgc ccacctcggc  78180
ctcccaaagt gctgagatta taggcgtgaa ccaccatgcc tggccatagc attatttcta  78240
atagtgaaaa attggaaaca tgctaagtgt ctatcaatat agcatgagtt agatttatga  78300
tgtcaccatt caattgaaac actacatatc tcccaaaaag aatggtgttc caatatggaa  78360
agatatctaa gatttattaa gagaaaaagc acattgcaga acactgggat cctatttgct  78420
ttttttttc tttttttgag acagagtctt gctctgtcac actgcaacct ccgcctcccg  78480
ggttcaagcg attctcctgc ctcagcctcc tgagtagctg ccaccatgcc cagctaattt  78540
ttgtgttttt agtagagaag ggtttcacc atgtttgtca ggctggtctt gaactcctga  78600
actcgtgatc cacctgcctc agcctcccaa agtgctgcga ttactggcat gagccaccgc  78660
acctggccat gaaatttttt ttttttttta aagagctgtt catattctta ttgcctagaa  78720
gatgtctgaa attacaccca agaaactctt tttgagacgg agtcttgctc tgttgtccag  78780
gctggagtgc aatggcgtga tcttggctca ctgaaacctc tgccttccag gttcaagcga  78840
ttctcctgct tcagccttct gagtagctgg gactacaagc gcccgccacc acatctggct  78900
aattttttgt atttttagta gagacagggt ttcaacatgt tggccaggct ggtcccgaac  78960
tcctaatctc aggtgatcca cccaccttgg cctctcaaag tgctgggatt acaggcatga  79020
gccactgcgc ccggctgaaa ctcttttttt ttcttttaag atggagtctc gctctgtcgc  79080
ccagacttga gtgcagtggt gtgatctcag ctcactgcaa gctctgcctc ccgggttcac  79140
accattctcc tgccctagcc tcccaagtag ctgggactac aggctcccgc caccacacct  79200
ggctaatttt ttgtattttt agtagagaca gggtttcacc atgttagcca gcatggtctc  79260
aatctcctga cttcgtgatc ctcctgcctc ggcctcccaa agtgctggga taccaggcat  79320
gagccaccgt gcccggccag aactcttaat agtagttatt tatgcacgct gggattggaa  79380
gacatttact ttttactgga tgtctttccg tattgtgtgc tttttttttt ttttttttat  79440
gtagggcata cattacttaa gtaattttaa agcctccata agtaagtgtg atttcctgcc  79500
catgtgtttg gcaaaaggaa ttgcattggt ggtagactta cattatagtc ttacctggag  79560
tagcacagga ggacccaagg ttaataggtg aacttcgagg caagccttag cattgaggtt  79620
gccatcagca ttgcttggtt gatgtgttca ttcttctggg atggattaca acctttactg  79680
gactttatac ttttcaccag taaggcttta aaaaaggagt tgaaacatta gagaataatt  79740
atccaggcag taatattcac tggtaaatag tcttccagcc tgtggcccaa ttggttgatt  79800
cttttacgtt aaagaatgca gcctcagctg ctctgcctat ggagtaggat tcttttattt  79860
actttcttaa taaacttgct tgcccctggc tccccccac caaaaaaaga aggcagcctc  79920
ccttttgcga atggtaattt cctatagttt cctcgtagaa ttgtggagtt acctatgctg  79980
aggttatagg ttagggtatt gagatccaga gttgccactt ctgaggtgtc acaactgcta  80040
atggtaaaac catttctaaa gcccagttct tgtgactttg tccagtgatt gcctgttcac  80100
cgtttcatgc tgccttccca tttgagcatt cccaggagga aggggaggtt gccagggacc  80160
tagtaccata gtccgacctt ggaatcgttg aatatgaggg aaagcgttgg cttctccctt  80220
ctttctccca aacattggaa gtatttttgg ctgttaaaaa gcacccccttg ttccatgtgg  80280
aatcccttgt ttaaaagaag taaaatatgt acctcctgtc ctccacagac ctgaggacca  80340
gtgtgatctc aagaaggtta caggtaaatg tagatgtctc taactgaaag gtggctttta  80400
```

```
caggttagag aaaagagaga accctgatct gaaggctatt ttatgaagta attaaaatgt  80460
tctaaacttt aaaaataact gctcaaataa ttgtgttgta tagttactta tcaactggag  80520
gggctgataa gtatttttct aaaacatttt taaggaaatt ttttcctatt ttctaatttg  80580
ctaattttgc tcaagtagtt tgttagatat tgttaatata gatgttggtt ataactgaat  80640
gaaagggaac aactactttg acattttgaa aaacaagctt cattttcttc tagtctaatg  80700
gatgggatcc caatgatatg tttcgatata atgaagaaaa ttatggtgta gtgtctacgt  80760
atgatagcag tttatcttcg tatacgtaag tttgaaaagt ttgtttttat tttagtgcat  80820
ttgtctttga ttttcatcag cttaatttat gatgaataaa tgtttgttag tttttaagtt  80880
aaacaattac atgaaataat ttttctctta ttaccaactg tgataaattt ccattaaaaa  80940
aagggaataa atgtagtttg cctataccct gtttttatgc tctaaacaaa ttttggtttt  81000
gtcttttttt ttcttttgag agggaatctc gctgtgtctc caggctggag tgcagtggtg  81060
caatctcggc tcactgcaac ctctgcatcc cgggttcaag cgattctcct gcctcagcct  81120
cccgagtagc tgggactata ggcgcgtgct accatgccca tctaatttct gtatttttag  81180
tagagacggg gtttcaccat gttggccagg atagtctcga tctcttcacc tcgtgatcca  81240
cctgcctcgg cctcccaaag tgctgggatt acaggtgtga gccactgtgc ctggccggtt  81300
ttgtcttcta agttgttaaa aaatatctaa atttgcaagg gcagagatta tggtgaacag  81360
tttaaccagt ttttgaaata tgttcctctg gagaaaaggt aacagaaaaa aaagttagaa  81420
ttttgattta taaatacaca gatcactata acttttagtt ttagttttag ttttagtttc  81480
tgtttttacc agtattctaa actctaaact ttcttagtag ttgattatga cagatacata  81540
aactgtggct ttaaaggact cattttgctt ttcttttcct catgtttcag agtgccctta  81600
gaaagagata actcagaaga atttttaaaa cgggaagcaa gggcaaacca gttagcagaa  81660
gaaattgagt caagtgccca gtacaaagct cgagtggccc tggaaaatga tgataggagt  81720
gaggaagaaa aatacacagc agttcagaga aattccagtg aacgtgaggg gcacagcata  81780
aacactaggt atttaaagga aatcatgatg cagtattttg gatacacaac tcaaggtctg  81840
tgtgagacgg tgtattgtta ttatatttcc tcttccttta atatagctta ggtagagaat  81900
gcaagtagaa ttggtttaag atctgttaga gaaaaggtta tggtgatctt ggaaaatatg  81960
cttttgagag taagctctgt ggagccaagt gttggtatat cacggtgagc aatccaagat  82020
cttgaagagc ttgttaaaat agttatctgg tgggggacac gtgtaacaat cacagcagta  82080
caatatgatt tgcttggtta aaggcatgtt caaagtacta ggaacataca gaatgaggag  82140
gagctagcat aacctgtaga gtcagagaaa acctcattga ggaggtgaca ttttgtgata  82200
agataatagg gtctttgaca cttagagaag agttgggaga agagtttatc acctgatgaa  82260
aagccatgta caagcatggc tatgagaaaa tttggccagc tcaggagagg gctggttgtt  82320
gcatgtgtct ggaacacagg atctgtgtca ggtgcagcag tggcagttga tagtaggaac  82380
tgaggtcatt aaaggacttg gcatgtcatg ctaaagagca ccctgttgga aggagatggg  82440
gtgaataaac cctggggcat tgaggactgg ctgagacaca gagaacagtt agtgcactga  82500
aatagttcaa ctgtgagaat ttggtaacca cctagttaag ggatgagcct gaggtttatt  82560
tgataactaa gtgacttaat ggatgtactg gtaagagaga gaggaaacat ggagcaagtt  82620
tgaggggaaa aacagtgact ccgtttgtgc agctaattgc atatgtgggc ttgtgggtct  82680
ttcatttatt cataaacgtg ttgagaaata cctgctacct atctagtaaa gtaagagatg  82740
```

```
catcctctct taaaggcagt cagcttagag tctggtgatt tgaattgaca tgtccactga  82800
tagatgttga cactgtgaga ctggcggttc agtttgaggt ttcatcagca ttgccgatat  82860
tggagccatg aaaaaccaaa gaacagccag tgagagaaga gatctcagag aaaataaaat  82920
tgagaaagtg aaggacaaaa aatgttgtga agatagacca agattgatgg aatcagccat  82980
agagaggtca agtgggatga gaatgagcac gcatctgtta aactttgtgc ttaggagcag  83040
aatctaaggg aagggacagt ccagaggtta gaactcaggg taagatggaa gaacaggggc  83100
atctgggagt gaggcagttt ggtttagtgt agaacctttt tgtaacaagc attcccttct  83160
gtctagatga cttttagata tgtttcattg gcttggtacc ttttagaata aaatgattta  83220
gaggatctct cattttcagg gaaaataaat atattcctcc tggacaaaga aatagagaag  83280
tcatatcctg gggaagtggg agacagaatt caccgcgtat gggccagcct ggatcgggct  83340
ccatgccatc aagatccact tctcacactt cagatttcaa cccgaattct ggttcagacc  83400
aaagagtagt taatggaggc aagtattttg accagacttg tcaatatcat tgataaaata  83460
gttttctaaa tacttaaaat acttaaaata gtttacataa ctgatatgaa tgtgcacttt  83520
aatgatttgg tgagtagctt tcacttcagc attacttaaa attggctttt gtggatatta  83580
aattagtaaa acattgtata tgtcattgac atatatatta tttagcatga tgaaatattc  83640
atgatgtact aagataaagt gctacattta acccaagaca atcacttggc caaaaacact  83700
tcacatataa agaaattgga aactttgggt aggttctcaa ttttaaaaac actggataat  83760
aaaatttttt agacataatt tatatggaaa attctaacct atgtgcaaca ctgtggttaa  83820
tatagatcaa ttttcattat ttgtttctat attatgctta cttcaagaaa ggatctgagg  83880
taacttataa tacaagacat gatcaagagt catgtgaaga aagtgactag agaaatttgc  83940
ttaaaaaaca acaaaaacaa cccttagtct aagggtggat gttacagttt agcaacttaa  84000
gtaaaagaaa cctgaatctt tagtaggaag acatttttta ctctacctct aaatctaggt  84060
tgaatatatc ttgtaggttg tggatctttt ccataaatca gggatactga acaacagttc  84120
tatggatggt atggaaatag taatagcaat agtatgttac taactttgtg ggaaaagagt  84180
ggacattcaa ttttagctat ttaaatttgg aaagttagat gaaaatagag aacactaagt  84240
ttccaatttc atttgttttc attgagtctt ttctccagaa ttcctctcca aatggacact  84300
cttgagtatt ttcagtactt aatattgggg gtgaaatttc tttgctcact gaggaaagat  84360
tttagttgtt tataaacaga attttaaagt taaaaaacct gaagggggct gagaaatata  84420
tgatacttaa gtgtgtggaa ccctatggag aggagacctg gactgtttga taagattaag  84480
gtaagtgata tgtaatgtta aatactagct gtatctttac ctaggcatat ccatcagtat  84540
aaatttattt ggtgatgact gctttgtagt tgcagtattt attaagcagt cgcttagata  84600
agtgtttaac tgtataaatt atttagaagg tctccctttt tctagtttaa tgaggtcaag  84660
actttttttt tgaaatagca atgaatatta tcatttgata ctcacaggag tcacaaactc  84720
tagaagagta atgttttatt tctacttaaa tgggacttgc ttaataagat tccaaactga  84780
gttctgggtt caagtgtaaa cctgatgaaa atcatagata attgtaagga accagcattt  84840
ctaattggat ataatagcta ctgcttattt tcgttatgcc tcagagttaa aactaataca  84900
gtaaataatc ttactcctga gtaggaatta ttgtgattta ttatgtgaaa ttatctagtg  84960
tatgttatat tcctttaaac aaccagttac tgagaaacag ttatagaagc aggattaata  85020
ggcaaagtct taactgtctt cttcaatagt gtgtatagat cctaattaac cctttgggaa  85080
cgtgtattca tttaaacaga cttaatctta aggaggttaa agtaaaatgt gaatttatgt  85140
```

cagttaagtt atgctaaaac ttatcacaaa tcaaatgact gtcctcaaag ggttaaaatg 85200
tacaagaaat catttttgtc attttacttt ttttctgttt actttttttcc ctcatttttt 85260
tctttagttt ttatactttc cttcatatca tttgttctgt caggtgttcc ctggccatcg 85320
ccttgcccat ctccttcctc tcgcccacct tctcgctacc agtcaggtcc caactctctt 85380
ccacctcggg cagccacccc tacacggccg ccctccaggc ccccctcgcg gccatccaga 85440
cccccgtctc acccctctgc tcatggttct ccagctcctg tctctactat gcctaaacgc 85500
atgtcttcag aaggtacaat accacaattt gttcatgttt ttgtttgtct ttgtttaact 85560
cctatgtgag tttataatta caaaatagtt tcctcttcat tatttaataa cctataattt 85620
ctgtgtttta actttagttt attaaaacta tttctattaa ccttttgttc attagagaga 85680
aatttgataa atgtgtgaag ctataaactc tcttgaattg ttgttaaaaa gggggtttat 85740
ctctgcctga taattatgct tctttacagc cccagaaggg tctgccccac agccttcccc 85800
ctccttattt gcactgtata cagtagttaa acaaatgaac tttcttcagc cagtcttgaa 85860
cttaggttca ttttacagct ctttggccaa ggtcctagtg aaccttccta ttggccataa 85920
gcagggatgg tgttttctgg gtcttttttg agagcgacag cccatgtagc tgactttgcg 85980
tgtctgccct tagattaaag tagttgattt ttagaatgcc agaagaattc taaatttaac 86040
tgagtaattt ttttaaagtt agctttgcaa tcttacatag tgaaaggctg ctttaatctg 86100
gaagaagtcc ttgatctgag ataaaattga taaaaacgac atatgaattt gaatatttag 86160
ctatttcttt cctcgtcaaa aataagaata aaatcttgta attcttattc agtatttggc 86220
gctaaatcca tcattgccac atatcaaata cagggatatg ttgtagaaag gtaacattct 86280
aatttaaatg ccacccatat attaaaaacc tgttttctga atcataatgt ccttttgata 86340
ctagttctga atatttgtgt taaaatttta atctgatttg ttcattaaaa ttagttaata 86400
ttgcttatgt tgggactaat aaagttttcc gcacaaaatg tgtttctcct gcttccctgg 86460
agaaaactgt attggctact tttaaataaa ttgttaccat ctaagcaggc aggtcatatg 86520
actttgactg aagcatctaa ccttgaagag caagttccac tgattttcaa ggtgacttct 86580
ttgctcaaaa gggccttaat agtggtcact aaatgcaaaa ttctgttgat atttttcttg 86640
tagtccatca tttgagtaag cgatgtttat ttaatgagaa tatattaaat aaaacatgat 86700
cattaatgac tgtgaacatc tttattacat taagatttaa ggactgctca tgtattaact 86760
tcacacagaa atatactttc tgtgtcattc agagatgttg aatatttcca tttgaaaatt 86820
atagtgtata acattagcat tcttctaaag atcatgttcg tgtttaaatt cctgttggaa 86880
gccaggcatg gtggctaacg cctgtaatct cagcactttg ggaggctgag gcaggtggat 86940
cacttgaggt caggagtttg agaccagcct ggccaacatg gtgaaacctc gtctctacta 87000
aaaataccca gctacttggg aggctgaggc aggagaatca cttgaacctg ggaggcagag 87060
gttgcagtga gttgagatcg taccactgca ctccagcctg ggcgacagag acagactctg 87120
tcttataaaa ataaaaataa aataataatt ctattggcaa catatattaa tttgaagttc 87180
taaagagttt ggcagccggg tgagagagtg aggagatttg gctttgacat tagggaagtt 87240
ttcgcttggt gttaacacca gtaggcttct ctgatgaggg ccattctgtc cactctttta 87300
cctgatagat tggtctaatg cacagtagac tgatttagaa agagtagtca ctagtggcat 87360
ggcagaatca ataatgtaga attttgacaa ttcatatagt gctgatttct cccccaaatg 87420
tcagttattt tggtcatcta ttaatagact aatacaagtc atccctttaa tagaattttc 87480

```
agctcacagc ctgctaagcc taagaaactg cttacaggtt actgcttact gttttaagcc  87540
gagttttaaa attgatgatc atgatagaag agataaataa actaaaattt tagagaaatt  87600
taagaagggt atgtacatat gttttagtgg tatcggggtg tatagggatt aatagtcttc  87660
tgtttaaatt tttttttct aattttagaa gtaatgtaga aaattcgggt cagggaaagg  87720
taaaatatat ggaaagttaa aaatatttta tcatgtagtc ataatttcta gtaacatatt  87780
tctttacaaa taagacatag ttgaaacaga ttgctacagt tcttttaaga gttgacatct  87840
tattgttgat ttcttaccac caacttcatc cctccctttc tttaaaaata aagggaaata  87900
ataaaattta tttataaaac tttgtggcat tccacaaaat aattctgaaa gaattagtat  87960
ggccaaaaaa atatgtatgg tgtttttttt ttttctattt ttaaccaagg aaaaactgta  88020
gagtgagtga gtgtgtgtgc atgtgtgtgt gaatgggtgt atttagcaga aaagtagtac  88080
tgatgaatat catggaattt atgtgatgtt cactgtttct tccttagggc ctccaaggat  88140
gtccccaaag gcccagcgac atcctcgaaa tcacagagtt tctgctggga ggggttccat  88200
atccagtggc ctagaatttg tatcccacaa cccacccagt gaagcagcta ctcctccagt  88260
agcaaggacc agtccctcgg ggggaacgtg gtcatcagtg gtcagtgggg gtaggtaaca  88320
cttgggcata atgatggtac tcattttgtc attacactag atataaagag ggctgagcta  88380
caactctgtt tgaggaagtg taagtatgta tatgttaaaa atagtagaat caccaggaat  88440
tgggaaaccc atatttttat tctgggctct accacttatt catcatatat taaagcaagt  88500
cagacactca ttctgaagtt gagatttcgc agtgagtaaa gtgttaataa ttcttgccta  88560
gtctacatta tgggattgtg atgagattcc tataaggttc ataaatacag atatattgta  88620
aaactataaa gttttgtaaa gtacctctct aatatgaggc aaacacagta tgtaacacta  88680
tttggaggga ccgtatttcc ttatcttttt agcagctttg tttatcagta cattctataa  88740
acatttattt ttggcttaca ttgtagtgtg tttctatagc atctgtatat ggcactaatt  88800
cccaactata tttccataat aaggaatatc aaatacaaat aaagggtcca agttttattt  88860
gtgattagca taaggaatat gctgacagca gctataaaag tataaaaatt aggctgggtg  88920
tggtggctca cgcctgtaat cccagcactt tgggaggctg aggtgggcgg atcacaaggt  88980
caggagatcg agaccatcct ggctaacacg gtgaaacccc gtccctacta aaagtacaaa  89040
aaaaattagc cgggcatggt ggcgggtgcc tgtagtccca gctacttggg aggctgaggc  89100
aggagaatgg catgaactcg ggaagcggag cttgcagtta gctgagatca cgccattgca  89160
ctccagcatg ggcaacagag caagactctg tctcaaaaaa aaaaaaaaaa aaaaagttta  89220
aaaactagac gttgacatga ttttacaata aggctgactg cttttgctac tttgccaatc  89280
agtccttagt gctttgttcc cataactgtg gtaagcaaga gcttacaaag aatacttaaa  89340
acaaacaaac aaacaaacaa aaaaaacact ttttctcttt taatcagtcc agagaacctt  89400
taaaagaaac aagatcggcc agttgctgtg gctcatgcct gtaatcccag cactttggga  89460
ggctgaggtg ggtggatcac ttgaggtcag gagttcaaga ctggcctgac caacatgatg  89520
aaaccccatc tctactaaaa atacaaaatt agctgagtgt ggtggctatt tgagaggctg  89580
aggcaggaga atcatttgaa cccaggaggt gaaggttgca gtgagccaag atcacaccat  89640
tgcactccag tctgggtgac aagagcgaaa ctctatctca aaaaaaagaa aaaagaaaca  89700
agatcttcaa gcttaaggaa acaaaaacaa aactcagctg tgttaaatct gtttttagtt  89760
gctatacatt tctgctcagc ttcatgtgat gcacattcat gtaattgtat cctaaattcc  89820
tttgtacttt ttattttctt ccttggtctt caattatctt aagactacca agaaaacaaa  89880
```

aattttaaaa atcttcttca gccggtcagg cgcagtggct cacggctgta atcccagcac 89940
ttggggaggc tgaggcgggt ggatcacgag gtcaggagtt caacaccagc ctggccaaca 90000
tggtgaaacg tcgtctctac taaaaataca aaaattagct gggcattgtg gcgcgttctt 90060
gtaatcccag ctgctcagga ggctgaggca ggagaattgc ttgaaccagg acccgggagg 90120
tgtaggttgc ggtgagcgga gatcgcgcca ctgcactcca gcctgggcta tagagtgaga 90180
ctccatttca aaaaaaaaaa aaaaaatctg cttcagctat tctgttaatc ttttgacatt 90240
acttagatgg tctggaaata aattttgaga ataacatgat tagaagtgag agagtataag 90300
catagttttg gagatacact cagaatagca ttatagattt tctcttttta ctaattggaa 90360
aaatggcagt tgttgaataa tagttttctt ccgtgaccct tgtgacttaa aaaaaaaaaa 90420
acactgaaat gaaataatcg aaccattttc tctaaacctt tgaatctgag ctctgcagtt 90480
aggtttataa tggtatatga aacctattag atatatactt ggaagtcata tgggatacaa 90540
accctgcttt tattatcttc cccttttgac taacttgggt ctcaagtttc cttaattact 90600
gcacagtgga ccttgatgtt gctataaaga atgtgtaggg ctgggcatgg tggctcatgc 90660
ctgtaatccc agcactttgg gaggccaagg taggcagatc acctgaggtc aggagtttga 90720
gaccagcctg gccagcatgg tgaaaccccg tctctactaa aaatacaaaa aaattagctg 90780
gttgtggtgg cgagtgcctt taatcccagc tactccagag gctgaggcag gagaatcact 90840
tgatacattt agttaggaga gaaaatcata cttatgttag taattgctgc tgttcttcat 90900
atacttgtgg ttttgattgc cagcaaattc ctaacatttt ggaaaagaaa acagtaatgg 90960
gataaagggt aagggctaga gaggacagtt ttatttacct agatcttcag agaagcctga 91020
agcctctttt aggaagtaac atttgaactg agaatgtaat aaatacattt tccctttctt 91080
ctagttccaa gattatcccc taaaactcat agacccaggt ctcccagaca gaacagtatt 91140
ggaaataccc ccagtgggcc agttcttgct tctccccaag ctggtattat tccaactgaa 91200
gctgttgcca tgcctattcc agctgcatct cctacgcctg ctagtcctgc atcgaacaga 91260
gctgttaccc cttctagtga gggtatgtaa caaagggctt ctggatccat aatctcagct 91320
gtgaaattga atgttagagg gtgatattat atgaaaaaat tctaggttat ttttattcat 91380
agacaagtat ttttagtgca catttaaaag tttatgtaaa ttttgatgtt gtttaatact 91440
actaatttaa tatagtgtct gtgttacaaa ggttaacatt cctgggtgtc aaatacctac 91500
ataaataaaa ttattggtgt ttcatatgac atctgcaaag gaaaaaaagc ctctgtttaa 91560
atgaaagcat tattttccaa aaacatagga aatcaaaatt attgttcagt gttttcttgt 91620
tttgcttttc taacttatct gaattttttt taaaaaattg ttttctagct aaagattcca 91680
ggcttcaaga tcagaggcag aactctcctg cagggaataa agaaaatatt aaacccaatg 91740
aaacatcacc tagcttctca aaagctgaaa acaaaggtta gagtttaaag agtcattaag 91800
cttaactgta ggaataggaa gaagtatgtc taatttcatg cccatacaga atatttttgt 91860
tcaacatttc ttcttactat tgtgatagat aaatgtattg cttgacaaat tccaaaatcc 91920
aaatttaata tttgaaatta ttttctgatc ttatatctta ttctaatttc tatcatctca 91980
tactaaaaag aatgtgatgt taaagtttaa aaataaacct gtgtcttaac agttcttaat 92040
tttacaggta tatcaccagt tgtttctgaa catagaaaac agattgatga tttaaagaaa 92100
tttaagaatg attttagggt aagtattgta ctaactgatg aatttgagtt ttagaaaata 92160
agcattacta aagatttatc tatttataaa aatgcgttat gtatacagtc agaaacatca 92220
aaccatatat gtagaaagca gaacattttt aaagtggtct ttgcctatcc tttaagtggg 92280
ataactaaaa tcatgagatt tggtaacaac aatatgtagg tatcaaatga gagtatagcc 92340
ctgacatttg aaaccaccat agcacagctt actatttgat ggtcatttgt actttgttca 92400
gtgaagctag atattagtag agcaaggcca agtcattaat aatctagtgt ggcaaatgga 92460
agatgtactg gactctggtg ttctgaggta gttggagatt tatactttgt acacaaatat 92520
attgtggtca aaatctttct gtaacattat ttctctgtct tagcacaggc tttacttaac 92580
atctctcctt gattgtcatt tcattctttt gcatgttatt tactataggt atcgaggtag 92640
attttgagac caaccaataa atcttcttga aacttagctt cttagaaagg aaaatctaaa 92700
taccagcctt ttaaaaaaag tagctgaatt aaaggatgag tgaaccaaag gcaaaggtag 92760
cctttcctca gcctgtgttt tagctttcta aatgttaaca atagcttcat tcttgactta 92820
ttggtaacat tcaaaatact acttattatt tcatacttta gcacatgtat ctattcagct 92880
ttaatgctat taacagttgt taacctaagt tttcatttgt tggcgggcac ggtggctcac 92940
acctgtaatc ctagcacttt gggaggccga ggtgggcaga tcacctaagg tcaggagttc 93000
gagaccagcc tggtcaacat ggtgaaaccc tgtcttgacc aaaaatagaa aaattagcta 93060
ggcatggtgg cgcacacttg taatcccagc tacttggcag gctgaggcag gataatcgct 93120
tgaacccagg agacagaggt tgcagtgagc cgagatcaca ccactccact ccatcctggg 93180
cgacagagca agactgcatc tcaaaaaaaa aaaaaaaaaa aaaaagtttt tcaatttgtt 93240
aaacaatagt taacacatac aaatgataca aagaatattg aatatgatca tgtgcccact 93300
acccagctta gtaaataaag cattctaaca cagttaaact cctcttatgt atctgcccct 93360
cctcagctgc ttccccctgt ttccttccaa aaggaagggt ttcttttctg tgcagttctt 93420
tatatttata ctgcatatga atatatctgt gagcaataga tgatattttg cataatctta 93480
aatttgctat aaagtctttt tttttttttt aattgatcat tcttgggtgt ttctcgcaga 93540
gggggatttg gcagggtcat aggacaatag tggagggaag gtcagcagat aaaaagtgaa 93600
caaaggtctc tggttttcct aggcagagga ccctgcggcc ttccgcagtg tttgtgtccc 93660
tgggtacttg agattaggga gtggtgatga ctcttaacga gcatgctgcc ttcaagcatc 93720
tgtttaacaa agcacatctt gcaccgccct taatccattt aaccctgagt gacacagcac 93780
atgtttcaga gagcacaggg ttgggggtaa ggtcatagat caacaggatc ccaaggcaga 93840
agaatctttc ttagtacaga acaaaatgaa aagtctacca tgtctacttc tttctccaca 93900
gacgcagcaa ccatccgatt tctcaatctt ttccccacct ttcccccttt tctattccac 93960
aaagccgcca ttgtcatcat ggcccgttct caataagctg ttgggtacac ctcccagacg 94020
gggtggtggc cgggcagagg ggctcctcac ttcccagaag gggcggccgg gcagaggtgc 94080
cccccacctc ccggacgggg cggctggctg ggcgggggct gaccccccac ctccctcccg 94140
gatggggcgg ctggccgggc gggggctgac ccccacctcc ctcccggacg ggttggctgc 94200
cgggtggaga tgctcctcac ttcccagacg gggtggctgc caggcggagg ggcttctcac 94260
ttctcagacg gggcggctgc cgggcagagg ggctcctcac ttctcagacg gggcggccag 94320
gcagagacgc tcctcacctc ccagacgggg tcgcggccgg gcagaggcgc tcctcacatc 94380
ccagacgggg cagcggggca gaggcgctcc ccacatctca gacgacgggt ggccgggcag 94440
agacgctcct cacttcctag acgggatggc ggccgggaag aggtgctcct cacttcccag 94500
actgggcagc cgggcagagg ggctcctcac atcccagacg atgggtggcc aggcagagac 94560
gctcctcact tcccagacgg ggtggcggcc gggcagaggc tgcaatctcg gcactttggg 94620

```
aggccaaggc aggtggctgg gaggtggagg ttgtagcgag ccgagatcac gccactgcac  94680
tccagcctgg gcaccattga gcactgagtg aacgagactc cgtctgcaat cccggcacct  94740
cgggaggccg aggctggcag atcactcgcg gttaggagct ggagaccagc ccggccaaca  94800
cagcgaaacc ccgtctccac caaaaaaata cgaaaaccag tcaggcgtgg cggcgcgggc  94860
ctgcaatcac aggcactagg caggctgagg caggagaatc aggcagggag gttgcagtga  94920
gccgagatgg cagcagtaca gtctagcttc ggctcggcat cagagggaga ccgtggaaag  94980
agagggagag ggagaccgtg gggagaagga gaaggagggg gagggggagg gggggagagg  95040
gagagggaca atgatgtctt gctgtaggta ttcttcccca tttgaatttt ttcctcagca  95100
ttattttttt taacatcatt cagtctcctc ttatactaca cttggattga atttaatatc  95160
tcatgaagaa aaaacatttc tactttgaag catgtgaatt agcatgtttt tataacagct  95220
ttattgagat ataatttaca tatataaata aaccgtttaa agtgtataaa tcagtggttt  95280
ttaatgagat ataatttaca tatataaatc aaccatttaa agtgtataaa tcagtggttt  95340
ttaaaatatt cacaatgttg tacaaccgtc ttctcagttg attttaaaac atactcttca  95400
cccccaaaag aaaccccgtg cccagtttag cagtcgttcc acatttgcct ccagcccttc  95460
tctttcccct actcccaacc ctaagcaacc gttaatctac tttctgtctc tatggatggg  95520
cttatttggg gcaaattcca tttcatacaa atggaataat aaaatatgtg gcttttatga  95580
ctggcttctt tcactcagag tagtgttata aaagttcatc catgttggag catgtttcag  95640
tacttcattt ctttttgtga ctgactaata ttccttgatg tggataatac cacattttgt  95700
ttatccatta atcagtttgt agctatttgt ggtgttctca ctgtttgact attctgaata  95760
acactgccac aaacatgagt gtgcagtttt tttctcgtcc tatcttttca tttcttttgt  95820
gtacctacct aggagttgaa ttgctgggtc atatggcaac tgtgtttaac cttttgagga  95880
actaccaagc tatttgccaa gatatctaca ctattttaca ttcccaccag cagggtatga  95940
gggtttctgt ttctccacat ccttgctaac acttattgtc ttgtcttttt tgattatagt  96000
catccttgtg ggtgtgaagt gttaacctca ttgtggcttt aatgtgcagt tctttcatgg  96060
ctaatgatgt tgaacatctt ttgtgtttat tggccattta tatatcttct ttggattgat  96120
gtctgttcaa atctttaccc attttaaaaa ttgagttgtc tttttattat tgggttgtgg  96180
gagttcttta tatattgtgt gtacaagtcc ctgttagata catggtttgc aaatgttttc  96240
tcctgttctg ttggttgtct ttttactttt tcatcccttg aagcacaaaa atttttaatt  96300
ttgatgaagt ccaatttatc tgattttgaa gtaagctttt ggtgtcgtat ctaagaaaat  96360
actgtttcat caatcattaa ggtttattac tcttctgggt ttttttaaga attacattta  96420
gaggtgtgat ccatttggag caactttttt tttcttttga cacagaatct cgctcttttg  96480
cttaggctgg agggcagtgg tgcaatcttg gctcacagca gcctcagcct cctgggctca  96540
aatgagtagc tggtactaca ggtgtgcacc accacacctt gctattaata acttttgtat  96600
ttttttgtag agacagaatt tcgccatgtt gcccaggctg gtctcaaaca cttggactca  96660
agtgacacgc ccacctcagc ctcccaaagt gaaaaattgc tttcaccttg cactgcggac  96720
tcgccctgaa ttctttcttg tgcaagatcc aagagccctc tctgggggtc tggatcggga  96780
cccctttcct ataacaatat tatgagaata acatttgatt ttttttaagt gaaacaaatt  96840
gttattaaaa aattaaaaaa ggtcatagga gagtgacttg gtgctcagcc cattttgagc  96900
agttatttaa tatagcataa ggtggggttc aaattcattc tttatattaa tttttttattt  96960
```

```
ctaattgaca cataaccata cacttataac catttttact gtgtaagttc agattcattc  97020
ttccgtatgt aggtattagt tgtcccagca ccatctgtta aaaagactat tcttggccag  97080
gcacagtggc tctcaacgcc tgtaatccca gcactttggg agtcccaagc aggcagatca  97140
catgaggtca ggagttcgaa accagtctga ccaaatggtg aaaccgcatg tctactaaaa  97200
atacaaaaat tacctgggtg tggtggcgca cacctgtagt ctagtcccac tactgtagtg  97260
gctgaggcag gagattcgct tgaacccagg aggtagaggt tgcagtgagc tgagatcatg  97320
cactccagtg tgggcgacag agtgagactc catctcaaaa aaaagactat tctttcctcc  97380
attgaattat cttcacatgc ttgttggaag tctgttgact acaaatgtga aagtttatta  97440
ctggactctg aattgtcctc cactgaatct ctatgtctta tccttatggc agtaccatac  97500
tgtcttgatt agagttactg tattttaaaa ggctgtactt tttcagttag cagaaaacat  97560
tttagctatc agcacaactt tctgtaaacc ttcattaatg cttgacttaa attccaagaa  97620
ggagcaacat aaaaagtctt atctctttag gagttttagt cttactactt ttaggtgcct  97680
gaataaccaa atgtattatt tagcctctta ctaataactc cttgatccat aggggcatac  97740
caggaagaaa agaagtggtt tttaaaaaat gagagtgggc cgggcacggt ggctgatacc  97800
tataatccta acactttggg aggctgaggc gggtggatca cttgaggtca ggagtttgag  97860
accagcctgg ataacatggc gaaaccctat ctttattaaa aatatataaa ttagccgggc  97920
atggtggcac atgcctgtaa tcccagctac tcaggaggct gaggcaggag aatcacttga  97980
atccaggagg tggaggttgc agtgatccga gattgcatca gtgggcgaca gagcgagaat  98040
ctgtctcaaa gaaaaaaaaa gagagtggaa aaaaaaaata tgtgtcccag aacttaaatt  98100
ttaattaaaa aaaaataaaa gagtgaactt tctaattgtt ctcttcagat aatataatgt  98160
tattctctta tgttttattg cgtatttcct gtgtaccaga tgctgttctt catgcttgta  98220
tgttaaatct tgtctaacat ctctgtcaag caagttctgt ttgtatctgc actgtgtata  98280
ttaggcagct tgggcaaaga gaagttaagt aatctgccca aactcacatg gctagtaagt  98340
aagagggctg accatctggt gtttaagctt ctagcagtgc tttgaatagt aactaatgca  98400
tagtgcatgc tgcactgtca gtcagtgatt cattagagct aacttcatga catgctcata  98460
gccccaaact gcatttgttc acaaatatct gtagtccttc atttaggcag aaatagaaat  98520
accttgtgtg tttgttgttc cttccctttt gagccatatg cagagtgctg atagctttat  98580
ttgtgtaaga attgctagta atttgatctg ttttgggtta ataatgtggg ttttagaggt  98640
aaatggacct aggtttgaat gttggcctct atacatcatg tgcgtaacat tgtggcatgc  98700
tatctacttc ccccaagcca aaatgggtta attttagaac ctgcttcata gtgttcctgt  98760
gagagctcga tgagatattg cctataaagt gtttagcata gtgcctagca catggtatgt  98820
attcaataca tgttcattct tactagcaaa atatagatga cccagtattg tacagagtat  98880
gtacaatggt gtcattgtac catttcatgt ggagtcacat aagaatttca gttttctgct  98940
gggcatgatg gctcactcct gtaatcccag cactttggga ggctgaggtg gatggatcag  99000
ctgaggtcag gagttccaga ccagcctggc cgacatgatg aaaccccatc tctactaaaa  99060
atacaaaaaa ttagccaggc gtggtggcag gtgcctgtaa tcccagctac tcgcaagact  99120
gaggcaggag aaatgcttga acccgggagg cggtggttgc catgagttaa gatcgtgccg  99180
ctgcactcca gcctgggcaa taagagcgaa actccgtctc caaaaaaaag aaaaaaaaag  99240
aacttaagtt ttccattaga tttagtatag tgcagagagg aaatacagca gagtgctata  99300
ttccatatat agcaatatag cattagaaca atatattcca atacagcaga gtgctatatt  99360
```

cagataccaa ctagtggact tgctatttgt aagatggcaa taatagtatc tacatcaaat 99420
agggctgttg tgaagactaa atgaataagt ctataaatag tttagaacag tgtctggaca 99480
ggtacagtgg ctcatgcctg aatcttagca ctttgggagg ctgagacagg tggatagctt 99540
gagctcaggc attaaagacc aacctgggta acatggtaaa accctgtttc tacaaaaaaa 99600
tacacacatt agccaggtgt ggtggcacat gctaatagta ccagctactc aggaggctga 99660
ggtgggagaa tcacttgagc ctgggagatg gaggttgcag tgaggtgagc ttgcaccact 99720
gcgctccagt ctgggcaacg gagtcagacc ctgtttggaa aaaaaaaaaa aagtgtccaa 99780
cccatagtaa gaaatgcaga tgtgtttgac attgtaagaa aaagcaacac caaaagtctg 99840
atttttgcct tcactcaaga actcttatga taattaaact ccgaagtcct tggcaatata 99900
tatagttggt ctgttatgtg gatcgcctct actaaagatt tttgtgaaca aatgaaagtt 99960
taagtagtaa gttcctacat cgtgacttaa attgccagtg tgcccacata aataccctgt 100020
caacatttgc ccttagccac ttgactcttt agctatattg gtaatgcagt aaagcttgcg 100080
atgcgccaga gttgcataat gctgtttgcc atgacaccaa gagccttggt aatgaaacca 100140
ttgaaattgg tttgcctata ctgaggctga agaggtatct tggctctcta attttaaggc 100200
aacctttttg gctgtgtagg tttctcttta gcttgtttct caccacctgg ggctgtggct 100260
taggtccgtt gtcctaacct gtggcttagg ttctgttttt gttgcttgta cttgctcccc 100320 ctttttcag ccattcctgt tttctttctt ttgtagagga tgccatctta aatcatcttc 100380
agccagtggt agcattttat tttttctggt ctgcaaactt aaaaacctca tcacttattt 100440
tgctaatatc tttgtcttct gttctttttg atggtccttg gttttgcagt ctactttaaa 100500
ggtttttatt tttttatggg tacatagtag acgtattatt catagggtct gtgagatatt 100560
tagataaagg catataatgt gtaataatca cattagggta aatggggtat ccatcaccat 100620
catcattcat catttctttg tgtaatgaac gttgcaattg tactccctca gttattctaa 100680
aaagtacaac aaattaatgc tgactgtagt caccctgctt tgttgtcaaa tactagatct 100740
tattcattct ttatttaact ttttaaattt taaacttatt ttatttattt atttttagac 100800
ggagtctcac tctgtcgcca ggctggagtg cggtggcgca gtctcaactc actgcaacct 100860
ccgcctccag ggttcaagtg attctcctgc ctcagcctcc tgactagctg gaactacagg 100920
cacgtgccac cacgcccagc taatttttgt atttttagta gagacggggt ttcactatgt 100980
tggctgggat ggtcttgatc tcttgacctt gtgatccggc tgccacagcc tcccaaagtg 101040
ctggggttgc aggcgtgagc caccgtgccc ggcctttaaa attattttaa atcattttaa 101100
tatctttttc atttctgcct ccggtcctgc agagttctta ttcgttcttt ctaaattttc 101160
tttgcaccca ctaatcacct catttccctt cttctcccca ttacccttcc caacttctgg 101220
taaccattct gctatctcca tgtgttcaat tgtttttatt tttagtgcct gcaaacgagt 101280
aagaatatgc aaagtttatc tttctgtccc tggcttattt tacttaacat aatgtcctcc 101340
agtgccatct acattgctgc aaatgacagg atctcattct tttttatggc tgaatggtaa 101400
tctattgtgt atatatacca cattttcttt ctccatttgt ctgtcagtgg acacgtaggt 101460
tgattccaaa tcttggctgt tgtgtatata gtgccgtagt aaacatggga gtgcagatat 101520
tccttcaata aactgatttc ctttctgagt atatacctag cagtgcaatt gctggatcat 101580
atggtagctc tatttttagt tttttgagga atttccatac tgttctccat agtggtttta 101640
ccaatttaca tgtccaccaa cagtgtgtga aggttcccct ttatccacat cgttaccagc 101700
atttgttatt gcctgtcttt tggataaaag ccattttaac tggggtgaga tgatatcttg 101760
ttgtagtttt aatttccatt tttctggtga tcagtagtat tgaatacctt tcatatacct 101820
gtttgccatt cataaataac gatgaggtct tgctgtttgg cccaggctgg tctcgaactc 101880
ctgggctcaa gcaatcctcc caccttggct tcccaaaatg ctgaaattat agttgtgagc 101940
cactgcacct ggccttgtat gtcttccttt ttttttgtt ttgttttgtt tttgagacag 102000
agtctcactt tgttgcccag gctggagcgt agtggtgtga tcttggctca ctgcgcccta 102060
cacctcccgg attcaagcaa ttctcctgcc tcctgccacc atgtctgcct aatttttgta 102120
tttttagtag agacgggatt tctccttgtt gcccaggctg gtcttgaact cctaacctca 102180
ggtgatttac ctgcctcagc ctcccaaagt gctaggatta caggcgtgag ctgctgcgcc 102240
cagcctgtat gtcgtctttt gagaaatgtc tattcagatc ttttgcccat ttttaattga 102300
gttactaaaa ttttccctat ggagttgctt gagtgccttt tatattctgg ttattgatcc 102360
cttgtcagat gagtagtttg caaatatttt ctcccattct gtgggctgtc tcttcacttt 102420
gttgatggtt tcctttgctg tgcagaagct ttttaacttg atgtgatccc atttgtccat 102480
ctttgctttg gttgcctgta cttttggggt attactcaag aaatctttgc ccagagtaat 102540
gtccctggga gtttaatgtt ttcttttagt agtttcatag tttgaggtct tagatttaaa 102600
tctttagtcc attttgattt gattttttt taatatggtg ggacacaggg gtctggtttc 102660
attcttctgc atatggatat ccagttttcc cagcaccatt tattgaagag actgtccttt 102720
ccccagtgta tgttcatggc ttctttgtgg aaaatgagtt cacttagacg tatggattca 102780
tttctgagtt ctctgttctg tttcattgat ctatatcttt ttttatgcca gtaccatgcc 102840
attttggtta caataatttg aagtcagata atgattcctc ccgttttgtt cattttgctc 102900
agtatggctt ttgctctttt gggcctttttg tggttcccta caaattttag aattattttt 102960
gtctacttct gtgaggaatg tcattggtat tttgataggg attgcactga atctgtagat 103020
tgctttgagt attatcaaca ttttagcaat attaattctt ctaatccata aacatggaat 103080
ctcttttcat gtttttctg tgtcatcaat ttcagtgttt taaagttgtc attatagaaa 103140
tcttttactc atttggttaa gtttattcct aagtatttta ttatatttgt agctattgta 103200
aatgggattg cgtttaaaaa atttttcaga ttgtttgctg ttaaatataa aaatgctcct 103260
gatttttgtg tgttgatttt tgtatcctgc aattttactg aatttgtttg tcagttctaa 103320
taggtttttc ttttttggag tctaggtttt tccaaatgta agatcatatt atctgcaaac 103380
aaggataatt tgacttcttc cattccagtg tggatgcttt ttatttcttt ctgttgtctg 103440
attgctccaa ttaggacttc cgagtattat gttgaataac aatggtgaaa gtgggcatcc 103500
ttgtcttgtt ccagatctta gaggaaagcc tttcagtttt tccctttttca gtatggtact 103560
agttatgggt ctgtcatata tggcttctgt tttgttgagg tatattcctt ctatacccag 103620
ttctttgggg ttttttgtt tgtttgtttt tgagatggag tctcactctg tcacccaggc 103680
tggagtgcag tggcgcaatg ttggctcact gcaagctcca cctcctgggt tcatgccgtt 103740
ctcctgcctc agcctcccga gtagctggga ctacaggtgt ccgctaacac gcccggctaa 103800
ttttttgtat ttttagtaga gacggggttt caccgtgtta gccaggatgg tctcgaactc 103860
ctgacctcat gatctgcccg tctcagcctc ccaaagtgct gggattacag gcgtgagcca 103920
ccacgcccgg ccaagggttt taatcataag gggatgtggc attttatgtg atataaatta 103980
tatatttata tcatgtgata tatatttata tcatacacag tataaataat atatatatat 104040
atttttagt ctttgtcttt tattctgtta agatgtacca tgtttattga tttgcgtatg 104100
tcgaaccatc cttgcatccc tgggatgaat cccacttagt catgatgaat gatcttttta 104160
atgtgttact gaattcggtt tgctagtatt atattgagga tttttgcata atgttcttca 104220
gagacactgg cttctagttt tcccttttg atgtgtcctt tggttttgta tagggtaata 104280
gtggccttgt agaatgagtt tagaagtatt ccctcttcct gtattgtgtt ggaatagttt 104340
gagtaggatt ggtattagtt cttctttaaa ggtttagtag aattcagcag tgaagccatc 104400
aggtccatgg cttttctttg ctgggagact atttcttata gctttgatct cgttacttgt 104460
tattggtctc gttacttgtt attgtatttg ggttttggat ttctttgtgg ttcagtcttg 104520
gtaggttgta tgtgtctagg aatttatcca tttcttcaag gttttccaat gtatcagcat 104580
atagatgctc atagtagtct ctaatgatcc tttgaatttc ggtggtaaca attataatgt 104640
ctcctttttc atctctcatt ttattatttg ggtttctct tttttttctg agtctggcta 104700
aaggtttgtc agttttgttt atctcttcaa aacaatttac tgttttattg atcttttgta 104760
ttttcttcat ttcaatttta tttatttctg ctttgatttt ttttatttct tctactgatt 104820
ttaggttttg tccttgcttt tctagttctt taggatgtat tggcagatga agtttttcca 104880
cttttttgat gtaggcactt actgctgtaa acattcctct tattgttgct tttactgtat 104940
cctataggtt ttgataagct gtgtttccat tttcatttgt ttcaaggaat tttccagttt 105000
tcttcttaat ttcttcatgg acccactggt cattcaggag catattgctt aattttcatg 105060
tatttgtata ctttccaaag ttcctcttgt tatctagtgt tattttattt tatttttatt 105120
tttgtttttt tgagatggag tctcgctctg tcacccatgc tggagtgtag tggcgcgatc 105180
tcggcttact gcaacctctg cctccccagt tcaagtgatt cttctgcctc agcctcctga 105240
gtagctggga ttacaggcat gtaccaccac tcctggctaa ttttttttg tatttttagt 105300 agagaggggg tttcaccatg ttggtcaagc tgatctcgaa ctcctgacct cagatgatcc 105360
acccaccttg gcctcctaaa gtgctggaat tacaggcatg agccaccgtg cccggcctct 105420
agtgttatct tattgtgatc agagaagata gttgatatga ttttaacttt tttgaatttt 105480
tatttattta tttgtttgtt tgtttgtttg tttgtaacag agtctcactc tgttacccag 105540
gctggagtac atgtcatgat cttggctcac ctgcaacctc cgccttcctg gctcaagcaa 105600
tcctcccacc ttagccttcc aagtagctgg gactacaggc acatgccgtc acatatggct 105660 gatattttg gatttttttt ttttttgtag agatggggct ttgcgatgtg tcccagggtt 105720
gtttcgaact cctgagctca agcaatccac ctatttcggc ctcccaaggt gctgggatta 105780
cagacatgag ccactgtgcc acgtcaaatc tttagacttg ttttgtggct taacataggg 105840
tctatctttg agagcaatcc atatgttgag gagaagaatg tgtattctat agctgttgga 105900
cacaatgttc tgtaaatatg tattgggcct atttggtcta tagagcaaat taggtctaat 105960
gtttctttgt tgattttctg tctgaatgat ctgtccattg ctgagagtgg ggtgttgaag 106020
tttccgactg ttactgaggt ctgtttctct tttttgctct aataatgttt gctttatata 106080
tctggatgct ccagtattgg ttgcatatgt atttatactt gttataacct cttgccgaat 106140
tgatcccttt atcattatac aataatcttc tttgtctgtt tttatagact ttgtctcaaa 106200
atctatttta tctaagcata gctactcctg ttcttttctg gtttccattt gcatggaata 106260
ttgttttcca gctcttcaat tttagtctat gtgtgatttt ataggtaaag tgtgtttctt 106320
gtaggcaatg gatctttggt tttttttttt ttttttttga gacagagttt tgctattgtt 106380
gcccaggctg gagggcaatg gcgctatctc agctcactgc aacctccgcc tcctgagttc 106440

```
aagcgattct cctgcctcag cctcccaagt agctgggatt acaggcgcct gccaccaagc 106500
ccagctaaat tttttgtatt ttcagtagag atggggtttc agtatgttcg tcaggctgtt 106560
cttgaactcc taacctcagg tgatttgcct gccttggcct cccaaagtcc tgggattaca 106620
ggcgtgagcc accgcaccca gcctttttttt taaatccatt tagccactct gtatcttttg 106680
attggagagt ttagtcgatt tacattcagt gttgttactg attagtgagg acttaactac 106740
taccattttg ttacttatta tctggttgtt ttgtagtcct actccctccc ttccccccttc 106800
tttttacttt cctcttcgct cctttttttcc ctccctccct tccttgtttt gaaagtgatt 106860
ttctctggtg gtatgtttta atttcctgct ttatattttt tgtgtatctg ttgtaggtgt 106920
ttttgattta agatcaccat gacagctggg tgcagtggtt cacacctgta atcccagcac 106980
tttgggaggc cgaggtgggt ggatcaagag gtcaggagat tgagaccagc ctggctaaca 107040
tggtgaaacc ccatctctac taaaaataca aaacttagcc aggcgtggag gcacgtgcct 107100
gtaatctcag atactcagga ggctgaggca ggagaattgc ttgaacccag gaggcagagg 107160
ttgcagtgag tcaatattgt gccactgcac cccagcctgg gcgacagagt gagactccgt 107220
ctcaaaaaaa aaaaaaaaaa agagatcaca taagggttgc aaataacatt ttataaccca 107280
ttattttaaa ccaatgacaa cttgaaactt tgattgcaaa aacaagcaag caaagagaaa 107340
actaataaaa actctacact tcatctgccc gctttttaac ttttgttgtt tttatttata 107400
tctttattat actatgtctt aaaaaactgt agttataagc caggcgcagt ggttcacgtg 107460
tgtaatccca gcactttggg aggctgaggt gggcggatca cctaaggtca ggagttcgag 107520
accagcctag ccaatatggc aaaacccccct ctctactaaa aatagaaaaa ttagccggac 107580
atggtggcgg gtgcctgtaa tcccagctac tcggaggctg aggcaggaga atcacttgaa 107640
cccaggaggc ccaggttgca gtgagccgag agtgcgccac tgcactccag tctgggcaac 107700
agagtaagac tgtctcaaaa aacaatacaa aacaaaacaa aaccctggcc tagtggctca 107760
cgcctaatcc cagcactttg gaaggcaaag gtggggcgaa tcacaaggtt aggagttcga 107820
gaccagcctg accaacgtgg tgaaactctg tctctactaa aaatacaaaa attagccagg 107880
cgtggtggca cgcacctgta atcctagcta ctcaggaggc tgaggcagga gaatcgcttg 107940
aacctgggag gcggaggttg cagttagccg agatcgcgcc actgccgtcc agcctgggca 108000
gcagagcaag actctgtctc acaaaaaaaa aaaaaattgt agttcttatt tttgaaaggt 108060
tcatttttta ttcttcctgc tcaaaatatg agtagtagtt tatacaccac aattacagtg 108120
ttacaatatt ctgtattttt ctgtgtactt gttaccagtg agtttttgca ccttcaggtg 108180
atttattatt gtttgttaac atccttttct tgcagattga agaacttttt tttttttttt 108240
tttttttga gacagagtca tgctctgtta ccagcctgga gtgcagtggt gccatcttgg 108300
ctcactacaa cctccaactc ccaggttcaa gcgattcttc tgcctcagcc tcccaagtag 108360
ctgggattac aagcatgtgc caccacgccc agctactttt tgtattttta gtaaagacgg 108420
ggttttgcca tatttgccag gctggtcttg agctcctgac ctcagggtga tccgcccgcc 108480
ttggcatcct aaagtgctag gattataagc gtgagtcatc gtgcccaact tggttgttta 108540
ttttcaaata gcctgaattc aagctcacta atgttttctg ctgcttgata catttctgct 108600
attgagagac tgatgcattt ttcagtttgt caattgaatt tttccacttt gggatttctg 108660
cttgattctt tttactaata attattgcag tctctttttt aaatttatag gattctgaat 108720
ttgttctctg tattatcttg gatttcgttg aactttctca aagcattcag cttgaattct 108780
gtctgaaagt tcacatatct cttatcactt gggaattggt cactggtgtc ctttattttt 108840
```

agttcatttg gtgaggtcat gttttctcag atggccttga tgcttgtgga tgttcatcag 108900
tgtctgggca ttgaagagtt gggtattctg ttctttgtag tctggttttg tttgtacgca 108960
ttcttttttt tttttttctg tttttgagac agagtctcgc tctgtcgccc aggctggagt 109020
gcagtggcac agtctttgct caccgcaacc tccgtctccc ggattcaagc aattctcctg 109080
cctcagcctc ctgagtagct gggattacag gtgcgtgcca ccacgcctgg ctaatttttg 109140
tatttttagt aaatatggtg tttcaccatg ttggtcaggc tggtctcgaa ctcctaacct 109200
cgtgatctgt ccgccttggc ctctcagagt gttgggatta caggcgttag ccactgcatc 109260
cggctcccat tcttcttgag aaggtttttc aagtattcaa agggaattaa gtgttgtcat 109320
ctaagtcttc gctcactgca gccatacatg cattagaggg caccccaaga ctagtaatgt 109380
tgtgactctg tagaggtatc accttggtag tcttggggaa gatctgggag aattccctgt 109440
attaccaggc agtctcttgt cctcttacat ttctccaaac aaatggagtc tctctttgtg 109500
ctgagctgct tggagtttgg ggaagggtga cacaagcact gccatggcca ccgtcactgg 109560
aactgtactt ggtctcaccc aaggcctgtg gcagctattt tctggccacc actgatgtta 109620
atttaaggcc caagggtgct ttagtcagta ggtgaagaat cctgcaagaa ctgggtcttt 109680
actttcagtg cagcaggttc ccttctggcc cagggtgtgt ctagaaatgc tgcccaggag 109740
ccagggcctg ggatcgggag ctttaggaat ctgctttatt gtactggggc tgagctggca 109800
cccacttgca agataaagtc ctttttactc ttctctcacc tcaagcaggt gggtctcccc 109860
atggacacca cagctgtgaa tgtgcggggt catatctgaa gctggcacaa tacgacatgg 109920
caccttgttt tttattcaag gcacaagggc tctttagtca gctggtggtg aatcctacta 109980
ggactaggta tttcccttca aggcaatggg ttcccttctg gtccagaata tgtctagaaa 110040
tgtcatctgg gagctatggc ctagaattga ggcttcagaa ctatgcttgg tgctttattt 110100
tactgtggct gaactagtat ccacattgca agacaaagtc ctccctactc ttccctctcc 110160
tcccagagct gtgagctgtg gtacctggag ttgggggaag gctggcacaa gcactcccct 110220
ggccacccta gctggtgtct cagtgggtca catgtacccc aagtccactg actatgagcc 110280
cagcacagta ccatgacttg tccaggaatt gcagtccttc tggtctagac tgcctttcaa 110340
gtttatttag gaccccagag gactttaccc acggtggtgg ggcttaccaa aattaagatt 110400
cttttggttt tttttggcag agtttcgctc ttattgccca ggctggagta tagtgacgca 110460
atctcagctc accacaacct ccgcctcccg ggttcaaata attctcctac ctcagcctcc 110520
tgagtagctg ggattaccgg catgcgctac cacctctggc taattttttt gtttttttagt 110580 agagatgagg tttctccatg ttggtcaggc tggtcttgaa ctcccgacct caggttatcc 110640
gtccgcctcg gcctcccaaa gtgctgggat tacagaccat agtgcccagc ccgaaattca 110700
gattctaatc actgggatgg acaattcccc tctgactagg gctagtctaa atactccctc 110760
tgtgggtgct ggctgaattc tgtcctatgc tgctttccac tgtgacaggg cagcactgag 110820
tttcaatgca aaatcccaca gtcatttctc tctctctccc ccgagcacac agattctttc 110880
tccaccccac actgcattgt gggggaatgt caggggtgtt ggaggggcag ttcaagacta 110940
tcttccttat cttttttggt gtctttttcc ttgataggat gtcaaaactg ggtactgtga 111000
tcgcttacct aatttttggt tcttatgaag gtgctttctt gtgtggatag ttgttcaatt 111060
tggtgctcct tgttggggat gatcactgga aggttctgtt tggccaccat gctctgtctc 111120
ttctcccctg ccatctcctt tttttactta ggggtttaga atgtctaact gaccaatatg 111180
tacagtcagg tctcattctg aattcaccta cttaatgacc ttccaagctg actaggccca 111240
gcgcttagtc cagcctccat gacggtccct ccacatccta attagcctcc ctccagttca 111300
tttcacacaa agctgctgtg ttcacctttc tgaactataa atctgcccag tactctaccc 111360
tacttaaaat tccgtataga ctgcccattt gccctgagaa ttaaaagcca aagtcctaaa 111420
cgtagctttt taaaactttt tttttttttt ttttaatttt tagatggagt cttgctctgt 111480
cacccaggct ggagtgcagt ggtgtgatct tggctcactg caacctccgc ctcctgggtt 111540
caagcaattc tcatatgtca gcctcccaag tagctgggat ttacacgtgt gccatcacgc 111600
ctggctaatt tttttttttt atctttagta gagacggagt ttcaccatgt tggccagtct 111660
ggtcttaaac tcctgacctc aagtgatcca cctgccttgg cttcccaaag tgctaggatg 111720
ataggtgtta gccactgcac gcagccctga acatagcttt taagttcctt tattgtcata 111780
ttccttttga cgagtctatc attttctgac tcacttgtac atgtgtgtct cacccttggt 111840
ccagccattg gtgcttttct ttacttcttt atttttgtta ttttatttta ttttattatt 111900
attttttaaa tgagacaggg tatcactatg ttgcccaggc tggtcttgaa ctcctgagct 111960
taagcagtct gcttgtctca gcctcccaaa gggctggaat tacagtgatg agctactgtg 112020
cccagctcat tggtgctatc tttttttttt tttttgagac ggagtctcgc tctgtcaccc 112080
aggctggagt gcagtggcgt gatcttggct cactgcagct ccacttccca ggttcacacc 112140
attctcctac ctcagcctcc cgagtagcag ggactatagg cgcctgccac catgcctggc 112200
taatttttgt atttttagta gagatggggt ttcagcgtgt gagccaagat ggtctcgatc 112260
tcctgacctc gtgatccgcc tgccttggcc tcccaaagtg ctgggattac aggcgtgagc 112320
caccgtgccc ggcccccatt ggtgctattg ttttatgtga tagagccagc ttctcccttt 112380
tctttggatt tttaaacata ctcttccttt tacttagact attctccatc ccaacacctt 112440
tcctaaactt ctttcacacc ttagactagc tgacacttta ctgagaaacc tttctttttt 112500
ataggttgct ttttctatag actctcttag catttactca ttttattgtg aagtgtctga 112560
tcttatttaa atgacaagta taagaggata gaaactattt catatttttc tcacccagca 112620
ggcacaattt ctgacatgtg gtaagcactc agtaaatatt gaactttaga ggctaggaca 112680
tttgagtgct ttggtgactg tggttgtgct atataggtac tctgttattg ttagtttata 112740
gtaaaagcat tactcttaaa gtatgaaaaa agccttattc agaacatttc atgcgtatag 112800
ttaatattac gtagcttgtg ctcatggcaa aaatgtatta ctaaagttat ttaagatatt 112860
taagtataat tgtttccttt atttagttac agccaagttc tacttctgaa tctatggatc 112920
aactactaaa caaaaataga gagggagaaa aatcaagaga tttgatcaaa gacaaaattg 112980
aaccaagtgc taaggattct ttcattgaaa atagcagcag caactgtacc agtggcagca 113040
gcaagccgaa tagccccagc atttcccctt caatacttag taacacggag cacaagaggg 113100
gacctgaggt cacttcccaa ggggttcaga cttccagccc agcatgtaaa caagagaaag 113160
acgataagga agagaagaaa gacgcagctg agtgagtaaa cctggaactt agaccatcct 113220
gttactcaat taactttttt ttttttaaag gcatttaggt ccttccaact gtgaagaatc 113280
catctggact tttagactac tttatacatt gcccttagtt tacaaacagc tagtccaaac 113340
aaatgacatc ttaagtaaat gaggttattg caccctgtgc tactcttctg ttcttcccct 113400
tttttgtacc ccagggctag aaaaacaagg cataaattaa gaaaagtttt tctgtaaatg 113460
aacaggagtt gaaaaattat caattcaggg gacctatctt tactggattc cactcattag 113520
tcaccctcac tgtgctgcta ggttgaaaaa ctgccactgt caaggagaga agcatgcggt 113580
gcttctactt ggaattcaaa atatttttca tcagaaactg tgttttagtt aatgtttaga 113640
tttgttaaga tagacttaat tctgcacatt cagtatatta attaaatgga cttttagggg 113700
ctaacctcag aacttaacta ccattgactt aggtgtttgg gtaccaaaca atccagttaa 113760
agctgaagtt ttggaatgca gcttattgat aaattgggga ctgcttattc ttgatttgag 113820
gcaatttttt tttacagcca tgactttttc caggtatgtc atgtaaaata tcttctcaca 113880
taagaattac tgcatgctag aatattggta tgttgactgg tagctcatac ctataatccc 113940
agcactctgg gaggtccaag caggtagatt acttgaggtt aggagttgaa gaccagcctg 114000
gccaacatgt gaaaccctgt ctgtactaaa aatacaaaaa ttagccaggc atggtggtag 114060
gtgcctgtat cccagctact cgggaggctg aggcaggaga attgcttgaa cccagaaggt 114120
ggaggctgca gtgagccgag atcatgccac tgcactccag cctgggtgac agagcgagac 114180
tctgtctcaa aaataaataa ataaataaat aaaaggatac tgttatgtta agaattgctt 114240
ttaaggatat ttcataagta gctactgtct tttcagctca agtgtttgtt gattggccag 114300
gcgtggtagc tcatacctgt aatcccagca ctttgggagg ctgagtcagg cagatcactt 114360
aaggtcagcg tggccaaaat ggtgaaaccc catctttact aaaaataaat attaaaaaaa 114420
attagctggg cgtggtggca gtctcctgta atcccagcta atcaggaggc taaggcaaga 114480
gaatggctta aactcgggag gcagaggttg cagtgagcca agattgcact gctgcactcc 114540
aacctgagca acagagtggg actctgtgaa ggaaaaaaaa aaagtatttt ttgattgcct 114600
ttgagaggaa cggttgtata ttactcagat ttttaaaaaa ttgttctttt atggctgtat 114660
tctttaaggg attaaggaat gggcaatata agtgtatatg tttcaataaa aacgattagt 114720
gatcttctag tgagaacagt ttaaatctat atttagcaat tttttttaaa ttgtcaggta 114780
tggaagattt tagagcaacg taaagtccat gtagatttca ctggccttta tatttttttt 114840
aggcaagtta ggaaatcaac attgaatccc aatgcaaagg agttcaaccc acgttccttc 114900
tctcaggtag gtttattact ttctttgagg ttatctagtc ccaaaaaaag aaaaattatt 114960
agtaatagtc cttcttccat acctgccatc tgaattttgt tttagtgtgc tgaaccaacc 115020
ttctttcttt tttttacatg gccattaatg aatacttttt aaacattaaa aaaaggtctt 115080
tgttttgtca tcaattagat gtgatcttgg gcaaatcttt gaatttctct gacccagaat 115140
ttgacgatgg ttggctagct aggctgtcag gtttatagat acgtcctctg cacctgaggg 115200
ttttgcatca ctggattcaa ccaaccatgg atcaaaaaca tagttaggat aatctatact 115260
gaacacatgc agacgtttcc ttgtcattat tccaaaacaa tacagtaaag catttacctt 115320
gttttaggta ttataaataa tctagagatg atgtaaagta tataggagga tatgcatagg 115380
ttgtatgcga atactacatg attttatgta agggacttga gcattccaag actttggtat 115440
cttcacaggg tactgtaacc aatcccccac agatactaag agatgactgt actattgtta 115500
ttattcgact gagatcataa gaagatatat ttatttttaa tttttaaaaa cacttccatc 115560
agtttcttaa aaatagctgc cactgttttt aatatttttt aattgacaaa gttttaagtt 115620
cctactgaaa catttttttct tttattgaaa tgtgaaaatt tatgtgctgt gtttttgttt 115680
tcaataaaag ggacatagtt aaagcaagta aaattagaaa gactgggaaa atccgtcttt 115740
aaattgcaat aatagttcat ctgttacctt gagataattg aatttattgt tgtttttgta 115800
gccaaagcct tctactaccc caacttcacc tcggcctcaa gcacaaccta gcccatctat 115860
ggtgggtcat caacagccaa ctccagttta tactcagcct gtttgttttg caccaaatat 115920

```
gatgtatcca gtcccagtga gcccaggcgt gcaagtaagt catagaattt gatgttcact 115980
tagcctcccc aattgtttgt atctgacacc aagcactctt taggttttca gtgacttgag 116040
ggtgtgatgg ttatgcatat gcatttgaaa cagacaggca tgcagagatt cagtgtgttg 116100
ttaagtatga ggacctaaat ctgagaatgt tttctgtgaa aaagatggtt tagatttact 116160
gtagtttggg gtttgttcct tttagctgtg ggtatgatct aattttttaa tgactaatgg 116220
agaatcagga aaccttctca tgcctagctc tctagcaata taaaactaag agtgacagaa 116280
taccttgtta ttatcatagg tgcctaatgt taattttttt tttaattctc tcaagccttt 116340
atacccaata cctatgacgc ccatgccagt gaatcaagcc aagacatata gagcaggtaa 116400
aggtgagaat aatcctgcct gtgtttgctt gtagtttgca tgctgcatga attgagtaac 116460
taagtttata atgaataaat agttgtagtt tagctctgac tttttgatga ggctatgcat 116520
tggcttttga tgaacaacat tacatagata ttcacatgga ttttatgaag aaaaacaggg 116580
gagaaaaaat gcccatcagt tgtgattata tagtatcctc ttcaaaaaga gtaattggag 116640
gcctggtgtg atggctcaca cctgtaattt tagcactttg ggaggccaag gcaggaggat 116700
tgcttgagct caggagccca agatcagcct ggacaacaga gactttgtct ctactaaaat 116760
tcaaaaaaat tagctgggca tggtggcata tgcctgtagc cccagctgtt tgggggactg 116820
aggcgagagg atcacttgag cccaggaagt agaggctgca gtgagctgtg attatgccac 116880
tgccctccag cctgggcgac agagtgagac cccgtctcaa acataaatac tggctgggca 116940
tggtggctta tgcctgtaat cccagcactt tgggaggccg aggtgggtgt atcacctgag 117000
gtcagtagtt tgagaccagc ctggccaaca tggcgaaacc ccatctctac taaaatacaa 117060
aaattagccg gacatggtgg cacctgccgc ctgtaatccc agctactagg tggggctgag 117120
gcaggagaat tgcttgaacc cgggaggcag gggttgcagt gagccaagat cgtgccactg 117180
cacttcagcc tgggcaacag agtgagactc catctcaaaa caaacaaaca aacaaaaaac 117240
aaacaaacaa aaaaaccaga ctaattggct ggacacagtg gctccatgcc tgatatccca 117300
gctggaggat gacttgaacc catgagttcg agagcagcat gggcaatata gtgagaccct 117360
atctcaaaaa aaaaaaaaaa agttaattcc aaagcttttt gatctgaaat ctgatttaaa 117420
tctgaactta aatttgaaga agagggtttg ctagattaat ttactagatt gctaaccttg 117480
ctttatatat acctacagtt atttccccaa agccagaatt tcttttgaag cagaggggca 117540
actaacttca accaatgtta agatcctatt agaaggatgt ttcggctagg cttggtggct 117600
cacgtgtaat tccagcactt tgagaggctg aggtgggcag atcacatgac cgggagtttt 117660
aagaccagcc tgggcaacat ggcaaaaacc tatctctgca aaaaaaaaat agaaatctta 117720
gccagccgtc atggtgtgct cctgtagtcc tagctacttg ggagactgag gtgggaggat 117780
caattgaaac cagaaggtcc aggctgcagg gaactgtgac tgcaccactg ggctccagct 117840
tgggtgaaag agcgaaaccc tgcctcaaaa agaaaaataa gatggatgtt tctgcattaa 117900
aattagggag ttgtcgtata atgtagttgc ataaactagt attctgtgct tgtgtggtta 117960
aagagccttc gtagaaaaaa tcccacattt ttcttaaaag gaaatctttt ggccaggtgt 118020
ggtggctcac atctgtaagc ccaacactct gggaagccga ggtgggcaga tcacttgagg 118080
tcaggagtac aaaaccatcc tggccaacat ggtgaaaacc cgtctctact aaaaatacaa 118140
agatcagctg ggcatggtgg tgcgtgcctg ggtgacagag cgagactccg tccaaaaaaa 118200
aaaaaaaaaa aaaagagttc ttttaatgtt ggaaaatgct aaagggtttt ttttttgcca 118260
accagttaat ttagagtgat taactgctat cagttgagaa actatagaaa gtagaataat 118320
```

ttatacagaa aagacatttc tcagtgccca ataattgcct ttctgacata aagttttcat 118380
ttttcctgaa ttaataagat ttcctcaatg tgttttttg ggtgttttgt gtgtgtgtgt 118440
gtgtgtgtgt gtgtgtgtgt gtgtgtgtgt gtatgtgttt gatacagggt cttgctttgc 118500
tgctgaggct ggaacgcagt ggcgctatca tggctcaatg cagccttgac ctcctgggct 118560
caagcgatcc tcccttctca gtcccctgga tagcgggggc tacaggtgca caccaccaca 118620
cctagctaat tttgtattt tttgtagaga tgggttttgc catgttgcct aggctggtct 118680
caaactcctg ggctcaagcg atctgcctgg ctctgcttcc caaagtgcct gcgcccagcc 118740
aattttctcc atgtttgacc taattgtgat ttcatagatg ttaactaaaa ctcttaattt 118800
tcgttttctc agtatgctat ttttttttt tttagccttg gaacatatga acctgttgaa 118860
agaactctgc ctgaaataat gtaatcaaat tatagagttt aatcttattt tgagggcctt 118920
tagaaattct gagaagaaag tgggtttttt tttttactgc cattttaatg tagtgttaag 118980
gtgttcatgt atcaccagca ggtgtagctg ttttcaatga ttacttaaaa caatgcaatg 119040
ggaacttttt gttgtcatta aaatataaaa ggttactgta gtaagagcaa gcatgacagt 119100
ttggctatct gatgggagag tcacattcta acttcaggag gtactgtctt tttaatagaa 119160
atgatatact cagagtctgg gcacggtggc tcacgcctgt aatccagcac tttgggaggc 119220
cgaggtgggc agatcacgag gtcaggagat caagaccatc ctggctaata cagtgaaacc 119280
gtgtctctac taaaaataca aacaattagc tgagcgtggt ggcaggtgcc tatagtccca 119340
gctactcggg aggctgaggc aggagaatgg catgaacctg ggaggcagag ctggcagtga 119400
gctgagatgg tgccactgca ctccagcctg ggtgacagag cgagactccg tctcaaaaaa 119460
aaaaaaaaaa aaaaaatagt agagaaaggg ctttgccatg ttggccgggc tggtcttgaa 119520
ctcctggcct caagtgatcc acctccctcg gcctcccaaa gtgctgggat tacaggtgtg 119580
agccactgct cctggcctga atataccact tttacctatc atcagttgat gaacatttgg 119640
attatttcct ttttctggca atgagtaatg cttttgtgga ttttcatgta caaattttca 119700
tatgaggctg ggagcagtgg ctcatgccta taatcccagc agtctgggag gctgaggtgg 119760
gcagatgact tgaggtcagg agtttgagac cagcctggcc aacatggtga aatcccatct 119820
ctactaaaaa tacaaaaatt acactggcat ggtagcgtgc acctataatc ccagctattc 119880
aggaggctga ggcaggagca tcagaatcgc ttgaacctgg gaggcggagg ctgcagtgag 119940
ctgagatcac accactgcac cccagcctga gtgaaagagt gagtctcaaa aaataaaaaa 120000
taaaattttt tttcatgtgg ccttagattt tcatttctcc taaagtagaa atgctgtgat 120060
ggaactgcca aacttttcca aagcagctgc atcattttgt atttctacca gtaatgtaca 120120
agtgttccag tttctccaca tcctcataaa taaccgatat gtctttggtt tgggttatgt 120180
ccattctagt ggttatgaag tgtcattgtg gttttttgtt tttttgtatt gttttgagat 120240
cgtgcccagg ctggagcaca gtggcacaat ctcggctcac tgcagccttc gcttcctggg 120300
ttcaagcaat tctcctgcct caccctccca gatagctggg gctgcaggca tacgccacca 120360
caccaggcta atttttatat tttttgtaga gatggagctt ctccgtgctt cccaggctgg 120420
tctcgaattc ctgagctcaa gcgatccccc tgcgtcagcc tccagagtag ctggggttat 120480
aggcgtgcac caccgcgctc ggcccatttt tgtattttta gtagagatgg aatttcacca 120540
tgttggccag gctggtcttg aactcctgac ctcaaatgat ccgcctgcct caccttccca 120600
aagtgctgag attttagacg cgaaccacca tgccctgact ataggttatc tttttacttg 120660

```
cttgatggtg ttctttgtaa cacagttttt aattttgatg aagttcaatt tatctgtttg 120720
tttttctttt tgttgctgtt gctcctgatg tcatatcaga caaagcattg cctaactcaa 120780
ggccacagag atttactcct atgaaacgcc tataaaactc ctatgatttt tatagtttag 120840
ctcttaacat ttaagtctac aatctctttt gagttaattt ttgtgtatga gatgagagta 120900
gtggtccagg tttttccttt tgcttgtgga tatccgttgt ccccacctca tttgttgaaa 120960
agactattct ttcctcttaa attgtttgtt tgtttattta tttttgagat ggagtgtcgc 121020
tctgatggag tggcgctaac ttagcttcac tgcaacctcc gcctctcaga ttcaagcgat 121080
tcccctgcct cagcctcctg agtagctgga attacagggg tgcgccacca cacccagcta 121140
atttttgtat ttttagtaga gacggggttt taccgtgttg gtcaggctgg tctcgaactc 121200
ctgatctcgt gatctgcctg tctcctggca ccctgggagg ctgagaggct gaggtgggag 121260
gatcacttga gctcaggagt ttgagaccag cctgtaccat tatgcctggc taattttaga 121320
atttatctta aagtataaaa tgtgaatcca atttatcttg ttctaaatga ctatccaaaa 121380
tgttttaacc agttttatta gtctgtaatt tacatacaag aaaatgctca tctttttatg 121440
tttacatttt aatgagtttt gacaaatata tttgctcatg taactacttg cttcatcagt 121500
gaagatggaa aacattgtgc ctgttcctct tctctgtcca actgtacttt attaccacta 121560
gctccagtta accagtaatc tgccttcttt tactatagat tagatttatc ctctttagat 121620
ttctttttct tttttttttt ttgattaggt tttttttttt cttttttttac gtaaaaaaat 121680
cttttttttgg agacgtctca ttatattgcc caggttggtc tcgaactctt gagctcacct 121740
cagcctccca gagtgctagg attacagatg tgagccacct cagccagccc ctagattttt 121800
tttttttttt taataaatgg aatcaaacag cgtgtaacag aggtgttcaa tcttttggct 121860
tccctgggtc atattggaag aagaattgtg ttgggccaca cataaaatac agtaacacta 121920
atgatagctg atgaacaaaa caaaaaaaaa tagcaaaact tataatgttt taagaaagtt 121980
tatgaatttg tgttgggcca cattcaaagc cgtcccagga cgcaagttgg acaagcttgg 122040
tatataattt catatgtgtg tcctaaacag tgtagtaatt tgaatttcat gttagtatca 122100
gcttattcct ttttgtttgt ttgtttgttt ttgagatgga gtcttgttct gtgtcccaga 122160
attggtctgc aattccactg cctcagcctc ccaagtagct gggattacag gcacgtgcca 122220
ccacacctgg ctaatttttg tctctctctc tttttttttt tttttttttt ttttttagca 122280
gagacgggat ttcaccatgt tggccaggct ggtctcaaac tcctgacccc aaatgatcca 122340
cctgccttgg cctcccaaag tgctgggatt acaggtgtga gtcaccgtgc ccagccagct 122400
tattcctttt tattgctggg tagcatttca ttttatgatt ataccacagt taatttaccc 122460
attactagtc gatgggcatt tgagttattg ccagcttttg gctattatga atgaagctgc 122520
tgtgagcatt tgtgtacaag tgtttgtgtt tttatttctt ttagttaaat acctagaatt 122580
ggaattgctg aggtatggta agtgcatatt tcattttttt aaaaaattta ttttattttt 122640
tatttattta tttttttga gatgaagtct cactctgttg cccaggctgg agttcagtgg 122700
cgtgatttca gctcatggca acctccctgt cccgggttca agcaattctc ccgcctcagc 122760
ctcccaagta gctgggatta caggcgcgca ccaccatgcc tggctaattt ttttgtattt 122820
ttagtagaga cggggtttca ccacgttggc caggctggtc tcgaactcct gaccacaagt 122880
gatccacccg ccccagcctc ccaaagtgtt gggattacag atgtgagcca ccacacactg 122940
cctggtaaat acatatttca attaataaga aactagcaat cttctaaagt gattgtgtca 123000
ttttacattc caactgatca ggtacatgtg taggttccat gtgttctgca tccttgccaa 123060
```

cacttggtat tgtgttatct ttttaatttc aacaggtcta atgggtgtct tatggtatct 123120
cattgtgatc ttaaatgtac atttctctga tgatgactga tccaggagca cctcatcatg 123180
tgtgtgtttg ttttcagctg tcaacctttt tttagtaaat ggttcaaatc ttttttccat 123240
tttatttatt tatttattta tttgatggaa tctcactcta ttgcccaggc tggaacgcag 123300
tggtgccatc ttggctcact gcaacctccg cctcccaggt tcaagcaatt cttacgcctt 123360
agcctcccaa gtagctggga ttacaggcat gcgccaccat gcctggctaa ttttgtattt 123420
ttagtgtagg tggggtttca ccatgttggt catgctggtc tctaactcct gacctcaggt 123480
gatctacctg cctcggcctc ccaaagtgct gagattacag gtgtgagcca ctgcgcctgt 123540
cctaataatt tctttttgtc tcaatgtttc tgcctgggtg cactggctca cgcctgtaat 123600
tccagcactt tgggaggcca acctggatgg atcatttgag ccaacagttt gagaccagcc 123660
tgaggaacat gacaaaaccc tgtctttgca aaaaaaaaaa agaaaaaaga aaaattagcc 123720
aggcacagaa gcgcattcct atggtcccag ctacttgggg ggctgaggtg ggacaatcgc 123780
ttgagcgagg ttgcgggggt ttggagggcg atggaggggt gatcgaggtt gcagtgagct 123840
gagattgcac tactgcactc cagcctgggc aatagagcca gaccctgtct cacaaaaaaa 123900
agaaaaaaaa gtcatgtttc ttttcttact gtgaaaataa agttactact tttagtaaat 123960
tattttaagt tatttatata ttctggttac aagtcctttc tcagaatatt gtgaatattt 124020
tctcccagtc tgcggttttt tttgaagagc cagtattgtt aattttaatg aagccttatt 124080
tatcaagctt ttctcttaag gttcatgctt ttttgtatca taataagaaa tcttttacgt 124140
accctaggtt atgaatgttt ttatggttag gtatatggtt gatttcaggt taggttttgt 124200
gtagggtgtg atgtaaaggt ctagcttcat tttctccacc ataaatattt actcggtttc 124260
tctggcacca gcctctgttt tccattggtg gctttatttt ttttctgttc ttgaaacaag 124320
agtctcgatc ttgttaccca ggctggagtg cagtagtgtg accttggctc actgcaacct 124380
ccacttccca gggtcaagcg attctgcctc agcctctcga gtagctagga ttacaggtgc 124440
ccgccactac acccagctaa tttgtatttt tttttttttt ttttttagta gagacagggt 124500
ctcaccatgt tggccaggct agtctcgaac tcctgacctc aggtgatctg ctcatctcag 124560
cctcccaaag ttctgggatt acaggcatga gccactgcgc ccagccatag tagctttatt 124620
gaattcagtt gactgtattg tatgtgtgtc tatttgtgaa ctgttttgtt gtattgatct 124680
ttgtatatat ccttatgcca attctctctt tattgctgtt actttgtaac caacctttaa 124740
gttcatatga gtctcccagt tttattctcg tcaaaattac tcttattctg cgttctttga 124800
atttgcaaat aaattttaga atcagcttgg gattgtgcac tgaatcttta tatcagttct 124860
gggagaaata tcttaacaat atggaatctt cattgaggtc atcatatact gctccattta 124920
tttaagtctt aagtttcacc agtgttttct agttttcttt gtatcagttt tgtgcctgct 124980
ttcttaaatt tatcccttaa tatttcatct gttttgtgct gttgtgagtt atattttaaa 125040
aactttcaac gtttgtttat tcgtaaatag agatgcactt gatttttgaa tattgacctt 125100
gtgtcttgat gtgttggtaa acccactgtt tctggcagcc ctttaagact taaacataca 125160
atcatgatct aatcaccatg ttggtgtttt tgggtttttt ttttttgtct tattgtactg 125220
gtgcattact gaaaaaggca tgagattttg ccatgctccc atttttaggg gtgagacatt 125280
gtctttcact attaagcata cagttaggtg ttacttcagt tcctaatttg cagaggtggg 125340
tttgttttct ttttaatcat gaatggttgt tggattatgt tcaaatactt atcatctact 125400
aagtatatca tattgaccag gaacagtggc tcatacctgt aacctcagag ctttgggagg 125460
ccaaggcagg aggatcgctt gaggccagga gttcaagacc aacctgggtg atgtaggaaa 125520
accccatatc tacaaaacaa tttaaaaatt tgctgggtgt ggtggcacac acctgtagtc 125580
ctaactactt gagaggctga ggaaggagaa ttgcttgagc ccagtagttt aaagcagcag 125640
tgagctgtga ttgtaccact gtactccagc ctgggtgaca gaaggagacc ctgtatttaa 125700
agtgtgtgtg tatgcgtgcg catagatgga tagataataa tgtaattcca ttatggtcat 125760
acaaactgat atgaaatgcc attttatcat ataacaagtg tctttttgtg gttgaatttg 125820
tttctggatt tttcactctg cttcactaat ctaataggac taccttctca tccactcact 125880
gccaacattg attttttttt tcagattacc ttgaattttc tgtttatttt tccatatgaa 125940
ctctataatt aacttactac taaaaaaatc agttgccttt ttaaaaccaa ctgatcttta 126000
aaatatatct tggctgggcc cggtggcagg cacctgtaat tctagctact tgggagactg 126060
aggcagaaga attgcttgaa cccaggaggc ggaagttgta gttgagttga gattgcgcac 126120
ctgtactcca gcctgggtga cagagcaaga ttccctctta aaaaaaaaaa aaaaaaaaag 126180
aaacagaaaa gataaatctt tttacaataa tttgttccaa ttagggtcca agtcaggctt 126240
gcaatttgga tttgtttata tgttgaagtc tttttttttt tttaattgtt tcatattgtg 126300
gtaacttttt tttttttttt ttgagatgga atcttggctc tgtcacctag gctggagtac 126360
agtggcacaa tctcaactca ctgcaacctc cccctctggg gttcaagcaa ttctcctgcc 126420
tcagcctccc aagtagccca gccttttttt tttgagacag agtctcgctc tgttgcccag 126480
gctggagtgc agtgatgcga tctcggctca ctgcaagctc cgcctcttgg gttcatgcca 126540
ttctcctgcc tcagcctcct gagtagctgg gactacattc gcccgccacc acacccggct 126600
aatttttttg tatttttagt agagacaggg tttcaccgtg ttagccagga tggtatcgat 126660
ctcctgacct cgtgatccgc ccgcctcggc ctcccaaagt gctgggatta caggtgtgag 126720
ccactgcgcc cggccttgta tttttaatag agatggggtt tcaccatgtt ggccagcccg 126780
gtcttgaact cctgacctca aatgatccac ccgcctcggc ctcccaaagt gctgggatta 126840
caggtgtgag ccatcgctct cagccttgcg gtaacttttt attacgaatg tattgagaca 126900
ttaataacct aggccagtca tgtttcatcc ctacccattg tctcttaaaa gctttgagtc 126960
cactggatta ttctgaagca aattctagac attgcatcag tttatccacc aacattttag 127020
tgtgtatctt taagttggtt ttggttttgt tttttgtttt tgagatgggg tctggctttg 127080
ttgcccaggc ttggagtgca gtagtgcaat catagctcac tgctgctgcg aattcctggt 127140
ctcaaaggat cctccctcct cagcctctca agtaactgtg actacaggca catgccacct 127200
tgccagcttt tcttttcttg tcttgtcttt cttcttcttt gttttttgt ttgtttttg 127260 ttttttttg agacagagtc tcaccatctt tctatcttgc ccaggctagt cctaaattcc 127320
agggcttaag ttatctttct acctcagcct cctaaagtgc taggattaca ggccagcact 127380
ttaggaggtg ctggatgagc catcacaccc agccaagtca taggtttttt tgtttgtttg 127440 tttttgaga cagtgtctaa ctctgtcacc caagctggag tgcagtggca tgatttcagc 127500
tcagtgcagt ctctaccaat tgggcttagg tggtcctccc acctcaacct cccaagtagc 127560
tgggactaaa ggtgcgcgcc accatacctg gctaattttt gtatttttg tagagacagg 127620 gtttcgaatt cctgagctca agcagtctgc ctgccttgac tcccaaggtg ccaggattac 127680
aggcatgagc cactgcactc agccctcaca gttttaatta cagtttttcc cttagttttt 127740
gtcttgttca tatccagctt gtcttgtatt tttttcccac gatctgaatt ttgctgactg 127800
tatccctgtg ttgatattta aagtagactt ctgtcccctg taatctttgt aaactgatag 127860
taaataatga aggcttgatc agattgggtt tttttttttt ttccccaatg tttcacagat 127920
gtgtgtactt tcagtgagga gtcatgtaat cagtcttttt cctgatagga gtagtcagtg 127980
agttcctaga tgttttatct atccaggaga taatatgtcc ctttagcgcc ttaatttttt 128040
tggtgtgttt tttagcagcc attgatgata attgtctagc ccaagatcag ttatttcctt 128100
aggggttgta aaatggtgac attcttttcc tttcatccct tcttcaatta ttgcctggaa 128160
tatttctata aagaaaaact ttcccatatc cagctgtttg gttaccctga ggtatagctt 128220
tcttaggaaa agtaatttaa aatgttaatc atttcccttt ttaaggcagt cttcaaaata 128280
atgagttggt tttctgttat cctccaaagg taaccagtga ggtggttttt ttgtcgttgg 128340
ttcttactat cagtataaac ttctggaatt tttttttttt ttttaatttt ttggagacaa 128400
ggtctggctc tgttacctag gctggagtgc agtgggatga tctgggcata ctgcagcctc 128460
aacttcccga gctaaggcaa tccccccacc tcagcctccc aagtagctgg gactacaggc 128520
aagcaccacc gtgcctggct taatttttgt atattttgca gagacagggt ttcaccatgt 128580
tgcccaggct ggtgtcgaac tcctgagctc aagcagtctg cctgtgtcag cctcacaaag 128640
tggtgggact acaggcatga gccaccatgg caggccagaa tcacaataaa cttataaatt 128700
aacttgagaa gaaatgattg atgtcttcat gatgttgagt cttcctgttc aagaacaaag 128760
tataccttca atagcatatt aaagtttatc cttggctgga tgcagtggct gacgcctgta 128820
atcccacctc tttgggaggc agaggtgggc agatcacctg aggtctggag ttcgagacca 128880
gcctggccaa catggtgaaa ccccgtctct actaaaaata ttttaaaaaa agtattagct 128940
gggtgtggtg tgcacctgta gtcccagcta ctctggaggc tgaggtagga gaatcgcttg 129000
aacccaggag gcagagagtg cagtgagtca agattgcacc actgcactcc agcttgggca 129060
accgagcgac actctgtctc aaagaaaata aataaataaa aataaagttt atctttaagg 129120
ttttgtacat ttttttcagt gtatgcctta ggtaggttct tttttaatgt tagtgtaacc 129180
cagggacttc tcttccattg catcttctaa gtaattactt atgaagtacc atatatgaag 129240
gctattgctg tttatatgtt agtttttacc ctgctccttt actaaattcc aatcctttga 129300
ggtattggat aaaaatattt ttagcatttt tcaaataaca ggcagagtca agggcttggt 129360
ttcttttctt cccctcctgt cccctaccct cccctttttt gagacagggt ctcacttctt 129420
cgccgaggct ggagtgcagt ggtgcagtta cggcttaccg cggcatctgc ctccctggct 129480
gaaaagttcc tcccacctca gcctcctgag tagctgggac catagatgca cagcaccgca 129540
gctggctaat atttttgtat tttttgtgga ggcagtgtct ccccatgttg cccagggtgg 129600
tcccaaactc atgagctcaa gcagtccgct cgccctggcc tcctaaagtg tagggattat 129660
aagcgtgagc cactgcgcct ggcctgggga tcatgtttta acatgagaat tagtggagac 129720
aaacacatga tatctaaata atagcaccat agtatacttg actagctttt taattatttt 129780
ttaaatatac aggaaggtaa taagtaacaa agtaataata gtgaatagtt taagctcagt 129840
tagcataatc gggcaaactt tcatttgata aaagtgataa gtagttttca gtggcttttt 129900
tgtttaccag aaggaggtgg tttttaaata cgtgcatcca agataaaata taaaaaaatg 129960
ttcaggtttg ctttcctaca tagataaaat aatatgtaac tagctctccc aaatttcagc 130020
aacagttagt gaatgtttag ccacaaattt gcagttaatt atataatcag ttcttaggat 130080
tttatgaaca agttctatat tctttgtgcc ttatacctag ttgtaagcag tcattccaca 130140

```
attattttcc tgaagtggct tggttaatgc cacaccagaa acaggtcaca gacaatagtg 130200
ctgtaagaaa tgtgtgagga aagaggcaca tgggaagtag ctagctcgtg ctggaggaac 130260
tggaaaaaaa cctcacatgg gagatgacag ttgagctgaa ttcttaacta gagttgtaac 130320
agggcgaggc ccttacatgc agaccacctg tgtggattaa gataagacat aaagtaatct 130380
tttaaaagaa ctattattta gaaacctggt atatgctaca tggtgctgtg ttatactggg 130440
tttgagaaag aatgggaagt gttacaagga ttcagtggtt ggaaattaag gaagatagaa 130500
agttagtgtt ggatctgttt tggctctttg gtcatgcctt tgtttttctc aaaatgaatg 130560
cagtgcccgt cccagaaaat accatatgag aagcgatttc ataatgctgt gagagtctgt 130620
tacagggact tgatcaagtc tgagggccat gagagaaagt ccctctgagg aagttgcttt 130680
caagctgaca cctgaaggat gaagcagaat tatcccagct gggatttggg aactggtgtt 130740
tgaggctgag gactagcatg catgatagga aaataaccca gagtggcaga agtgggagtg 130800
gtatgagatg gcatcagaga cgcagattca gggtcaaatc attcagagcc tcctagacca 130860
tgtgaacaca tgtattatgc tgtggagata ctgtttaata ggcagtctgc tttttttct 130920
gcagtaccaa atatgcccca acagcggcaa gaccagcatc atcagagtgc catgatgcac 130980
ccagcgtcag cagcgggccc accgattgca gccaccccac cagcttactc cacgcaatat 131040
gttgcctaca gtcctcagca gttcccaaat cagccccttg ttcagcatgt gccacattat 131100
cagtctcagg taaggctggt aaggcctaac tcttaatttt tgtaccatat aaaaaaactt 131160
ttaatatggt aaagggattt tcctttataa tttttgcttt tgtgtgatgg tagggtagat 131220
agctaaggac ttggggaccc ttttcaatat atattcgaag gttactgatg attgtaagag 131280
gttcagagga aacagccaag aaagatttga gagtttacag ctgtttctgg aaatctggaa 131340
accatggagt taaaaatctt aactaaagtc tgcttggctc tatttgcagt gttaatgtgc 131400
tttctttatt ttttgtttga acacagcatc ctcatgtcta tagtcctgta atacagggta 131460
atgctagaat gatggcacca ccaacacacg cccagcctgg tttagtatct tcttcagcaa 131520
ctcagtacgg ggctcatgag cagacgcatg cgatgtatgg taggaagcac tttgtttgtc 131580
tcttccagtg tgtgtgactc ttcttaattt aagtttctga aaacatactc tatctaagaa 131640
taacctgacc ttttatgaca ttgagggtca agaatctgaa ggaaaagatg aacccatttc 131700
tttgcctgac ttgctttata acttttggca aatagtttct acttctgtac ctggtcttca 131760
gatctctttc ctgctttaac taaaatgtaa tgatgtatat aatggcaaag catctttgtg 131820
gagaaaggta cctttctcct cttcctcatc aatattatgc tttggtatat cctgcctacg 131880
acatgcaaga gaattttata ataataaaag cataaaggtg ttctccagca tgaaaacatt 131940
ttgcttcact acttgatctg agggtcactg gcattacata tttttttgc tgtttgttat 132000
aatgataata ctatgtttct acatcatgct gtattttaat ggttgaatat tatgtcatat 132060
tagatatatt ttagacatga gtcacacttt aaatataacc aatgtgaaca gaatgctgaa 132120
atgaaaatga gaagtatttt atgtaaaact aagcagtatt tatatgtgag aataataagc 132180
aaaaaaaccc atcttcgttt tgtgactaaa cagagaaatt tgtgtagatc aacttagcag 132240
ctgtctaaag taccaaaata atagattttt cactgttgat aatttaaaat aaaatgtcca 132300
tttgtatatc ttatgataca gaattaatgg attgcttcaa atgtttttca gaatatgttt 132360
ttaaatagta ctgatttcat taagatgttt tgttctgaat atttctgaga actaccgtag 132420
tgtcgtttag ttttcctatt tgcgtttttg gttgtttgga gtaggggata attttggttt 132480
attcatacag ttgaaaagtg tactgctatg agaatgagat tatggttaca tgtaactaca 132540
```

tgggcatttc atttttaaag cctctttgaa ctttttgaaa tactaagaat ataaaatttt 132600
tattttttaa gtttagatgt cctgaacgag tatgtttagg caaaattgag ttatttaaga 132660
atttataggc tgggcgcagt ggctcacgcc tgtaatccca gcactttggg aggccaaggc 132720
tggcggatca tgaggtcagg agatcgagac cagcctggcc aacatggtga aaccccatct 132780
ctactaaaaa tccaaaaaat tggccgggtg tggtggcatg tgcctgtagt cccggctact 132840
tcggaggctg aggcaacaga attgcttgaa cccgggaggc agaggttgca gtgagccgag 132900
atcgcgccac tacactctag cctgagcgac agagtgagac tccatctcca aaaaaaaaaa 132960
aaaaaaaaaa gaatttacag atttctggca aaccttcttc ttgagacatt actacttttc 133020
ataccacctc tgtccttttt gaagaataaa agttttaaca ttccgtaggt taatgagaat 133080
aggacttggg cagcagcaat catccttcct gtcacctgta acccacagct tatgctttct 133140
tcctggaggt tcttgtctgc cacaaaggct cactgctgat aggaatttgt atatgatcaa 133200
aggtgtttag ttttataaaa cagttaagtc cagtcttaat tttccacatt atcactttca 133260
attttgtatt gtggattacg cattttaaat aaaaaattgt gtgattgcta cattttggaa 133320
aacatttttt tcaagaggcc catccgtaat ttaattgtaa aagatactga caaactaact 133380
tggtttatta ttttggttat gaccccgtca tttgacttgt ctttagttgt cttaacgggg 133440
actgaatatg cgtgcaaagg cacgattgat ttatcatgct ggcttttatg caacttgtat 133500
atattttaac aatttttcctg tttgctaaag gcttaggtta aaagttcatt atgattgttt 133560
atacatttct ggtgaataca tcatgattta acaagtggaa agaacatctc tttccttcca 133620
ttttctggca tactcccctt ggaatcagat ctgaaacttt taagctaaaa tttccattgc 133680
atttggagag tagttatttg tgtatgcatg cttttgagac attgtagcaa taatactgta 133740
atgttgagcc gaatctttct cctcattgtg ttcattcact gccaacatct ggcttcatct 133800
tttggatgaa tgttcattgg ttttgaaaca gcctataggg taaatactgt gtttgaggta 133860
cagatgattt tcataactac ttcctagaac atgtccattt gaagagcagt ggggccttag 133920
accccaaagt ccatttatgt gtgggcaaat aggaaatgtt gcaaacaaaa caaagcacta 133980
gatctaatgt ccagtgaaat ctggaatgaa ctagtcatta gagccggttc tttcatgcca 134040
ggaaaaagtt actcagccaa atctgaacta ctctcctgca gtttacacag gtggtattta 134100
attgctgtct gtatggaggc aggctaggag caaggctgtg gacttgttgt gattgtcact 134160
agttaatcaa gattcccttt gtggtgctta agaccctaaa aaggacacta ggagctgggc 134220
atggtggctg acacctgtaa tccaagaact tggggaggct gaagtggagg atcgcttagc 134280
ccaggtgttc aagaccagtc taggcaagat ggcgagatcc catctctacc aaaaaaaaaa 134340
aaaaaaaaaa aaaaaaaaag cccagtcatg gtggcacatg cctgtagtcc cacctacaca 134400
ggaagctgag atgggaggat cacttgagtc caggactttg aggctacagt gagctatcat 134460
ggcaccactg taatccagcc tgggtgacag agcaagaccc tgtctctatt taaaaaaaag 134520
aaaacataag aaagaattgt tttgttctat gccatcataa gccataattt aatctgctta 134580
agcatgttct tcattaaatc tgcagtgatt tatttgaatt attagacttt caaagcctta 134640
ttatatcaaa tataaacaaa atttgaagta cattcttata aactacaaca aacttacata 134700
gaagtgttaa ttttatactc atcttccctg aacaatttat attttataaa tatattaaat 134760
atattgtaat aaattttctc aaaggaacca aatactttga gtatgaattg tgcttttctt 134820
tttaagctac atcatatcta ggtttttaaa acatttaatg caaacagaag aacatgcacc 134880
cagatgttgg tgacaatttt atgtcacctt ttctcattca ttaattgtta tagccatagc 134940
caaaggcatt gaaaacatag gaccactaat gactgcaaaa tgaaatcctg attattgttt 135000
ttaaattttt agtatgttta atacacatat gctaacatta ctgaacagtt aaatgataaa 135060
ataggataat tattttattc taaaaaagta ttgaccttga cctctttcta gctatcttag 135120
aaagggcttt tgtcaaaaac cttatctctt tgatgtctct ttttttgaga tggagtctct 135180
ccctgtcgcc caggctggag tgcagtggcg tgatctcagc tcactgcacg ctccgcctcc 135240
tgcgttcacg ccattctcct acctcagcct cccgagtagc taggactaca ggcgcccgcc 135300
accatgcccg gctaattttt tgtattttgt ttagtagaga tggggtttca ctgtgttagc 135360
caggatggtc ttgatctcct gacctcgtga tccgcctgcc tcagcctccc aaagtgctgg 135420
gattacaggc gtgagccact gtgcccagcc tctttttttt tttttatttt ttatttattt 135480
tttatttttt ttttaatttt tgagaaggag tctccctctg ccacccaggc tggagtgcag 135540
tggcgcgatc tcagctccct gcaaactccg cctcctgggt tcaagcagtt ctcctgcctc 135600
agcctcctga gtagctggga ctacaggtgc ccgccaccac acctggctaa tttttgtgtt 135660
tttagtagag acagggtttc accatgttgg tcaggctggt cttgaattcc cgacctcagg 135720
tgatccaccc acctcagcct cccaaagtgc tgggattaca ggcgtgagcc actgccccgg 135780
cctctttgat gtctcttaat ctaacttcca tcattgcctc taccccatcc cttctaagaa 135840
gttactttaa tttttttttcc tctcacatct actctttttt tttttttttt ttttttttg 135900 aggtagtctc actctgtcac ccattctgaa gtgcagcggt gcgatctcag ctcactgcaa 135960
catctgcctc ccaggttcaa gcggtttttc tgcctcagcc tcccgagtag gtgggactac 136020
aggtgtgcgc caccacgacc ggccaatttt tgtattttta gtagagacgg ggtttcaccg 136080
tcttggccag gctgatctcg aacttctgac cttgtgattt gtctgcctag gcctcccaaa 136140
gtgctgggat tacagatgtg agccaccacg cccagcctca catctactct tctaatccat 136200
ctaattttgt tttatggtga tgcttttacc tttcagaaac agtaataata caacttttcc 136260
gactaactag agccattagg aagaattaga tccagaatcc ttttttgatt tgtttttggt 136320
agtttaatgc agataagtaa gaaaatatag ttaagttaaa aaaaaaaaaa atgaaaagca 136380
tccataatcc ctccacctga caactgcctt ttaacatttt gatgtgtatc cttccaggtg 136440
tatttaaata cactcaaata ccctacccct ttatgtagac atgttttaat aagaaataat 136500
attcatgttt atattcttgc tatgatccta aatttttgga tccattacta gataatcttt 136560
caggataatg acatttccat tagtaatgtt tttgcaaaat tgtgtgtcta ttgaattaaa 136620
cttgtaaaat agttttattt tggtacatga tttatatcaa ggttgttcag tagaatgcca 136680
tgttggtgtt tttattagat aatgatttta ttccttttac ttttaagcaa gtcagcatga 136740
caacttgaca cctaagtaca gaagaacagt gtcttccggt ttagtccttt cttttaaaat 136800
tctgtagcag tgtttaaagt gcttgtcatc tcttatgaaa atgaattatg catgaataca 136860
aaaagaaatt actaatatgt caacctttcc agaaaatttg gaaaatgcac acctcaaaag 136920
gctaatttac ctttctattt cccaaattca gcatgtccca aattaccata caacaaggag 136980
acaagccctt ctttctactt tgccagtgag ttgggttttt tatactaatt tttaattgta 137040
cagtaaaaca ctttttaaag gatacatgtt aagggagtag acttgttgaa caatattttc 137100
cttgtgccag tcaaattatt gaaagtactt atatatataa ataattcagt ttttaaaatg 137160
gaaataccca atttaagaag gctggagtta atgaaaaatg gagttgtttc agaaatcaat 137220
ttttgcatac caagcaaatg tgactgggaa atgcctaata ttttccttgt tagagaaact 137280
tcctaaacag ctttatacac acacacacac acacacacac acacacacac aaacacacac 137340
acccaagcca caagcttggt ataaatttaa aatgtttatt tatacacaca cacacacaca 137400
cacacacaca cacacacacc ccaagccaca agcttggtat aaacttaaaa tgtttattta 137460
tattctgata agatgaaatt tatgcctacc aggattttta attgaatagg attgatgaaa 137520
tactaaggga aaaacttttc agtcctgtgc atggctaaag gtttaaaata ctcaggaagg 137580
gccaggcacg gtggctcaca cctgtaatcc cagtgctttg ggaggctgag gcgggtggat 137640
catctgaggt cagcagttca agaccagcct agccaacatg gtaaaactcc atctctacta 137700
aaaaatacaa aaatcagcca tgcatgctgg catgcgccta taatctcagc tactagggag 137760
gctgagacag gagaattgct tgaacttggg aggcagaggt tgcagtgagc cgaagtcgtg 137820
ccactccact ccagcctggg tggcagagcg aaattctgtc tcaaaaaata aaatattcag 137880
gaagcagacc cctcaggata tcttgagctt aagcaagaga tcatgacctc tcaggtcatt 137940
atcttggaca gcacaggtcc cctctcccca cctggcaaaa agtacagaaa tagttgctcc 138000
ttcatggaga aagtctgggc agagctttct tctggaaatg aacttttaag gtacattttt 138060
cctatttgta gggcaatttg taaaaataag ggccggacgt ggtggctcac gcctgtaatc 138120
ccagtacttt gggaggccga ggtgggtgga ttgcttgagg ccaggagttc gagaacagcc 138180
tggccaacat ggtgaaaccc tatctctacc aaagcatggt ggcacgcacc tgtagtccca 138240
gctacttggg aggcggaggc acaagagttc catgaaccct ggaggtggag gttgcagtga 138300
gctgagattg taccactgca ctcaggcctg ggcaacagag agagactctg tctcaaaata 138360
aaaaataaaa ataaggctag tcttggactt tggtatttaa ataggaagga gtactaatat 138420
ttgtagaaat cctttagaaa tttgtgccat taatattgtc accttgtatg aaatgttgtg 138480
ttctagagga tattaaggat tcaaatttta tgttaggcac attttgagtt attttggggt 138540
gactcaatgt ctgactctac taaatgccat attagcattt aaaatgcatt tgaccttaaa 138600
tctttgttaa ttatgccatg acttggtatc caaaaataag ctgatacata catacataca 138660
tatatgtgtg tgtgtgtgtg tgtgtgtgta tatatatata tatgtatgtg tgtatatata 138720
atttatttgg tgctaggaaa tgttaaattt aatcctttaa tagatgctct ttaaaaagga 138780
gtcttgctgt atgtatatac tattaaaggg gaaactatgt ctgtgattgt agtgtgtaaa 138840
agatagtagg tgattttatt atgtactcaa tttgaggtct caaatgtagt tatcctcacc 138900
atcttactgt ctctgttagt agtttggtgt tgttttcctg gtaagtagct aaggtcctta 138960
atcattaaca cctaagcctt aattgcctta gcacaacttc ccctaaaagg gagtatcagt 139020
actttttaaa agaaactaac agttgggctg ctaatttaat ctgctgcttc atttcccccct 139080
gttctaagcc attttatgat ggtttggtca agttgccttt tattcccctt ttagagtttt 139140
caactttcct tcacttccct ttttctgaat ttaacatcag atttacaagt tggaagattt 139200
tgttttgttt tataagtttt gcaatgctgg tgatctctta tgacttgtgc atccaaagtc 139260
aaaatgacaa aacctagtta caaattaaac acacagcttt ctgtacttaa tttgcttcag 139320
tgagatcaca gctgaggaaa ctagttctgg aatgtggtta gtgttattaa ggatttttga 139380
ctgatcatat gtttagaatc ttaaatattt atgtcaagga acactgagtg ggaaacttct 139440
ggactaggtc tggaccaaag aagcatatgt ctttgattat ctttaatcta aaagatttta 139500
tgaagactaa agttttataa atagaagttt aactgatgaa taaatcagta ttacaaataa 139560
aattaacttt atttttaacc tctctgggat ctttagccag aatgagcata tataacaaaa 139620
gcagtgaaat aatatgtgtg ggtcagaacc cactgccctt cccactccac tctccttttc 139680
cctgattctc ctgtgttttt tccttcttta ccttatcttg gttccttttt tttttttttt 139740
cttttgagat ggagtctcac tctgtcgtcc aggctggagt gcagtggtgc gatctcggct 139800
cactgcaacc tccgcctcct aggttcaagc aattctctgc ctcagcttcc agagtagctg 139860
ggattacagg cgcctgctgc cacacccagc taattttttt tgtattttta gtagagacag 139920
ggtttcacca tcttggccag gctggtcttg aactcctgac ctcgtgatca cctacctcgg 139980
cccctggttc ctttttgtc tctcttgtct tccaagctat ttttttcctt ggcttttaaa 140040
ttttcttcct accctgcttt gtgtcactgt cacttaactg gcctatcaag gaaccgaact 140100
gtatttttgt tactagtatt gatttaaagt ataagtttca catttctccc aatttattat 140160
tattatttat ttatttattt gtttatttta ttttttgaga cggagtttcg ctcttgttgc 140220
ccaagctgga gtgcaatggt gtgatgtcgg ttcactgcaa cctccacctc ccgggttcaa 140280
gctattctcc ttccccactc tccctagtag ctgtgattac aggtgcctgc caccacgccc 140340
agctaatttt tgtattttta gtagagacag ggtttcgccg tgttggccaa gctggtctcg 140400
aactcctaac ctcaggtgat ccgcccgcct cggcctccca aaatgctggg attacaagcg 140460
tgagccaccg tgcccggctc catttctccc aatttcaaat tcaaggagga aaagaattcc 140520
tgattaaggt acttctttca gatcttttga gctagaacaa aaaaacaaag ggaaatattt 140580
ctaattaact ctttttaaat tttgtttaca acgtatgata catattttac acatcctttg 140640
tggtttttgt tcgtcttgtt tttaatcaat gccttgcaag tttaccggta tttaggtagg 140700
gaaaggattt tgtttttgtt tttttaaaca aagcctatgt acattcactc agcttgggta 140760
tttgtgctat gcatgcaaat tagctataga ttagaaaacc gtattatagt ctttaaatac 140820
tggtaaactt aaattgcaga gatgcctttt aaaaatgcat agtaaaaata tttcatcttt 140880
acttttctct tcaaatgatt ttaagatttt tacatttttc cagttgatga ataacttaaa 140940
ttatgagatt tcatgggcat aattattttc tatatttatt gttacttttt aatattctta 141000
atactttgct tagaaggtat ttaaaagtga aatttcaaac tttttagtac aaaatttctt 141060
gaataaataa agttacaaaa aaaaaacaaa aacctctgag attccgtact gtatctttat 141120
gaacctccat gaacagaatt tgggatttgg gaattgcttt tccttagaca gatttagatt 141180
gttacaaatg acatttttaa gaggctgggg tggcggtagg ggttagtgct aatggtttaa 141240
cagtagggga ccatggacaa ctgtagacat cactatccag tagaacattt tgtggctggg 141300
cgcggtggct cacgcctgta gtcccagcac tttgggaggc caagacaagt ggatcacctg 141360
aggtcaggag ttcaagacca gccagaccaa catggtgaaa ccctgtctct actaaaaata 141420
caaaaaagtt agccaggcgc gcctgtagtc ctagctactc aggaggctga cacaggagaa 141480
tcgcttgaac ccgggaggca gaggttgcgg tgagctgata tcacgccact gcactccacc 141540
ctgggcaaca gagcgagact ccgtctcaaa acaacaacaa aactgcactg tccaccgtat 141600
tagctactta gctacatgtg gctttttat tattcaaaaa taaattttta ggccgggtgc 141660
agttgctcac acctgtaatc ccaacacttt gggaggccga gatggacgga tcacttgagg 141720
ccaggagttt gagaccagcc tggccaacat ggtgaaaccc cgtctctact aaaaatacaa 141780
aaattagcca ggtaatccca gctactcaga ggctgaagca ggagtatcac tttaacccag 141840
gaggcggagg ctgcagtgag ccgagatcgc tccactgcac tccagcctgg gtgacagcaa 141900
gactgggtct caaaaataaa caaacatggc cgggcgcagt ggctcatgcc tgtaatccca 141960
gcactttggg aggccgaggc ggatggatca cttgaggcca gtagttcgag accagcctgg 142020
ccaacatggt gaaacccgtc tctactaaaa atacaaaaat cagccaggca tggtgatgct 142080
tgcctatagt tccagctact cggcaggctg aggcaggaga atcgcttgaa cccgggaggc 142140
ggaggttgca gtgagccgag atggtgcccc tgcactccag cctgggcaac agagcgagac 142200
tctgtcaaaa attaaacaaa taaatacatt tttaaaatga acgtaagatt tttacaagta 142260
caacaaactc aggttcgaaa tttacatcaa atcttttaga ccaagtcagt gcctatacaa 142320
cttggaggag ctggaagtaa acttaatgag tatgatgatg atggagggcc tgttaataag 142380
ccaccaagtt agaaaaaaag gactgtctta tagacttatg ggactgtgaa gctcaggaag 142440
gcttcatcgt ttgtacatca tttgttctag ctcccagaag acgttcacta ctcttaaaaa 142500
cattcagaga ctatgttgcc acagttttct tgttaaaata ttctggcata tgttaattcc 142560
tacagtctgg aaaattttcc cagtgtataa acaaagctgc tgtatccagt ctaaactgga 142620
tatgaaggaa tattaatgcc agctgtggca ttggcagtgg atgcacaggt gatcctagaa 142680
ctggctcttt gccttgccct ttcccctgct aagagatagc tttgcagctg gagacgtaac 142740
tgttagggct ggagagttgg tggcccttag ccctacaaca cctaggatta tagaactgct 142800
ccatgtgcct agcctaaccc tctgcacacc atttacgtgg aatataccca gagccgtcta 142860
tgctggtgac tcggcagcct tgcctaccag actgctggaa ctagggtgcc tcttcccaaa 142920
gctgtgcttg cttctctcac caatcagtcc tgcatatgtc tgtgtttgct aacacgttat 142980
atgaagaatg tggggaacta ttttggaatc atttctgtgt atgggcttat tatcttgagg 143040
gattttagga tttgtttctc aagagagggc tgggaactat accttgctag agttgtcttg 143100
agaacgctct attctcagct cattgcctcg tggaggttag ttttttatca tcggtgtgct 143160
gtccatagtc actggaagca gtgaacacat cctactctgc ttctgattct caacttactg 143220
tttttgaagc acatgaacag gccaggcacg gtggctcacg tctgtaatcc cagcactttg 143280
ggaggctgaa gtgggcggat catttgaggt caggagtttg agatcagcct ggccagcatg 143340
gcgaaacccc atctctacta aaaatacaaa aattagctgg gcgtggtggc acatgcctgt 143400
aatctcagct actcgggagg ctgaggcagg agaattgctt gaacctggga ggcagaggtt 143460
gcagtgagcc tgggcaacag agtgagtgag acttatatct caaaaaaaaa caaaaaacaa 143520
aaaactgaaa gacatgaaga aatggttttt gtaccaaggt ttggcccacg ctgagattca 143580
caaagaactg gctttcagtt cttatcttta ttttgattta aactggccca tcatgttgtc 143640
ctttgaagtt agtctagtaa atttctttcc aaagggctgg ggcactcaga agggagttta 143700
cttttctata tttatttcat aaagcaaaga tgggagatcc tccattaggg cttgggaaag 143760
taaactgagt ggcagaaggg ctcctgtgat tagctgagag agactgtggt ccttcggccc 143820
tgatgataga tccctggcct tgccacatac catacacagt gcccgcaccc ccatccccca 143880
ccacacccaa tatagtctgt gccctcagga cattgctcca gggcagtagc atggtgaggt 143940
tagcctgatg atggccttga gctaaagagt gtgcacctaa aatgcacttg tttgagtagt 144000
ttctgcctat gccttcaagt tgcctttttg ggaaaaccta gtgaccgtta agagtaaatg 144060
caaactaatt tgattttaat atcatatgta gagctgtatt atatgaacca aatgctagtc 144120
tgttaagcaa tagctacact tattttttca agacaatgga tggtttaaat ggagtcatct 144180
atagaaattg gtagtggcgt gagttatgca ttgtaaccat caagaaagtt cagttgatga 144240
agtgtagagg agcgatggag gttgtcagac atcggttgtg tacatgctcc tttttctttc 144300
actttagttt ccacgggctc ccttgctcag cagtatgcgc accctaacgc taccctgcac 144360
ccacatactc cacaccctca gccttcagct acccccactg gacagcagca aagccaacat 144420
ggtggaagtc atcctgcacc cagtcctgtt caggtaaggg caactcagag gtctgcatgg 144480
agtggcttct ttatcctagt atctgagtgc tttcttcagg tgccaggtat cgcatcgtca 144540
gaacacatgg catgtccacc ctcgtgaaga tggatacagc tgtgccccctg gggtggtggt 144600 tttaagaatc acatttaaag gctgggcgca gtggctcacg cctgtaatcc caccactttg 144660
ggaggccgag gcgggtggat cacgaggtca ggagattgag accatcctgg cgaacactgt 144720
gaaactccgt ctctaataaa aatacaaaaa aattagccgg gcgtggtggt gggcgcctgt 144780
agtcccagct tctcgggagg ctgaggaagg agaatggcgt gaacccggga ggcggagctt 144840
gcagtgagca gagatcgcgc cactgcactc cagcttggac aacagcgaga ctctgtctca 144900
aaaaaataaa aaattaaaaa aaatcacatt taagatacat gttgataata aggtgattgg 144960
ataagctctg gaaacttgca gtaatgaaaa atcaaattta acataaagtt cataaggcaa 145020
attcctattt gcttgggact ttttaatttc taaggtttat gtgatgaggt tattttccta 145080
tgagcttctt gaattatgtt tgctaatgga ggcagttaaa gatgtctttg atatctatca 145140
gttccctggg gcagtagtct tttttgactt tagtatgtat gctcagaagt ttctaactgc 145200
cagactgaga atcaggcttc tgtaccctag aaaggagttg tccagatggg aggcacctcc 145260
agccttgctc ttaccaccct gtacattctc ctgtactttc cagtgaccct catcataggc 145320
ccaagtgtgc aaagcttagc tttgtgggta tcccttggct gcttttcatt aaagaagttt 145380
tcctctcaat tctttcctgt cgctttgcag caccatcagc accaggccgc ccaggctctc 145440
catctggcca gtccacagca gcagtcagcc atttaccacg cggggcttgc gccaactcca 145500
ccctccatga cacctgcctc caacacgcag tcgccacaga atagtttccc agcagcacaa 145560
cagactgtct ttacgatcca tccttctcac gttcagccgg cgtataccaa cccaccccac 145620
atggcccacg tacctcaggt aataccagct ttagccaact ttctgtgaag gccaagtaga 145680
atgtgaaggt tatcagtaag cagctagagg ctctcccagc taggaaaccc tgtgtgtcat 145740
gccatttgcc tgtctccctt tccctctcaa atacacgtga tctggcccta agggaatgtt 145800
tgtgtggttt tgtcatggga tcagtgaagg tgctgattgg tcagtccttt agttttccaa 145860
ctgagacctt aaaaatatct ttgactctgg aatgcaaccc agtccttctt tcctttctgt 145920
gtctgctttg ctatgtctat atagcctcac tactatatat atgtgtacat atatattccc 145980
ctacacactt accttggaag ccaggcaggg atgatggcct tcacagagtc tcagctctcc 146040
gaagtgacta ccggggcctg tcaacttgat tgttactcac atgagttcca gacacatctc 146100
tccaattgtt ttccctggtt atccatatat ctgctttgac cataagttgt actcttgaga 146160
gggcttggcc ttggacattg gtgcagtgta actagaagct ggaagcaccc aggtggtccc 146220
atttttcttt aagagcagcc ctggaagcac tttggagctc acctccagtg taagctgcta 146280
caggtgaaag gtgtgcttgc catctcagtg gttgctgtct gcatcagctg ctgacaaagg 146340
tccctgcact ccagggccca ggggattgtc ttaatgagga gaaggagctg cactgaagtt 146400
gggctctaac gctggccttg aggccctccc tggggctgtt acgggtgaat tggctgtatt 146460
agatgtctct gctactttca taacagaact ctctgaggcg ggtctaagtg agacctgcca 146520
caatgaattc catttcctgt taaatagtgc gccagtgagg ctctggcaag gtgtgggcta 146580
gagatgcgac tcagttggat ctatctctca gaaggctacc ttgtaagtag agttccacag 146640
ctctgggaag tttgggcgtc ctcaccctgc aaagtttagg ttctgtggtg tagcgcactg 146700
cagttgattt gctttttgat agtggggagg gaagccggtt tggtccgtgt gggccagcgt 146760
ggtttggtgg agtcagcttc ataagagctg gggtcctgta ggtgtctacc agaggctggt 146820
ggctaagtag gcatgtgaac ttacatgtaa gtcagggatc cctaaaacct cactctgttt 146880
ttgtgctgaa agggcaaaaa ggttaacaca gggaagctca aatttgccat gtgcccgttt 146940
gaatatgtga gagtaaaaac ggcatttcat ccaaggctta tcgtagtcta gaacagtgca 147000
cagtgtggga aaaaggaaac aagggctctt cctggccctg ccaacccccct gcagagctgg 147060
aatccagctg tttgggctga ctaaaatcac ctttccaact tgacagtgag tgagaccagg 147120
ttgaacttgg tacagagacg ctgggctggc ccagatgact tcaggttact cctttccatc 147180
tcactggagc cattaaaaac tccaactcct cctcctcctc ctgctccatc agcatatctc 147240
tgagagagtc acgggggcct aagagtctct tttcactgcc tggtgagcag accagaagca 147300
gagggagaga ggcaaatgaa cagaggtcca agtaattcac atacttgact gtgacagtct 147360
ctgcttatta atgtaatctg ttttcctatt tgaaagggat gttatctgca aaactacctc 147420
aggccccaca tggcagcctg attctgaagc atcattgaat cttgtatgat attaagttga 147480
gaaagctgcc cttggatcca gtgtctaatc tttgtgaaga tcttacccca tacatagaat 147540
acaatgatca gaaatgtcaa gggttaggac agcacagccc tgacttctac ccaggctcac 147600
ttgttgcctg ctccctgacc cttgcaggat ctgcccaaag gtgaagcgcg tcttcaggtc 147660
aatagataat ctactagaga ttgtccccag agaacagaac tgggccctga ggcccaccgt 147720
tgccctttcc tgagagtccc agcccagtga aaggaacaca gttgacatgt tgttgaagcc 147780
ggagatgttg cctgtatgcg taaaagagct ctctgtttca ggctcatgta cagtcaggaa 147840
tggttccttc tcatccaact gcccatgcgc caatgatgct aatgacgaca cagccacccg 147900
gcggtcccca ggccgccctc gctcaaagtg cactacagcc cattccagtc tcgacaacag 147960
cgcatttccc ctatatgacg caccccttcag gtgaggcgtg tgtgtgcagg ggccgccggg 148020
gcaccccaaa gcattctgct cgcacaggtg gaatggcagg cagggccagt gcttcaagcc 148080
ccgcatttga gaactagcaa gacccgtcca ggagtgtgca caggagggac tgtgacgatc 148140
agttcagcat cagggcctga ggcttccggg agccgagtct gtgtgtgttc tgatggtata 148200
caggatttgg cttgatgaga agcagcagca gcagcaacag cagcctgatg catgcctagg 148260
actcagttgg ccttccttgt tatgacaggc tggacagggc agtgttttcc ttcctgagtc 148320
ccaaaagtct gacatgtggg gggttattac catggcagag tttgattgta gctctggaga 148380
agatactgct gagaaagcgc tgtggatgga ctggctttga gtgtagcgtt agccccagcc 148440
cctgaacagg ggagagcgcc ctgtgattgt gctctactac ttgatggctg ccatggcgat 148500
acttcacagt ctgacctgtt attctgaaag caatactggt gcttggctaa tatttgggga 148560
gggggtttgt taaggccttt ttttctaccc catgaacaag tcttctggga gttttatctg 148620
aagtggtttt acgtctgact ggtttgtttc tacccaccca cccaaccctc cccactttgg 148680
tgcagatggg agggggaaaa gcgaattcaa ttttgagttt tgttcagcta gcacgaggat 148740
agtttacaat catgtgctgc agagacacta ggctgatgtg tggtgttgcc agttttctgt 148800
ttcaatgttc gcttttcttt ttacagtaca agcccaccac caacagcagt tgtaaggctg 148860
ccctggagga accgaaaggc caaattccct cctcccttct actgcttcta ccaactggaa 148920
gcacagaaaa ctagaatttc atttattttg tttttaaaat atatatgttg atttcttgta 148980
acatccaata ggaatgctaa cagttcactt gcagtggaag atacttggac cgagtagagg 149040
catttaggaa cttgggggct attccataat tccatatgct gtttcagagt cccgcaggta 149100

```
ccccagctct gcttgccgaa actggaagtt atttattttt taataaccct tgaaagtcat 149160
gaacacatca gctagcaaaa gaagtaacaa gagtgattct tgctgctatt actgctaaaa 149220
aaaaaaaaaa aaaaaaatca agacttggaa cgccctttta ctaaacttga caaagtttca 149280
gtaaattctt accgtcaaac tgacggatta ttatttataa atcaagtttg atgaggtgat 149340
cactgtctac agtggttcaa cttttaagtt aagggaaaaa cttttacttt gtagataata 149400
taaaataaaa acttaaaaaa aatttaaaaa ataaaaaaag ttttaaaaac tgatcaagtt 149460
agtgtgtgtc tgtataagct acttctttgt aggatactta atatcaaagc aggtgtgcta 149520
agggtgcatt ttgaatatcc cggaaggtag ctgtgaaatg atttttcttc ttcaccctta 149580
gttctggttc aaggtatctc tagaaaaaga caagactgag ctattctctt tggtggatta 149640
gagatctgct tcaggaggag gaaggttggc cagagttggg cagcactgaa attccacatc 149700
ctcgggctga caccgattct gtaagcttcc tttttaatat ctcctgaacc aaaatgagtg 149760
tcattagctg gaagttccca attcgggcat ttttctactt taccagtagg gggcaggaga 149820
cactcagaaa aaaattgcaa taaagaaatc cagagggcat gaaggctgaa aagatacaaa 149880
gatgtacaaa gctgcttatt gacatggatg gactcataag catttgttag tattcccaga 149940
ttgcaacggg gaggacaaag ggaagagcga gtatttgggc agggcaagga ttttgtagag 150000
acaccatggt cttaatagag cctttaaata ttatgacagc aaatcaagat tctgaaaact 150060
ttttaattca catatagcaa tttgtacatt atagcaaaat ttgcattatt caagaataag 150120
ttacttgtac agtacataaa acaatacata aaaatttgcc aaataccttc tgcctataat 150180
gatacaagat gaatccactt tatgttatca caatgtgctg tatattctaa ccaaacacag 150240
gatgtcagat gtgtccttgt taatatactc gcaagttcct ctagcttgtg ggagatgtta 150300
gagctaacac atttgcagta agggacttag tcctgaatag aaagcatgaa ggaatctcag 150360
gcaaccctca gggaagagtc caaggccttg actttaggtt aagaaactgt tatgtaaaaa 150420
tagtgttctc tggcccaaga ttttaatgat tgctattcct ttttcctacg gtccagaaat 150480
gatcaaaggc agaagattta taccagataa agccatatgg attgctggtc taaaattcaa 150540
ggcaggttag ttgacttaat tctttggtgc tggtgactgt tagtttgtaa aagttcaata 150600
agtcagatga aggaagggat ggtgccggga gctgtcaagc tgtactggtg gggtctgtaa 150660
ttagagctaa ctggagggat catgatgtct actgtccagt ttggtgttga gccatggctc 150720
tcggtagaag ttgccggctg gggcctggtc aggactggaa ggagagtggt gggatgtgct 150780
gtgcctatgg tgggctagct gcagccagtg gggtgcctgc cccacactgc tgcccacccc 150840
ttcatcagct gattctgctc ccacataaag aaaggtgttg gcttagtgtc acttcttcct 150900
agagccatgg gagttttctg tcagcatgtt tttgagctgt cctggtaact tggacgggaa 150960
gcagtctgga ggtgggtgcc ttccaaatct ctgccacaga a                   151001
```

<210> SEQ ID NO 5
<211> LENGTH: 863
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t

<400> SEQUENCE: 5

```
gtctgtcggg gctctctccc cgccccctcc ggatcctggg naagnacggn ggacggggtg     60
gagacaagtg ggccttggcc cccgcacccc tctgcgttcg tgtccgaggc ggcggcgggg    120
gctcccgaac tcccctgaaa tcgtggggct ccatgtggcc tccggcagcg ttccaccctc    180
ccccacctgg ggaagggaag gggtggggag tgcccggccc cgtcccggcc ttcctccttc    240
ccccgccaga cctctccggc gcgcgggtgg tggccgatcc gcattgctgt tcgaggccgc    300
agtggagaag gcgcctgtgg aacatcgagg tcgaaacagt aacaaaggac tgcctcagtc    360
tacgatttct tttgatggaa tctatgcaaa tatgaggatg gttcatatac ttacatcagt    420
tgttggctcc aaatgtgaag tacaagtgaa aaatggaggt atatatgaag gagtttttaa    480
aacttacagt ccgaagtgtg atttggtact tgatgccgca catgagaaaa gtacagaatc    540
cagttcgggg ccgaaacgtg aagaaataat ggagagtatt ttgttcaaat gttcagactt    600
tgttgtggta cagtttaaag atatggactc cagttatgca aaaagagatg cttttactga    660
ctctgctatc agtgctaaag tgaatggcga acacaaagag aaggaccctg cagcccctgg    720
atgcaggtga actcacagcc aatgagggaa ctggaggctt tgnaaaatga cgtatctaat    780
ggatggaacc caaagatatg tttcgtttaa tgaaaaaaat tatggcgcag gggccaccgt    840
tgaaagcagt ttatttcgga tac                                            863
```

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 27
<212> TYPE: DNA
<213> ORGANISM: Artificial sequence
<220> FEATURE:
<223> OTHER INFORMATION: Primer

<400> SEQUENCE: 11
accaaagagt agttaatgga ggtgttc 27

<210> SEQ ID NO 12
<211> LENGTH: 19
<212> TYPE: DNA
<213> ORGANISM: Artificial sequence
<220> FEATURE:
<223> OTHER INFORMATION: Primer

<400> SEQUENCE: 12
agaaggtggg cgagaggaa 19

<210> SEQ ID NO 13
<211> LENGTH: 19
<212> TYPE: DNA
<213> ORGANISM: Artificial sequence
<220> FEATURE:
<223> OTHER INFORMATION: Probe

<400> SEQUENCE: 13
ctggccatcg ccttgccca 19

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cgtttgcata gattccatca 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
cttcacattt cgatccaaca 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tcatatatgc ctccgttttt 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gtggacacca caccataatt 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctggattcaa tttcttctgc 20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
tgtactgagc actggattca 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gtcatcattc tcaagggcga 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ggtcatcatt ctcaagggcg 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ttcttcctca ctccggtcat 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
ggtgatgttt cacttgcttt 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gtcatcaatc tgttttctgt 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
gtgacttttc tccttctcta 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
gcttccgttt tatctttaat 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
agcacttgct tccgttttat 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tgctgctgct gtcaatgaaa 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
aatgtcgatt tcctaacctg 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gaccaaaggc tgattgggaa 20

<210> SEQ ID NO 31

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggaccaaagg ctgattggga 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
caggactgta cacatgagga 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
cactaaacca ggctgagcat 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ctgttagcat tcctatcaga 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gtccaaaaca tcctccactg 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
tgcctctact cggtccaaaa 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
ccctacatgc ctctactcgg 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
agccacaagt ccctacatgc 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gttcatgact ctcaagggcc 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
acttctgtca agtttagtaa 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
agttttccct taacttaaaa 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
gacaaaatga gccagtttta 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
aatctgtgtt ttccctttcg 20

<210> SEQ ID NO 44
<211> LENGTH: 20
<212> TYPE: DNA

-continued

```
<213> ORGANISM: Artificial sequence
<220> FEATURE:
<223> OTHER INFORMATION: Synthetic oligonucleotide

<400> SEQUENCE: 44

tagcaccagg tatgcccatg                                            20


<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45

catggttatc tatggcagca                                            20
```

METHODS FOR REDUCING ATAXIN-2 EXPRESSION

SEQUENCE LISTING

The present application is being filed along with a Sequence Listing in electronic format. The Sequence Listing is provided as a file entitled BIOL0281USC1SEQ_ST25.txt, created on May 18, 2021, which is 348 KB in size. The information in the electronic format of the sequence listing is incorporated herein by reference in its entirety.

FIELD

Provided are methods for reducing expression of Ataxin-2 mRNA, and optionally reducing expression of Ataxin-2 protein, in an animal. Such methods are useful to prevent or ameliorate at least one symptom of a neurodegenerative disease. Such symptoms include loss of motor function, reduced CMAP amplitude, denervation, and loss of motor neurons. Such neurodegenerative diseases include spinocerebellar ataxia type 2 (SCA2), amyotrophic lateral sclerosis (ALS), and parkinsonism.

BACKGROUND

Ataxin-2 is a protein encoded by the ATXN2 gene. Ataxin-2 is expressed systemically and is located in the cytoplasm. It is thought that Ataxin-2 interacts with the endoplasmic reticulum and is involved in the regulation of RNA stability. The ATXN2 gene includes a CAG trinucleotide repeat expansion. Normally, the CAG trinucleotide repeat is repeated approximately 22 times. CAG expansions of more than 22 repeats are associated with certain neurodegenerative diseases.

Spinocerebellar ataxia type 2 (SCA2) is an autosomal dominant neurodegenerative disease characterized by progressive functional and cell loss of neurons in the cerebellum, brain stem, and spinal cord. The cause of SCA2 is CAG expansion in the ATXN2 gene resulting in polyglutamine (polyQ) expansion in the ataxin-2 protein. Patients with SCA2 are characterized by progressive cerebellar ataxia, slow saccadic eye movements, and other neurologic features such as neuropathy (Pulst, S. M. (ed.), *Genetics of Movement Disorders*. Elsevier, Inc., Amsterdam, 2003, pp. 19-34.). Moderate CAG expansion in the ATXN2 gene is also associated with parkinsonism or amyotrophic lateral sclerosis (ALS) indistinguishable from the idiopathic forms of these diseases (Kim et al., *Arch. Neurol.,* 2007, 64: 1510-1518; Ross et al., *Hum. Mol. Genet.,* 2011, 20: 3207-3212; Corrado et al., *Hum. Genet.,* 2011, 130: 575-580; Elden et al., *Nature,* 2010, 466: 1069-1075; Van Damme et al., *Neurology,* 2011, 76: 2066-2072).

The pathogenic functions of polyQ disease proteins that occur with polyQ expansion may be attributed to the gain of toxicity associated with the development of intranuclear inclusion bodies or with soluble toxic oligomers (Lajoie et al., *PLoS One,* 2011, 5: e15245). While SCA2 patient brains are characterized by loss of Purkinje cells, SCA2 Purkinje cells lack inclusion bodies indicating polyQ-expanded ataxin-2 may cause toxicity that is unrelated to inclusion body formation (Huynh et al., *Ann. Neurol.,* 1999, 45: 232-241). Functions gained in polyQ-expanded ataxin-2 may include anomalous accumulation in Golgi bodies (Huynh et al., *Hum. Mol. Genet.,* 2003, 12: 1485-1496), gain-of-normal functions (Duvick et al., *Neuron,* 2010, 67: 929-935), and sequestering of transcription factors (TFs) and glyceraldehyde-3-phosphate dehydrogenase like for other polyQ proteins (Yamanaka et al., *Methods Mol. Biol.,* 2010: 648, 215-229; Koshy et al., *Hum. Mol. Genet.,* 1996, 5: 1311-1318; Burke et al., *Nat. Med.,* 1996, 2: 347-350). Some normal functions of ataxin-2 have been characterized. Ataxin-2 is present in stress granules and P-bodies suggesting functions in sequestering mRNAs and protein translation regulation during stress (Nonhoff et al., *Mol. Biol. Cell,* 2007, 18: 1385-1396). Ataxin-2 overexpression interfered with the P-body assembly, while underexpression interfered with stress granule assembly (Nonhoff et al., *Mol. Biol. Cell,* 2007, 18: 1385-1396). Interactions with polyA-binding protein 1, the RNA splicing factor A2BP1/Fox1 and polyribosomes further support roles for ataxin-2 in RNA metabolism (Shibata et al., *Hum. Mol. Genet.,* 2000, 9: 1303-1313; Ciosk et al., *Development,* 2004, 131: 4831-4841; Satterfield et al., *Hum. Mol. Genet.,* 2006, 15: 2523-2532). Ataxin-2 is a regulator of EGF receptor internalization and signaling by the way of its interactions with SRC kinase and the endocytic protein CIN85 (Nonis et al., *Cell Signal.,* 2008, 20: 1725-1739). Ataxin-2 also interacts with the ALS-related protein TDP-43 in an RNA-dependent manner and familial and sporadic ALS associates with the occurrence of long normal CAG repeat expansion ATXN2 (Elden et al., *Nature,* 2010, 466: 1069-1075; Van Damme et al., *Neurology,* 2011, 76: 2066-2072).

Currently there is a lack of acceptable options for treating neurodegenerative diseases including neurodegenerative diseases associated with a CAG expansion in Ataxin-2. It is therefore an object herein to provide methods for the treatment of such diseases.

SUMMARY OF THE INVENTION

Provided herein are methods for reducing expression of Ataxin-2 mRNA, and optionally reducing the amount of Ataxin-2 protein, in an animal. In certain embodiments, compounds useful for modulating expression of Ataxin-2 mRNA are oligomeric compounds. In certain embodiments, the oligomeric compound comprises a modified oligonucleotide.

In certain embodiments, Ataxin-2 mRNA expression is reduced in a cell or tissues. In certain embodiments, the cell or tissue is in an animal. In certain embodiments, the animal is a human. In certain embodiments, the amount of Ataxin-2 protein is reduced. Such reduction can occur in a time-dependent manner or in a dose-dependent manner.

Also provided are methods useful for ameliorating at least one symptom of ALS. In certain embodiments, such symptoms include loss of motor function, reduced CMAP amplitude, denervation, and loss of motor neurons.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

"Administering" means providing a pharmaceutical agent to an animal. "Administered prior to the detection of the at least one symptom" is prophylactic administration and means providing the pharmaceutical agent to an animal before a symptom of ALS is apparent through observation or clinical diagnosis.

"ALS" or "amyotrophic lateral sclerosis" means a progressive neurodegenerative disease that affects nerve cells in the brain and the spinal cord. ALS causes progressive degeneration of motor neurons, eventually resulting in their death. There are familial and sporadic forms of ALS. "At least one symptom of ALS" includes loss of motor function, reduced CMAP amplitude, denervation, and loss of motor neurons.

"Animal" means a human or non-human animal.

"Antisense activity" means any detectable and/or measurable change attributable to the hybridization of an oligomeric compound to its target nucleic acid. In certain embodiments, antisense activity is a decrease in the amount or expression of a target nucleic acid or protein encoded by such target nucleic acid compared to target nucleic acid levels or target protein levels in the absence of the oligomeric compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the oligomeric compound.

"Ameliorate" or "amelioration" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom is loss of motor function, reduced CMAP amplitude, denervation, and loss of motor neurons. In certain embodiments, amelioration of these symptoms results in improved motor function, increased or stabilized CMAP amplitude, preservation or increase in innervation, and reduced motor neuron loss.

"Bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^{m}$C) and guanine (G).

Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Gapmer" means an oligomeric compound comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Identifying an animal having ALS" means identifying an animal having been diagnosed with ALS or predisposed to develop ALS. Individuals predisposed to develop ALS include those having one or more risk factors for developing ALS include having a genetic predisposition for ALS including mutations in any of ATXN2, SOD1, C9ORF72, FUS, and TDP43. Diagnosis may be accomplished by any method including evaluating an individual's medical history or standard clinical tests or assessments, such as, electromyography (EMG), nerve conduction velocity (NCV), and magnetic resonance imaging (MRI), and genetic testing of ATXN2, SOD1, C9ORF72, FUS, and/or TDP43.

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage ("phosphodiester internucleoside linkage"). Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"Non-bicyclic sugar moiety" means a modified sugar moiety that comprises a modification, such as a substitutent, that does not form a bridge between two atoms of the sugar to form a second ring.

"MOE" means methoxyethyl. "2'-MOE" means a —$OCH_2CH_2OCH_3$ group at the 2' position of a furanosyl ring.

"Nucleobase" means an unmodified nucleobase or a modified nucleobase. As used herein "an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e. no additional nucleosides are present between those that are linked).

"Oligomeric compound" means a compound comprising an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Reducing or inhibiting the expression or amount" refers to a reduction or blockade of the expression or amount relative to the expression or amount in an untreated or control sample and does not necessarily indicate a total elimination of expression or amount.

"Single-stranded" in reference to an oligomeric compound means such a compound that is not paired with a second oligomeric compound to form a duplex.

"Standard cell assay" means the assay described in Example 1 and reasonable variations thereof "Standard in vivo experiment" means the procedure described in Example 2 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. Modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1. A method comprising administering to an animal having ALS an oligomeric compound comprising a modified oligonucleotide, wherein the modified oligonucleotide consists of 12 to 30 linked nucleosides, and wherein the modified oligonucleotide has a nucleobase sequence that is complementary to an Ataxin-2 nucleic acid.

Embodiment 2. A method comprising identifying an animal having ALS and administering to the animal having ALS an oligomeric compound comprising a modified oligonucleotide, wherein the modified oligonucleotide consists of 12 to 30 linked nucleosides, and wherein the modified oligonucleotide has a nucleobase sequence that is complementary to the nucleobase sequence of an Ataxin-2 nucleic acid.

Embodiment 3. The method of embodiment 1 or 2, wherein the modified oligonucleotide has a nucleobase sequence that is at least 90% complementary to the Ataxin-2 nucleic acid.

Embodiment 4. The method of embodiment 1 or 2, wherein the modified oligonucleotide has a nucleobase sequence that is at least 95% complementary to the Ataxin-2 nucleic acid.

Embodiment 5. The method of embodiment 1 or 2, wherein the modified oligonucleotide has a nucleobase sequence that is 100% complementary to the Ataxin-2 nucleic acid.

Embodiment 6. The method of any of embodiments 1-5 wherein the administering results in amelioration of at least one symptom of ALS.

Embodiment 7. The method of any of embodiments 1-6 wherein the oligomeric compound is administered prior to the detection of the at least one symptom.

Embodiment 8. The method of embodiment 6 or 7, wherein the at least one symptom of ALS is loss of motor function, reduced CMAP amplitude, denervation, and loss of motor neurons.

Embodiment 9. The method of any of embodiments 6-8, wherein the amelioration is the slowing of progression of at least one symptom.

Embodiment 10. The method of any of embodiments 6-9, wherein the amelioration is the delay of onset of at least one symptom.

Embodiment 11. The method of any of embodiments 6-10, wherein the amelioration is the reduction of severity of at least one symptom.

Embodiment 12. The method of any of embodiments 6-11, wherein the amelioration is the reduction of frequency of at least one symptom.

Embodiment 13. The method of any of embodiments 1-12, wherein expression of Ataxin-2 mRNA is reduced in the animal.

Embodiment 14. The method of any of embodiments 1-13, wherein the amount of Ataxin-2 protein is reduced in the animal.

Embodiment 15. The method of any of embodiments 1-14, wherein the animal is a human.

Embodiment 16. The method of any of embodiments 1-15, wherein the nucleobase sequence of Ataxin-2 nucleic acid is SEQ ID NO: 3, the complement of SEQ ID NO: 4, or SEQ ID NO: 5.

Embodiment 17. The method of any of embodiments 1-16, wherein the oligomeric compound is single-stranded.

Embodiment 18. The method of any of embodiment 1-17, wherein the modified oligonucleotide comprises at least one modified nucleoside.

Embodiment 19. The method of embodiment 18, wherein the modified oligonucleotide comprises at least one modified nucleoside comprising a modified sugar moiety.

Embodiment 20. The method of embodiment 19, wherein the modified oligonucleotide comprises at least one modified nucleoside comprising a bicyclic sugar moiety.

Embodiment 21. The method of embodiment 20, wherein the modified oligonucleotide comprises at least one modified nucleoside comprising a bicyclic sugar moiety having a 2'-4' bridge, wherein the 2-4' bridge is selected from —O—$CH_2$—; —O—$CH_2$—$CH_2$; and —O—$CH(CH_3)$—.

Embodiment 22. The method of any of embodiments 18-21, wherein the modified oligonucleotide comprises at least one modified nucleoside comprising a modified non-bicyclic sugar moiety.

Embodiment 23. The method of embodiment 22, wherein the modified oligonucleotide comprises at least one modified nucleoside comprising a non-bicyclic sugar moiety comprising a 2'-MOE or 2'-OMe.

Embodiment 24. The method of any of embodiments 18-23, wherein the modified oligonucleotide comprises at least one modified nucleoside comprising a sugar surrogate.

Embodiment 25. The method of any of embodiments 1-24, wherein the modified oligonucleotide comprises at least one modified nucleoside comprising a sugar surrogate selected from a morpholino, a PNA, a F-HNA, a THP, or a modified THP.

Embodiment 26. The method of any of embodiments 1-25, wherein the modified oligonucleotide has a sugar motif comprising:

a 5'-region consisting of 1-5 linked 5'-nucleosides;

a central region consisting of 6-10 linked central region nucleosides; and a 3'-region consisting of 1-5 linked 3'-region nucleosides; wherein each of the 5'-region nucleosides and each of the 3'-region nucleosides comprises a modified sugar moiety and each of the central region nucleosides comprises an unmodified DNA sugar moiety.

Embodiment 27. The method of any of embodiments 1-26, wherein the modified oligonucleotide comprises at least one modified internucleoside linkage.

Embodiment 28. The method of embodiment 27, wherein each internucleoside linkage of the modified oligonucleotide is a modified internucleoside linkage.

Embodiment 29. The method of embodiment 27 or 28, wherein at least one internucleoside linkage is a phosphorothioate internucleoside linkage.

Embodiment 30. The method of embodiment 27 or 29, wherein the modified oligonucleotide comprises at least one unmodified phosphodiester internucleoside linkage.

Embodiment 31. The method of embodiment 27, wherein each internucleoside linkage is either an unmodified phosphodiester internucleoside linkage or a phosphorothioate internucleoside linkage.

Embodiment 32. The method of any of embodiment 28, wherein each internucleoside linkage is a phosphorothioate internucleoside linkage.

Embodiment 33. The method of any of embodiments 1-32, wherein the modified oligonucleotide comprises at least one modified nucleobase.

Embodiment 34. The method of embodiment 33, wherein the modified nucleobase is a 5-methylcytosine.

Embodiment 35. The method of any of embodiments 1-34, wherein each nucleobase of each nucleoside of the modified oligonucleotide is either an unmodified nucleobase or is a 5-methylcytosine. Embodiment 36. The method of any of embodiments 1-35 wherein the oligomeric compound comprises a conjugate group.

Embodiment 37. The method of any of embodiments 1-16 or 18-36, wherein the oligomeric compound is paired with a second oligomeric compound to form a duplex.

I. Certain Oligonucleotides

In certain embodiments, the provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, $NH_2$, $N_3$, $OCF_3$, $OCH_3$, $O(CH_2)3NH_2$, $CH_2CH{=}CH_2$, $OCH_2CH{=}CH_2$, $OCH_2CH_2OCH_3$, $O(CH_2)_2$ $SCH_3$, $O(CH_2)_2ON(R_m)(R_{11})$, $O(CH_2)_2O(CH_2)_2N(CH_3)_2$, and N-substituted acetamide ($OCH_2C({=}O)$—$N(R_m)(R_n)$), where each $R_m$ and $R_{11}$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C({=}O)$—$N(H)CH_3$ ("NMA").

In certain embodiments, a 2'-substituted nucleoside or 2'-non-bicyclic modified nucleoside comprises a sugar moiety comprising a non-bridging 2'-substituent group selected from: F, $OCH_3$, and $OCH_2CH_2OCH_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'—$(CH_2)_2$-2', 4'—$(CH_2)_3$-2', 4'—$CH_2$—O-2' ("LNA"), 4'-$CH_2$—S-2', 4'—$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'—$CH_2$—N(R)-2', 4'—$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J. Org. Chem.,* 2009, 74, 118-134), 4'-$CH_2$—$C({=}CH_2)$-2' and analogs thereof (see e.g., Seth et al., U.S. Pat. No. 8,278,426), 4'-$C(R_aR_b)$—N(R)—O-2', 4'—$C(R_aR_b)$—O—N(R)-2', 4'—$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a){=}C(R_b)$—, —$C(R_a){=}N$—, —$C({=}NR_a)$—, —C(=O)—, —C(=S)—, —O—, —$Si(R_a)_2$—, —$S({=}O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S({=}O)_2$-$J_1$), or sulfoxyl ($S({=}O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

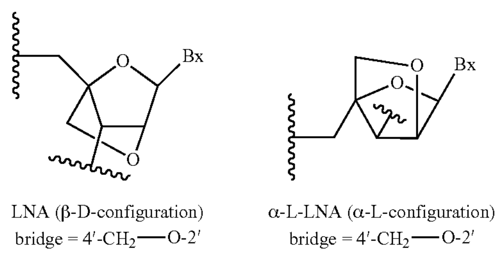

α-L-methyleneoxy (4'-$CH_2$—O-2') or α-L-LNA bicyclic nucleosides have been incorporated into antisense oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

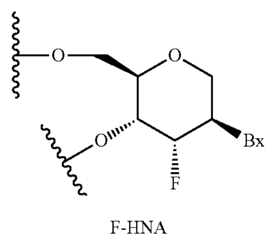

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

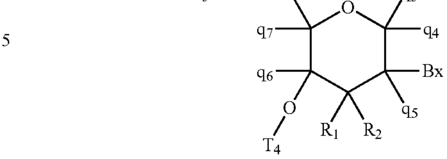

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(═X)$J_1$, OC(═X)$NJ_1J_2$, $NJ_3$C(═X)$NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

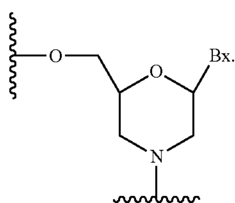

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C{\equiv}C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et at, *Angewandte Chemie, International Edition,* 1991, 30, 613; Sanghvi, Y. S., Chapter 15*, Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino ($—CH_2—N(CH_3)—O—CH_2—$), thiodiester, thionocarbamate ($—O—C(=O)(NH)—S—$); siloxane ($—O—SiH_2—O—$); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI ($3'-CH_2—N(CH_3)—O-5'$), amide-3 ($3'-CH_2—C(=O)—N(H)-5'$), amide-4 ($3'-CH_2—N(H)—C(=O)-5'$), formacetal ($3'-O—CH_2—O-5'$), methoxypropyl, and thioformacetal ($3'-S—CH_2—O-5'$). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleoside comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Lengths

It is possible to increase or decrease the length of an oligonuclotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that $X \leq Y$.

For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

D. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugage Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugage Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Duplexed Oligomeric Compounds

In certain embodiments, oligomeric compounds described herein comprise an oliognucleotide, having a nucleobase sequence complementary to that of a target nucleic acid. Oligomeric compounds are single-strands and in certain embodiments, oligomeric compounds are single stranded. In certain embodiments, a single-stranded oligomeric compound comprises or consists of a modified oligonucleotide and optionally a conjugate group. In certain embodiments, an oligomeric compound is paired with a second oligomeric compound to form a duplex. Such duplexed oligomeric compounds comprise a first oligomeric compound having a region complementary to a target nucleic acid and a second oligomeric compound having a region complementary to the first oligomeric compound. In certain embodiments, the first oligomeric compound of a duplexed oligomeric compound comprises or consists of (1) a modified or unmodified oligonucleotide and optionally a conjugate group and (2) a second modified or unmodified oligonucleotide and optionally a conjugate group. Either or both oligomeric compounds of a duplexed oligomeric compound may comprise a conjugate group. The oligonucleotides of duplexed oligomeric compounds may include non-complementary overhanging nucleosides.

IV. Antisense Activity

In certain embodiments, oligomeric compounds are capable of hybridizing to a target nucleic acid, resulting in at least one antisense activity. In certain embodiments, oligomeric compounds selectively affect one or more target nucleic acid. Such selective oligomeric compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an oligomeric compound to a target nucleic acid results in recruitment of a protein that cleaves the target nucleic acid. For example, certain oligomeric compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are oligomeric compounds that are sufficiently "DNA-like" to elicit RNase H activity. In certain embodiments, one or more non-DNA-like nucleoside in the gap of a gapmer is tolerated.

In certain antisense activities, an oligomeric compound or a portion of an oligomeric compound is loaded into an RNA-induced silencing complex (RISC), ultimately resulting in cleavage of the target nucleic acid. For example, certain oligomeric compounds result in cleavage of the target nucleic acid by Argonaute. Oligomeric compounds that are loaded into RISC are RNAi compounds. RNAi compounds may be double-stranded (siRNA) or single-stranded (ssRNA).

In certain embodiments, hybridization of an oligomeric compound to a target nucleic acid does not result in recruitment of a protein that cleaves that target nucleic acid. In certain embodiments, hybridization of the oligomeric compound to the target nucleic acid results in alteration of splicing of the target nucleic acid. In certain embodiments, hybridization of an oligomeric compound to a target nucleic acid results in inhibition of a binding interaction between the target nucleic acid and a protein or other nucleic acid. In certain embodiments, hybridization of an oligomeric compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, oligonucleotides described herein are complementary to a target nucleic acid comprising a single-nucleotide polymorphism (SNP). In certain such embodiments, the oligonucleotide is capable of modulating expression of one allele of the SNP-containing target nucleic acid to a greater or lesser extent than it modulates another allele. In certain embodiments, an oligonucleotide hybridizes to a (SNP)-containing target nucleic acid at the single-nucleotide polymorphism site.

In certain embodiments, oligonucleotides are at least partially complementary to more than one target nucleic acid. For example, oliognucleotides described herein may mimic microRNAs, which typically bind to multiple targets.

A. Complementarity/Mismatches to the Target Nucleic Acid

It is possible to incroduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. Ataxin-2

In certain embodiments, oligomeric compounds comprise or consist of any oligonucleotide comprising a region that is complementary to a target nucleic acid, wherein the target nucleic acid is Ataxin-2. In certain embodiments, Ataxin-2 nucleic acid has the sequence set forth in GENBANK Accession No. NM_002973.3 (incorporated herein as SEQ ID NO: 3), the complement of GENBANK Accession No. NT_009775.17 truncated from nucleotides 2465000 to U.S. Pat. No. 2,616,000 (incorporated herein as SEQ ID NO: 4) and GENBANK Accession No. BX410018.2 (incorporated herein as SEQ ID NO: 5).

In certain embodiments, contacting a cell with an oligonucleotide complementary to SEQ ID NO: 3, the complement of SEQ ID NO: 4, or SEQ ID NO: 5 reduces expression of Ataxin-2 mRNA. In certain embodiments, contacting a cell with an oligomeric compound complementary to SEQ ID NO: 3, the complement of SEQ ID NO: 4, or SEQ ID NO: 5 ameliroates one or more symptoms of ALS. In certain embodiments, the symptom is loss of motor function, reduced CMAP amplitude, denervation, and loss of motor neurons.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in CNS tissue, including brain tissue, such as cortex, cerebellum, and pons.

VI. Certain Pharmaceutical Compositions

In certain embodiments, described herein are pharmaceutical compositions comprising one or more oligomeric compound or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS.

In certain embodiments, pharmaceutical compositions comprise one or more or oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: In Vitro Inhibition of Ataxin-2

Modified oligonucleotides that are 100% complementary to a mouse Ataxin-2 transcript were tested for their effects on mouse Ataxin-2 mRNA expression in vitro. The modified oligonucleotides listed in Table 1 target mouse Ataxin-2 pre-mRNA, designated herein as SEQ ID NO: 1 (GENBANK Accession No. NT_078458.6 truncated from nucleotides 8174000 to 8280000) and/or mouse Ataxin-2 mRNA, designated herein as SEQ ID NO: 2 (GENBANK Accession No. NM_009125.2). "Start site" indicates the 5'-most nucleoside of the indicated target sequence to which each oligonucleotide is complementary. "Stop site" indicates the 3'-most nucleoside of the indicated target sequence to which each oligonucleotide is complementary. The modified oligonucleotides listed in Table 1 were tested at various doses in bEND cells and primary mouse cortical neurons. bEND cells and neurons were electroporated or incubated, respectively, with 5 different concentrations of each modified oligonucleotide, ranging from 0.25 to 20 μM. After 24 hours for the bEND cells and after 96 hours for the neurons, RNA was isolated from the bEND cells. After an additional 72 hours, RNA was isolated from the neurons. Ataxin-2 mRNA levels were measured by quantitative real-time PCR. Mouse Ataxin-2 primer/probe set RTS3642 was used to measure mRNA levels. The primer/probe sequences are: forward primer: 5'-ACCAAAGAGTAGTTAATGGAGGTGTTC-3' (SEQ ID NO: 11); reverse primer: 5'-AGAAGGTGGGCGAGAGGAA-3' (SEQ ID NO: 12; and probe: 5'-CTGGCCATCGCCTTGCCCA-3' (SEQ ID NO: 13). Ataxin-2 mRNA levels were normalized to total RNA as measured using Ribogreen. Results are presented as percent the half maximal inhibitory concentration ($IC_{50}$) for each oligonucleotide. The oligonucleotides in Table 1 inhibited Ataxin-2 in both cell types in a dose responsive manner.

TABLE 1

$IC_{50}$ values of modified oligonucleotides complementary to mouse Ataxin-2

| Isis No. | Sequence | SEQ ID NO: 1 Start site | SEQ ID NO: 1 Stop site | SEQ ID NO: 2 Start site | SEQ ID NO: 2 Stop site | b.END cells IC50 (μM) | neurons IC50 (μM) | SEQ ID NO. |
|---|---|---|---|---|---|---|---|---|
| 708135 | $^{m}C_{es}\ G_{eo}\ T_{eo}\ T_{eo}\ T_{eo}\ G_{ds}\ ^{m}C_{ds}\ A_{ds}\ T_{ds}\ A_{ds}\ G_{ds}\ A_{ds}\ T_{ds}\ T_{ds}\ ^{m}C_{ds}\ ^{m}C_{eo}\ A_{eo}\ T_{es}\ ^{m}C_{es}\ A_{e}$ | 37434 | 37453 | 714 | 733 | 7.9 | 1.4 | 14 |
| 708137 | $^{m}C_{es}\ T_{eo}\ T_{eo}\ ^{m}C_{eo}\ A_{eo}\ ^{m}C_{ds}\ A_{ds}\ T_{ds}\ T_{ds}\ T_{ds}\ ^{m}C_{ds}\ G_{ds}\ A_{ds}\ T_{ds}\ ^{m}C_{ds}\ ^{m}C_{eo}\ A_{eo}\ A_{es}\ ^{m}C_{es}\ A_{e}$ | n/a | n/a | 762 | 781 | 2.8 | 1.7 | 15 |
| 708140 | $T_{es}\ ^{m}C_{eo}\ A_{eo}\ T_{eo}\ A_{eo}\ T_{ds}\ A_{ds}\ T_{ds}\ G_{ds}\ ^{m}C_{ds}\ ^{m}C_{ds}\ T_{ds}\ ^{m}C_{ds}\ ^{m}C_{ds}\ G_{ds}\ T_{eo}\ T_{eo}\ T_{es}\ T_{es}\ T_{e}$ | 37965 | 37984 | 790 | 809 | 6.9 | 1.2 | 16 |
| 708188 | $G_{es}\ T_{eo}\ G_{eo}\ G_{eo}\ A_{eo}\ ^{m}C_{ds}\ A_{ds}\ ^{m}C_{ds}\ ^{m}C_{ds}\ A_{ds}\ ^{m}C_{ds}\ A_{ds}\ ^{m}C_{ds}\ ^{m}C_{ds}\ A_{ds}\ T_{eo}\ A_{eo}\ A_{es}\ T_{es}\ T_{e}$ | 67431 | 67450 | 1156 | 1175 | 8.4 | 6.6 | 17 |
| 708205 | $^{m}C_{es}\ T_{eo}\ G_{eo}\ G_{eo}\ A_{eo}\ T_{ds}\ T_{ds}\ ^{m}C_{ds}\ A_{ds}\ A_{ds}\ T_{ds}\ T_{ds}\ T_{ds}\ ^{m}C_{ds}\ T_{ds}\ T_{eo}\ ^{m}C_{eo}\ T_{es}\ G_{es}\ ^{m}C_{e}$ | 67988 | 68007 | 1267 | 1286 | 7 | 3.9 | 18 |
| 708206 | $T_{es}\ G_{eo}\ T_{eo}\ A_{eo}\ ^{m}C_{eo}\ T_{ds}\ G_{ds}\ A_{ds}\ G_{ds}\ ^{m}C_{ds}\ A_{ds}\ ^{m}C_{ds}\ T_{ds}\ G_{ds}\ G_{ds}\ A_{eo}\ T_{eo}\ T_{es}\ ^{m}C_{es}\ A_{e}$ | 67999 | 68018 | 1278 | 1297 | 3.3 | 1.5 | 19 |
| 708212 | $G_{es}\ T_{eo}\ ^{m}C_{eo}\ A_{eo}\ T_{eo}\ ^{m}C_{ds}\ A_{ds}\ T_{ds}\ T_{ds}\ ^{m}C_{ds}\ T_{ds}\ ^{m}C_{ds}\ A_{ds}\ A_{ds}\ G_{ds}\ G_{eo}\ G_{eo}\ ^{m}C_{es}\ G_{es}\ A_{e}$ | 68028 | 68047 | 1307 | 1326 | 3.4 | 1.3 | 20 |
| 708213 | $G_{es}\ G_{eo}\ T_{eo}\ ^{m}C_{eo}\ A_{eo}\ T_{ds}\ ^{m}C_{ds}\ A_{ds}\ T_{ds}\ T_{ds}\ ^{m}C_{ds}\ T_{ds}\ ^{m}C_{ds}\ A_{ds}\ A_{ds}\ G_{eo}\ G_{eo}\ G_{es}\ ^{m}C_{es}\ G_{e}$ | 68029 | 68048 | 1308 | 1327 | 10.3 | 0.8 | 21 |
| 708217 | $T_{es}\ T_{eo}\ ^{m}C_{eo}\ T_{eo}\ T_{eo}\ ^{m}C_{ds}\ ^{m}C_{ds}\ T_{ds}\ ^{m}C_{ds}\ A_{ds}\ ^{m}C_{ds}\ T_{ds}\ ^{m}C_{ds}\ ^{m}C_{ds}\ G_{ds}\ G_{eo}\ T_{eo}\ ^{m}C_{es}\ A_{es}\ T_{e}$ | 68043 | 68062 | 1322 | 1341 | 4.4 | 7.5 | 22 |
| 708299 | $G_{es}\ G_{eo}\ T_{eo}\ G_{eo}\ A_{eo}\ T_{ds}\ G_{ds}\ T_{ds}\ T_{ds}\ T_{ds}\ ^{m}C_{ds}\ A_{ds}\ ^{m}C_{ds}\ T_{ds}\ T_{ds}\ G_{eo}\ ^{m}C_{eo}\ T_{es}\ T_{es}\ T_{e}$ | 75837 | 75856 | 2233 | 2252 | 4.2 | 3.4 | 23 |
| 708307 | $G_{es}\ T_{eo}\ ^{m}C_{eo}\ A_{eo}\ T_{eo}\ ^{m}C_{ds}\ A_{ds}\ A_{ds}\ T_{ds}\ ^{m}C_{ds}\ T_{ds}\ G_{ds}\ T_{ds}\ T_{ds}\ T_{ds}\ T_{eo}\ ^{m}C_{eo}\ T_{es}\ G_{es}\ T_{e}$ | 76374 | 76393 | 2303 | 2322 | 3.6 | 3.4 | 24 |
| 708318 | $G_{es}\ T_{eo}\ G_{eo}\ A_{eo}\ ^{m}C_{eo}\ T_{ds}\ T_{ds}\ T_{ds}\ T_{ds}\ ^{m}C_{ds}\ T_{ds}\ ^{m}C_{ds}\ ^{m}C_{ds}\ T_{ds}\ T_{ds}\ ^{m}C_{eo}\ T_{eo}\ ^{m}C_{es}\ T_{es}\ A_{e}$ | 85004 | 85023 | 2400 | 2419 | 3.5 | 1.3 | 25 |
| 708320 | $G_{es}\ ^{m}C_{eo}\ T_{eo}\ T_{eo}\ ^{m}C_{eo}\ ^{m}C_{ds}\ G_{ds}\ T_{ds}\ T_{ds}\ T_{ds}\ A_{ds}\ T_{ds}\ ^{m}C_{ds}\ T_{ds}\ T_{eo}\ T_{eo}\ A_{es}\ A_{es}\ T_{e}$ | 85032 | 85051 | 2428 | 2447 | 6.3 | 3.5 | 26 |
| 708321 | $A_{es}\ G_{eo}\ ^{m}C_{eo}\ A_{eo}\ ^{m}C_{eo}\ T_{ds}\ T_{ds}\ G_{ds}\ ^{m}C_{ds}\ T_{ds}\ T_{ds}\ ^{m}C_{ds}\ ^{m}C_{ds}\ G_{ds}\ T_{ds}\ T_{eo}\ T_{eo}\ T_{es}\ A_{es}\ T_{e}$ | 85039 | 85058 | 2435 | 2454 | 9.6 | 5.7 | 27 |

TABLE 1-continued

| IC$_{50}$ values of modified oligonucleotides complementary to mouse Ataxin-2 | | | | | | | | |
|---|---|---|---|---|---|---|---|---|
| | | SEQ ID NO: 1 | | SEQ ID NO: 2 | | b.END cells | neurons | SEQ |
| Isis No. | Sequence | Start site | Stop site | Start site | Stop site | IC50 (μM) | IC50 (μM) | ID NO. |
| 708325 | $T_{es}\ G_{eo}\ {}^{m}C_{eo}\ T_{eo}\ G_{eo}\ {}^{m}C_{ds}\ T_{ds}\ G_{ds}\ {}^{m}C_{ds}\ T_{ds}\ G_{ds}\ T_{ds}\ {}^{m}C_{ds}\ A_{ds}\ A_{ds}\ T_{eo}\ G_{eo}\ A_{es}\ A_{es}\ A_{e}$ | 85067 | 85086 | 2463 | 2482 | 7.3 | 1.7 | 28 |
| 708343 | $A_{es}\ A_{eo}\ T_{eo}\ G_{eo}\ T_{eo}\ {}^{m}C_{ds}\ G_{ds}\ A_{ds}\ T_{ds}\ T_{ds}\ T_{ds}\ {}^{m}C_{ds}\ {}^{m}C_{ds}\ T_{ds}\ A_{ds}\ A_{eo}\ {}^{m}C_{eo}\ {}^{m}C_{es}\ T_{es}\ G_{e}$ | 86390 | 86409 | 2662 | 2681 | 3.7 | 2.9 | 29 |
| 708378 | $G_{es}\ A_{eo}\ {}^{m}C_{eo}\ {}^{m}C_{eo}\ A_{eo}\ A_{ds}\ A_{ds}\ G_{ds}\ G_{ds}\ {}^{m}C_{ds}\ T_{ds}\ G_{ds}\ A_{ds}\ T_{ds}\ T_{ds}\ G_{eo}\ G_{eo}\ G_{es}\ A_{es}\ A_{e}$ | 92235 | 92254 | 3083 | 3102 | 6.2 | 2.8 | 30 |
| 708379 | $G_{es}\ G_{eo}\ A_{eo}\ {}^{m}C_{eo}\ {}^{m}C_{eo}\ A_{ds}\ A_{ds}\ A_{ds}\ G_{ds}\ G_{ds}\ {}^{m}C_{ds}\ T_{ds}\ G_{ds}\ A_{ds}\ T_{ds}\ T_{eo}\ G_{eo}\ G_{es}\ G_{es}\ A_{e}$ | 92236 | 92255 | 3084 | 3103 | 5.5 | 2.3 | 31 |
| 708386 | ${}^{m}C_{es}\ A_{eo}\ G_{eo}\ G_{eo}\ A_{eo}\ {}^{m}C_{ds}\ T_{ds}\ G_{ds}\ T_{ds}\ A_{ds}\ {}^{m}C_{ds}\ A_{ds}\ {}^{m}C_{ds}\ A_{ds}\ T_{ds}\ G_{eo}\ A_{eo}\ G_{es}\ G_{es}\ A_{e}$ | 92966 | 92985 | 3132 | 3151 | 4.7 | 1.1 | 32 |
| 708393 | ${}^{m}C_{es}\ A_{eo}\ {}^{m}C_{eo}\ T_{eo}\ A_{eo}\ A_{ds}\ A_{ds}\ {}^{m}C_{ds}\ {}^{m}C_{ds}\ A_{ds}\ G_{ds}\ G_{ds}\ {}^{m}C_{ds}\ T_{ds}\ G_{ds}\ A_{eo}\ G_{eo}\ {}^{m}C_{es}\ A_{es}\ T_{e}$ | 93025 | 93044 | 3191 | 3210 | 7.2 | 2.9 | 33 |
| 708458 | ${}^{m}C_{es}\ T_{eo}\ G_{eo}\ T_{eo}\ T_{eo}\ A_{ds}\ G_{ds}\ {}^{m}C_{ds}\ A_{ds}\ T_{ds}\ T_{ds}\ {}^{m}C_{ds}\ {}^{m}C_{ds}\ T_{ds}\ A_{ds}\ T_{eo}\ {}^{m}C_{eo}\ A_{es}\ G_{es}\ A_{e}$ | 104505 | 104524 | 4011 | 4030 | 5.5 | 3.9 | 34 |
| 708461 | $G_{es}\ T_{eo}\ {}^{m}C_{eo}\ {}^{m}C_{eo}\ A_{eo}\ A_{ds}\ A_{ds}\ A_{ds}\ {}^{m}C_{ds}\ A_{ds}\ T_{ds}\ {}^{m}C_{ds}\ {}^{m}C_{ds}\ T_{ds}\ {}^{m}C_{ds}\ {}^{m}C_{eo}\ A_{eo}\ {}^{m}C_{es}\ T_{es}\ G_{e}$ | 104533 | 104552 | 4039 | 4058 | 5.2 | 2.1 | 35 |
| 708462 | $T_{es}\ G_{eo}\ {}^{m}C_{eo}\ {}^{m}C_{eo}\ T_{eo}\ {}^{m}C_{ds}\ T_{ds}\ A_{ds}\ {}^{m}C_{ds}\ T_{ds}\ {}^{m}C_{ds}\ G_{ds}\ G_{ds}\ T_{ds}\ {}^{m}C_{ds}\ {}^{m}C_{eo}\ A_{eo}\ A_{es}\ A_{es}\ A_{e}$ | 104545 | 104564 | 4051 | 4070 | 3.1 | 0.5 | 36 |
| 708463 | ${}^{m}C_{es}\ {}^{m}C_{eo}\ {}^{m}C_{eo}\ T_{eo}\ A_{eo}\ {}^{m}C_{ds}\ A_{ds}\ T_{ds}\ G_{ds}\ {}^{m}C_{ds}\ {}^{m}C_{ds}\ T_{ds}\ {}^{m}C_{ds}\ T_{ds}\ A_{ds}\ {}^{m}C_{eo}\ T_{eo}\ {}^{m}C_{es}\ G_{es}\ G_{e}$ | 104552 | 104571 | 4058 | 4077 | 7.3 | 4.5 | 37 |
| 708468 | $A_{es}$ Go ${}^{m}C_{eo}\ {}^{m}C_{eo}\ A_{eo}\ {}^{m}C_{ds}\ A_{ds}\ A_{ds}\ G_{ds}\ T_{ds}\ {}^{m}C_{ds}\ {}^{m}C_{ds}\ {}^{m}C_{ds}\ T_{ds}\ A_{ds}\ {}^{m}C_{eo}\ A_{eo}\ T_{es}\ G_{es}$ m$C_{e}$ | 104562 | 104581 | 4068 | 4087 | 1.7 | 2.6 | 38 |
| 708481 | $G_{es}\ T_{eo}\ T_{eo}\ {}^{m}C_{eo}\ A_{eo}\ T_{ds}\ G_{ds}\ A_{ds}\ {}^{m}C_{ds}\ T_{ds}\ {}^{m}C_{ds}\ T_{ds}\ {}^{m}C_{ds}\ A_{ds}\ A_{ds}\ G_{eo}\ G_{eo}\ G_{es}\ {}^{m}C_{es}\ {}^{m}C_{e}$ | 104665 | 104684 | 4171 | 4190 | 6.2 | 1.3 | 39 |
| 708491 | $A_{es}\ {}^{m}C_{eo}\ T_{eo}\ T_{eo}\ {}^{m}C_{eo}\ T_{ds}\ G_{ds}\ T_{ds}\ {}^{m}C_{ds}\ A_{ds}\ A_{ds}$ Gas $T_{ds}\ T_{ds}\ T_{ds}\ A_{eo}\ G_{eo}\ T_{es}\ A_{es}\ A_{e}$ | 104771 | 104790 | 4277 | 4296 | 12.8 | 7 | 40 |
| 708503 | $A_{es}\ G_{eo}\ T_{eo}\ T_{eo}\ T_{eo}\ T_{ds}\ {}^{m}C_{ds}\ {}^{m}C_{ds}\ {}^{m}C_{ds}\ T_{ds}\ T_{ds}\ A_{ds}\ A_{ds}\ {}^{m}C_{ds}\ T_{ds}\ T_{eo}\ A_{eo}\ A_{es}\ A_{es}\ A_{e}$ | 104875 | 104894 | 4381 | 4400 | 7.7 | 2.2 | 41 |
| 708511 | $G_{es}\ A_{eo}\ {}^{m}C_{eo}\ A_{eo}\ A_{eo}\ A_{ds}\ A_{ds}\ T_{ds}\ G_{ds}\ A_{ds}\ G_{ds}\ {}^{m}C_{ds}\ {}^{m}C_{ds}\ A_{ds}\ G_{ds}\ T_{eo}\ T_{eo}\ T_{es}\ T_{es}\ A_{e}$ | 8800 | 8819 | n/a | n/a | 5.8 | 5.1 | 42 |
| 708512 | $A_{es}\ A_{eo}\ T_{eo}\ {}^{m}C_{eo}\ T_{eo}\ G_{ds}\ T_{ds}\ G_{ds}\ T_{ds}\ T_{ds}\ T_{ds}\ T_{ds}\ {}^{m}C_{ds}\ {}^{m}C_{ds}\ {}^{m}C_{ds}\ T_{eo}\ T_{eo}\ T_{es}\ {}^{m}C_{es}\ G_{e}$ | 11550 | 11569 | n/a | n/a | 6.3 | 2.8 | 43 |
| 708522 | $T_{es}\ A_{eo}\ G_{eo}\ {}^{m}C_{eo}\ A_{eo}\ {}^{m}C_{ds}\ {}^{m}C_{ds}\ A_{ds}\ G_{ds}\ G_{ds}\ T_{ds}\ A_{ds}\ T_{ds}\ G_{ds}\ {}^{m}C_{ds}\ {}^{m}C_{eo}\ {}^{m}C_{eo}\ A_{es}\ T_{es}\ G_{e}$ | 39657 | 39676 | n/a | n/a | 4.4 | 1.4 | 44 |
| 708540 | ${}^{m}C_{es}\ A_{eo}\ T_{eo}\ G_{eo}\ G_{eo}\ T_{ds}\ T_{ds}\ A_{ds}\ T_{ds}\ {}^{m}C_{ds}\ T_{ds}\ A_{ds}\ T_{ds}\ G_{ds}\ G_{ds}\ {}^{m}C_{eo}\ A_{eo}\ G_{es}\ {}^{m}C_{es}\ A_{e}$ | 89861 | 89880 | n/a | n/a | 5.3 | 3.8 | 45 |

Subscripts: "e" indicates a 2'-MOE modified nucleoside, "d" a 2'-deoxynucleoside, "o" indicates a phosphate intemucleoside linkage, and "s" indicates a phosphorothioate intemucleoside linkage.
Superscript "m" preceding a "C" indicates a 5-methylcytosine.

Example 2: In Vivo Reduction of Ataxin-2 mRNA in Mice

Select oligonucleotides described in Table 1 above were tested for antisense activity in vivo. Female C57Bl/6 mice each received a single intracerebroventricular bolus (ICVB) injection of 500 ug of one of the oligonucleotides listed in the table below or PBS vehicle alone. Each treatment group consisted of 3 or 4 animals. Two weeks later, the animals were sacrificed, and RNA was isolated from the cortex, cerebellum, and spinal cord. Ataxin-2 mRNA levels were measured by RT-qPCR, as described in Example 1, and the resulting values were normalized to GAPDH levels. The average inhibition of Ataxin-2 mRNA levels for each treatment group, relative to the PBS treated group, are shown in the table below. The results show that the oligonucleotides in the table below inhibited Ataxin-2 mRNA levels in the cortex, cerebellum, and the spinal cord.

TABLE 2

| Inhibition of Ataxin-2 in wild type mice | | | |
|---|---|---|---|
| | Inhibition of Ataxin-2 mRNA (%) | | |
| Isis No. | Cortex | Cerebellum | Spinal Cord |
| 708137 | 63 | 60 | 76 |
| 708140 | 57 | 57 | 70 |
| 708206 | 45 | 50 | 77 |
| 708212 | 31 | 27 | 56 |
| 708213 | 49 | 33 | 69 |
| 708318 | 91 | 75 | 89 |
| 708386 | 39 | 29 | 62 |
| 708462 | 78 | 66 | 81 |
| 708468 | 52 | 27 | 64 |
| 708481 | 71 | 67 | 82 |
| 708522 | 50 | 48 | 62 |

Example 3: Effect of Ataxin-2 Modified Oligonucleotides on CMAP in an ALS Model, SOD1G$^{93A}$ Mice Isis No. 708137 (see Table 1 above) was tested for its effects on compound muscle action potential (CMAP) in SOD1$^{G93A}$ mutant mice. SOD1$^{G93A}$ mutant mice express the human G93A SOD1 variant and early denervation (or loss of motor units) was reported in the fast-twitch muscles of the SOD1$^{G93A}$ mutant mice (Frey et al., 2000; Pun et al., 2006). In order to test the effect of Isis No. 708137 on the motor units of the fast-twitch muscle tibialis anterior (TA), CMAP was measured, which is a functional measurement of motor units represented by the summation of all action potentials in a given area of the muscle upon stimulation of the sciatic nerve. Baseline CMAP measurements were performed on both the left and right TA muscles on five week old wild type and SOD1$^{G93A}$ mutant mice one day before each mouse received an ICVB injection of 500 μg of Isis No. 708137 or of vehicle alone. Each treatment group consisted of 11 or 12 animals. CMAP measurements were also performed at 7, 9, and 10 weeks of age (2, 4, and 5 weeks following oligonucleotide treatment). Each CMAP measurement was performed by stimulating the sciatic nerve percutaneously by single pulses of 0.1 ms duration (VikingQuest NCS/EMG Portable EMG machine) delivered through a pair of needle electrodes placed at the sciatic notch. The CMAP was recorded with the recording electrode placed subdermally on the muscle belly of the TA muscle. A reference electrode was placed near the ankle and ground electrode at the midline. Disposable monopolar needle electrodes (25 mm, 28G; catalog #902-DMF25-TP, Natus Medical Inc., San Carlos, CA) were used for both stimulating and recording. The CMAP trace used for analysis from a given animal or leg was obtained from 4 stimuli. The CMAP value of an individual animal at a given time point represents the averaged peak-to-peak amplitude of both left and right legs. The results shown in the table below are the average CMAP values of all animals in each treatment group. Data were analyzed with two-way ANOVA. The results in the table below show that treatment with an oligonucleotide targeting Ataxin-2 partially rescued motor function in SOD1$^{G93A}$ mutant mice. The differences between the treated and untreated SOD1$^{G93A}$ mutant mice were determined to be significant at 7, 9, and 10 weeks of age.

TABLE 3

| CMAP in SOD1$^{G93A}$ mice | | | |
|---|---|---|---|
| Mice | Treatment | Age (weeks) | CMAP (mV) |
| WT | Vehicle | 5 | 84 |
| | | 7 | 89 |
| | | 9 | 86 |
| | | 10 | 84 |
| SOD1$^{G93A}$ | Vehicle | 5 | 83 |
| | | 7 | 73 |
| | | 9 | 49 |
| | | 10 | 43 |
| | Isis No. 708137 | 5 | 84 |
| | | 7 | 83 |
| | | 9 | 65 |
| | | 10 | 52 |

Example 4. Effect of Ataxin-2 Modified Oligonucleotides on Denervation in an ALS Model, SOD1G93A Mice Histological analysis of neuromuscular junctions was performed on anterior tibialis muscles of SOD1$^{G93A}$ mice treated with Isis No. 708137 or vehicle at 9 weeks of age as described in Example 3 above.

Anterior tibialis muscles were dropped-fixed in 10% neutral formalin at room temperate for 1 hour and subsequently transferred to PBS at 4° C. overnight to remove fixatives. Tissues were then cryoprotected by immersing in 30% sucrose in PBS at 4° C. overnight prior to embedding in Tissue Tek OCT compound for cryosectioning. Twenty-am thick sections were stained for neuromuscular junctions (NMJs) with rabbit anti-vesicular acetylcholine transporter (VAChT) antibody (1:200; synaptic system) followed by Alexa Fluor 594-conjugated α-bungarotoxin (Invitrogen) for acetylcholine receptors (AChRs). NMJs were visualized and imaged with confocal microscope (Olympus). Fully innervated NMJs were defined by complete overlap of presynaptic (i.e., VAChT) and postsynaptic endplate (i.e., AChR) labeling. Partially innervated NMJs were the postsynaptic endplates with partial occupancy of presynaptic terminals. Denervated NMJs were endplates devoid of presynaptic labeling. For each sample, 50-100 NMJs were examined and the proportions of each NMJ category were quantified. Data was the average of 4 samples from each treatment group. The results in the table below show that treatment with an oligonucleotide complementary to Ataxin-2 partially ameliorated denervation in SOD1$^{G93A}$ mutant mice.

TABLE 4

| Innervation in SOD1$^{G93A}$ mice | | | |
|---|---|---|---|
| Mice | Treatment | Innveration (% of NMJs) | |
| SOD1$^{G93A}$ | Vehicle | Fully Innervated | 32 |
| | | Partially Innvervated | 11 |
| | | Denervated | 57 |
| SOD1$^{G93A}$ | Isis No. 708137 | Fully Innverated | 44 |
| | | Partially Innverated | 24 |
| | | Denervated | 32 |

The invention claimed is:

1. A method comprising administering to an animal having ALS an oligomeric compound comprising a modified oligonucleotide, wherein the nucleobase sequence of the modified oligonucleotide is at least 90% complementary to the nucleobase sequence of an Ataxin-2 nucleic acid, wherein the animal has ALS associated with a SOD1 or TDP43 mutation, and wherein the modified oligonucleotide consists of 12 to 30 linked nucleosides; the animal does not have a polyglutamine (polyQ) expansion in the Ataxin-2 protein; and the administering results in amelioration of at least one symptom of ALS.

2. The method of claim 1, wherein the nucleobase sequence of the modified oligonucleotide is at least 90% complementary to an Ataxin-2 nucleic acid having the nucleobase sequence of SEQ ID NO: 3, SEQ ID NO: 4, or SEQ ID NO: 5.

3. The method of claim 1, wherein the oligomeric compound is administered prior to detection of the at least one symptom.

4. The method of claim 1, wherein the at least one symptom of ALS is loss of motor function, reduced CMAP amplitude, denervation, or loss of motor neurons.

5. The method of claim 1, wherein the amelioration of at least one symptom of ALS results in slowing of progression of at least one symptom, delaying onset of at least one symptom, or reducing severity or frequency of at least one symptom.

6. The method of claim 1, wherein the amount of Ataxin-2 mRNA and/or Ataxin-2 protein is reduced in the animal following administration of the oligomeric compound.

7. The method of claim 1, wherein the oligomeric compound is single-stranded.

8. The method of claim 1, wherein the modified oligonucleotide comprises at least one modified nucleoside comprising a bicyclic sugar moiety, at least one modified nucleoside comprising a non-bicyclic sugar moiety, or at least one modified nucleoside comprising a sugar surrogate.

9. The method of claim 8, wherein the bicyclic sugar moiety has a 2'-4' bridge, wherein the 2-4' bridge is selected from —O—$CH_2$—; —O—$CH_2$—$CH_2$—; and —O—CH($CH_3$)—.

10. The method of claim 8, wherein the non-bicyclic sugar moiety comprises a 2'-MOE or 2'-OMe.

11. The method of claim 8, wherein the sugar surrogate is selected from a morpholino, a PNA, a F-HNA, a THP, or a modified THP.

12. The method of claim 1, wherein the modified oligonucleotide has a sugar motif comprising:

a 5'-region consisting of 1-5 linked 5'-region nucleosides;

a central region consisting of 6-10 linked central region nucleosides; and a 3'-region consisting of 1-5 linked 3'-region nucleosides; wherein each of the 5'-region nucleosides and each of the 3'-region nucleosides comprises a modified sugar moiety and each of the central region nucleosides comprises an unmodified DNA sugar moiety.

13. The method of claim 1, wherein at least one internucleoside linkage is a phosphorothioate internucleoside linkage.

14. The method of claim 1, wherein each internucleoside linkage is either an unmodified phosphodiester internucleoside linkage or a phosphorothioate internucleoside linkage.

15. The method of claim 1, wherein the modified oligonucleotide comprises at least one 5-methylcytosine.

16. The method of claim 1, wherein the oligomeric compound comprises a conjugate group.

17. The method of claim 1, wherein the oligomeric compound is paired with a second oligomeric compound to form a duplex.

18. The method of claim 1, wherein the administering is to the central nervous system.

19. The method of claim 18, wherein the administering is intrathecal administration or intracerebroventricular administration.

20. The method of claim 1, wherein the nucleobase sequence of the modified oligonucleotide is at least 95% or is 100% complementary to an Ataxin-2 nucleic acid having the nucleobase sequence of SEQ ID NO: 3, SEQ ID NO: 4, or SEQ ID NO: 5.

21. The method of claim 1, wherein the animal does not have a CAG expansion in the ATXN2 gene of more than 22 repeats.

22. A method comprising identifying an animal having ALS and administering to the animal having ALS an oligomeric compound comprising a modified oligonucleotide, wherein the nucleobase sequence of the modified oligonucleotide is at least 90% complementary to the nucleobase sequence of an Ataxin-2 nucleic acid, wherein the animal has ALS associated with a SOD1 or TDP43 mutation, and wherein the modified oligonucleotide consists of 12 to 30 linked nucleosides; the animal does not have a polyglutamine (polyQ) expansion in the Ataxin-2 protein; and the administering results in amelioration of at least one symptom of ALS.

23. The method of claim 22, wherein the nucleobase sequence of the modified oligonucleotide is at least 90% complementary to an Ataxin-2 nucleic acid having the nucleobase sequence of SEQ ID NO: 3, SEQ ID NO: 4, or SEQ ID NO: 5.

24. The method of claim 22, wherein the oligomeric compound is administered prior to detection of the at least one symptom.

25. The method of claim 22, wherein the at least one symptom of ALS is loss of motor function, reduced CMAP amplitude, denervation, or loss of motor neurons.

26. The method of claim 22, wherein the amelioration of at least one symptom of ALS results in slowing of progression of at least one symptom, delaying onset of at least one symptom, or reducing severity or frequency of at least one symptom.

27. The method of claim 22, wherein the amount of Ataxin-2 mRNA and/or Ataxin-2 protein is reduced in the animal following administration of the oligomeric compound.

28. The method of claim 22, wherein the oligomeric compound is single-stranded.

29. The method of claim 22, wherein the modified oligonucleotide comprises at least one modified nucleoside comprising a bicyclic sugar moiety, at least one modified nucleoside comprising a non-bicyclic sugar moiety, or at least one modified nucleoside comprising a sugar surrogate.

30. The method of claim 29, wherein the bicyclic sugar moiety has a 2'-4' bridge, wherein the 2-4' bridge is selected from —O—$CH_2$—; —O—$CH_2$—$CH_2$—; and —O—CH($CH_3$)—.

31. The method of claim 29, wherein the non-bicyclic sugar moiety comprises a 2'-MOE or 2'-OMe.

32. The method of claim 29, wherein the sugar surrogate is selected from a morpholino, a PNA, a F-HNA, a THP, or a modified THP.

33. The method of claim 22, wherein the modified oligonucleotide has a sugar motif comprising:

a 5'-region consisting of 1-5 linked 5'-region nucleosides;

a central region consisting of 6-10 linked central region nucleosides; and a 3'-region consisting of 1-5 linked 3'-region nucleosides; wherein each of the 5'-region nucleosides and each of the 3'-region nucleosides comprises a modified sugar moiety and each of the central region nucleosides comprises an unmodified DNA sugar moiety.

34. The method of claim 22, wherein at least one internucleoside linkage is a phosphorothioate internucleoside linkage.

35. The method of claim 22, wherein each internucleoside linkage is either an unmodified phosphodiester internucleoside linkage or a phosphorothioate internucleoside linkage.

36. The method of claim 22, wherein the modified oligonucleotide comprises at least one 5-methylcytosine.

37. The method of claim 22, wherein the oligomeric compound comprises a conjugate group.

38. The method of claim 22, wherein the oligomeric compound is paired with a second oligomeric compound to form a duplex.

39. The method of claim 22, wherein the administering is to the central nervous system.

40. The method of claim 39, wherein the administering is intrathecal administration or intracerebroventricular administration.

41. The method of claim 22, wherein the nucleobase sequence of the modified oligonucleotide is at least 95% or is 100% complementary to an Ataxin-2 nucleic acid having the nucleobase sequence of SEQ ID NO: 3, SEQ ID NO: 4, or SEQ ID NO: 5.

42. The method of claim 22, wherein the animal does not have a CAG expansion in the ATXN2 gene of more than 22 repeats.

43. A method of reducing Ataxin 2 RNA in an animal, comprising administering to the animal an oligomeric compound wherein the oligomeric compound comprises a modified oligonucleotide, wherein the modified oligonucleotide consists of 12 to 30 linked nucleosides, and wherein the modified oligonucleotide has a nucleobase sequence comprising at least 12 contiguous nucleobases of any one of SEQ ID NOS: 14-45.

44. The method of claim 1, wherein the animal is a human.

45. The method of claim 22, wherein the animal is a human.

* * * * *